(12) United States Patent
Springer et al.

(10) Patent No.: US 7,737,152 B2
(45) Date of Patent: Jun. 15, 2010

(54) 6-CARBOARYL-OXY-PYRAZIN-2-YL-CARBOARYL-AMINES AND COMPOSITIONS COMPRISING SAID COMPOUNDS

(75) Inventors: Caroline Joy Springer, Sutton (GB); Ion Niculescu-Duvaz, Sutton (GB); Esteban Roman Vela, Granada (ES); Adrian Liam Gill, Macclesfield (GB); Richard David Taylor, Slough (GB); Richard Malcolm Marais, London (GB)

(73) Assignee: The Wellcome Trust Limited, London (GB)

( * ) Notice: Subject to any disclaimer, the term of this patent is extended or adjusted under 35 U.S.C. 154(b) by 0 days.

(21) Appl. No.: 11/722,612

(22) PCT Filed: Dec. 22, 2005

(86) PCT No.: PCT/GB2005/005011
§ 371 (c)(1),
(2), (4) Date: Aug. 9, 2007

(87) PCT Pub. No.: WO2006/067466
PCT Pub. Date: Jun. 29, 2006

(65) Prior Publication Data
US 2008/0015191 A1 Jan. 17, 2008

Related U.S. Application Data

(60) Provisional application No. 60/637,892, filed on Dec. 22, 2004.

(30) Foreign Application Priority Data
Dec. 22, 2004 (GB) .................. 0428082.2

(51) Int. Cl.
*A61K 31/4965* (2006.01)
(52) U.S. Cl. .................. 514/255.06; 544/405; 546/235; 585/26
(58) Field of Classification Search ............ 514/255.06; 544/405; 548/235; 585/26
See application file for complete search history.

(56) References Cited

U.S. PATENT DOCUMENTS

| 4,666,828 | A | 5/1987 | Gusella |
|---|---|---|---|
| 4,683,202 | A | 7/1987 | Mullis |
| 4,801,531 | A | 1/1989 | Frossard |
| 5,192,659 | A | 3/1993 | Simons |
| 5,272,057 | A | 12/1993 | Smulson et al. |
| 5,521,073 | A | 5/1996 | Davis et al. |
| 5,691,364 | A | 11/1997 | Buckman et al. |
| 5,877,020 | A | 3/1999 | Alitalo |
| 5,879,672 | A | 3/1999 | Davis et al. |
| 5,882,864 | A | 3/1999 | An et al. |
| 6,030,831 | A | 2/2000 | Godowski et al. |
| 6,034,103 | A | 3/2000 | Buckman et al. |
| 6,218,529 | B1 | 4/2001 | An et al. |
| 2003/0060629 | A1 | 3/2003 | Kuo et al. |
| 2004/0102455 | A1 | 5/2004 | Burns et al. |
| 2004/0235862 | A1 | 11/2004 | Burns et al. |

FOREIGN PATENT DOCUMENTS

| GB | 2400101 | 10/2004 |
|---|---|---|
| WO | WO 98/52559 | 11/1998 |
| WO | WO 01/17995 | 3/2001 |
| WO | WO 02/24681 | 3/2002 |
| WO | WO 02/060492 | 8/2002 |
| WO | WO 03/031406 | 4/2003 |
| WO | WO 03/037891 | 5/2003 |
| WO | WO 03/056036 | 7/2003 |
| WO | WO 2004/052868 | 6/2004 |
| WO | WO 2005/003101 | 1/2005 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, p. 18.*

(Continued)

*Primary Examiner*—James O Wilson
*Assistant Examiner*—Douglas M Willis
(74) *Attorney, Agent, or Firm*—Michael Best & Friedrich LLP

(57) ABSTRACT

The present invention pertains to certain 6-carboaryloxy-pyrazin-2-yl-carboaryl-amines of the following formula, and pharmaceutically acceptable salts thereof, which, inter alia, inhibit RAF (e.g., B-RAF) activity, inhibit cell proliferation, treat cancer, etc., wherein Q is independently $-N=$; $R^{P3}$ is independently a group of the formula $-J^1-L^1-Z$; $-J^1L^1-Z$ is independently $-NH-Z$; Z is independently $C_{6-14}$carboaryl and is independently unsubstituted or substituted; $R^{P2}$ is independently $-H$; $R^{P5}$ is independently a group of the formula $-W-Y$; W is independently $-O-$; Y is independently $C_{6-14}$ carboaryl and is independently unsubstituted or substituted; and $R^{P6}$ is independently $-H$. The present invention also pertains to pharmaceutical compositions comprising such compounds.

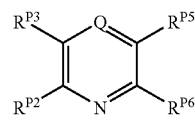

27 Claims, No Drawings

OTHER PUBLICATIONS

Wolff, Manfred E., Ed. Burger's Medicinal Chemistry and Drug Discovery—Fifth Edition, New York: John Wiley & Sons, 1996, vol. 1, pp. 975-976.*

Adams, R.H., et al, 1999, "Roles of ephrinB ligands and EphB receptors in cardiovascular development: demarcation of arterial/venous domains, vascular morphogenesis, and sprouting angiogenesis", *Genes Dev.*, vol. 13, pp. 295-306.

Angerer, L.M., et al, 1987, "Demonstration of tissue-specific gene expression by in situ hybridization", *Methods in Enzymology*, vol. 152, pp. 649-661.

Bartlett, J.M.S., 2004, "Fluorescence In Situ Hybridization: Technical Overview," in: Molecular Diagnosis of Cancer, Methods and Protocols, 2nd ed. (Series: Methods in Molecular Medicine), pp. 77-88.

Berge et al., 1977, "Pharmaceutically Acceptable Salts," *J. Pharm. Sci.*, vol. 66, pp. 1-19.

Brooks, P.C., et al, 1994, "Integrin $\alpha_v\beta_3$ antagonists promote tumor regression by inducing apoptosis of angiogenic blood vessels", *Cell*, vol. 79, pp. 1157-1164.

Brose, M.S., et al, 2002, "*BRAF* and *RAS* mutations in human lung cancer and melanoma", *Cancer Research*, vol. 62, pp. 6997-7000.

Brückner, K., et al, 1997, "Tyrosine phosphorylation of transmembrane ligands for Eph receptors", *Science*, vol. 275, pp. 1640-1643.

Bruder, J.T., et al, 1992, "Serum-, TPA-, and Ras-induced expression from Ap-1/Ets-driven promotors requires Raf-1 kinase", *Genes & Development*, vol. 6, pp. 545-556.

Calipel, A., et al., 2003, "Mutation of B-Raf in Human Choroidal Melanoma Cells Mediates Cell Proliferation and Transformation through the MEK/ERK Pathway", *J. Biol. Chem.*, vol. 278, pp. 42409-42418.

Cantrell, D.A., 2003, "GTPases and T cell activation", *Immunological Reviews*, vol. 192, pp. 122-130.

Chan, A.C., et al, 1996, "Regulation of antigen receptor signal tgransdu8ction by protein tyrosine kinases", *Current Opin. Immunol.*, vol. 8, pp. 394-401.

Cohen, Y., et al, 2003, "Lack of BRAF mutation in primary uveal melanoma", *Invest. Ophthalmol. Vis. Sci.*, vol. 44, pp. 2876-2878.

Colville-Nash, P.R., et al, 1992, "Angiogenesis and rheumatoid arthritis: pathogenic and therapeutic implications", *Annals of the Rheum. Dis.*, vol. 51, pp. 919-925.

Cooper, J.A., 1994, "Membrane-associated tyrosine kinases as molecular switches", *Sem. Cell Biology*, vol. 5, pp. 377-387.

Courtneidge, S.A., et al, 1993, "The Src family of protein tyrosine kinases: regulation and functions", *Development 1993 Supplement*, pp. 57-64.

Cowley, S., et al, 1994, "Activation of MAP kinase kinase is necessary and sufficient for PC12 differentiation and for transformation of NIH 3T3 cells", *Cell*, vol. 77, pp. 841-852.

Davies, H., et al, 2002, "Mutations of the *BRAF* gene in human cancer", *Nature*, vol. 417, pp 949-954.

Davis, S., et al, 1996, "Isolation of angiopoietin-1, a ligand for the TIE2 receptor, by secretion-trap expression cloning", *Cell*, vol. 87, pp. 1161-1169.

Denekamp, J., 1993, "Review article: angiogenesis, neovascular proliferation and vascular pathophysiology as targets for cancer therapy", *British Journal of Radiology*, vol. 66, pp. 181-196.

Dickson, B., et al, 1992, "Raf functions downstream of Ras1 in the sevenless signal transduction pathway", *Nature*, vol. 360, pp. 600-603.

Dumas, J., 2001, "Protein kinase inhibitors: emerging pharmacophores 1997-2000" Expert Opinion on Therapeutic Patents, Ashley Publications, vol. 11, No. 3, pp. 405-429.

Fidler, I.J., et al, 1994, "The implications of angiogenesis for the biology and therapy of cancer metastasis", *Cell*, vol. 79, pp. 185-188.

Folkman, J., 1992, "The role of angiogenesis in tumor growth", *Cancer Biology*, vol. 3, pp. 65-71.

Folkman, J., 1997, "Angiogenesis and angiogenesis inhibition: an overview", *EXS*, vol. 79, pp. 1-8.

Folkman, J., et al, 1992, "Angiogensis", *Journal of Biol. Chem.*, vol. 267, pp. 10931-10934.

Folkman, J., et al, 1995, "Angiogenesis in cancer, vascular, rheumatoid and other disease", *Nature Medicine*, vol. 1, pp. 27-31.

Friedlander, et al, 1995, "Definition of two angiogenic pathways by distinct $\alpha_v$ integrins", *Science*, vol. 270, pp. 1500-1502.

Gale, et al, 1999, "Growth factors acting via endothelial cell-specific receptor tyrosine kinases: VEGFs, angiopoietins, and ephrins in vascular development", *Genes Dev.*, vol. 13, pp. 1055-1066.

Genot, E., et al, 2000, "Ras regulation and function in lymphocytes", *Curr. Opin. Immunol.*, vol. 12, pp. 289-294.

Gorden, A., et al, 2003, "Analysis of *BRAF* and *N-RAS* mutations in metastatic malanoma tissues", *Cancer Research*, vol. 63, pp. 3955-3957.

Helbling, P.M., et al, 2000, "The receptor tyrosine kinase EphB4 and ephrin-B ligands restrict angiogenic growth of embryonic veins in *Xenopus laevis*", *Development*, vol. 127, pp. 269-278.

Hingorani, S. R., et al., 2003, "Suppression of $BRAF^{V599E}$ in Human Melanoma Abrogates Transformation", *Cancer Research*, vol. 63, pp. 5198-5202.

Holland, S.J., et al, 1996, "Bidirectional signalling through the EPH-family receptor Nuk and its transmembrane ligands", *Nature*, vol. 383, pp. 722-725. Holland, S.J., et al., 1996, Nature, vol. 383, pp. 722-725.

Ingber, et al, 1990,"Synthetic analogues of fumagillin that inhibit angiogenesis and suppress tumour growth", *Nature*, vol. 348, pp. 555-557.

Kahlon, R., et al, 1992, "Angiogenesis in atherosclerosis", *Can. J. Cardiol.*, vol. 8, pp. 60-64.

Karasarides, M., et al., 2004, "B-RAF is a therapeutic target in melanoma", *Oncogene*, vol. 23, pp. 6292-6298.

Kolch, W., et al, 1991, "Raf-1 protein kinase is required for growth of induced NIH/3T3 cells", *Nature*, vol. 349, pp. 426-428.

Lemonnier, J., et al, 2001, "Role of N-cadherin and protein kinase C in osteoblast gene activation inducted by the S252W fibroblast growth factor receptor 2 mutation in apert craniosynostosis", *J. Bone & Min. Research*, vol. 16, pp. 832-845.

Liu, W., et al, 2004, "Effects of overexpression of ephrin-B2 on tumour growth in human colorectal cancer", *British Journal of Cancer*, vol. 90, pp. 1620-1626.

Mansour, S.J., et al, 1994, "Transformation of mammalian cells by constitutively active MAP kinase kinase", *Science*, vol. 265, pp. 966-970.

Marais, R., et al, 1997, "Differential regulation of Rad-1, A-Raf, and B-Raf by oncogenic Ras and tyrosine kinases", *J. of Biol. Chem.*, vol. 272, pp. 4378-4383.

McMahon, G., 2000, "VEGF receptor signaling in tumor angiogenesis", *The Oncologist*, vol. 5, pp. 3-10.

Meyers, G.A., et al, 1996, "FGFR2 Exon IIIa and IIIc mutations in Crouzon, Jackson-Weiss, and Pfeiffer syndromes: Evidence for Missense changes, insertions, and a deletion due to alternative RNA splicing", *Am. J. Hum. Genet.*, vol. 58, pp. 491-498.

Mineo, T.C., et al, 2004, "Prognostic impact of VEGF, CD31, CD34, and CD105 expression and tumour vessel invasion after radical surgery for IB-IIA non-small cell lung cancer", *J. Clin. Pathol.*, vol. 57, pp. 591-597.

Mustonen, T., et al, 1995, "Endothelial receptor tyrosine kinases involved in angiogenesis", *J. Cell Biol.*, vol. 129, pp. 895-898.

Nakamoto, M., et al, 2002, "Diverse roles for the Eph family of receptor tyrosine kinases in carcinogenesis", *Micros. Res. and Tech.*, vol. 59, pp. 58-67.

O'Reilly, M.S., et al, 1994, "Angiostatin: A novel angiogenesis inhibitor that mediates the suppression of metastases by a Lewis lung carcinoma", *Cell*, vol. 79, pp. 315-328.

Orre, M., et al, 1999, "VEGF, VEGFR-1, VEGFR-2, microvessel density and endothelial cell proliferation in tumours of the ovary", *Int. J. Cancer*, vol. 84, pp. 101-108.

Ozawa, F., et al, 2001, "Growth factors and their receptors in pancreatic cancer", *Teratog. Carcinog. & Mutagen.*, vol. 21, pp. 27-44.

Pabst, B., et al, 1999, "Analysis of K-*ras* mutations in pancreatic tissue after fine needle aspirates", *Anticancer Research*, vol. 19, pp. 2481-2484.

Partanen, J., et al, 1992, "A novel endothelial cell surface receptor tyrosine kinase with extracellular epidermal growth factor homology domains", *Mol. Cell. Biol.*, vol. 12, pp. 1698-1707.

Partanen, J., et al, 1999, "Functions of Tie1 and Tie2 receptor tyrosine kinases in vascular development", *Current Topics in Microbiol. Immunol.*, vol. 237, pp. 159-172.

Paulson, R.F., et al, 1995, "Receptor tyrosine kinases and the regulation of hematopoiesis", *Semin. Immunol.*, vol. 7, pp. 267-277.

Peacock, D.J., et al, 1992, "Angiogenesis inhibition suppresses collagen arthritis", *J. Exp. Med.*, vol. 175, pp. 1135-1138.

Peacock, D.J., et al, 1995, "A novel angiogenesis inhibitor suppresses rat adjuvant arthritis", *Cell. Immun.*, vol. 160, pp. 178-184.

Peters, K.G., 1998, "Vascular endothelial growth factor and the angiopoietins", *Circ. Res.*, vol. 83, pp. 342-343.

Pinedo, H.M., et al, 2000, "Translational research: The role of VEGF in tumor angiogenesis", *The Oncologist*, vol. 5, pp. 1-2.

Plomp, A.S., et al, 1998, "Pfeiffer syndrome type 2: Further delineation and review of the literature", *Am. J. Med. Gen.*, vol. 75, pp. 245-251.

Powers, C.J., et al, 2000, "Fibroblast growth factors, their receptors and signaling", *Endocrine-Related Cancer*, vol. 7, pp. 165-197.

Prix, L., et al, 2002, "Diagnostic biochip array for fast and sensitive detection of K-*ras* mutations in stool", *Clinical Chemistry*, vol. 48, pp. 428-435.

Rajagopalan, H., et al, 2002, "RAF/RAS oncogenes and mismatch-repair status", *Nature*, vol. 418, p. 934.

Shin, D., et al, 2001, "Expression of EphrinB2 identifies a stable genetic difference between arterial and venous vascular smooth muscle as well as endothelial cells, and marks subsets of microvessels at sites of adult neovascularization", *Dev. Biol.*, vol. 230. pp. 139-150.

Singer, G., et al, 2003, "Mutations in BRAF and KRAS characterize the development of low-grade ovarian serous carcinoma", *J. Nat. Can. Inst.*, vol. 95, pp. 484-486.

Sumimoto, H. et al., 2004, "Inhibition of growth and invasive ability of melanoma by inactivaiton of mutated BRAF with lentivirus-mediated RNA interference", *Oncogene*, vol. 23, pp. 6031-6039.

Suri, C., et al, 1996, "Requisite role of angiopoietin-1, a ligand for the TIE2 receptor, during embryonic angiogenesis", *Cell*, vol. 87, pp. 1171-1180.

Tang, X.X., et al, 1999, "Coexpression of transcripts encoding EPHB receptor protein tyrosine kinases and their Ephrin-B ligands in human small cell lung carincoma[1]", *Clin. Can. Res.*, vol. 5, pp. 455-460.

Tang, X.X., et al, 1999, "High-level expression of EPHB6, EFNB2, and EFNB3 is associated with low tumor stage and high TrkA exp0ression in human neuroblastomas", *Clin. Can. Res.*, vol. 5, pp. 1491-1496.

Taraboletti, G., et al, 1995, "Inhibition of angiogenesis and murine hemangioma growth by batimastat, a synthetic inhibitor of matrix metalloproteinases", *J. Nat. Can. Instit.*, vol. 87, pp. 293-298.

Wan, P.T.C., et al, 2004, "Mechanism of activation of the RAF-ERK signaling pathway by oncogenic mutations of B-RAF", *Cell*, vol. 116, pp. 855-867.

Wang, H.U., et al, 1998, "Molecular distinction and angiogenic interaction between embryonic arteries and veins revealed by ephrin-B2 and its receptor Eph-B4", *Cell*, vol. 93, pp. 741-753.

Wellbrock, C., et al., 2004, "$^{V599E}$B-RAF is an Oncogene in Melanocytes", *Cancer Research*, vol. 64, pp. 2338-2342.

Wilks, A.F., 1990, "Structure and function of the protein tyrosine kinases", *Progress in Growth Factor Research*, vol. 2, pp. 97-111.

Yancopoulos, G.D., et al, 1998, "Vasculogenesis, angiogenesis, and growth factors: ephrins enter the fray at the border", *Cell*, vol. 93, pp. 661-664.

Yu, K., et al, 2000, "Loss of fibroblast growth factor receptor 2 ligand-binding specificity in Apert syndrome", *Proc. Natl. Acad. Sci. U.S.A.*, vol. 97, pp. 14536-14541.

\* cited by examiner

6-CARBOARYL-OXY-PYRAZIN-2-YL-CARBOARYL-AMINES AND COMPOSITIONS COMPRISING SAID COMPOUNDS

CROSS-REFERENCE TO RELATED APPLICATIONS

This application is a national stage filing under 35 U.S.C. 371 of International Application No. PCT/GB2005/005011, filed on Dec. 22, 2005, which claims priority benefits to United Kingdom Application No. 0428082.2, filed Dec. 22, 2004, and to U.S. Provisional Application No. 60/637,892, filed Dec. 22, 2004; the contents of each of which are incorporated herein by reference in their entirety.

TECHNICAL FIELD

The present invention pertains generally to the field of therapeutic compounds for treating proliferative conditions, cancer, etc., and more specifically to certain pyrazines and pyridines and derivatives thereof which, inter alia, inhibit RAF (e.g., B-RAF) activity. The present invention also pertains to pharmaceutical compositions comprising such compounds, and the use of such compounds and compositions, e.g., both in vitro and in vivo, to inhibit RAF (e.g., B-RAF) activity, to inhibit receptor tyrosine kinase (RTK) activity, to inhibit cell proliferation, to induce cell death, and in the treatment of diseases and conditions that are ameliorated by the inhibition of RAF, RTK, etc., proliferative conditions such as cancer (e.g., colorectal cancer, melanoma), etc.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

RAF, Proliferative Conditions, and Cancer

Mutations in genes that directly or indirectly control cell growth and differentiation are generally considered to be the main cause of cancer. Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation.

RAF is key downstream target for the RAS GTPase and mediates the activation of the MAP kinase cascade consisting of RAF-MEK-ERK. Activated ERK is a kinase that subsequently targets a number of proteins responsible for mediating, amongst other things, the growth, survival and transcriptional functions of the pathway. These include the transcription factors ELK1, C-JUN, the Ets family (including Ets 1, 2, and 7), and the FOS family. The RAS-RAF-MEK-ERK signal transduction pathway is activated in response to many cell stimuli including growth factors such as EGF, PDGF, KGF etc. Because the pathway is a major target for growth factor action, the activity of RAF-MEK-ERK has been found to be upregulated in many factor dependent tumours. The observation that about 20% of all tumours have undergone an activating mutation in one of the ras proteins indicates that the pathway is more broadly important in tumorigenesis. There is growing evidence that activating mutations in other components of the pathway also occur in human tumours. This is true for RAF.

The RAF oncogene family includes three highly conserved genes termed A-RAF, B-RAF and C-RAF (also called Raf-1). RAF genes encode protein kinases that play important regulatory roles in signal transduction processes that regulate cell proliferation. RAF genes code for highly conserved serine-threonine-specific protein kinases, which are recruited to the plasma membrane following direct binding to the Ras small Guanine-nucleotide binding proteins and this is the initiating event in RAF activation. RAF proteins are part of a signal transduction pathway believed to consist of receptor tyrosine kinases, adaptor proteins and exchange factors, p21 RAS, RAF protein kinases, Mek1 (ERK activator or MAPKK) kinases and ERK (MAPK) kinases, which ultimately phosphorylate several cellular substrates, including transcription factors. Signaling through this pathway can mediate differentiation, proliferation or oncogenic transformation in different cellular contexts. Thus, RAF kinases are believed to play a fundamental role in the normal cellular signal transduction pathway, coupling a multitude of growth factors to their net effect, cellular proliferation. Because RAF proteins are direct downstream effectors of RAS protein function, therapies directed against RAF kinases are believed to be useful in treatment of RAS-dependent tumors.

The RAF kinases are differentially regulated and expressed; C-RAF is the most thoroughly characterized and is expressed in all organs and in all cell lines that have been examined. A-RAF and B-RAF also appear to be ubiquitous, but are most highly expressed in urogenital and brain tissues, respectively. Because B-RAF is highly expressed in neural tissues it was once thought to be limited to these tissues but it has since been found to be more widely expressed. Although all RAF proteins can bind to active RAS, B-RAF is most strongly activated by oncogenic RAS, and may be the primary target of oncogenic RAS in transformed cells.

Recent evidence indicates that mutational activation of B-RAF is found in a number of different tumours including more than 65% of malignant melanomas, more than 10% of colorectal cancers (Davies, H., et al., 2002, *Nature*, Vol. 417, pp. 949-954; Rajagopalan, H. et al., 2002, *Nature*, Vol. 418, p. 934), ovarian cancers (Singer, G., et al., 2003, *J. Natl. Cancer Inst.*, Vol. 95, pp. 484-486) and papillary thyroid cancers (Brose, M., et al., 2002, *Cancer Res.*, Vol. 62, pp. 6997-7000;

Cohen, Y., et al., 2003, *Invest. Opthalmol. Vis. Sci.*, Vol. 44, pp. 2876-2878). A range of different B-RAF mutations have been identified in different tumours with the most common being a V600E mutation (which was originally assigned as V599E) in the so-called activation loop of the kinase domain (Davies, H., et al., 2002, *Nature*, Vol. 417, pp. 949-954).

Other mutations of B-RAF found associated with human cancers may not necessarily activate B-RAF directly but do upregulate the activity of the RAS-RAF-MEK-ERK pathway by mechanisms which are not fully understood but may involve cross-talk with other RAF isoforms, such as C-RAF (Wan, P., et al., 2004, *Cell*, Vol. 116, pp. 855-867). In such cases, inhibition of RAF activity would remain a beneficial aim in cancer treatment.

In addition to link between B-RAF and certain cancers, there is a significant amount of evidence to indicate a more broad inhibition of RAF activity could be beneficial as an antitumour therapy. Blocking the pathway at the level of B-RAF would be effective at counteracting the upregulation of this pathway caused by tumorigenic ras mutations and also in tumours responding to growth factor action via this pathway. Genetic evidence in *Drosophila* and *C. elegans* indicates that RAF homologues are essential for ras dependent actions on differentiation (Dickson, B., et al., 1993, *Nature*, Vol. 360, pp. 600-603). Introduction of constitutively active MEK into NIH3T3 cells can have a transforming action whilst expression of dominant negative MEK proteins can suppress the tumorigenicity of RAS transformed cell lines (Mansour, S. J., et al., 1994, *Science*, Vol. 265, pp. 966-970; Cowely, S., et al., 1994, *Cell*, Vol. 77, pp. 841-852). Expression of activated versions of B-RAF in fibroblasts and melanocytes causes them to acquire elevated ERK, to grow in a mitogen independent manner and to grow as tumours in nude mice, demonstrating the oncogenic potential of mutant B-RAF (Davies, H., et al., 2002, *Nature*, Vol. 417, pp. 949-954; Wellbrock, C., et al., 2004, *Cancer Research*, Vol. 64, pp. 2338-2342). Expression of a dominant negative RAF protein has also been found to inhibit ras dependent signalling as has suppression of RAF expression using an antisense oligonucleotide construct (Koch, W., et al., 1991, *Nature*, Vol. 349, pp. 426-428; Bruder, T. T., et al., 1992, *Genes and Development*, Vol. 6, pp. 545-556). Depletion of B-RAF protein in melanoma cells that express oncogenic versions of B-RAF using RNA interference technology blocks their constitutive ERK signalling, blocks their proliferation, induces death in some, but not all lines and prevents the cells from growing as tumours in nude mice (Calipel, A., et al., 2003, *J. Biol. Chem.*, Vol. 278, pp. 42409-42418; Hingorani, S. R., et al., 2003, *Cancer Research*, Vol. 63, pp. 5198-5202; Karasarides, M., et al., 2004, *Oncogene*, Vol. 23, pp. 6292-6298; Sumimoto, H et al., 2004, *Oncogene*, Vol. 23, pp. 6031-6039).

This and other evidence suggests that inhibition of RAF (e.g., B-RAF) activity would be beneficial in the treatment of cancer, and that inhibition of RAF (e.g., B-RAF) activity could be particularly beneficial in those cancers containing a constitutively activated B-RAF mutation.

The RAF-MEK-ERK pathway functions downstream of many receptors and stimuli indicating a broad role in regulation of cell function. For this reason inhibitors of RAF may find utility in other disease conditions that are associated with upregulation of signalling via this pathway. The RAF-MEK-ERK pathway is also an important component of the normal response of non-transformed cells to growth factor action. Therefore inhibitors of RAF may be of use in diseases where there is inappropriate or excessive proliferation of normal tissues. These include, but are not limited to glomerulonephritis and psoriasis. The cellular signalling pathway of which RAF is a part has also been implicated in inflammatory disorders characterized by T-cell proliferation (T-cell activation and growth), such as tissue graft rejection, endotoxin shock, and glomerular nephritis.

RAF (e.g., B-RAF) has been shown to be a valid therapeutic target in hyperproliferative disorders such as cancer. Activated versions of RAF (e.g., B-RAF) are able to transform mammalian cells, allowing them to take on the characteristics of cancer cells and the growth of these cells becomes dependent on the mutant RAF (e.g., B-RAF) protein. Inhibition of RAF (e.g., B-RAF) activity in human cancer cell lines that express the mutant forms of RAF (e.g., B-RAF) blocks their growth and ultimately induces their death.

Angiogenesis

Chronic proliferative diseases are often accompanied by profound angiogenesis, which can contribute to or maintain an inflammatory and/or proliferative state, or which leads to tissue destruction through the invasive proliferation of blood vessels. (Folkman, 1997, *EXS*, Vol. 79, pp. 1-81; Folkman, 1995, *Nature Medicine*, Vol. 1, pp. 27-31; Folkman and Shing, 1992, *J. Biol. Chem.*, Vol. 267, p. 10931.)

Angiogenesis is generally used to describe the development of new or replacement blood vessels, or neovascularisation. It is a necessary and physiological normal process by which the vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, 1992, *Ann. Rhum. Dis.*, Vol. 51, p. 919). In diabetes (and in many different eye diseases), new vessels invade the macula or retina or other ocular structures, and may cause blindness (Brooks et al., 1994, *Cell*, Vol. 79, p. 1157). The process of atherosclerosis has been linked to angiogenesis (Kahlon et al., 1992, *Can. J. Cardiol.*, Vol. 8, p. 60). Tumor growth and metastasis have been found to be angiogenesis-dependent (Folkman, 1992, *Cancer Biol.*, Vol. 3, p. 65; Denekamp, 1993, *Br. J. Rad.*, Vol. 66, p. 181; Fidler and Ellis, 1994, *Cell*, Vol. 79, p. 185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly et al., 1994, *Cell*, Vol. 79, p. 315; Ingber et al., 1990, *Nature*, Vol. 348, p. 555), ocular diseases (Friedlander et al., 1995, *Science*, Vol. 270, p. 1500), arthritis (Peacock et al., 1992, *J. Exp. Med.*, Vol. 175, p. 1135; Peacock et al., 1995, *Cell. Immun.*, Vol. 160, p. 178) and hemangioma (Taraboletti et al., 1995, *J. Natl. Cancer Inst.*, Vol. 87, p. 293).

RTKs

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

FGFR

The fibroblast growth factor (FGF) family of signaling polypeptides regulates a diverse array of physiologic functions including mitogenesis, wound healing, cell differentiation and angiogenesis, and development. Both normal and malignant cell growth as well as proliferation are affected by changes in local concentration of these extracellular signaling molecules, which act as autocrine as well as paracrine factors. Autocrine FGF signaling may be particularly important in the progression of steroid hormone-dependent cancers and to a hormone independentstate (Powers et al., 2000, *Endocr. Relat. Cancer*, Vol. 7, pp. 165-197).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Ozawa et al., 2001, *Teratog. Carcinog. Mutagen.*, Vol. 21, pp. 27-44).

The two prototypic members are acidic fibroblast growth factor (aFGF or FGF1) and basic fibroblast growth factors (bFGF or FGF2), and to date, at least twenty distinct FGF family members have been identified. The cellular response to FGFs is transmitted via four types of high affinity transmembrane tyrosine-kinase fibroblast growth factor receptors numbered 1 to 4 (FGFR-1 to FGFR-4). Upon ligand binding, the receptors dimerize and auto- or trans-phosphorylate specific cytoplasmic tyrosine residues to transmit an intracellular signal that ultimately reaches nuclear transcription factor effectors.

Disruption of the FGFR-1 pathway should affect tumor cell proliferation since this kinase is activated in many tumor types in addition to proliferating endothelial cells. The overexpression and activation of FGFR-1 in tumor-associated vasculature has suggested a role for these molecules in tumor angiogenesis.

FGFR-2 has high affinity for the acidic and/or basic fibroblast growth factors, as well as the keratinocyte growth factor ligands. FGFR-2 also propagates the potent osteogenic effects of FGFs during osteoblast growth and differentiation. Mutations in FGFR-2, leading to complex functional alterations, were shown to induce abnormal ossification of cranial sutures (craniosynostosis), implying a major role of FGFR signaling in intramembraneous bone formation. For example, in Apert (AP) syndrome, characterized by premature cranial suture ossification, most cases are associated with point mutations engendering gain-of-function in FGFR-2 (Lemonnier et al., 2001, *J. Bone Miner. Res.*, Vol. 16, pp. 832-845).

Several severe abnormalities in human skeletal development, including Apert, Crouzon, Jackson-Weiss, Beare-Stevenson cutis gyrata, and Pfeiffer syndromes are associated with the occurrence of mutations in FGFR-2. Most, if not all, cases of Pfeiffer Syndrome (PS) are also caused by de novo mutation of the FGFR-2 gene (Meyers et al., 1996, *Am. J. Hum. Genet.*, Vol. 58, pp. 491-498; Plomp et al., 1998, *Am. J. Med. Genet.*, Vol. 75, 245-251), and it was recently shown that mutations in FGFR-2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of FGFR-2 (Yu et al., 2000, *Proc. Natl. Acad. Sci. U.S.A.*, Vol. 97, pp. 14536-14541).

Activating mutations of the FGFR-3 receptor tyrosine kinase such as chromosomal translocations or point mutations produce deregulated, constitutively active, FGFR-3 receptors which have been involved in multiple myeloma and in bladder and cervix carcinomas (Powers, C. J., et al., 2000, *Endocr. Rel. Cancer*, Vol. 7, p. 165). Accordingly, FGFR-3 inhibition would be useful in the treatment of multiple myeloma, bladder and cervix carcinomas.

VEGFR

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al., 2000, *The Oncologist*, Vol. 5 (90001), pp. 1-2). VEGFR(s) are protein tyrosine kinases (PTKs). PTKs catalyze the phosphorylation of specific tyrosyl residues in proteins involved in the regulation of cell growth and differentiation. (Wilks, A. F., 1990, *Progress in Growth Factor Research*, Vol. 2, pp. 97-111; Courtneidge, S. A., 1993, *Dev. Supp.l*, pp. 57-64; Cooper, J. A., 1994, *Semin. Cell Biol.*, Vol. 5(6), pp. 377-387; Paulson, R. F., 1995, *Semin. Immunol.*, Vol. 7(4), pp. 267-277; Chan, A. C., 1996, *Curr. Opin. Immunol.*, Vol. 8(3), pp. 394-401).

Three PTK receptors for VEGF have been identified: VEGFR-1 (Flt-1), VEGFR-2 (Flk-1 or KDR), and VEGFR-3 (Flt-4). These receptors are involved in angiogenesis and participate in signal transduction (Mustonen, T., et al., 1995, *J. Cell Biol.*, Vol. 129, pp. 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G., 2000, *The Oncologist*, Vol. 5(90001), pp. 3-10).

Inhibition at the kinase domain binding site of VEGFR-2 would block phosphorylation of tyrosine residues and serve to disrupt initiation of angiogenesis.

TIE

Angiopoieten 1 (Ang1), a ligand for the endothelium-specific receptor tyrosine kinase TIE-2 is a novel angiogenic factor (Davis et al., 1996, *Cell*, Vol. 87, pp. 1161-1169; Partanen et al., 1992, *Mol. Cell. Biol.*, Vol. 12, pp. 1698-1707; U.S. Pat. Nos. 5,521,073; 5,879,672; 5,877,020; and 6,030, 831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of anEGF-like domain and an immunoglobulin (IG)

like domain, which consists of extracellular folding units, stabilized by intra-chain disulfide bonds (Partanen et al., 1999, *Curr. Topics Microbiol. Immunol.*, Vol. 237, pp. 159-172). Unlike VEGF, which functions during the early stages of vascular development, Ang1 and its receptor TIE-2 function in the later stages of vascular development, i.e., during vascular remodelling (remodelling refers to formation of a vascular lumen) and maturation (Yancopoulos et al., 1998, *Cell*, Vol. 93, pp. 661-664; Peters, K. G., 1998, *Circ. Res.*, Vol. 83(3), pp. 342-343; Suri et al., 1996, *Cell*, Vol. 87, pp. 1171-1180).

Consequently, inhibition of TIE-2 would be expected to serve to disrupt remodelling and maturation of new vasculature initiated by angiogenesis thereby disrupting the angiogenic process.

Eph

The largest subfamily of receptor tyrosine kinases (RTKs), the Eph family, and their ligands (ephrins), play important roles in physiologic and pathologic vascular processes. Both the Ephs (receptors) and ephrins (ligands) are divided into two groups, A and B subfamilies (Eph Nomenclature Committee, 1997). The binding of ephrin ligands to Eph receptors is dependent on cell-cell interactions. The interactions of ephrins and Ephs have recently been shown to function via bi-directional signalling. The ephrins binding to Eph receptors initiate phosphorylation at specific tyrosine residues in the cytoplasmic domain of the Eph receptors. In response to Eph receptor binding, the ephrin ligand also undergoes tyrosine phosphorylation, so-called 'reverse' signalling (Holland, S. J., et al., 1996, *Nature*, Vol. 383, pp. 722-725; Bruckner et al., 1997, *Science*, Vol. 275, pp. 1640-1643).

Eph RTKs and their ephrin ligands play important roles in embryonic vascular development. Disruption of specific Eph receptors and ligands (including ephrin-B2) leads to defective vessel remodelling, organisation, and sprouting resulting in embryonic death (Wang, H. U., et al., 1998, *Cell*, Vol. 93, pp. 741-753; Adams, R. H., et al., 1999, *Genes Dev*, Vol. 13, pp. 295-306; Gale and Yancopoulos, 1999, *Genes Dev*, Vol. 13, pp. 1055-1066; Helbling, P. M., et al., 2000, *Development*, Vol. 127, pp. 269-278). Coordinated expression of the Eph/ephrin system determines the phenotype of embryonic vascular structures: ephrin-B2 is present on arterial endothelial cells (ECs), whereas EphB4 is present on venous ECs (Gale and Yancopoulos, 1999, *Genes Dev*, Vol. 13, pp. 1055-1066; Shin, D., et al., 2001, *Dev Biol*, Vol. 230, pp. 139-150). Recently, specific Ephs and ephrins have been implicated in tumour growth and angiogenesis.

The Ephs and ephrins have been found to be overexpressed in many human tumours. In particular, the role of EphB2 has been identified in small cell lung carcinoma (Tang, X. X., et al., 1999, *Clin Cancer Res*, Vol. 5, pp. 455-460), human neuroblastomas (Tang, X. X., et al., 1999, *Clin Cancer Res*, Vol. 5, pp. 1491-1496) and colorectal cancers (Liu, W., et al., 2004, *Brit. J. Canc.*, Vol. 90, pp. 1620-1626), and higher expression levels of Ephs and ephrins, including EphB2, have been found to correlate with more aggressive and metastatic tumours (Nakamoto, M. and Bergemann, A. D., 2002, *Microsc. Res Tech*, Vol. 59, pp. 58-67).

Consequently, inhibition of EphB2 would be expected to serve to disrupt angiogenesis, and in particular in certain tumours where over-expression occurs.

The inventors have discovered compounds that, e.g., inhibit RAF (e.g., B-RAF) activity and/or are useful in the treatment of, e.g., proliferative conditions, cancer, etc.

There is a recognized need for more and better treatments for proliferative conditions (e.g., cancer) which offer, for example, one or more the following benefits:
(a) improved activity;
(b) improved efficacy;
(c) improved specificity;
(d) reduced toxicity (e.g., cytotoxicity);
(e) complement the activity of other treatments (e.g., chemotherapeutic agents);
(f) reduced intensity of undesired side-effects;
(g) fewer undesired side-effects;
(h) simpler methods of administration (e.g., route, timing, compliance);
(i) reduction in required dosage amounts;
(j) reduction in required frequency of administration;
(k) increased ease of synthesis, purification, handling, storage, etc.;
(l) reduced cost of synthesis, purification, handling, storage, etc.

Thus, one aim of the present invention is the provision of active compounds that, offer one or more of the above benefits.

SUMMARY OF THE INVENTION

One aspect of the invention pertains to active compounds, specifically, certain pyrazines and pyridines and derivatives thereof, as described herein.

Another aspect of the invention pertains to a composition comprising an active compound as described herein and a pharmaceutically acceptable carrier or diluent.

Another aspect of the present invention pertains to a method of inhibiting RAF (e.g., B-RAF) activity in a cell, e.g., in vitro or in vivo, comprising contacting the cell with an effective amount of an active compound, as described herein.

Another aspect of the present invention pertains to a method of inhibiting receptor tyrosine kinase (RTK) activity, such as FGFR, Tie, VEGFR and/or Eph activity, for example, FGFR-1, FGFR-2, FGFR-3, Tie2, VEGFR-2 and/or EphB2 activity, in a cell, e.g., in vitro or in vivo, comprising contacting the cell with an effective amount of an active compound, as described herein.

Another aspect of the present invention pertains to a method of regulating (e.g., inhibiting) cell proliferation (e.g., proliferation of a cell), inhibiting cell cycle progression, promoting apoptosis, or a combination of one or more these, e.g., in vitro or in vivo, comprising contacting cells (or the cell) with an effective amount of an active compound, as described herein.

Another aspect of the present invention pertains to a method for the treatment comprising administering to a subject in need of treatment a therapeutically-effective amount of an active compound, as described herein, preferably in the form of a pharmaceutical composition.

Another aspect of the present invention pertains to an active compound as described herein for use in a method of treatment of the human or animal body by therapy.

Another aspect of the present invention pertains to use of an active compound, as described herein, in the manufacture of a medicament for use in treatment.

In one embodiment, the treatment is treatment of a disease or condition (e.g., cancer) that is characterised by the up-regulation and/or activation of RAF (e.g., B-RAF), and/or is ameliorated by the inhibition of RAF (e.g., B-RAF).

In one embodiment, the treatment is treatment of a disease or condition (e.g., cancer) that is characterised by the up-regulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of a disease or condition that is characterised by inappropriate, excessive, and/or undesirable angiogenesis.

In one embodiment, the treatment is treatment of a proliferative condition, e.g., cancer.

Another aspect of the present invention pertains to a kit comprising (a) an active compound, as described herein, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

One aspect of the present invention pertains to compounds which may be described as "pyrazine and pyridines and derivatives thereof", and their surprising and unexpected RAF (e.g., B-RAF) inhibitory, anti-proliferative, and anti-cancer properties.

Compounds

One aspect of the present invention pertains to compounds of the following formula:

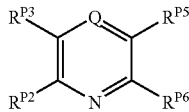

wherein:
Q is independently —N= or —CH=;
one of $R^{P2}$ and $R^{P3}$ is independently a group of the formula -$J^1$-$L^1$-Z;
  wherein:
  if Q is —N=, then -$J^1$-$L^1$-Z is independently:
    —NH—Z,
    —O—Z, or
    —S—Z;
  if Q is —CH=, then -$J^1$-$L^1$-Z is independently:
    —NH—(CH$_2$)$_n$—Z, wherein n is independently 0 or 1,
    —O—Z, or
    —S—Z;

Z is independently:
  $C_{6-14}$carboaryl,
  $C_{5-14}$heteroaryl,
  $C_{3-12}$carbocyclyl,
  $C_{3-12}$heterocyclyl;
  and is independently unsubstituted or substituted;
the other of $R^{P2}$ and $R^{P3}$ is independently —H, —NHR$^{N1}$, or —NHC(=O)R$^{N2}$;
wherein:
  R$^{N1}$, if present, is independently —H or aliphatic saturated $C_{1-4}$alkyl;
  R$^{N2}$, if present, is independently —H or aliphatic saturated $C_{1-4}$alkyl;
one of $R^{P5}$ and $R^{P6}$ is independently a group of the formula —W—Y;
  wherein:
  W is independently:
    a covalent bond;
    —NR$^{N4}$, —O—, —S—, —C(=O)—, —CH$_2$—;
    —NR$^{N4}$—CH$_2$—, —O—CH$_2$—, —S—CH$_2$—, —C(=O)—CH$_2$—, —(CH$_2$)$_2$—;
    —CH$_2$—NR$^{N4}$—, —CH$_2$—O—, —CH$_2$—S—, or —CH$_2$—C(=O)—;
  wherein:
    R$^{N4}$, if present, is independently —H or aliphatic saturated $C_{1-4}$alkyl;
  Y is independently:
    $C_{6-14}$carboaryl,
    $C_{5-14}$heteroaryl,
    $C_{3-12}$carbocyclyl,
    $C_{3-12}$heterocyclyl;
    and is independently unsubstituted or substituted;
the other of $R^{P5}$ and $R^{P6}$ is independently —H;

and pharmaceutically acceptable salts, solvates, amides, esters, ethers, N-oxides, chemically protected forms, and prodrugs thereof.

Pyrazines

In one embodiment, Q is —N=, and the compounds may be referred to as "pyrazines":

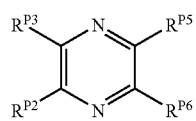

It is not intended that the central pyrazine ring be fused to any other rings.

In one embodiment, Q is —N= and one of $R^{P2}$ and $R^{P3}$ is independently —NH—Z, as in, for example:

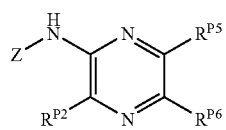

In one embodiment, Q is —N= and one of $R^{P2}$ and $R^{P3}$ is independently —O—Z or —S—Z.

In one embodiment, Q is —N= and one of $R^{P2}$ and $R^{P3}$ is independently —O—Z.

In one embodiment, Q is —N= and one of $R^{P2}$ and $R^{P3}$ is independently —S—Z.

In one embodiment:
Q is —N=;
$R^{P2}$ is independently —H;
$R^{P3}$ is independently: —NH—Z, —O—Z, or —S—Z;
$R^{P5}$ is independently a group of the formula —W—Y; and
$R^{P6}$ is independently —H;

as in, for example:

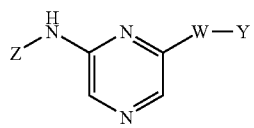

Pyridines

In one embodiment, Q is —CH=, and the compounds may be referred to as "pyridines":

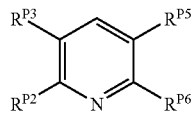

It is not intended that the central pyridine ring be fused to any other rings.

In one embodiment, Q is —CH= and one of $R^{P2}$ and $R^{P3}$ is independently —NH—(CH$_2$)$_n$—Z, wherein n is independently 0 or 1, as in, for example:

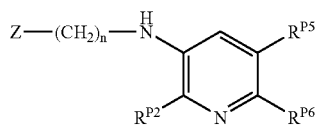

In one embodiment, Q is —CH= and one of $R^{P2}$ and $R^{P3}$ is independently —NH—Z (i.e., n is 0), as in, for example:

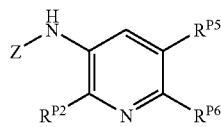

In one embodiment, Q is —CH= and one of $R^{P2}$ and $R^{P3}$ is independently —NH—CH$_2$—Z (i.e., n is 1), as in, for example:

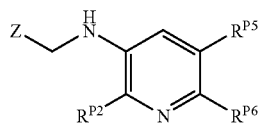

In one embodiment, Q is —CH= and one of $R^{P2}$ and $R^{P3}$ is independently —O—Z or —S—Z.

In one embodiment, Q is —CH= and one of $R^{P2}$ and $R^{P3}$ is independently —O—Z.

In one embodiment, Q is —CH= and one of $R^{P2}$ and $R^{P3}$ is independently —S—Z.

The Other of $R^{P2}$ and $R^{P3}$ and the Other of $R^{P5}$ and $R^{P6}$: Positions In one embodiment:
$R^{P3}$ is independently a group of the formula -J$^1$-L$^1$-Z; and
$R^{P2}$ is independently —H, —NHR$^{N1}$, or —NHC(=O)R$^{N2}$.

In one embodiment:
$R^{P3}$ is independently —H, —NHR$^{N1}$, or —NHC(=O)R$^{N2}$; and
$R^{P2}$ is independently a group of the formula -J$^1$-L$^1$-Z.

In one embodiment:
$R^{P5}$ is independently a group of the formula —W—Y; and
$R^{P6}$ is independently —H.

In one embodiment:
$R^{P3}$ is independently a group of the formula -J$^1$-L$^1$-Z;
$R^{P2}$ is independently —H, —NHR$^{N1}$, or —NHC(O)R$^{N2}$;
$R^{P5}$ is independently a group of the formula —W—Y; and
$R^{P6}$ is independently —H;

as in, for example, the following formula:

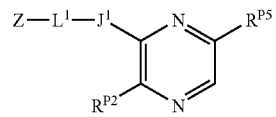

In one embodiment:
$R^{P3}$ is independently —H, —NHR$^{N1}$, or —NHC(=O)R$^{N2}$;
$R^{P2}$ is independently a group of the formula -J$^1$-L$^1$-Z;
$R^{P5}$ is independently a group of the formula —W—Y; and
$R^{P6}$ is independently —H;

as in, for example, the following formula:

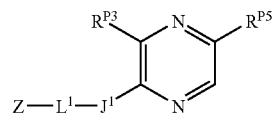

The Other of $R^{P2}$ and $R^{P3}$

As described above, the other of $R^{P2}$ and $R^{P3}$ is independently —H, —NHR$^{N1}$, or —NHC(=O)R$^{N2}$, wherein:

$R^{N1}$, if present, is independently —H or aliphatic saturated C$_{1-4}$alkyl;
$R^{N2}$, if present, is independently —H or aliphatic saturated C$_{1-4}$alkyl.

In one embodiment, $R^{N1}$, if present, is independently —H, -Me, or -Et.

In one embodiment, $R^{N2}$, if present, is independently —H, -Me, or -Et.

In one embodiment, the other of $R^{P2}$ and $R^{P3}$ is independently —H, —NH$_2$, —NHMe, —NHEt, —NHC(=O)Me, or —NHC(=O)Et.

In one embodiment, $R^{N1}$, if present, is independently —H or -Me.

In one embodiment, $R^{N2}$, if present, is independently —H or -Me.

In one embodiment, the other of $R^{P2}$ and $R^{P3}$ is independently —H, —NH$_2$, —NHMe, or —NHC(=O)Me.

In one embodiment, $R^{N1}$, if present, is independently —H.

In one embodiment, $R^{N2}$, if present, is independently —H.

In one embodiment, the other of $R^{P2}$ and $R^{P3}$ is independently —H.

In one embodiment, $R^{N1}$, if present, is independently other than —H.

In one embodiment, $R^{N2}$, if present, is independently other than —H.

The Group W

The group W is independently:
a covalent bond;
—$NR^{N4}$—, —O—, —S—, —C(=O)—, —$CH_2$—;
—$NR^{N4}$—$CH_2$—, —O—$CH_2$—, —S—$CH_2$—, —C(=O)—$CH_2$—, —$(CH_2)_2$—;
—$CH_2$—$NR^{N4}$—, —$CH_2$—O—, —$CH_2$—S—, or —$CH_2$—C(=O)—;

wherein $R^{N4}$, if present, is independently —H or aliphatic saturated $C_{1-4}$alkyl.

In one embodiment, W is independently:
a covalent bond;
—$NR^{N4}$—, —O—, —S—, —C(=O)—, or —$CH_2$—.

In one embodiment, W is independently: a covalent bond, —$NR^{N4}$—, —O—, —S—, or —C(=O)—.

In one embodiment, W is independently: a covalent bond, —$NR^{N4}$—, —O—, or —S—.

In one embodiment, W is independently: a covalent bond, —$NR^{N4}$— or —O—.

In one embodiment, W is independently: a covalent bond.
In one embodiment, W is independently: —$NR^{N4}$—.
In one embodiment, W is independently: —O—.
In one embodiment, W is independently: —S—.
In one embodiment:
Q is —N=,
$R^{P2}$ is independently —H;
$R^{P3}$ is independently: —NH—Z;
$R^{P5}$ is independently a group of the formula —W—Y;
W is independently a covalent bond; and
$R^{P6}$ is independently —H;

as in, for example:

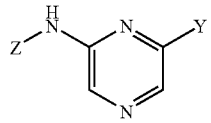

In one embodiment:
Q is —N=,
$R^{P2}$ is independently —H;
$R^{P3}$ is independently: —NH—Z;
$R^{P5}$ is independently a group of the formula —W—Y;
W is independently —$NR^{N4}$—; and
$R^{P6}$ is independently —H;

as in, for example:

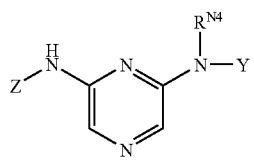

In one embodiment:
Q is —N=,
$R^{P2}$ is independently —H;
$R^{P3}$ is independently: —NH—Z;

$R^{P5}$ is independently a group of the formula —W—Y;
W is independently —O—; and
$R^{P6}$ is independently —H;

as in, for example:

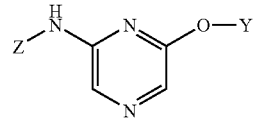

In one embodiment:
Q is —N=,
$R^{P2}$ is independently —H;
$R^{P3}$ is independently: —NH—Z;
$R^{P5}$ is independently a group of the formula —W—Y;
W is independently —S—; and
$R^{P6}$ is independently —H;

as in, for example:

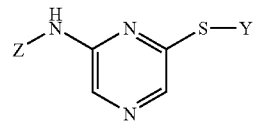

in one embodiment, $R^{N4}$, if present, is independently —H or aliphatic saturated $C_{1-4}$alkyl.

In one embodiment, $R^{N4}$, if present, is independently —H, -Me, or -Et.

In one embodiment, $R^{N4}$, if present, is independently —H or -Me.

In one embodiment, $R^{N4}$, if present, is independently —H.

The Group Y

The group Y is independently:
$C_{6-14}$carboaryl,
$C_{5-14}$heteroaryl,
$C_{3-12}$carbocyclyl, or
$C_{3-12}$heterocyclyl;
and is independently unsubstituted or substituted.

In one embodiment, Y is independently:
$C_{6-14}$carboaryl, or
$C_{5-14}$heteroaryl;
and is independently unsubstituted or substituted.

In one embodiment, Y is independently:
$C_{6-12}$carboaryl, or
$C_{5-12}$heteroaryl;
and is independently unsubstituted or substituted.

In one embodiment, Y is independently:
$C_{6-10}$carboaryl, or
$C_{5-10}$heteroaryl;
and is independently unsubstituted or substituted.

In one embodiment, Y is independently:
monocyclic or bicyclic $C_{6-10}$carboaryl, or
monocyclic or bicyclic $C_{5-10}$heteroaryl;
and is independently unsubstituted or substituted.

In one embodiment, the bicyclic groups are selected from "5-6" fused rings and "6-6" fused rings, e.g., as in benzimidazole and naphthalene, respectively.

In one embodiment, Y is independently:
monocyclic $C_6$carboaryl, or
monocyclic $C_{5-6}$heteroaryl;
and is independently unsubstituted or substituted.

In one embodiment, the heteroaryl groups have 1, 2, or 3 aromatic ring heteroatoms, e.g., selected from nitrogen and oxygen.

In one embodiment, the heteroaryl groups have 1 aromatic ring heteroatom, e.g., selected from nitrogen and oxygen.

In one embodiment, the heteroaryl groups have 2 aromatic ring heteroatoms, e.g., selected from nitrogen and oxygen.

In one embodiment, the heteroaryl groups have 3 aromatic ring heteroatoms, e.g., selected from nitrogen and oxygen.

In one embodiment, Y is independently derived from: benzene, naphthylene, pyridine, pyrrole, furan, thiophene, or thiazole; and is independently unsubstituted or substituted.

In one embodiment, Y is independently: phenyl, naphthyl, pyridyl, pyrrolyl, furanyl, thiophenyl, or thiazolyl; and is independently unsubstituted or substituted.

The phrase "derived from," as used in this context, pertains to compounds which have the same ring atoms, and in the same orientation/configuration, as the parent heterocycle, and so include, for example, hydrogenated (e.g., partially saturated, fully saturated), carbonyl-substituted, and other substituted derivatives. For example, "pyrrolidone" and "N-methyl pyrrole" are both derived from "pyrrole". In further embodiments, the phrase "derived from" (or similar language) is replaced with the word "is", as in, for example: In one embodiment, Y is independently: benzene, naphthylene, pyridine, pyrrole, furan, thiophene, or thiazole; and is independently unsubstituted or substituted.

In one embodiment, Y is independently derived from: benzene, naphthylene, pyridine, or pyrrole; and is independently unsubstituted or substituted.

In one embodiment, Y is independently: phenyl, naphthyl, pyridyl, or pyrrolyl; and is independently unsubstituted or substituted.

In one embodiment, Y is independently naphthyl; and is independently unsubstituted or substituted.

In one embodiment, Y is independently phenyl; and is independently unsubstituted or substituted.

In one embodiment, Y is independently a group of the formula:

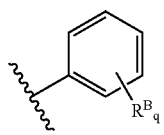

wherein:
q is independently an integer from 0 to 5; and, each $R^B$ is independently a substituent, for example, as defined under the heading "The Group Y: Substituents".

In one embodiment, q is independently 0, 1, 2, 3, 4, or 5; or: 1, 2, 3, 4, or 5.

In one embodiment, q is independently 0, 1, 2, 3, or 4; or: 1, 2, 3, or 4.

In one embodiment, q is independently 0, 1, 2, or 3; or: 1, 2, or 3.

In one embodiment, q is independently 0, 1, or 2; or: 1 or 2.

In one embodiment, q is independently 0 or 1.

In one embodiment, q is independently 1.

In one embodiment, q is independently 0.

In one embodiment, q is independently 1, and the substituent (e.g., $R^B$) is in a meta or para position.

In one embodiment, Y is independently:
$C_{3-12}$carbocyclyl (e.g., saturated $C_{3-12}$cycloalkyl, $C_{3-12}$cycloalkenyl), or
$C_{3-12}$heterocyclyl;
and is independently unsubstituted or substituted.

In one embodiment, Y is independently:
$C_{5-10}$carbocyclyl (e.g., saturated $C_{3-10}$cycloalkyl, $C_{3-10}$cycloalkenyl), or
$C_{5-10}$heterocyclyl;
and is independently unsubstituted or substituted.

In one embodiment, Y is independently:
monocyclic or bicyclic $C_{3-12}$carbocyclyl (e.g., saturated $C_{3-12}$cycloalkyl, $C_{3-12}$cycloalkenyl), or
monocyclic or bicyclic $C_{3-12}$heterocyclyl;
and is independently unsubstituted or substituted.

In one embodiment, Y is independently:
$C_{5-8}$carbocyclyl (e.g., saturated $C_{6-8}$cycloalkyl, $C_{5-8}$cycloalkenyl), or
$C_{5-8}$heterocyclyl;
and is independently unsubstituted or substituted.

In one embodiment, Y is independently:
monocyclic $C_{5-8}$carbocyclyl (e.g., saturated $C_{5-8}$cycloalkyl, $C_{5-8}$cycloalkenyl), or
monocyclic $C_{5-8}$heterocyclyl;
and is independently unsubstituted or substituted.

In one embodiment, the heterocyclyl groups have 1, 2, or 3 aromatic ring heteroatoms, e.g., selected from nitrogen and oxygen.

In one embodiment, the heterocyclyl groups have 1 aromatic ring heteroatom, e.g., selected from nitrogen and oxygen.

In one embodiment, the heterocyclyl groups have 2 aromatic ring heteroatoms, e.g., selected from nitrogen and oxygen.

In one embodiment, the heterocyclyl groups have 3 aromatic ring heteroatoms, e.g., selected from nitrogen and oxygen.

In one embodiment, Y is independently derived from: cyclopentane (e.g., cyclopentyl), cyclohexane (e.g., cyclohexyl), tetrahydrofuran, tetrahydropyran, dioxane, pyrrolidine, piperidine, or piperzine; and is independently unsubstituted or substituted (including, e.g., piperidinone, dimethyltetrahydropyran, etc.).

In one embodiment, Y is independently: cyclopentyl, cyclohexyl, tetrahydrofuranyl, tetrahydropyranyl, dioxanyl, pyrrolidinyl, piperidinyl, or piperzinyl; and is independently unsubstituted or substituted (including, e.g., piperidinonyl, dimethyltetrahydropyranyl, etc.).

In one embodiment, Y is independently as defined above under the heading "The Group Z".

In one embodiment, Y is independently selected from those (core groups) exemplified under the heading "Some Preferred Embodiments" and is independently unsubstituted or substituted, for example, with one or more substituents independently selected from those substituents exemplified under the heading "Some Preferred Embodiments."

The Group Y: Substituents

The group Y is independently unsubstituted or substituted.

In one embodiment, Y is independently unsubstituted.

In one embodiment, Y is independently substituted.

In one embodiment, Y is independently unsubstituted or substituted with one or more (e.g., 1 to 5; 1 to 4; 1 to 3; 1 or 2; 2 to 5; 2 to 4; 2 or 3; 1; 2; 3; 4; 5) substituents.

In one embodiment, the substituents on Y (e.g., $R^B$) are independently selected from the following:

(1) carboxylic acid; (2) ester; (3) amido or thioamido; (4) acyl; (5) halo; (6) cyano; (7) nitro; (8) hydroxy; (9) ether; (10) thiol; (11) thioether; (12) acyloxy; (13) carbamate; (14) amino; (15) acylamino or thioacylamino; (16) aminoacylamino or aminothioacylamino; (17) sulfonamino; (18) sulfonyl; (19) sulfonate; (20) sulfonamido; (21) $C_{5-20}$aryl-$C_{1-7}$alkyl; (22) $C_{5-20}$aryl; (23) $C_{3-20}$heterocyclyl; (24) $C_{1-7}$alkyl; (25) oxo; (26) imino; (27) hydroxyimino; (28) phosphate; (29) bi-dentate di-oxy groups.

Note that in one embodiment, Y is substituted at two positions by a (29) bi-dentate di-oxy group (—O—R—O—), for example, an oxy-$C_{1-3}$alkyl-oxy group, wherein the $C_{1-3}$alkyl is unsubstituted or substituted, for example, with halogen, for example fluorine. Examples of such bi-dentate di-oxy groups include —O—$CH_2$—O—, —O—$CH_2$—$CH_2$—O—, —O—$CH_2$—$CH_2$—$CH_2$—O—, —O—$CF_2$—O—, and —O—$CF_2$—$CF_2$—O—. In such cases, Y is also optionally substituted by one or more other substituents as described herein.

In one embodiment, the substituents on Y (e.g., $R^B$) are independently selected from the following:
(1) —C(=O)OH;
(2) —C(=O)$OR^1$, wherein $R^1$ is independently as defined in (21), (22), (23) or (24);
(3) —C(=O)$NR^2R^3$ or —C(=S)$NR^2R^3$, wherein each of $R^2$ and $R^3$ is independently —H; or as defined in (21), (22), (23) or (24); or $R^2$ and $R^3$ taken together with the nitrogen atom to which they are attached form a ring having from 3 to 7 ring atoms;
(4) —C(=O)$R^4$, wherein $R^4$ is independently —H, or as defined in (21), (22), (23) or (24);
(5) —F, —Cl, —Br, —I;
(6) —CN;
(7) —$NO_2$;
(8) —OH;
(9) —$OR^5$, wherein $R^5$ is independently as defined in (21), (22), (23) or (24);
(10) —SH;
(11) —$SR^6$, wherein $R^6$ is independently as defined in (21), (22), (23) or (24);
(12) —OC(=O)$R^7$, wherein $R^7$ is independently as defined in (21), (22), (23) or (24);
(13) —OC(=O)$NR^8R^9$, wherein each of $R^8$ and $R^9$ is independently —H; or as defined in (21), (22), (23) or (24); or $R^8$ and $R^9$ taken together with the nitrogen atom to which they are attached form a ring having from 3 to 7 ring atoms;
(14) —$NR^{10}R^{11}$, wherein each of $R^{10}$ and $R^{11}$ is independently —H; or as defined in (21), (22), (23) or (24); or $R^{10}$ and $R^{11}$ taken together with the nitrogen atom to which they are attached form a ring having from 3 to 7 ring atoms;
(15) —$NR^{12}$C(=O)$R^{13}$ or —$NR^{12}$C(=S)$R^{13}$, wherein $R^{12}$ is independently —H; or as defined in (21), (22), (23) or (24); and $R^{13}$ is independently —H, or as defined in (21), (22), (23) or (24);
(16) —$NR^{14}$C(=O)$NR^{15}R^{16}$ or —$NR^{14}$C(=S)$NR^{15}R^{16}$, wherein $R^{14}$ is independently —H; or as defined in (21), (22), (23) or (24); and each of $R^{15}$ and $R^{16}$ is independently —H; or as defined in (21), (22), (23) or (24); or $R^{15}$ and $R^{16}$ taken together with the nitrogen atom to which they are attached form a ring having from 3 to 7 ring atoms;
(17) —$NR^{17}SO_2R^{18}$, wherein $R^{17}$ is independently —H; or as defined in (21), (22), (23) or (24); and $R^{18}$ is independently —H, or as defined in (21), (22), (23) or (24);
(18) —$SO_2R^{19}$, wherein $R^{19}$ is independently as defined in (21), (22), (23) or (24);
(19) —$OSO_2R^{20}$ and wherein $R^{20}$ is independently as defined in (21), (22), (23) or (24);
(20) —$SO_2NR^{21}R^{22}$, wherein each of $R^{21}$ and $R^{22}$ is independently —H; or as defined in (21), (22), (23) or (24); or $R^{21}$ and $R^{22}$ taken together with the nitrogen atom to which they are attached form a ring having from 3 to 7 ring atoms;
(21) $C_{5-20}$aryl-$C_{1-7}$alkyl, for example, wherein $C_{5-20}$aryl is as defined in (22); unsubstituted or substituted, e.g., with one or more groups as defined in (1) to (28);
(22) $C_{5-20}$aryl, including $C_{6-20}$-carboaryl and $C_{5-20}$heteroaryl; unsubstituted or substituted, e.g., with one or more groups as defined in (1) to (28);
(23) $C_{3-20}$heterocyclyl; unsubstituted or substituted, e.g., with one or more groups as defined in (1) to (28);
(24) $C_{1-7}$alkyl, including:
saturated $C_{1-7}$alkyl;
unsaturated $C_{2-7}$alkyl, e.g., $C_{2-7}$alkenyl and $C_{2-7}$alkynyl;
cyclic $C_{3-7}$alkyl, e.g., $C_{3-7}$cycloalkyl $C_{3-7}$cycloalkenyl, $C_{3-7}$cycloalkynyl;
aliphatic (linear or branched) $C_{1-7}$alkyl;
unsubstituted $C_{1-7}$alkyl;
substituted $C_{1-7}$alkyl, e.g., substituted with one or more groups as defined in (1) to (23) and (25) to (28),
e.g., halo-$C_{1-7}$alkyl;
e.g., amino-$C_{1-7}$alkyl (e.g., —$(CH_2)_w$-amino, w is 1, 2, 3, or 4);
e.g., carboxy-$C_{1-7}$alkyl (e.g., —$(CH_2)_w$—COOH, w is 1, 2, 3, or 4);
e.g., acyl-$C_{1-7}$alkyl (e.g., —$(CH_2)_w$—C(=O)$R^4$, w is 1, 2, 3, or 4);
e.g., hydroxy-$C_{1-7}$alkyl (e.g., —$(CH_2)_w$—OH, w is 1, 2, 3, or 4);
e.g., $C_{1-7}$alkoxy-$C_{1-7}$alkyl (e.g., —$(CH_2)_w$—O—$C_{1-7}$alkyl, w is 1, 2, 3, or 4);
(25) =O;
(26) =$NR^{23}$, wherein $R^{23}$ is independently —H; or as defined in (21), (22), (23) or (24);
(27) =$NOR^{24}$, wherein $R^{24}$ is independently —H; or as defined in (21), (22), (23) or (24);
(28) —P(=O)$(OR^{25})_2$ and —OP(=O)$(OR^{25})_2$, wherein each $R^{25}$ is independently —H; or as defined in (21), (22), (23) or (24);
(29) —O—$R^{26}$—O—, wherein $R^{26}$ is independently saturated $C_{1-3}$alkyl, and is independently unsubstituted or substituted with one or more (e.g., 1, 2, 3, 4) substituents as defined in (5).

In one embodiment, the substituents on Y (e.g., $R^B$) are independently selected from the following:
(1) —C(=O)OH;
(2) —C(=O)OMe, —C(=O)OEt, —C(=O)O(iPr), —C(=O)O(tBu); —C(=O)O(cPr); —C(=O)$OCH_2CH_2OH$, —C(=O)$OCH_2CH_2OMe$, —C(=O)$OCH_2CH_2OEt$; —C(=O)OPh, —C(=O)$OCH_2Ph$;
(3) —(C=O)$NH_2$, —(C=O)$NMe_2$, —(C=O)$NEt_2$, —(C=O)N(iPr)$_2$, —(C=O)N$(CH_2CH_2OH)_2$; —(C=O)-morpholino, —(C=O)NHPh, —(C=O)NHCH$_2$Ph;
(4) —C(=O)H, —(C=O)Me, —(C=O)Et, —(C=O)(tBu), —(C=O)-cHex, —(C=O)Ph; —(C=O)CH$_2$Ph;
(5) —F, —Cl, —Br, —I;
(6) —CN;
(7) —$NO_2$;
(8) —OH;
(9) —OMe, —OEt, —O(iPr), —O(tBu), —OPh, —OCH$_2$Ph; —OCF$_3$, —OCH$_2$CF$_3$; —OCH$_2$CH$_2$OH, —OCH$_2$CH$_2$OMe, —OCH$_2$CH$_2$OEt; —OCH$_2$CH$_2$NH$_2$, —OCH$_2$CH$_2$NMe$_2$, —OCH$_2$CH$_2$N(iPr)$_2$; —OPh-Me, —OPh-OH, —OPh-OMe, —OPh-F, —OPh-Cl, —OPh-Br, —OPh-I;

(10) —SH;

(11) —SMe, —SEt, —SPh, —SCH$_2$Ph;

(12) —OC(=O)Me, —OC(=O)Et, —OC(=O)(iPr), —OC(=O)(tBu); —OC(=O)(cPr); —OC(=O)CH$_2$CH$_2$OH, —OC(=O)CH$_2$CH$_2$OMe, —OC(=O)CH$_2$CH$_2$OEt; —OC(=O)Ph, —OC(=O)CH$_2$Ph;

(13) —OC(=O)NH$_2$, —OC(=O)NHMe, —OC(=O)NMe$_2$, —OC(=O)NHEt, —OC(=O)NEt$_2$, —OC(=O)NHPh, —OC(=O)NCH$_2$Ph;

(14) —NH$_2$, —NHMe, —NHEt, —NH(iPr), —NMe$_2$, —NEt$_2$, —N(iPr)$_2$, —N(CH$_2$CH$_2$OH)$_2$; —NHPh, —NHCH$_2$Ph; piperidino, piperazino, morpholino;

(15) —NH(C=O)Me, —NH(C=O)Et, —NH(C=O)nPr, —NH(C=O)Ph, —NHC(=O)CH$_2$Ph; —NMe(C=O)Me, —NMe(C=O)Et, —NMe(C=O)Ph, —NMeC(=O)CH$_2$Ph;

(16) —NH(C=O)NH$_2$, —NH(C=O)NHMe, —NH(C=O)NHEt, —NH(C=O)NPh, —NH(C=O)NHCH$_2$Ph; —NH(C=S)NH$_2$, —NH(C=S)NHMe, —NH(C=S)NHEt, —NH(C=S)NPh, —NH(C=S)NHCH$_2$Ph;

(17) —NHSO$_2$Me, —NHSO$_2$Et, —NHSO$_2$Ph, —NHSO$_2$PhMe, —NHSO$_2$CH$_2$Ph; —NMeSO$_2$Me, —NMeSO$_2$Et, —NMeSO$_2$Ph, —NMeSO$_2$PhMe, —NMeSO$_2$CH$_2$Ph;

(18) —SO$_2$Me, —SO$_2$CF$_3$, —SO$_2$Et, —SO$_2$Ph, —SO$_2$PhMe, —SO$_2$CH$_2$Ph;

(19) —OSO$_2$Me, —OSO$_2$CF$_3$, —OSO$_2$Et, —OSO$_2$Ph, —OSO$_2$PhMe, —OSO$_2$CH$_2$Ph;

(20) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;

(21) —CH$_2$Ph, —CH$_2$Ph-Me, —CH$_2$Ph-OH, —CH$_2$Ph-F, —CH$_2$Ph-Cl;

(22) -Ph, -Ph-Me, -Ph-OH, -Ph-OMe, -Ph-NH$_2$, -Ph-F, -Ph-Cl, -Ph-Br, -Ph-I;
 pyridyl, pyrazinyl, pyrimidinyl, pyridazinyl, furanyl, thiophenyl, pyrrolyl, imidazolyl, pyrazolyl, oxazolyl, thiazolyl, thiadiazolyl;

(23) pyrrolidinyl, imidazolidinyl, pyrazolidinyl, piperidinyl, piperazinyl, azepinyl, tetrahydrofuranyl, tetrahydropyranyl, morpholinyl, azetidinyl;

(24) -Me, -Et, -nPr, -iPr, -nBu, -iBu, -sBu, -tBu, -nPe; -cPr, -cHex; —CH=CH$_2$, —CH$_2$—CH=CH$_2$; —CF$_3$, —CHF$_2$, —CH$_2$F, —CCl$_3$, —CBr$_3$, —CH$_2$CH$_2$F, —CH$_2$CHF$_2$, and —CH$_2$CF$_3$; —CH$_2$OH, —CH$_2$OMe, —CH$_2$OEt, —CH$_2$NH$_2$, —CH$_2$NMe$_2$; —CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$;

(25) =O;

(26) =NH, =NMe; =NEt;

(27) =NOH, =NOMe, =NOEt, =NO(nPr), =NO(iPr), =NO(cPr), =NO(CH$_2$-cPr);

(28) —OP(=O)(OH)$_2$, —P(=O)(OH)$_2$, —OP(=O)(OMe)$_2$, —P(=O)(OMe)$_2$;

(29) —O—CH$_2$—O—, —O—CH$_2$—CH$_2$—O—, —O—CH$_2$—CH$_2$—CH$_2$—O—, —O—CF$_2$—O—, and —O—CF$_2$—CF$_2$—O—.

In one embodiment, the substituents on Y (e.g., R$^B$) are independently selected from substituents as defined above for (2), (3), (4), (5), (6), (8), (14), (15), (16), (17), (20), (24) and (29).

In one embodiment, the substituents on Y (e.g., R$^B$) are independently selected from substituents as defined above for (3), (14), (15), (16), (17), (20), (24) (e.g., acyl-C$_{1-7}$alkyl, e.g. acyl-CH$_2$—), and (29).

In one embodiment, the substituents on Y (e.g., R$^B$) are independently selected from substituents as defined above for (3), (15), (16), and (24) (e.g., acyl-C$_{1-7}$alkyl, e.g., acyl-CH$_2$—).

In one embodiment, the substituents on Y (e.g., R$^B$) are independently selected from substituents as defined above for (3), (15), and (16).

In one embodiment, the substituents on Y (e.g., R$^B$) are independently selected from substituents as defined above for (15) and (16).

In one embodiment, the substituents on Y (e.g., R$^B$) are independently selected from:

(2) —C(=O)OMe, —C(=O)OEt, —C(=O)O(iPr), —C(=O)O(tBu); —C(=O)O(cPr); —C(=O)OCH$_2$CH$_2$OH, —C(=O)OCH$_2$CH$_2$OMe, —C(=O)OCH$_2$CH$_2$OEt; —C(=O)OPh, —C(=O)OCH$_2$Ph;

(3) —(C=O)NH$_2$, —(C=O)NMe$_2$, —(C=O)NEt$_2$, —(C=O)N(iPr)$_2$, —(C=O)N(CH$_2$CH$_2$OH)$_2$; —(C=O)-morpholino, —(C=O)NHPh, —(C=O)NHCH$_2$Ph;

(4) —C(=O)H, —(C=O)Me, —(C=O)Et, —(C=O)(tBu), —(C=O)-cHex, —(C=O)Ph; —(C=O)CH$_2$Ph;

(5) —F, —Cl, —Br, —I;

(6) —CN;

(8) —OH;

(14) —NH$_2$, —NHMe, —NHEt, —NH(iPr), —NMe$_2$, —NEt$_2$, —N(iPr)$_2$, —N(CH$_2$CH$_2$OH)$_2$; —NHPh, —NHCH$_2$Ph; piperidino, piperazino, morpholino;

(15) —NH(C=O)Me, —NH(C=O)Et, —NH(C=O)Pr, —NH(C=O)Ph, —NHC(=O)CH$_2$Ph; —NMe(C=O)Me, —NMe(C=O)Et, —NMe(C=O)Ph, —NMeC(=O)CH$_2$Ph;

(16) —NH(C=O)NH$_2$, —NH(C=O)NHMe, —NH(C=O)NHEt, —NH(C=O)NPh, —NH(C=O)NHCH$_2$Ph; —NH(C=S)NH$_2$, —NH(C=S)NHMe, —NH(C=S)NHEt, —NH(C=S)NPh, —NH(C=S)NHCH$_2$Ph;

(17) —NHSO$_2$Me, —NHSO$_2$Et, —NHSO$_2$Ph, —NHSO$_2$PhMe, —NHSO$_2$CH$_2$Ph; —NMeSO$_2$Me, —NMeSO$_2$Et, —NMeSO$_2$Ph, —NMeSO$_2$PhMe, —NMeSO$_2$CH$_2$Ph;

(20) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;

(24) -Me, -Et, -nPr, -iPr, -nBu, -iBu, -sBu, -tBu, -nPe; -cPr, -cHex; —CH=CH$_2$, —CH$_2$—CH=CH$_2$; —CF$_3$, —CHF$_2$, —CH$_2$F, —CCl$_3$, —CBr$_3$, —CH$_2$CH$_2$F, —CH$_2$CHF$_2$, and —CH$_2$CF$_3$; —CH$_2$OH, —CH$_2$OMe, —CH$_2$OEt, —CH$_2$NH$_2$, —CH$_2$NMe$_2$; —CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$.

In one embodiment, the substituents on Y (e.g., R$^B$) are independently selected from:

(2) —C(=O)OMe, —C(=O)OEt, —C(=O)O(tBu);

(3) —(C=O)NH$_2$;

(4) —C(=O)H;

(5) —F, —Cl, —Br, —I;

(6) —CN;

(8) —OH;

(14) —NH$_2$, —NHPh;

(15) —NH(C=O)Me, —NH(C=O)Et, —NH(C=O)Pr, —NH(C=O)Ph, —NHC(=O)CH$_2$Ph, —NHC(=O)CH(Me)Ph, —NHC(=O)(thiophenyl), —NHC(=O)CH$_2$(thiophenyl), —NHC(=O)furanyl;

(16) —NH(C=O)NH$_2$, —NH(C=O)NHMe, —NH(C=O)NHEt, —NH(C=O)NPh, —NH(C=O)NHCH$_2$Ph; —NH(C=S)NH$_2$, —NH(C=S)NHMe, —NH(C=S)NHEt, —NH(C=S)NPh, —NH(C=S)NHCH$_2$Ph;
(17) —NHSO$_2$Me, —NHSO$_2$Et, —NHSO$_2$Ph, —NHSO$_2$PhMe, —NHSO$_2$CH$_2$Ph; —NMeSO$_2$Me, —NMeSO$_2$Et, —NMeSO$_2$Ph, —NMeSO$_2$PhMe, —NMeSO$_2$CH$_2$Ph;
(20) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;
(24) —CH$_2$OH.

In one embodiment, the substituents on Y (e.g., $R^B$) are (or at least one of the substituents on Y is) independently selected from:
—C(=O)NR$^2$, R$^3$,
—NR$^{12}$C(=O)R$^{13}$,
—NR$^{12}$C(=S)R$^{13}$,
—NR$^{14}$C(=O)NR$^{15}$R$^{16}$,
—NR$^{14}$C(=S)NR$^{11}$R$^{16}$,
—NR$^{17}$SO$_2$R$^{18}$,
—SO$_2$NR$^{21}$R$^{22}$, and
—C$_{1-7}$alkyl-C(=O)—R$^4$ (e.g., —CH$_2$—C(=O)—R$^4$) (e.g., where R$^4$ is as defined in (22)).

In one embodiment, the substituents on Y (e.g., $R^B$) are (or at least one of the substituents on Y is) independently selected from:
—NR$^{12}$C(=O)R$^{13}$,
—NR$^{12}$C(=S)R$^{13}$,
—NR$^{14}$C(=O)NR$^{15}$R$^{16}$, and
—NR$^{14}$C(=S)NR$^{15}$R$^{16}$, In one embodiment, the substituents on Y (e.g., $R^B$) are (or at least one of the substituents on Y is) independently selected from:
—NR$^{14}$C(=O)NR$^{15}$R$^{16}$, and
—NR$^{14}$C(=S)NR$^{15}$R$^{16}$.

In one embodiment, Y is independently a group of the formula:

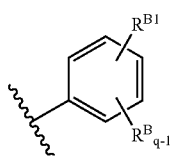

wherein:
q is independently an integer from 1 to 5; and
each $R^B$ is independently a substituent, for example, as defined under the heading "The Group Y: Substituents"; and
$R^{B1}$ is independently a substituent, for example, as defined under the heading "The Group Y: Substituents".

In one embodiment, $R^{B1}$ is selected from:
—C(=O)NR$^2$R$^3$,
—NR$^{12}$C(=O)R$^{13}$,
—NR$^{12}$C(=S)R$^{13}$,
—NR$^{14}$C(=O)NR$^{15}$R$^{16}$
—NR$^{14}$C(=S)NR$^{15}$R$^{16}$,
—NR$^{17}$SO$_2$R$^{18}$,
—SO$_2$NR$^{21}$R$^{22}$, and
—C$_{1-7}$alkyl-C(=O)—R$^4$ (e.g., —CH$_2$—C(=O)—R$^4$) (e.g., where R$^4$ is as defined in (22)).

In one embodiment, the substituents on Y (e.g., $R^B$) are independently selected from those exemplified in the section entitled "Some Preferred Embodiments."

In one embodiment, the substituents on Y (e.g., $R^B$) are independently as defined for the substitutents on Z (e.g., $R^A$) under the heading "The Group Z: Substituents."

The Group Z
The group Z is independently:
C$_{6-14}$carboaryl,
C$_{5-14}$heteroaryl,
C$_{3-12}$carbocyclyl, or
C$_{3-12}$heterocyclyl;
and is independently unsubstituted or substituted.

In one embodiment, Z is independently:
C$_{6-14}$carboaryl, or
C$_{5-14}$heteroaryl;
and is independently unsubstituted or substituted.

In one embodiment, Z is independently:
C$_{6-12}$carboaryl, or
C$_{5-12}$heteroaryl;
and is independently unsubstituted or substituted.

In one embodiment, Z is independently:
C$_{6-10}$carboaryl, or
C$_{5-10}$heteroaryl;
and is independently unsubstituted or substituted.

In one embodiment, Z is independently:
monocyclic or bicyclic C$_{6-10}$carboaryl, or
monocyclic or bicyclic C$_{5-10}$heteroaryl;
and is independently unsubstituted or substituted.

In one embodiment, the bicyclic groups are selected from "5-6" fused rings and "6-6" fused rings, e.g., as in benzimidazole and naphthalene, respectively.

In one embodiment, Z is independently:
monocyclic C$_6$carboaryl, or
monocyclic C$_{5-6}$heteroaryl;
and is independently unsubstituted or substituted.

In one embodiment, the heteroaryl groups have 1, 2, or 3 aromatic ring heteroatoms, e.g., selected from nitrogen and oxygen.

In one embodiment, the heteroaryl groups have 1 aromatic ring heteroatom, e.g., selected from nitrogen and oxygen.

In one embodiment, the heteroaryl groups have 2 aromatic ring heteroatoms, e.g., selected from nitrogen and oxygen.

In one embodiment, the heteroaryl groups have 3 aromatic ring heteroatoms, e.g., selected from nitrogen and oxygen.

In one embodiment, Z is independently derived from: benzene (e.g., phenyl), naphthalene (e.g., naphthyl), fluorene, indan, pyrrole, pyridine, furan, thiophene, oxazole, isoxazole, oxadiazole, thiazole, isothiazole, thiadiazole, imidazole, pyrazole, pyridazine, pyrimidine, pyrazine, tetrazole, benzofuran, isobenzofuran, chroman, indole, isoindole, 2,3-dihydro-1H-indole, benzimidazole, 1,3-dihydrobenzimidazole, benzoxazole, benzothiofuran, benzothiazole, benzothiadiazole, quinoline, isoquinoline, pyridopyridine, quinoxaline, 1,2,3,4-tetrahydroquinoxaline, 1,3-dihydroisobenzofuran, benzo[1,3]dioxole, 2,2-difluoro-benzo[1,3]dioxole, 2,3-dihydro-benzo[1,4]dioxine, 2,2,3,3,-tetrafluoro-2,3-dihydro-benzo[1,4]dioxine, 3,4-dihydro-2H-benzo[b][1,4]dioxepine, benzodiazepine, carbazole, acridine; and is independently unsubstituted or substituted (including, e.g., 1,3-dihydrobenzimidazol-2-one; 1,3-dihydro-indol-2-one, 3H-isobenzofuran-1-one, indan-1-one, 3,4-dihydro-naphthalene-1-one, etc.).

In one embodiment, Z is independently: phenyl, naphthyl, fluorenyl, indanyl (e.g., -4-yl, -5-yl, -6-yl, -7-yl), pyrrolyl, pyridinyl, furanyl, thiophenyl, oxazolyl, isoxazolyl, oxadiazolyl, thiazolyl, isothiazolyl, thiadiazolyl, imidazolyl, pyrazolyl, pyridazinyl, pyrimidinyl, pyrazinyl, tetrazolyl, benzofuranyl, isobenzofuranyl, chromanyl, indolyl, isoindolyl, 2,3-dihydro-1H-indolyl, benzimidazolyl, 1,3-dihydrobenzimidazolyl, benzoxazolyl, benzothiofuranyl, benzothiazolyl, benzothiadiazolyl, quinolinyl, isoquinolinyl, pyridopyridinyl, quinoxalinyl, 1,2,3,4-tetrahydroquinoxalinyl, 1,3-dihydro-isobenzofuranyl, benzo[1,3]dioxolyl, 2,2-difluoro-benzo[1,3]dioxolyl, 2,3-dihydro-benzo[1,4]dioxinyl, 2,2,3,3,-tetrafluoro-2,3-dihydro-benzo[1,4]dioxinyl, 3,4-dihydro-2H-benzo[b][1,4]dioxepinyl, benzodiazepinyl, carbazolyl, or acridinyl; and is independently unsubstituted or substituted (including, e.g., 1,3-dihydrobenzimidazol-2-one-yl; 1,3-dihydro-indol-2-one-yl, 3H-isobenzofuran-1-one-yl (e.g., -4-yl, -5-yl, -6-yl, -7-yl), indan-1-one-yl (e.g., -4-yl, -5-yl, -6-yl, -7-yl), 3,4-dihydro-naphthalene-1-one-yl (e.g., -5-yl, -6-yl, -7-yl, -8-yl) etc.).

In one embodiment, Z is independently derived from: benzene (e.g., phenyl), pyrrole (e.g., pyrolyl), pyridine, furan, thiophene, oxazole, isoxazole, thiadiazole, oxadiazole, thiazole, isothiazole, imidazole, pyrazole, pyridazine, pyrimidine, pyrazine, or tetrazole; and is independently unsubstituted or substituted.

In one embodiment, Z is independently: phenyl, pyrrolyl, pyridinyl, furanyl, thiophenyl, oxazolyl, isoxazolyl, thiadiazolyl, oxadiazolyl, thiazolyl, isothiazolyl, imidazolyl, pyrazolyl, pyridazinyl, pyrimidinyl, pyrazinyl, or tetrazolyl; and is independently unsubstituted or substituted.

In one embodiment, Z is independently derived from: benzene (e.g., phenyl), pyridine, thiadiazole, oxazole, thiazole, or pyrazole; and is independently unsubstituted or substituted.

In one embodiment, Z is independently: phenyl, pyridinyl, thiadiazolyl, oxazole, thiazolyl, or pyrazolyl; and is independently unsubstituted or substituted.

In one embodiment, Z is independently naphthyl, and is independently unsubstituted or substituted.

In one embodiment, Z is independently phenyl, and is independently unsubstituted or substituted.

In one embodiment, Z is independently a group of the following formula:

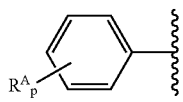

wherein:
p is independently an integer from 0 to 5; and
each $R^A$ is independently a substituent, for example, as defined under the heading "The Group Z: Substituents".

In one embodiment, p is independently 0, 1, 2, 3, 4, or 5; or: 1, 2, 3, 4, or 5.

In one embodiment, p is independently 0, 1, 2, 3, or 4; or: 1, 2, 3, or 4.

In one embodiment, p is independently 0, 1, 2, or 3; or: 1, 2, or 3.

In one embodiment, p is independently 0, 1, or 2; or: 1 or 2.
In one embodiment, p is independently 0 or 1.
In one embodiment, p is independently 1.
In one embodiment, p is independently 0.
In one embodiment, Z is independently:
$C_{3-12}$carbocyclyl (e.g., saturated $C_{3-12}$cycloalkyl, $C_{3-12}$cycloalkenyl), or
$C_{3-12}$heterocyclyl;
and is independently unsubstituted or substituted.

In one embodiment, Z is independently:
$C_{5-10}$carbocyclyl (e.g., saturated $C_{3-10}$cycloalkyl, $C_{3-10}$cycloalkenyl), or
$C_{5-10}$heterocyclyl;
and is independently unsubstituted or substituted.
In one embodiment, Z is independently:
monocyclic or bicyclic $C_{3-12}$carbocyclyl (e.g., saturated $C_{3-12}$cycloalkyl, $C_{3-12}$cycloalkenyl), or
monocyclic or bicyclic $C_{3-12}$heterocyclyl;
and is independently unsubstituted or substituted.
In one embodiment, Z is independently:
$C_{5-8}$carbocyclyl (e.g., saturated $C_{5-8}$cycloalkyl, $C_{5-8}$cycloalkenyl), or
$C_{5-8}$heterocyclyl;
and is independently unsubstituted or substituted.
In one embodiment, Z is independently:
monocyclic $C_{5-8}$carbocyclyl (e.g., saturated $C_{5-8}$cycloalkyl, $C_{5-8}$cycloalkenyl), or
monocyclic $C_{5-8}$heterocyclyl;
and is independently unsubstituted or substituted.
In one embodiment, the heterocyclic groups have 1, 2, or 3 aromatic ring heteroatoms, e.g., selected from nitrogen and oxygen.

In one embodiment, the heterocyclic groups have 1 aromatic ring heteroatom, e.g., selected from nitrogen and oxygen.

In one embodiment, the heterocyclic groups have 2 aromatic ring heteroatoms, e.g., selected from nitrogen and oxygen.

In one embodiment, the heterocyclic groups have 3 aromatic ring heteroatoms, e.g., selected from nitrogen and oxygen.

In one embodiment, Z is independently derived from: cyclopentane (e.g., cyclopentyl), cyclohexane (e.g., cyclohexyl), tetrahydrofuran, tetrahydropyran, dioxane, pyrrolidine, piperidine, or piperzine; and is independently unsubstituted or substituted (including, e.g., piperidinone, dimethyltetrahydropyran, etc.).

In one embodiment, Z is independently: cyclopentyl, cyclohexyl, tetrahydrofuranyl, tetrahydropyranyl, dioxanyl, pyrrolidinyl, piperidinyl, or piperzinyl; and is independently unsubstituted or substituted (including, e.g., piperidinonyl, dimethyltetrahydropyranyl, etc.).

In one embodiment, Z is independently as defined above under the heading "The Group Y".

In one embodiment, Z is independently selected from those (core groups) exemplified under the heading "Some Preferred Embodiments" and is independently unsubstituted or substituted, for example, with one or more substituents independently selected from those substituents exemplified under the heading "Some Preferred Embodiments."

The Group Z: Substituents

In one embodiment, the substituents on Z (e.g., $R^A$) are independently as defined for the substitutents on Y (e.g., $R^B$) under the heading "The Group Y: Substituents."

In one embodiment, the substituents on Z (e.g., $R^A$) are independently as defined for the substitutents on Y (e.g., $R^B$) under the heading "The Group Y: Substituents," with the proviso that the compound is not 4-[6-(3,4,5-trimethoxy-phenyl)-pyrazin-2-yl-amino]-benzonitrile or a salt or solvate thereof (see, e.g., compound 32302 on page 41 of Burns, C. J., et al., 2002, "Methods of Inhibiting Kinases," published international patent application publication number WO 02/060492 A1 published 8 Aug. 2002).

In one embodiment, the substituents on Z (e.g., $R^A$) are independently as defined for the substitutents on Y (e.g., $R^B$)

under the heading "The Group Y: Substituents," but with proviso that substituents on Z are not (6) cyano (—CN).

In one embodiment, the substituents on Z (e.g., $R^4$) are independently selected from substituents as defined above for (1), (2), (3), (4), (5), (7), (8), (9), (10), (11), (12), (13), (14), (15), (16), (17), (18), (19), (20), (21), (22), (23), (24), (25), (26), (27), (28), and (29).

In one embodiment, the substituents on Z (e.g., $R^4$) are independently selected from substituents as defined above for (1), (2), (3), (4), (5), (8), (9), (10), (11), (12), (13), (14), (15), (17), (18), (20), (21), (22), (23), (24), and (29).

In one embodiment, the substituents on Z (e.g., $R^4$) are independently selected from substituents as defined above for (2), (5), (8), (9), (10), (11), (12), (18), (22), (23), (24), and (29).

In one embodiment, the substituents on Z (e.g., $R^4$) are independently selected from:

(1) —C(=O)OH;
(2) —C(=O)OMe, —C(=O)OEt, —C(=O)O(iPr), —C(=O)O(tBu); —C(=O)O(cPr); —C(=O)OCH₂CH₂OH, —C(=O)OCH₂CH₂OMe, —C(=O)OCH₂CH₂OEt; —C(=O)OPh, —C(=O)OCH₂Ph;
(3) —(C=O)NH₂, —(C=O)NMe₂, —(C=O)NEt₂, —(C=O)N(iPr)₂, —(C=O)N(CH₂CH₂OH)₂; —(C=O)-morpholino, —(C=O)NHPh, —(C=O)NHCH₂Ph;
(4) —C(=O)H, —(C=O)Me, —(C=O)Et, —(C=O)(tBu), —(C=O)-cHex, —(C=O)Ph; —(C=O)CH₂Ph;
(5) —F, —Cl, —Br, —I;
(8) —OH;
(9) —OMe, —OEt, —O(iPr), —O(tBu), —OPh, —OCH₂Ph; —OCF₃, —OCH₂CF₃; —OCH₂CH₂OH, —OCH₂CH₂OMe, —OCH₂CH₂OEt; —OCH₂CH₂NH₂, —OCH₂CH₂NMe₂, —OCH₂CH₂N(iPr)₂; —OPh-Me, —OPh-OH, —OPh-OMe, —OPh-F, —OPh-Cl, —OPh-Br, —OPh-I;
(10) —SH;
(11) —SMe, —SEt, —SPh, —SCH₂Ph;
(12) —OC(=O)Me, —OC(=O)Et, —OC(=O)(iPr), —OC(=O)(tBu); —OC(=O)(cPr); —OC(=O)CH₂CH₂OH, —OC(=O)CH₂CH₂OMe, —OC(=O)CH₂CH₂OEt; —OC(=O)Ph, —OC(=O)CH₂Ph;
(13) —OC(=O)NH₂, —OC(=O)NHMe, —OC(=O)NMe₂, —OC(=O)NHEt, —OC(=O)NEt₂, —OC(=O)NHPh, —OC(=O)NCH₂Ph;
(14) —NH₂, —NHMe, —NHEt, —NH(iPr), —NMe₂, —NEt₂, —N(iPr)₂, —N(CH₂CH₂OH)₂; —NHPh, —NHCH₂Ph; piperidino, piperazino, morpholino;
(15) —NH(C=O)Me, —NH(C=O)Et, —NH(C=O)nPr, —NH(C=O)Ph, —NHC(=O)CH₂Ph; —NMe(C=O)Me, —NMe(C=O)Et, —NMe(C=O)Ph, —NMeC(=O)CH₂Ph;
(17) —NHSO₂Me, —NHSO₂Et, —NHSO₂Ph, —NHSO₂PhMe, —NHSO₂CH₂Ph; —NMeSO₂Me, —NMeSO₂Et, —NMeSO₂Ph, —NMeSO₂PhMe, —NMeSO₂CH₂Ph;
(18) —SO₂Me, —SO₂CF₃, —SO₂Et, —SO₂Ph, —SO₂PhMe, —SO₂CH₂Ph;
(20) —SO₂NH₂, —SO₂NHMe, —SO₂NHEt, —SO₂NMe₂, —SO₂NEt₂, —SO₂-morpholino, —SO₂NHPh, —SO₂NHCH₂Ph;
(21) —CH₂Ph, —CH₂Ph-Me, —CH₂Ph-OH, —CH₂Ph-F, —CH₂Ph-Cl;
(22) -Ph, -Ph-Me, -Ph-OH, -Ph-OMe, -Ph-NH₂, -Ph-F, -Ph-Cl, -Ph-Br, -Ph-I; pyridyl, pyrazinyl, pyrimidinyl, pyridazinyl, furanyl, thiophenyl, pyrrolyl, imidazolyl, pyrazolyl, oxazolyl, thiazolyl, thiadiazolyl;
(23) pyrrolidinyl, imidazolidinyl, pyrazolidinyl, piperidinyl, piperazinyl, azepinyl, tetrahydrofuranyl, tetrahydropyranyl, morpholinyl, azetidinyl;
(24) -Me, -Et, -nPr, -iPr, -nBu, -iBu, -sBu, -tBu, -nPe; -cPr, -cHex; —CH=CH₂, —CH₂—CH=CH₂; —CF₃, —CHF₂, —CH₂F, —CCl₃, —CBr₃, —CH₂CH₂F, —CH₂CHF₂, and —CH₂CF₃; —CH₂OH, —CH₂OMe, —CH₂OEt, —CH₂NH₂, —CH₂NMe₂; —CH₂CH₂OH, —CH₂CH₂OMe, —CH₂CH₂OEt, —CH₂CH₂CH₂NH₂, —CH₂CH₂NMe₂.

In one embodiment, the substituents on Z (e.g., $R^4$) are independently selected from:

(2) —C(=O)OMe, —C(=O)OEt, —C(=O)O(iPr), —C(=O)O(tBu); —C(=O)O(cPr); —C(=O)OCH₂CH₂OH, —C(=O)OCH₂CH₂OMe, —C(=O)OCH₂CH₂OEt; —C(=O)OPh, —C(=O)OCH₂Ph;
(5) —F, —Cl, —Br, —I;
(8) —OH;
(9) —OMe, —OEt, —O(iPr), —O(tBu), —OPh, —OCH₂Ph; —OCF₃, —OCH₂CF₃; —OCH₂CH₂OH, —OCH₂CH₂OMe, —OCH₂CH₂OEt; —OCH₂CH₂NH₂, —OCH₂CH₂NMe₂, —OCH₂CH₂N(iPr)₂; —OPh-Me, —OPh-OH, —OPh-OMe, —OPh-F, —OPh-Cl, —OPh-Br, —OPh-I;
(10) —SH;
(11) —SMe, —SEt, —SPh, —SCH₂Ph;
(12) —OC(=O)Me, —OC(=O)Et, —OC(=O)(iPr), —OC(=O)(tBu); —OC(=O)(cPr); —OC(=O)CH₂CH₂OH, —OC(=O)CH₂CH₂OMe, —OC(=O)CH₂CH₂OEt; —OC(=O)Ph, —OC(=O)CH₂Ph;
(18) —SO₂Me, —SO₂CF₃, —SO₂Et, —SO₂Ph, —SO₂PhMe, —SO₂CH₂Ph;
(22) -Ph, -Ph-Me, -Ph-OH, -Ph-OMe, -Ph-NH₂, -Ph-F, -Ph-Cl, -Ph-Br, -Ph-I; pyridyl, pyrazinyl, pyrimidinyl, pyridazinyl, furanyl, thiophenyl, pyrrolyl, imidazolyl, pyrazolyl, oxazolyl, thiazolyl, thiadiazolyl;
(23) pyrrolidinyl, imidazolidinyl, pyrazolidinyl, piperidinyl, piperazinyl, azepinyl, tetrahydrofuranyl, tetrahydropyranyl, morpholinyl, azetidinyl;
(24) -Me, -Et, -nPr, -iPr, -nBu, -iBu, -sBu, -tBu, -nPe; -cPr, -cHex; —CH=CH₂, —CH₂—CH=CH₂; —CF₃, —CHF₂, —CH₂F, —CCl₃, —CBr₃, —CH₂CH₂F, —CH₂CHF₂, and —CH₂CF₃; —CH₂OH, —CH₂OMe, —CH₂OEt, —CH₂NH₂, —CH₂NMe₂; —CH₂CH₂OH, —CH₂CH₂OMe, —CH₂CH₂OEt, —CH₂CH₂CH₂NH₂, —CH₂CH₂NMe₂.

In one embodiment, the substituents on Z (e.g., $R^4$) are independently selected from the following:

(5) —F, —Cl, —Br, —I;
(9) —OMe, —OEt, —OCF₃;
(20) —SO₂-morpholino;
(22) -Ph, pyridyl, furanyl, pyrrolyl, oxazolyl, thiadiazolyl; and
(24) -Me, -Et, -tBu, —CF₃, —CH₂OH.

In one embodiment, the substituents on Z (e.g., $R^4$) are independently selected from those substituents exemplified under the heading "Some Preferred Embodiments."

Some Preferred Classes of Compounds

All plausible combinations of the embodiments described above are explicitly disclosed herein, as if each combination was individually and explicitly recited.

Some preferred classes of compounds, defined by particular combinations of the above embodiments, are described next.

In one embodiment:
Q is independently —N=;
one of $R^{P2}$ and $R^{P3}$ is independently —NH—Z;

wherein:
Z is independently: $C_{6-14}$carboaryl or $C_{5-14}$heteroaryl, and is independently unsubstituted or substituted;
the other of $R^{P2}$ and $R^{P3}$ is independently —H, —NH$_2$, —NHMe, —NHEt, —NHC(=O)Me, or —NHC(=O)Et;
one of $R^{P5}$ and $R^{P6}$ is independently a group of the formula —W—Y;
wherein:
W is independently: a covalent bond, —NR$^{N4}$—, —O—, or —S—;
$R^{N4}$, if present, is independently —H, -Me, or -Et;
Y is independently: $C_{6-14}$carboaryl or $C_{5-14}$heteroaryl, and is independently unsubstituted or substituted; and;
the other of $R^{P5}$ and $R^{P6}$ is independently —H.
In one embodiment, W is independently: a covalent bond.
In one embodiment, W is independently: —NR$^{N4}$—.
In one embodiment, W is independently: —O—.
In one embodiment, W is independently: —S—.
In one embodiment:
Q is —N=,
$R^{P2}$ is independently —H;
$R^{P3}$ is independently: —NH—Z;
Z is independently: $C_{6-14}$carboaryl or $C_{5-14}$heteroaryl, and is independently unsubstituted or substituted;
$R^{P5}$ is independently a group of the formula —W—Y;
W is independently a covalent bond;
Y is independently: $C_{6-14}$carboaryl (e.g., phenyl, naphthyl) or $C_{5-14}$heteroaryl, and is independently unsubstituted or substituted; and
$R^{P6}$ is independently —H.
In one embodiment:
Q is —N=,
$R^{P2}$ is independently —H;
$R^{P3}$ is independently: —NH—Z;
Z is independently: $C_{6-14}$carboaryl or $C_{5-14}$heteroaryl, and is independently unsubstituted or substituted;
$R^{P5}$ is independently a group of the formula —W—Y;
W is independently —NR$^{N4}$—;
$R^{N4}$ is independently —H or aliphatic saturated $C_{1-4}$alkyl;
Y is independently: $C_{6-14}$carboaryl (e.g., phenyl, naphthyl) or $C_{5-14}$heteroaryl, and is independently unsubstituted or substituted; and
$R^{P6}$ is independently —H.
In one embodiment:
Q is —N=,
$R^{P2}$ is independently —H;
$R^{P3}$ is independently: —NH—Z;
Z is independently: $C_{6-14}$carboaryl or $C_{5-14}$heteroaryl, and is independently unsubstituted or substituted;
$R^{P5}$ is independently a group of the formula —W—Y;
W is independently —O—;
Y is independently: $C_{6-14}$carboaryl (e.g., phenyl, naphthyl) or $C_{5-14}$heteroaryl, and is independently unsubstituted or substituted; and
$R^{P6}$ is independently —H.
In one embodiment:
Q is —N=,
$R^{P2}$ is independently —H;
$R^{P3}$ is independently: —NH—Z;
Z is independently: $C_{6-14}$carboaryl or $C_{5-14}$heteroaryl, and is independently unsubstituted or substituted;
$R^{P5}$ is independently a group of the formula —W—Y;
Y is independently: $C_{6-14}$carboaryl (e.g., phenyl, naphthyl) or $C_{5-14}$heteroaryl, and is independently unsubstituted or substituted; and
W is independently —S—; and
$R^{P6}$ is independently —H.

In one embodiment:
Q is independently —N=;
one of $R^{P2}$ and $R^{P3}$ is independently —NH—Z;
wherein:
Z is independently phenyl, and is independently unsubstituted or substituted;
the other of $R^{P2}$ and $R^{P3}$ is independently —H, —NH$_2$, —NHMe, —NHEt, —NHC(=O)Me, or —NHC(=O)Et;
one of $R^{P5}$ and $R^{P6}$ is independently a group of the formula —W—Y;
wherein:
W is independently: a covalent bond, —NR$^{N4}$—, —O—, or —S—;
$R^{N4}$, if present, is independently —H, -Me, or -Et;
Y is independently phenyl, and is independently unsubstituted or substituted; and
the other of $R^{P5}$ and $R^{P6}$ is independently —H;
as in, for example, the following formula:

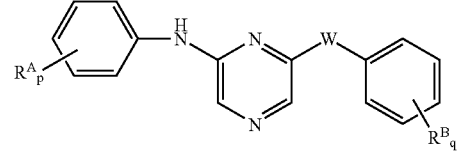

In one embodiment:
Q is independently —N=;
one of $R^{P2}$ and $R^{P3}$ is independently —NH—Z;
wherein:
Z is independently phenyl, and is independently unsubstituted or substituted;
the other of $R^{P2}$ and $R^{P3}$ is independently —H, —NH$_2$, —NHMe, —NHEt, —NHC(=O)Me, or —NHC(=O)Et;
one of $R^{P5}$ and $R^{P6}$ is independently a group of the formula —W—Y;
wherein:
W is independently: a covalent bond or —NR$^{N4}$;
$R^{N4}$, if present, is independently —H, -Me, or -Et;
Y is independently phenyl, and is independently unsubstituted or substituted; and.
the other of $R^{P5}$ and $R^{P6}$ is independently —H;
as in for example, the following formula:

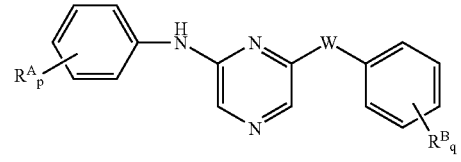

In one embodiment:
Q is independently —N=;
one of $R^{P2}$ and $R^{P3}$ is independently —NH—Z;
wherein:
Z is independently phenyl, and is independently unsubstituted or substituted;
the other of $R^{P2}$ and $R^{P3}$ is independently —H, —NH$_2$, —NHMe, —NHEt, —NHC(=O)Me, or —NHC(=O)Et;
one of $R^{P6}$ and $R^{P6}$ is independently a group of the formula —W—Y;

wherein:
W is independently: a covalent bond;
Y is independently phenyl, and is independently unsubstituted or substituted; and.
the other of $R^{P9}$ and $R^{P6}$ is independently —H;
as in, for example, the following formula:

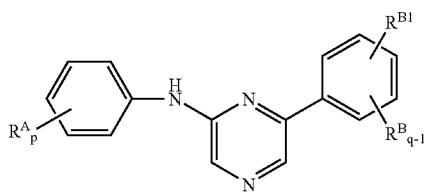

Molecular Weight

In one embodiment, the compound has a molecular weight of 250 to 1000.

In one embodiment, the bottom of range is 275; 300; 325; 350; 375; 400; 425; 450.

In one embodiment, the top of range is 900; 800; 700; 600; 500.

In one embodiment, the range is 250 to 900.
In one embodiment, the range is 250 to 800.
In one embodiment, the range is 250 to 700.
In one embodiment, the range is 250 to 600.
In one embodiment, the range is 250 to 500.

Some Preferred Embodiments

All plausible combinations of the embodiments described above are explicitly disclosed herein.

Examples of some preferred "pyrazine" compounds (wherein Q is —N═; -$J^1$-$L^1$- is —NH—; Z is phenyl and is optionally substituted; W is a covalent bond; and Y is phenyl and is optionally substituted) are shown below.

| No. | Code | Structure |
|---|---|---|
| 1. | CJS 371 | 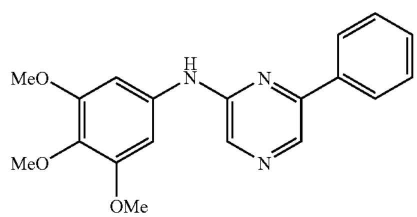 |
| 2. | CJS 350 | 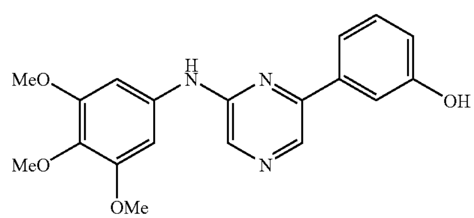 |
| 3. | CJS 351 | 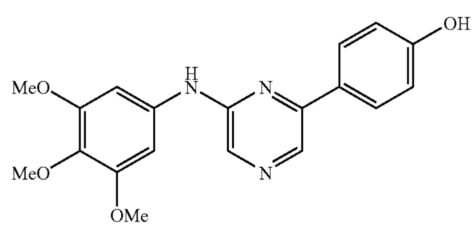 |
| 4. | CJS 357 | 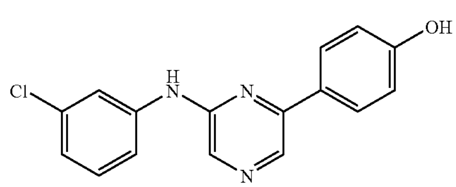 |
| 5. | CJS 377 | 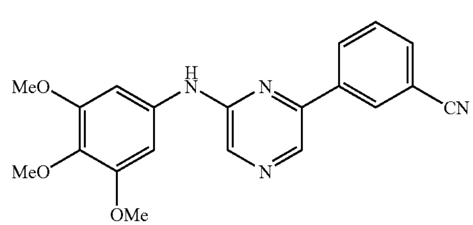 |

-continued
| No. | Code | Structure |
|---|---|---|
| 6. | CJS 374 | 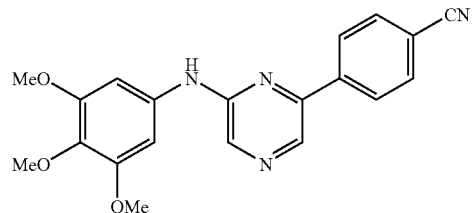 |
| 7. | CJS 364 | 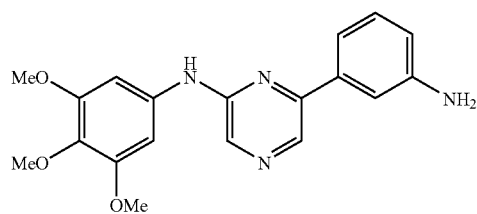 |
| 8. | CJS 366 | 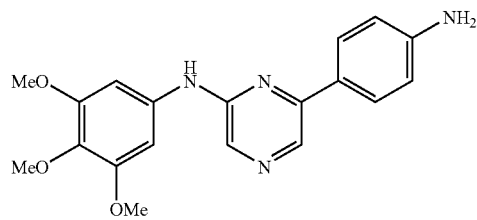 |
| 9. | CJS 355 | 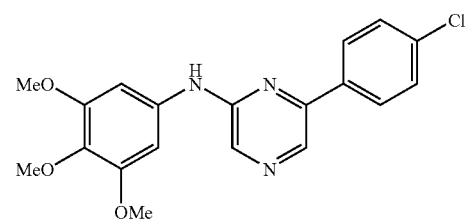 |
| 10. | CJS 362 | 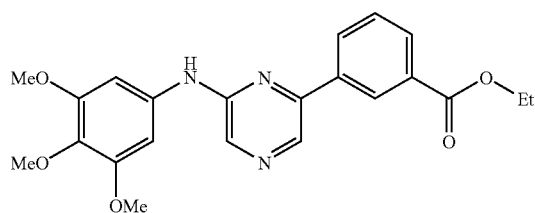 |
| 11. | CJS 365 | 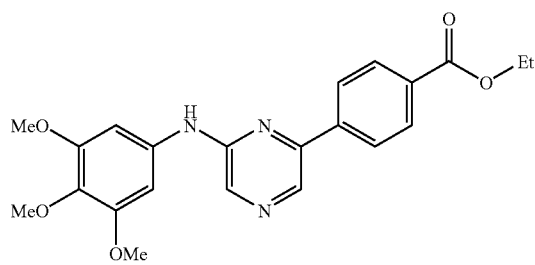 |

-continued

| No. | Code | Structure |
|---|---|---|
| 12. | CJS 372 | (structure) |
| 13. | CJS 359 | (structure) |
| 14. | CJS 400 | (structure) |
| 15. | CJS 495 | (structure) |
| 16. | CJS 702 | (structure) |
| 17. | CJS 703 | (structure) |

-continued

| No. | Code | Structure |
|---|---|---|
| 18. | CJS 711 | 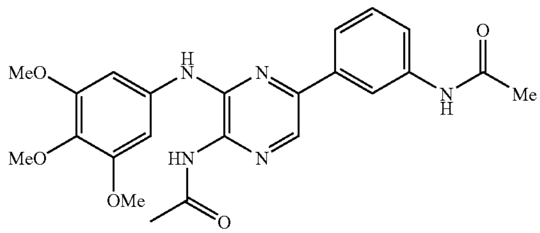 |
| 19. | CJS 352 | 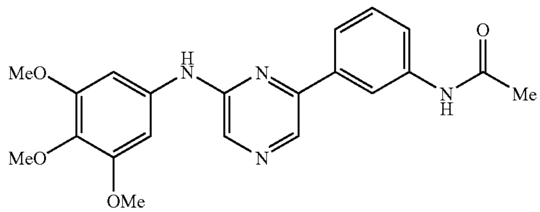 |
| 20. | CJS 354 | 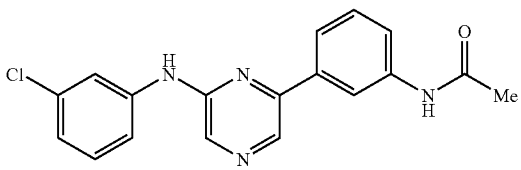 |
| 21. | CJS 367 | 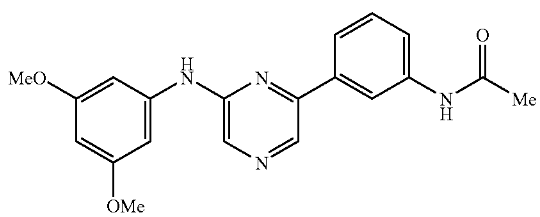 |
| 22. | CJS 368 | 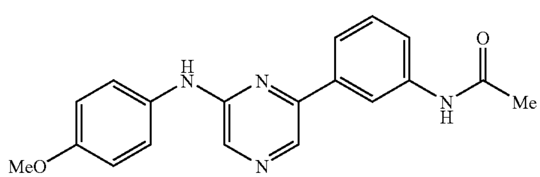 |
| 23. | CJS 369 | 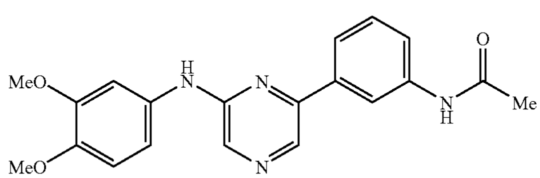 |
| 24. | CJS 370 | 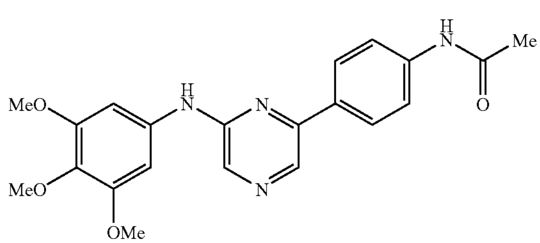 |

| No. | Code | Structure |
|-----|------|-----------|
| 25. | CJS 383 | 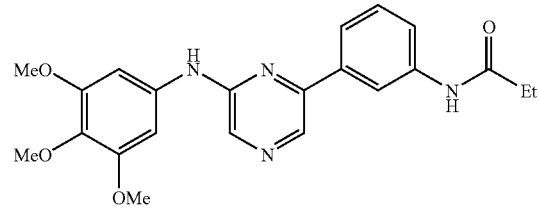 |
| 26. | CJS 384 | 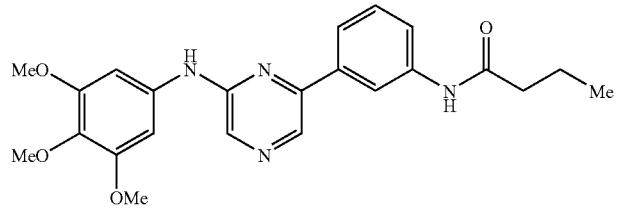 |
| 27. | CJS 385 | 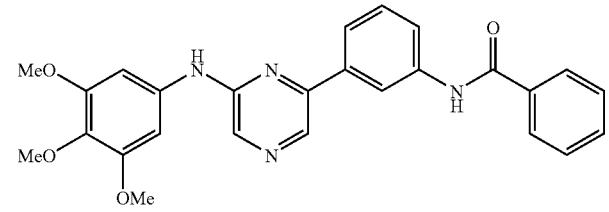 |
| 28. | CJS 386 | 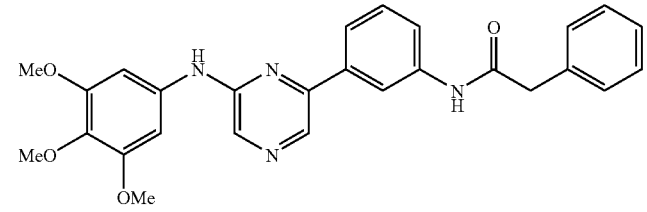 |
| 29. | CJS 387 | 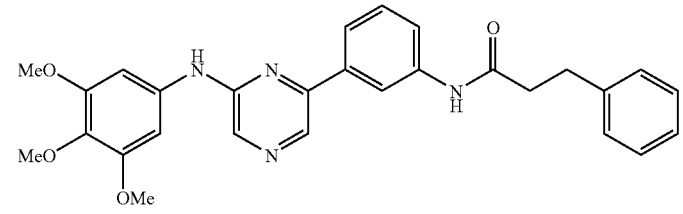 |
| 30. | CJS 388 | 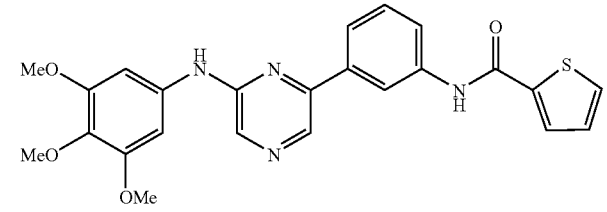 |
| 31. | CJS 389 | 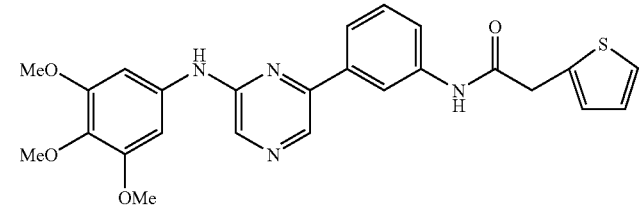 |

-continued

| No. | Code | Structure |
|---|---|---|
| 32. | CJS 390 | 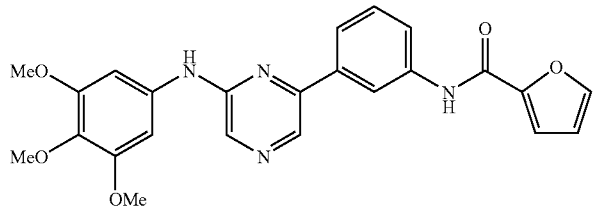 |
| 33. | CJS 392 | 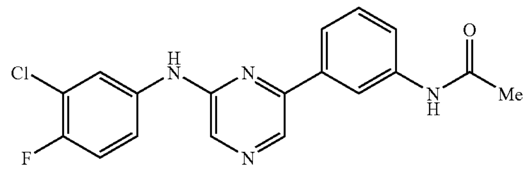 |
| 34. | CJS 393 | 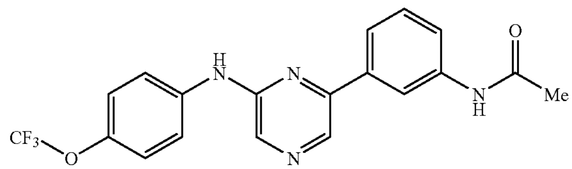 |
| 35. | CJS 394 | 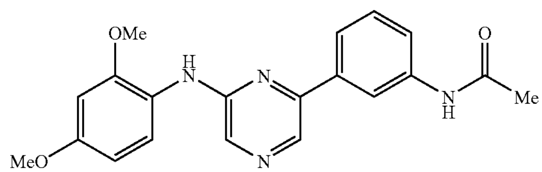 |
| 36. | CJS 407 | 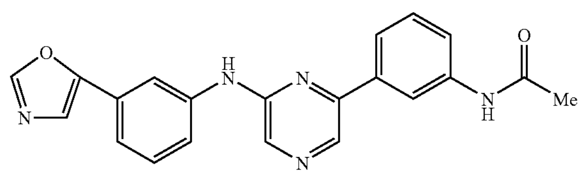 |
| 37. | CJS 409 | 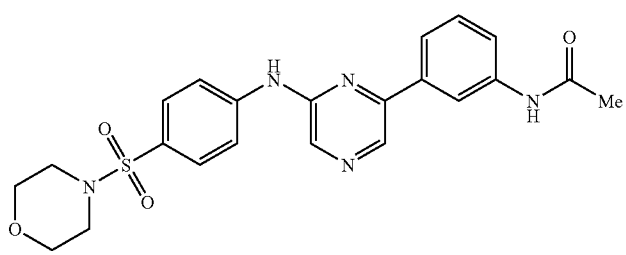 |
| 38. | CJS 438 | 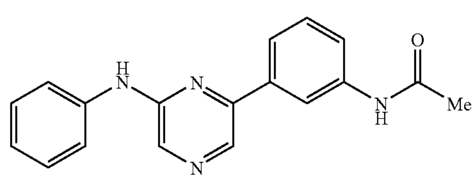 |

-continued
| No. | Code | Structure |
|---|---|---|
| 39. | CJS 441 | 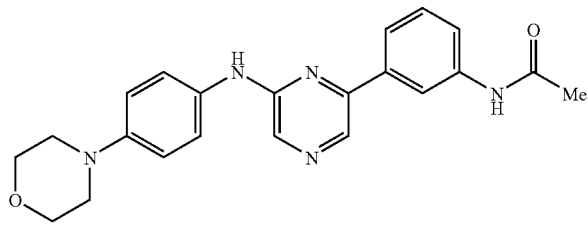 |
| 40. | CJS 442 | 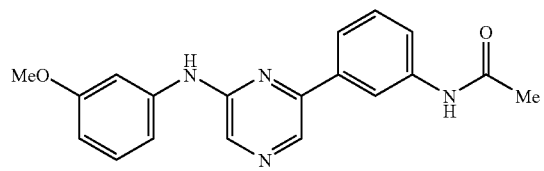 |
| 41. | CJS 444 | 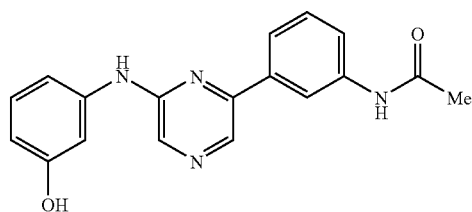 |
| 42. | CJS 446 | 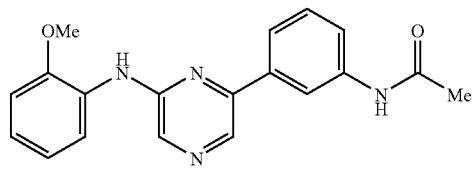 |
| 43. | CJS 481 | 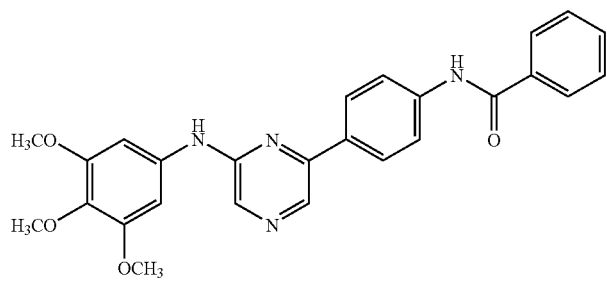 |
| 44. | CJS 496 | 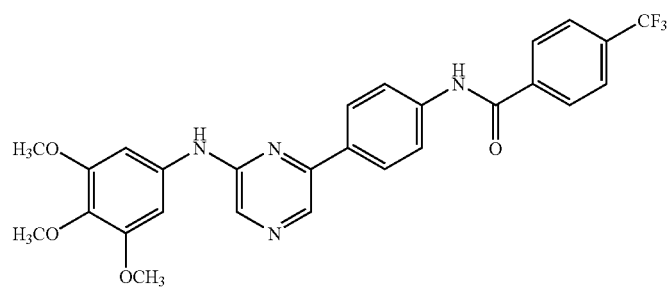 |

-continued
| No. | Code | Structure |
|---|---|---|
| 45. | CJS 497 | 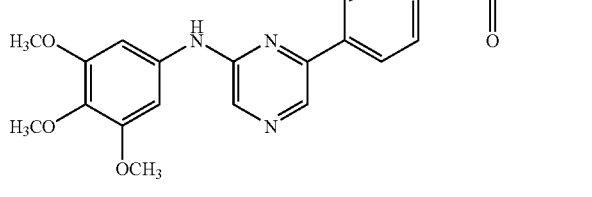 |
| 46. | CJS 501 | 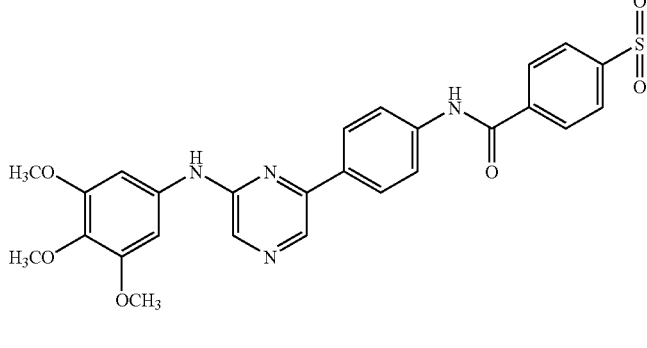 |
| 47. | CJS 502 | 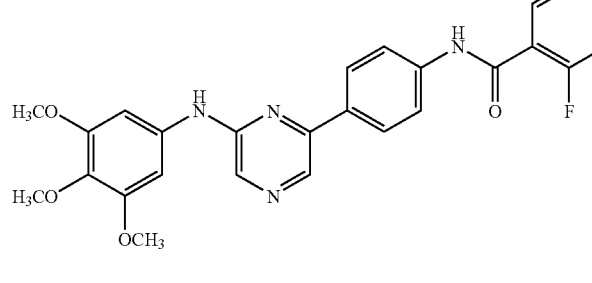 |
| 48. | CJS 375 | 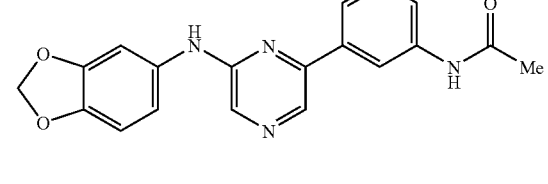 |
| 49. | CJS 416 | 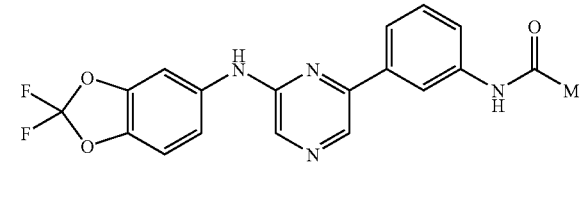 |
| 50. | CJS 391 | 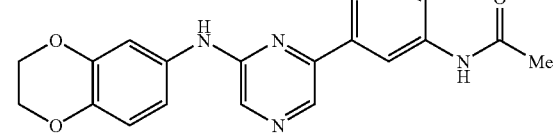 |

| No. | Code | Structure |
|---|---|---|
| 51. | CJS 415 | 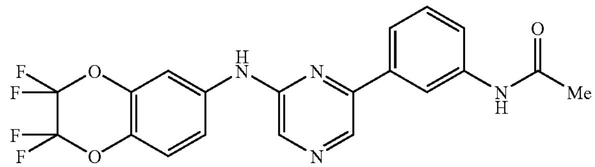 |
| 52. | CJS 408 | 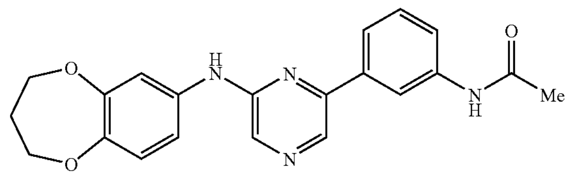 |
| 53. | CJS 380 | 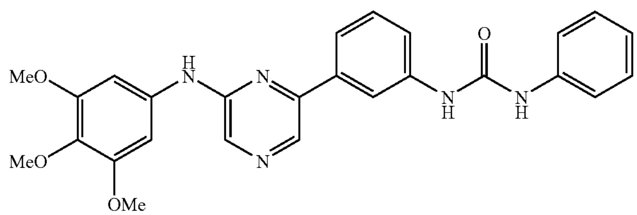 |
| 54. | CJS 457 | 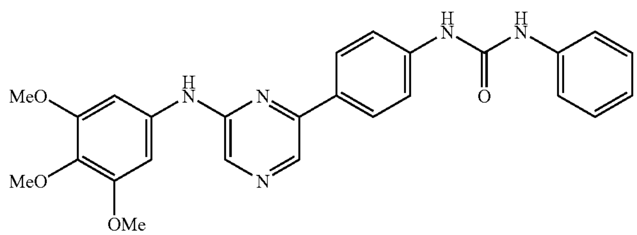 |
| 55. | CJS 459 | 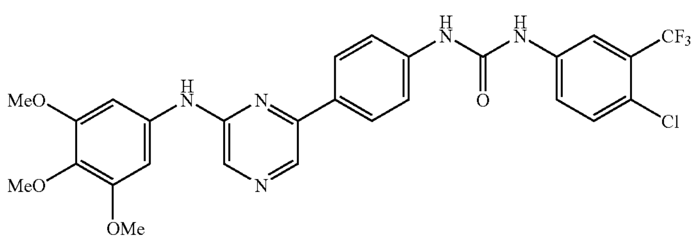 |
| 56. | CJS 469 | 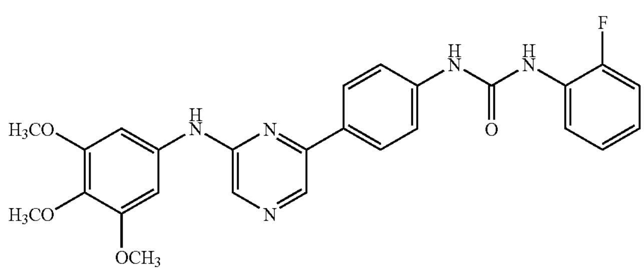 |
| 57. | CJS 470 | 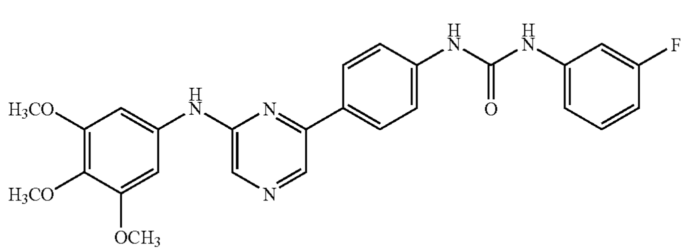 |

-continued

-continued

| No. | Code | Structure |
|---|---|---|
| 58. | CJS 471 | 3,4,5-trimethoxyphenyl-NH-pyrazine-C6H4-NHC(O)NH-C6H4-4-F |
| 59. | CJS 472 | 3,4,5-trimethoxyphenyl-NH-pyrazine-C6H4-NHC(O)NH-C6H4-3-Cl |
| 60. | CJS 473 | 3,4,5-trimethoxyphenyl-NH-pyrazine-C6H4-NHC(O)NH-C6H4-4-Cl |
| 61. | CJS 474 | 3,4,5-trimethoxyphenyl-NH-pyrazine-C6H4-NHC(O)NH-C6H4-3-CF3 |
| 62. | CJS 475 | 3,4,5-trimethoxyphenyl-NH-pyrazine-C6H4-NHC(O)NH-C6H4-4-CF3 |
| 63. | CJS 476 | 3,4,5-trimethoxyphenyl-NH-pyrazine-C6H4-NHC(O)NH-C6H3-3,4-F2 |

-continued
| No. | Code | Structure |
|---|---|---|
| 64. | CJS 477 | 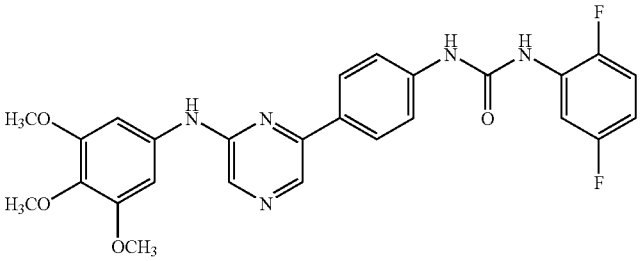 |
| 65. | CJS 466 | 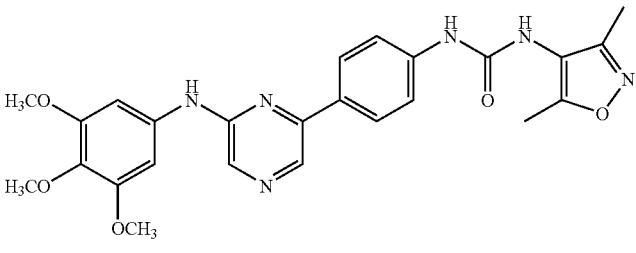 |
| 66. | CJS 467 | 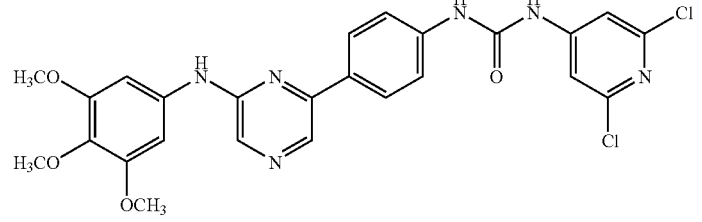 |
| 67. | CJS 468 | 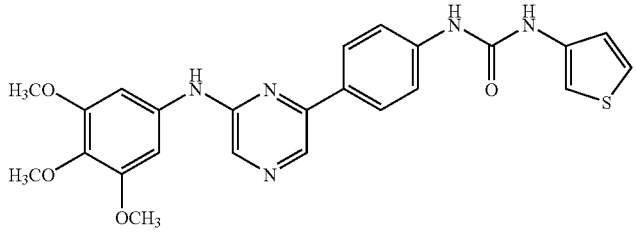 |
| 68. | CJS 382 | 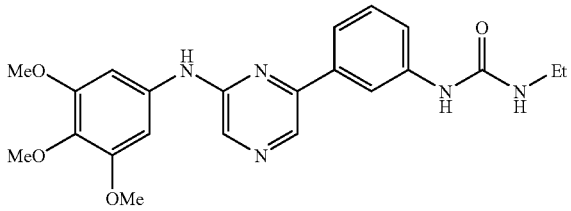 |
| 69. | CJS 378 | 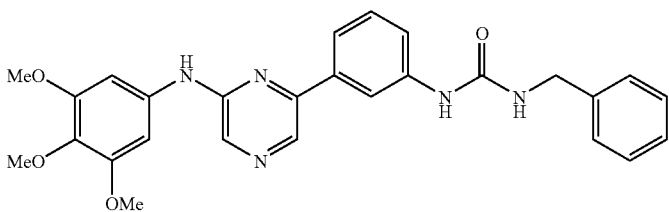 |

-continued
| No. | Code | Structure |
|---|---|---|
| 70. | CJS 381 | 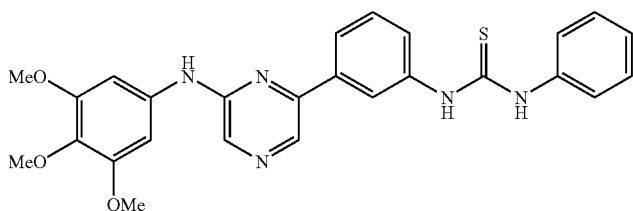 |
| 71. | CJS 379 | 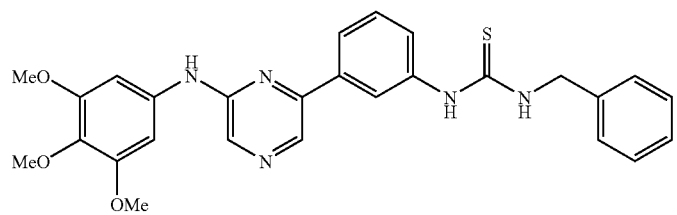 |
| 72. | CJS 479 | 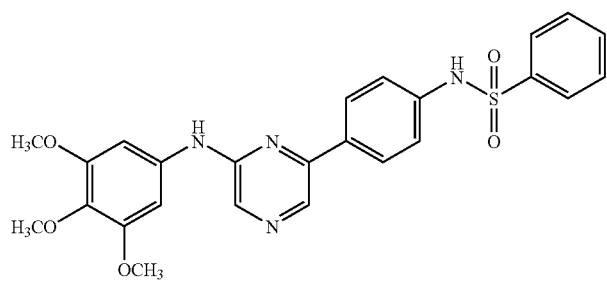 |
| 73. | CJS 482 | 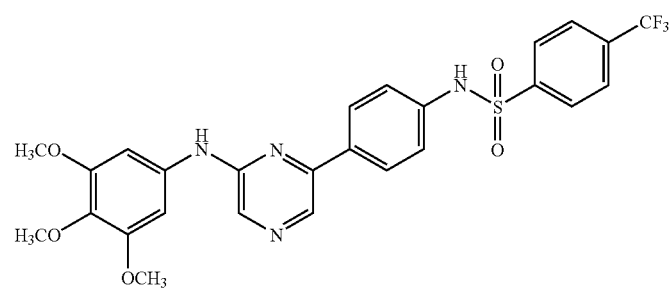 |
| 74. | CJS 483 | 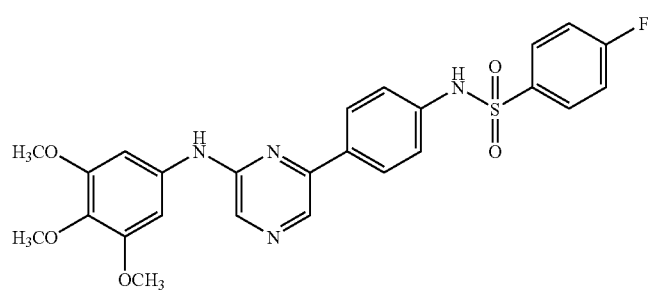 |

-continued
| No. | Code | Structure |
|---|---|---|
| 75. | CJS 484 | 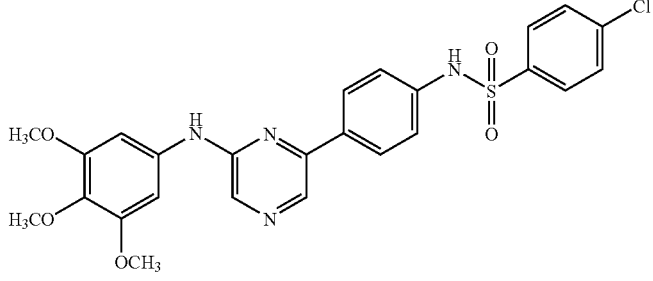 |
| 76. | CJS 486 | 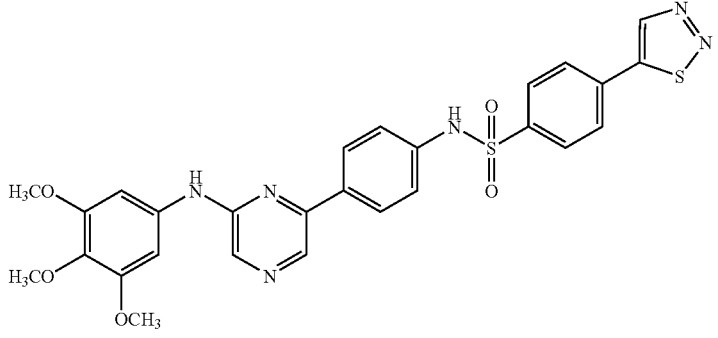 |
| 77. | CJS 488 | 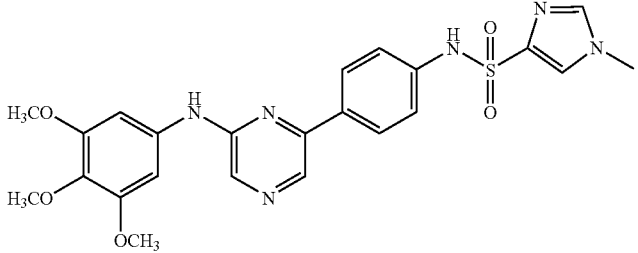 |
| 78. | CJS 490 | 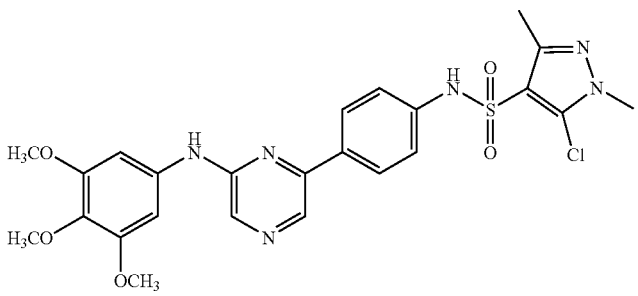 |
| 79. | CJS 491 | 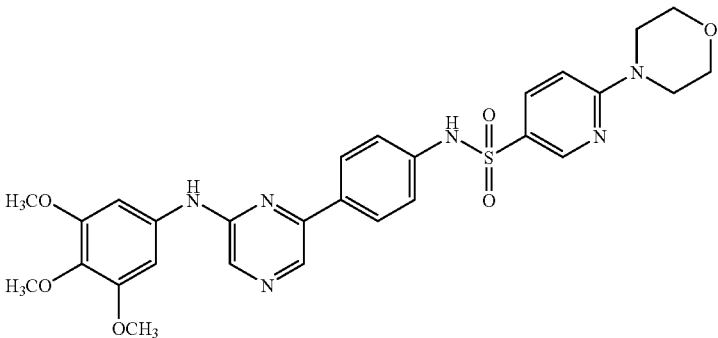 |

Examples of some preferred "pyrazine" compounds (wherein Q is —N═; -J$^1$-L$^1$- is —NH—; Z is phenyl and is optionally substituted; W is a covalent bond; and Y is naphthyl and is optionally substituted) are shown below.

| No. | Code | Structure |
|---|---|---|
| 80. | CJS 439 | 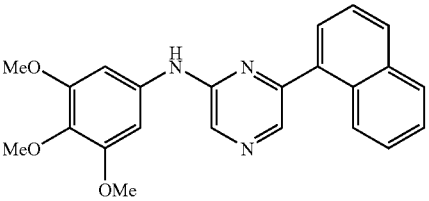 |
| 81. | CJS 440 | 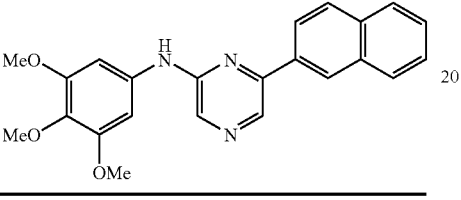 |

Examples of some preferred "pyrazine" compounds (wherein Q is —N═; -J$^1$-L$^1$- is —NH—; Z is phenyl and is optionally substituted; W is a covalent bond; and Y is C$_{5-6}$heteroaryl and is optionally substituted) are shown below.

| No. | Code | Structure |
|---|---|---|
| 82. | CJS 361 | 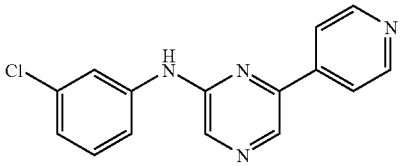 |
| 83. | CJS 363 | 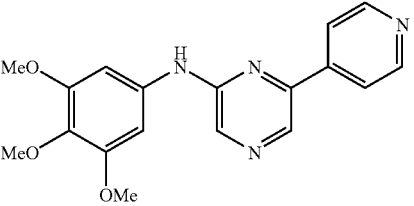 |
| 84. | CJS 373 | 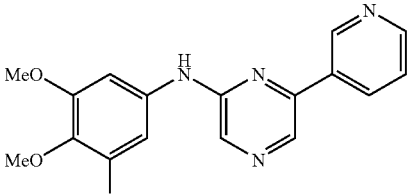 |
| 85. | CJS 398 | 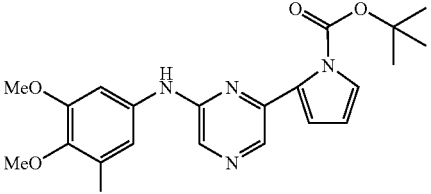 |

Examples of some preferred "pyrazine" compounds (wherein Q is —N═; -J$^1$-L$^1$- is —NH—; Z is C$_{5-10}$heteroaryl and is optionally substituted; W is a covalent bond; and Y is phenyl and is optionally substituted) are shown below.

| No. | Code | Structure |
|---|---|---|
| 86. | CJS 410 | 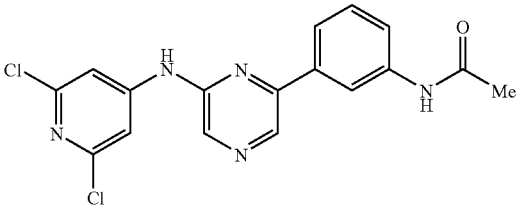 |
| 87. | CJS 413 | 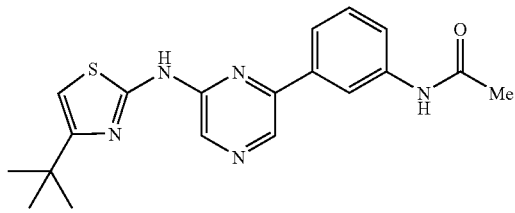 |

-continued

| No. | Code | Structure |
|-----|------|-----------|
| 88. | CJS 411 | 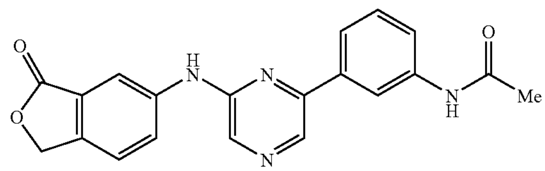 |

Examples of some preferred "pyrazine" compounds (wherein Q is —N=; -J¹-L¹- is —NH—; Z is phenyl and is optionally substituted; W is —O—; and Y is phenyl and is optionally substituted) are shown below.

| No. | Code | Structure |
|-----|------|-----------|
| 89. | CJS 430 | 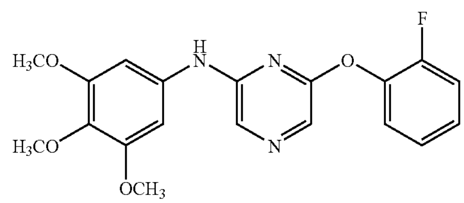 |
| 90. | CJS 454 | 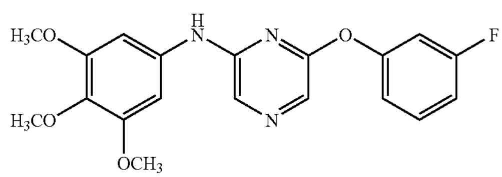 |
| 91. | CJS 480 | 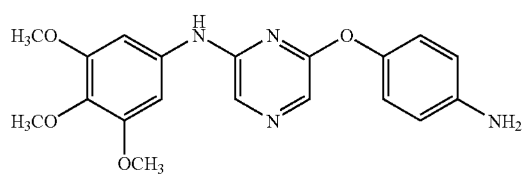 |
| 92. | CJS 489 | 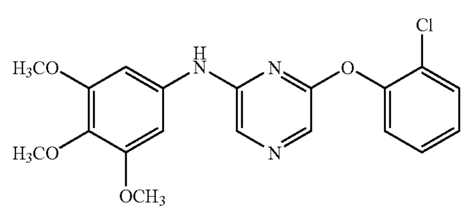 |
| 93. | CJS 492 | 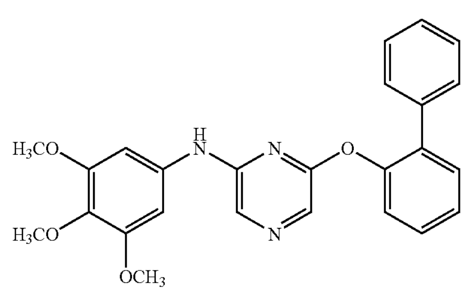 |

| No. | Code | Structure |
|---|---|---|
| 94. | CJS 493 | 3,4,5-trimethoxyphenyl-NH-pyrazinyl-O-(3-biphenyl) |
| 95. | CJS 494 | 3,4,5-trimethoxyphenyl-NH-pyrazinyl-O-(4-biphenyl) |
| 96. | CJS 504 | 3,4,5-trimethoxyphenyl-NH-pyrazinyl-O-(3-chlorophenyl) |
| 97. | CJS 508 | 3,4,5-trimethoxyphenyl-NH-pyrazinyl-O-(3-acetylphenyl) |
| 98. | CJS 509 | 3,4,5-trimethoxyphenyl-NH-pyrazinyl-O-(4-acetylphenyl) |
| 99. | CJS 514 | 3,4,5-trimethoxyphenyl-NH-pyrazinyl-O-(3-(C(=NOH)CH$_3$)phenyl) |
| 100. | CJS 515 | 3,4,5-trimethoxyphenyl-NH-pyrazinyl-O-(4-(C(=NOH)CH$_3$)phenyl) |
| 101. | CJS 718 | 3,4,5-trimethoxyphenyl-NH-pyrazinyl-O-phenyl |

| No. | Code | Structure |
|---|---|---|
| 102. | CJS 522 | (structure) |
| 103. | CJS 505 | (structure) |
| 104. | CJS 506 | (structure) |
| 105. | CJS 464 | (structure) |
| 106. | CJS 465 | (structure) |

Examples of some preferred "pyrazine" compounds (wherein Q is —N═; -J$^1$-L$^1$- is —NH—; Z is phenyl and is optionally substituted; W is —O—; and Y is naphthyl and is optionally substituted) are shown below.

| No. | Code | Structure |
|---|---|---|
| 107. | CJS 485 | (structure) |

| No. | Code | Structure |
|---|---|---|
| 108. | CJS 487 | 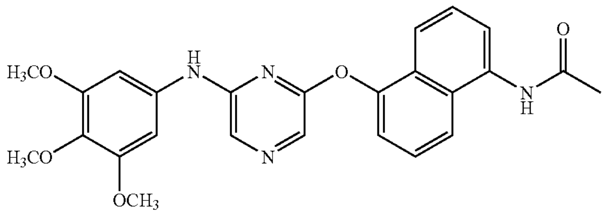 |
| 109. | CJS 706 | 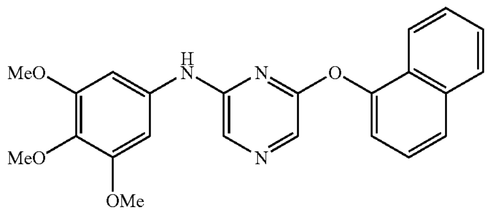 |
| 110. | CJS 717 | 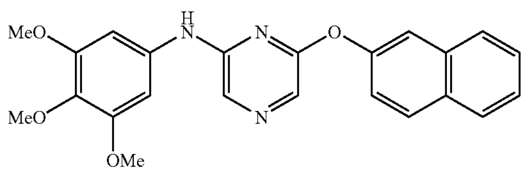 |
| 111. | CJS 727 | 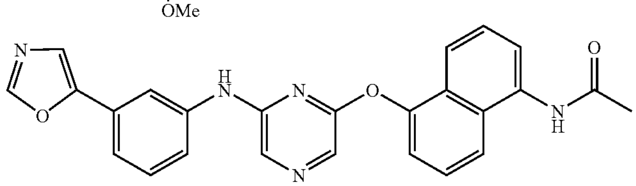 |
| 112. | CJS 734 | 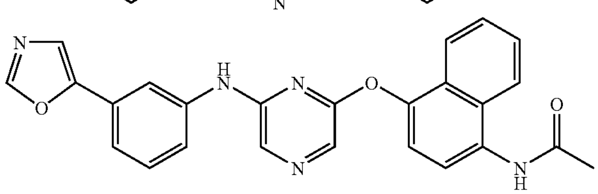 |
| 113. | CJS 712 | 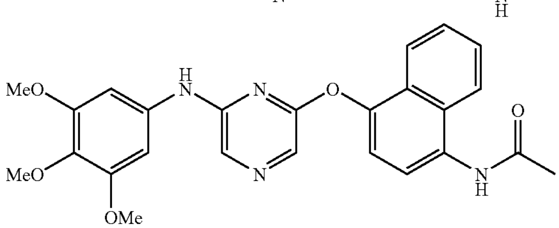 |

Examples of some preferred "pyrazine" compounds (wherein Q is —N═; -J$^1$-L$^1$- is —NH—; Z is C$_{5-10}$heteroaryl and is optionally substituted; W is —O—; and Y is naphthyl and is optionally substituted) are shown below.

| No. | Code | Structure |
|---|---|---|
| 114. | CJS 728 | 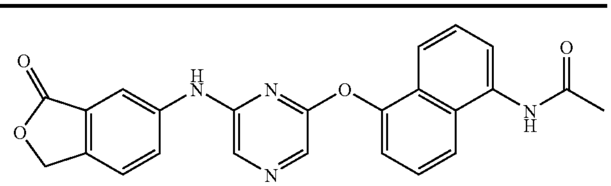 |

Examples of some preferred "pyrazine" compounds (wherein Q is —N=; -J$^1$-L$^1$- is —NH—; Z is phenyl and is optionally substituted; W is —O—; and Y is C$_{6-10}$carboaryl and is optionally substituted, e.g., with oxo (=O) or hydroxyimino (=NOH)) are shown below.

| No. | Code | Structure |
|---|---|---|
| 115. | CJS 510 | 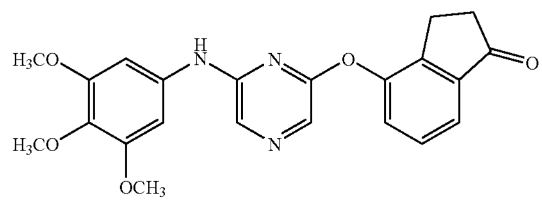 |
| 116. | CJS 511 | 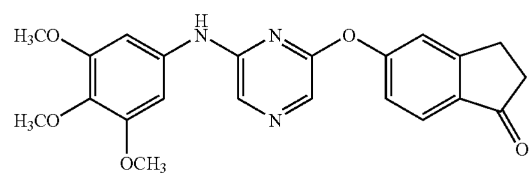 |
| 117. | CJS 512 | 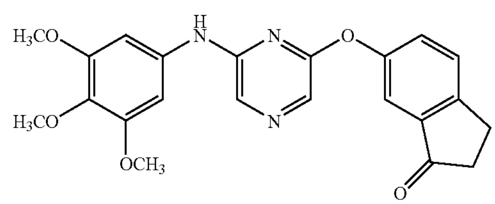 |
| 118. | CJS 513 | 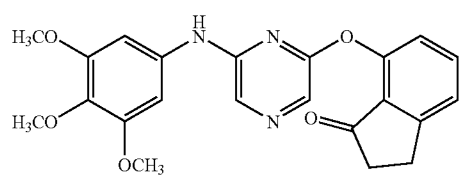 |
| 119. | CJS 516 | 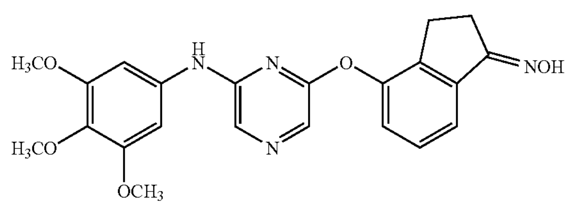 |
| 120. | CJS 517 | 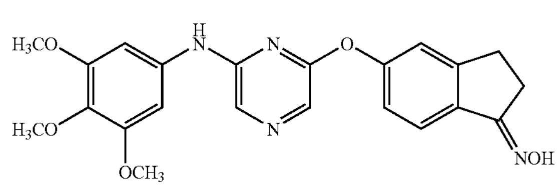 |
| 121. | CJS 724 | 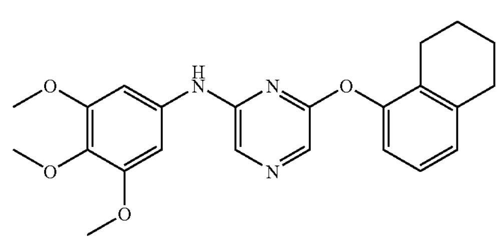 |

| No. | Code | Structure |
|---|---|---|
| 122. | CJS 428 | (structure) |
| 123. | CJS 429 | (structure) |
| 124. | CJS 519 | (structure) |
| 125. | CJS 520 | (structure) |

Examples of some preferred "pyrazine" compounds (wherein Q is —N=; -J$^1$-L$^1$- is —NH—; Z is phenyl and is optionally substituted; W is —O—; and Y is C$_{5-10}$heteroaryl and is optionally substituted) are shown below.

| No. | Code | Structure |
|---|---|---|
| 126. | CJS 719 | (structure) |
| 127. | CJS 721 | (structure) |
| 128. | CJS 523 | (structure) |

-continued

| No. | Code | Structure |
|---|---|---|
| 129. | CJS 524 | 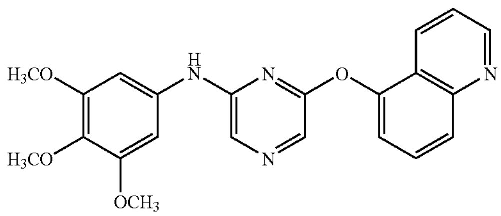 |
| 130. | CJS 525 | 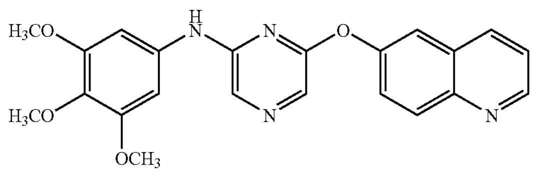 |
| 131. | CJS 526 | 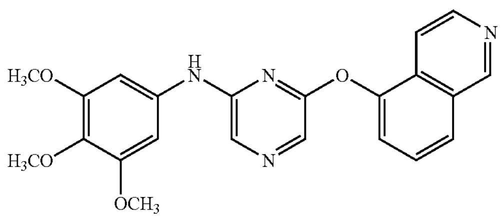 |
| 132. | CJS 725 | 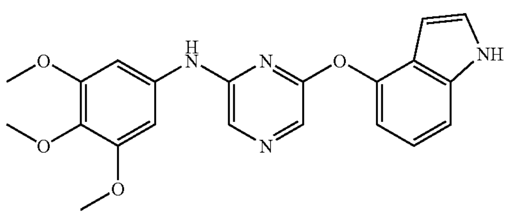 |
| 133. | CJS 426 | 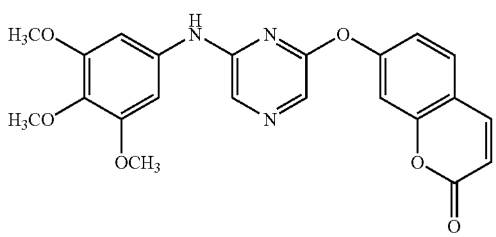 |

Examples of some preferred "pyrazine" compounds (wherein Q is —N═; -J$^1$-L$^1$- is —NH—; Z is phenyl and is optionally substituted; W is —NH—; and Y is phenyl and is optionally substituted) are shown below.

| No. | Code | Structure |
|---|---|---|
| 134. | CJS 448 | 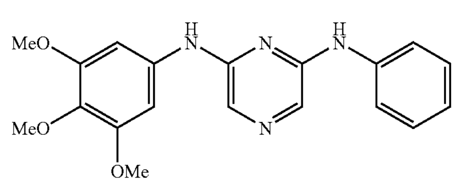 |

| No. | Code | Structure |
|---|---|---|
| 135. | CJS 461 | 3,4,5-trimethoxyphenyl-NH-pyrazine-NH-3,4,5-trimethoxyphenyl |
| 136. | CJS 462 | 3,4,5-trimethoxyphenyl-NH-pyrazine-NH-4-hydroxyphenyl |
| 137. | CJS 707 | 3,4,5-trimethoxyphenyl-NH-pyrazine-NH-3-fluorophenyl |
| 138. | CJS 709 | 3,4,5-trimethoxyphenyl-NH-pyrazine-NH-4-fluorophenyl |
| 139. | CJS 447 | 3,4,5-trimethoxyphenyl-NH-pyrazine-NH-(4-acetamidophenyl) |
| 140. | CJS 449 | 3,4,5-trimethoxyphenyl-NH-pyrazine-NH-(3-acetamidophenyl) |

Examples of some preferred "pyrazine" compounds (wherein Q is —N=; -J$^1$-L$^1$- is —NH—; Z is phenyl and is optionally substituted; W is —NH—; and Y is $C_{5-6}$ heteroaryl and is optionally substituted) are shown below.

| No. | Code | Structure |
|---|---|---|
| 141. | CJS 705 | 3,4,5-trimethoxyphenyl-NH-pyrazine-NH-(4-pyridyl) |

Examples of some preferred "pyrazine" compounds (wherein Q is —N=; -J$^1$-L$^1$- is —NH—; Z is phenyl and is optionally substituted; W is —S—; and Y is $C_{6-14}$ carboaryl (e.g., naphthyl) and is optionally substituted) are shown below.

| No. | Code | Structure |
|---|---|---|
| 142. | CJS 723 | 3,4,5-trimethoxyphenyl-NH-pyrazine-S-(1-naphthyl) |

Examples of some preferred "pyridine" compounds are shown below.

| No. | Code | Structure |
|---|---|---|
| 143. | CJS 402 | 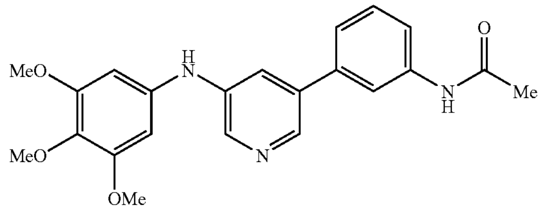 |
| 144. | CT077151 | 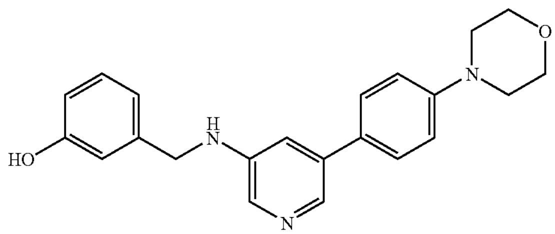 |
| 145. | CT077171 | 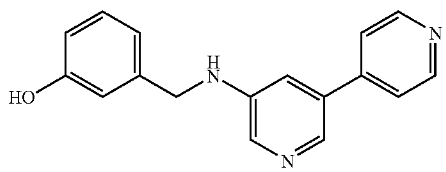 |
| 146. | CT077200 | 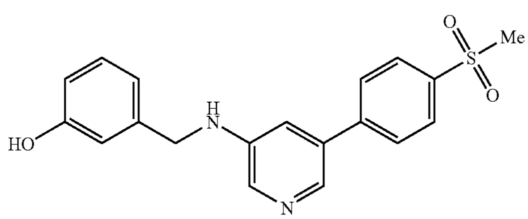 |
| 147. | CT077201 | 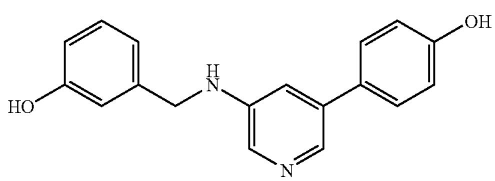 |
| 148. | CT077210 | 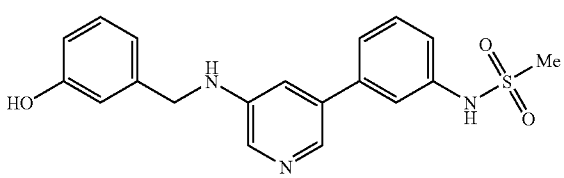 |
| 149. | CT077211 | 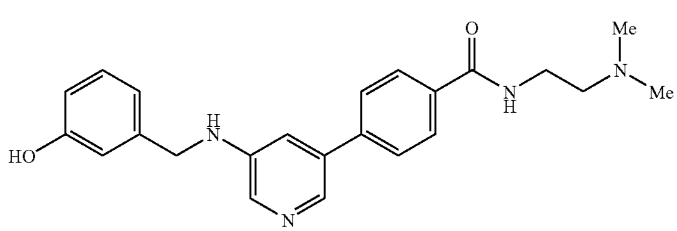 |

| No. | Code | Structure |
|---|---|---|
| 150. | CT077220 | 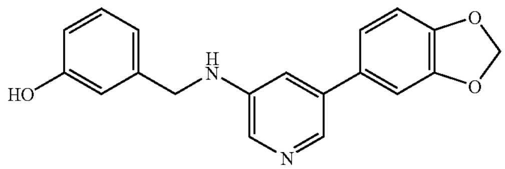 |

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond. Compounds and/or groups may be partially unsaturated or fully unsaturated.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked ring atoms, more preferably 3 to 8 covalently linked ring atoms, yet more preferably 5 to 6 covalently linked ring atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring," as used herein, pertains to an aromatic ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 (e.g., 1, 2, 3, 4) ring heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene, decalin, etc.), bridged (e.g., as in norbornane, adamantane, etc.), spiro (e.g., as in spiro [3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl. Note that the first prefix may vary according to other limitations; for example, for unsaturated alkyl groups, the first prefix must be at least 2; for cyclic and branched alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl (C$_4$), pentenyl (C$_5$), and hexenyl (C$_6$).

Alkynyl: The term "alkynyl," as used herein, pertains to an alkyl group having one or more carbon-carbon triple bonds. Examples of groups of alkynyl groups include C$_{2-4}$alkynyl, C$_{2-7}$alkynyl, C$_{2-20}$alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl," as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g., partially unsaturated, fully unsaturated), which moiety has from 3 to 20 carbon atoms (unless otherwise specified), including from 3 to 20 ring atoms. Thus, the term "cycloalkyl" includes the sub-classes cycloalkyenyl and cycloalkynyl. Preferably, each ring has from 3 to 7 ring atoms. Examples of groups of cycloalkyl groups include C$_{3-20}$cycloalkyl, C$_{3-15}$cycloalkyl, C$_{3-10}$cycloalkyl, C$_{3-7}$cycloalkyl.

Examples of cycloalkyl groups include, but are not limited to, those derived from:

saturated monocyclic hydrocarbon compounds:
cyclopropane (C$_3$), cyclobutane (C$_4$), cyclopentane (C$_5$), cyclohexane (C$_6$), cycloheptane (C$_7$), methylcyclopropane (C$_4$), dimethylcyclopropane (C$_5$), methylcyclobutane (C$_5$), dimethylcyclobutane (C$_6$), methylcyclopentane (C$_6$), dimethylcyclopentane (C$_7$), methylcyclohexane (C$_7$), dimethylcyclohexane (C$_8$), menthane (C$_{10}$);

unsaturated monocyclic hydrocarbon compounds:
cyclopropene (C$_3$), cyclobutene (C$_4$), cyclopentene (C$_5$), cyclohexene (C$_6$), methylcyclopropene (C$_4$), dimethylcyclopropene (C$_5$), methylcyclobutene (C$_5$), dimethylcyclobutene (C$_6$), methylcyclopentene (C$_6$), dimethylcyclopentene (C$_7$), methylcyclohexene (C$_7$), dimethylcyclohexene (C$_8$);

saturated polycyclic hydrocarbon compounds:
thujane (C$_{10}$), carane (C$_{10}$), pinane (C$_{10}$), bornane (C$_{10}$), norcarane (C$_7$), norpinane (C$_7$), norbornane (C$_7$), adamantane (C$_{10}$), decalin (decahydronaphthalene) (C$_{10}$);

unsaturated polycyclic hydrocarbon compounds:
camphene (C$_{10}$), limonene (C$_{10}$), pinene (C$_{10}$);

polycyclic hydrocarbon compounds having an aromatic ring:
indene (C$_9$), indane (e.g., 2,3-dihydro-1H-indene) (C$_9$), tetraline (1,2,3,4-tetrahydronaphthalene) (C$_{10}$), acenaphthene (C$_{12}$), fluorene (C$_{13}$), phenalene (C$_{13}$), acephenanthrene (C$_{15}$), aceanthrene (C$_{16}$), cholanthrene (C$_{20}$).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., C$_{3-20}$, C$_{3-7}$, C$_{5-6}$, etc.) denote the number of ring atoms, or range of number of ring atoms. For example, the term "C$_{5-6}$carbocyclyl," as used herein, pertains to a carbocyclyl group having 5 or 6 ring atoms. Examples of groups of carbocyclyl groups include C$_{3-20}$carbocyclyl, C$_{3-10}$carbocyclyl, C$_{5-10}$carbocyclyl, C$_{3-7}$carbocyclyl, and C$_{5-7}$carbocyclyl.

Examples of carbocyclic groups include, but are not limited to, those described above as cycloalkyl groups; and those described below as carboaryl groups.

The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., C$_{3-20}$, C$_{3-7}$, C$_{5-6}$, etc.) denote the number of ring atoms, or range of number of ring atoms, whether carbon atoms or heteroatoms. For example, the term "C$_{5-6}$heterocyclyl," as used herein, pertains to a heterocyclyl group having 5 or 6 ring atoms. Examples of groups of heterocyclyl groups include C$_{3-20}$heterocyclyl, C$_{5-20}$heterocyclyl, C$_{3-15}$heterocyclyl, C$_{5-15}$heterocyclyl, C$_{3-12}$heterocyclyl, C$_{5-12}$heterocyclyl, C$_{3-10}$heterocyclyl, C$_{5-10}$heterocyclyl, C$_{3-7}$heterocyclyl, C$_{5-7}$heterocyclyl, and C$_{5-6}$heterocyclyl.

Examples of (non-aromatic) monocyclic heterocyclyl groups include, but are not limited to, those derived from:

N$_1$: aziridine (C$_3$), azetidine (C$_4$), pyrrolidine (tetrahydropyrrole) (C$_5$), pyrroline (e.g., 3-pyrroline, 2,5-dihydropyrrole) (C$_5$), 2H-pyrrole or 3H-pyrrole (isopyrrole, isoazole) (C$_5$), piperidine (C$_6$), dihydropyridine (C$_6$), tetrahydropyridine (C$_6$), azepine (C$_7$);

O$_1$: oxirane (C$_3$), oxetane (C$_4$), oxolane (tetrahydrofuran) (C$_5$), oxole (dihydrofuran) (C$_5$), oxane (tetrahydropyran) (C$_6$), dihydropyran (C$_6$), pyran (C$_6$), oxepin (C$_7$);

S$_1$: thiirane (C$_3$), thietane (C$_4$), thiolane (tetrahydrothiophene) (C$_5$), thiane (tetrahydrothiopyran) (C$_6$), thiepane (C$_7$);

O$_2$: dioxolane (C$_5$), dioxane (C$_6$), and dioxepane (C$_7$);

O$_3$: trioxane (C$_6$);

N$_2$: imidazolidine (C$_5$), pyrazolidine (diazolidine) (C$_5$), imidazoline (C$_5$), pyrazoline (dihydropyrazole) (C$_5$), piperazine (C$_6$);

N$_1$O$_1$: tetrahydrooxazole (C$_5$), dihydrooxazole (C$_5$), tetrahydroisoxazole (C$_5$), dihydroisoxazole (C$_5$), morpholine (C$_6$), tetrahydrooxazine (C$_6$), dihydrooxazine (C$_6$), oxazine (C$_6$);

N$_1$S$_1$: thiazoline (C$_5$), thiazolidine (C$_5$), thiomorpholine (C$_6$);

N$_2$O$_1$: oxadiazine (C$_6$);

O$_1$S$_1$: oxathiole (C$_5$) and oxathiane (thioxane) (C$_6$); and,

N$_1$O$_1$S$_1$: oxathiazine (C$_6$).

Examples of substituted (non-aromatic) monocyclic heterocyclyl groups include those derived from saccharides, in cyclic form, for example, furanoses (C$_5$), such as arabinofuranose, lyxofuranose, ribofuranose, and xylofuranse, and pyranoses (C$_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

The term "aryl," as used herein, pertains to a monovalent moiety obtained by removing a hydrogen atom from an aromatic ring atom of an aromatic compound, which moiety has from 3 to 20 ring atoms (unless otherwise specified) (and so includes, e.g., indan-5-yl, 1,2,3,4-tetrahydronaphthalen-5-yl, etc.). Preferably, each ring has from 5 to 7 ring atoms.

In this context, the prefixes (e.g., C$_{3-20}$, C$_{5-7}$, C$_{5-6}$, etc.) denote the number of ring atoms, or range of number of ring atoms, whether carbon atoms or heteroatoms. For example, the term "C$_{5-6}$aryl," as used herein, pertains to an aryl group having 5 or 6 ring atoms. Examples of groups of aryl groups include C$_{5-20}$aryl, C$_{5-15}$aryl, C$_{5-12}$aryl, C$_{5-10}$aryl, C$_{5-7}$aryl, C$_{5-6}$aryl, C$_5$aryl, and C$_6$aryl.

The ring atoms may be all carbon atoms, as in "carboaryl groups." Examples of carboaryl groups include C$_{3-20}$carboaryl, C$_{5-20}$carboaryl, C$_{5-15}$carboaryl, C$_{5-12}$carboaryl, C$_{5-10}$carboaryl, C$_{5-7}$carboaryl, C$_{5-6}$carboaryl, C$_5$carboaryl, and C$_6$carboaryl.

Examples of carboaryl groups include, but are not limited to, those derived from benzene (i.e., phenyl) (C$_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups." Examples of heteroaryl groups include $C_{3-20}$heteroaryl, $C_{5-20}$heteroaryl, $C_{5-15}$heteroaryl, $C_{5-12}$heteroaryl, $C_{5-10}$heteroaryl, $C_{5-7}$heteroaryl, $C_{5-6}$heteroaryl, $C_5$heteroaryl, and $C_6$heteroaryl.

Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_6$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:
$C_9$heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);
$C_{10}$heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);
$C_{11}$heterocyclic groups (with 2 fused rings) derived from benzodiazepine ($N_2$);
$C_{13}$heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and,
$C_{14}$heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methylpyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N═ group may be substituted in the form of an N-oxide, that is, as —N(→O)═ (also denoted —N⁺(→O⁻)═). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (═O) groups on ring carbon atoms.

Monocyclic examples of such groups include, but are not limited to, those derived from:
$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$C_{10}$: tetralone, decalone;
$C_{14}$: anthrone, phenanthrone;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$); benzodiazepinone ($C_{11}$); benzodiazepinedione ($C_{11}$);
$N_4$: purinone ($C_9$) (e.g., guanine).

Still more examples of cyclic groups which bear one or more oxo (═O) groups on ring carbon atoms include, but are not limited to, those derived from:
cyclic anhydrides (—C(═O)—O—C(═O)— in a ring), including but not limited to maleic anhydride ($C_5$), succinic anhydride ($C_5$), and glutaric anhydride ($C_6$);
cyclic carbonates (—O—C(═O)—O— in a ring), such as ethylene carbonate ($C_5$) and 1,2-propylene carbonate ($C_5$);
imides (—C(═O)—NR—C(═O)— in a ring), including but not limited to, succinimide ($C_5$), maleimide ($C_5$), phthalimide, and glutarimide ($C_6$);
lactones (cyclic esters, —O—C(═O)— in a ring), including, but not limited to, β-propiolactone, γ-butyrolactone, δ-valerolactone (2-piperidone), and ε-caprolactone;
lactams (cyclic amides, —NR—C(═O)— in a ring), including, but not limited to, β-propiolactam ($C_4$), γ-butyrolactam (2-pyrrolidone) ($C_5$), δ-valerolactam ($C_6$), and ε-caprolactam ($C_7$);
cyclic carbamates (—O—C(═O)—NR— in a ring), such as 2-oxazolidone ($C_5$);
cyclic ureas (—NR—C(═O)—NR— in a ring), such as 2-imidazolidone ($C_5$) and pyrimidine-2,4-dione (e.g., thymine, uracil) ($C_6$).

Includes Other Forms

Unless otherwise specified, a reference to a particular group also includes the well known ionic, salt, solvate, and protected forms thereof. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and transforms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: ketolenol (illustrated below), imine/enamine, amide/imino alcohol, amidine/amidine, nitroso/oxime, thioketonelenethiol, N-nitroso/hydroxyazo, and nitro/aci-nitro.

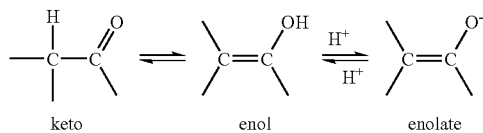

keto enol enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate forms thereof.

Chemically Protected Forms

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$-trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

Unless otherwise specified, a reference to a particular compound also includes prodrugs thereof.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of compounds of the present invention are described herein. These and/or other well known methods may be modified and/or adapted in known ways in order to facilitate the synthesis of additional compounds within the scope of the present invention.

In one approach, the target compound is synthesised in two steps from a 2,6-dihalopyrazine or 3,5-dihalopyridine. This approach can also be extended to 2,5-dihalopyrazines and 2,5-dihalopyridines, and although this approach is exemplified using a dichloro compound, other halogens (e.g., Br, I) may be used.

In a first approach (via b1), a combination of amination chemistry and Suzuki coupling is performed to produce the desired compound (d1), whereas in a second strategy (via c1), the steps are reversed (i.e., Suzuki coupling to give c1 is followed by amination).

Amination reactions are typically performed under inert atmospheres (e.g., argon or nitrogen) and anhydrous conditions, in the presence of suitable catalysts and ligands. As catalysts, palladium catalysts are preferred, but other metal-based catalysts are also acceptable. Examples of palladium catalysts suitable for this reaction include: tris(dibenzylideneacetone)dipalladium(0) (also known as Pd(0)$_2$ dba$_3$) and palladacycles. Examples of suitable ligands include: 1,3-(diphenylphosphino)propane (dppp), 2,2'-bis(diphenylphosphino)-1,1'-binaphtyl (BINAP), 2(dicyclohexyl)phoshino-2' (dimethylamino)biphenyl, 1,3-bis(2,6-di-isopropylphenyl)-4,5-dihydroimidazoliurm tetrafluoroborate, and 1,3-bis(2,4,6-trimethylphenyl)-4,5-dihydroimidazolium tetrafluoroborate). Amination reactions are typically performed at a temperature about 80-110° C. using degassed, dry and aprotic solvents such as 1,4-dioxane or toluene. Conventional heating or microwave irradiation may be employed. Potassium tert-butoxide, sodium tert-butoxide and cesium carbonate are preferred as bases, and the reaction times usually fall within the range of 3-24 hours. If microwave heating is used, reaction times are considerably shorter (e.g., 15-60 minutes).

In a second step of the first approach, intermediate b1 is reacted with an appropriate boronic acid (Suzuki coupling) or boronic ester to furnish the desired compound (d1). This step is typically performed in the presence of a palladium catalyst, a base and a solvent. Examples of suitable palladium catalysts include: [1,1'-bis(diphenylphosphino) ferrocene]dichloropalladium II complex with dichloromethane 1:1 (PdCl$_2$.dppf: DCM 1:1), palladium (II) bis(benzonitrile)dichloride (PdCl$_2$.(bn)$_2$), tetrakis(triphenylphosphine) palladium(0) (Pd (PPh$_3$)$_4$) and palladium acetate (Pd(Oac)$_2$). As a base, sodium carbonate is preferred, and toluene and ethyleneglycol-dimethylether (DME) are preferred as solvents. The reaction mixture is subsequently heated, e.g., to 80-100° C. (using, e.g., conventional heating or microwave irradiation), and reaction times generally fall within the range of 3-24 hours. If microwave heating is used, reaction times are considerably shorter (e.g., 15-60 minutes).

Alternatively, the two steps are reversed, e.g., the Suzuki coupling is performed first (producing c1), followed by the amination step, to yield final product d1, with both the Suzuki coupling reaction and the amination reaction as described above.

An example of such a method is illustrated in the following scheme.

Scheme 1

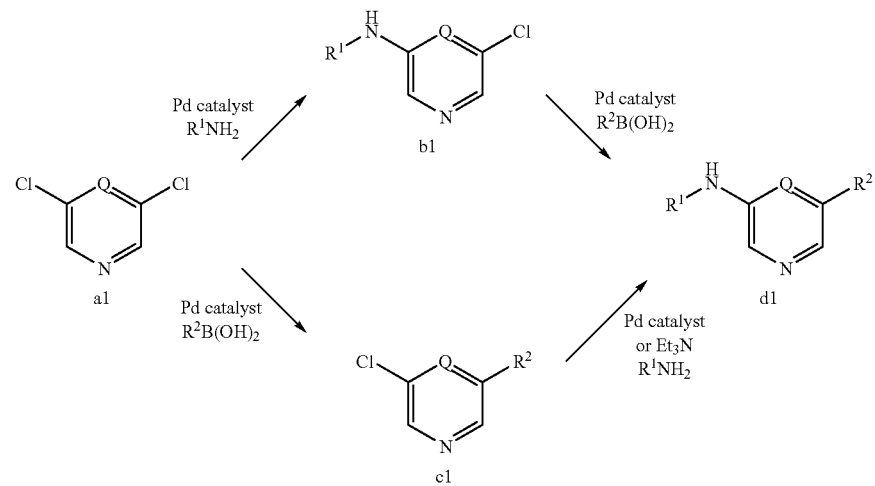

Q is N (pyrazine) or CH (pyridine)

In another approach, 3,5-dihalopyridine is reacted with different benzylic amines in the presence of suitable bases (e.g., triethylamine) to afford pyridine halide (b3). The pyridine halide (b3) is subsequently reacted via Suzuki coupling, as described above, to give the desired product (c3). Alternatively, the two steps can be reversed, performing the Suzuki coupling first and the reaction with benzylic amines afterwards. This approach can also be extended to 2,5-dihalopyridines, and although this approach is exemplified using a dibromo compound, other halogens (e.g., Cl, I) may be used.

An example of such a method is illustrated in the following scheme.

Scheme 2

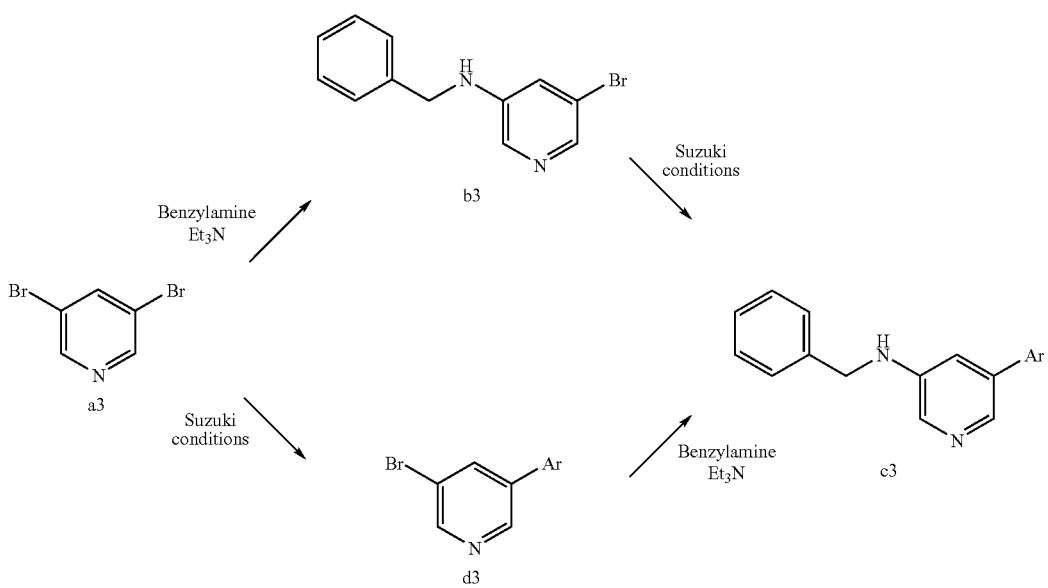

In another approach, urea and thiourea compounds (b4) are prepared by reaction of corresponding amines (a4) (e.g., CJS 364 and CJS 366) with an isocyanate or thioisocyanate.

An example of such a method is illustrated in the following scheme.

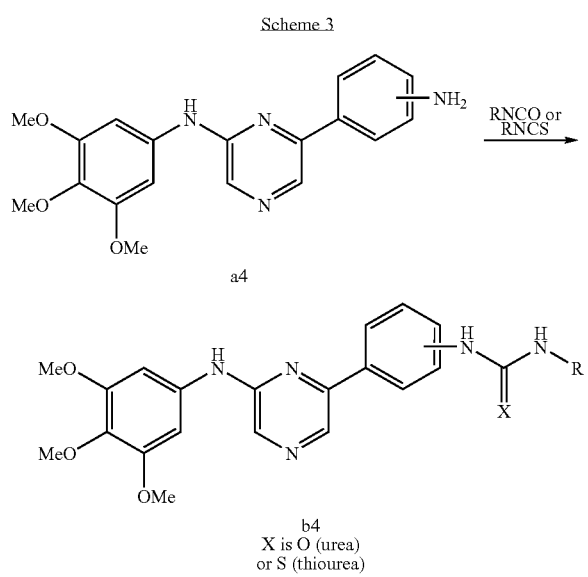

In another approach, amide compounds (a5) are prepared by reaction of phenylamines (e.g., CJS 364, CJS 366) with an acid halide (e.g., acid chloride) or acid anhydride.

An example of such a method is illustrated in the following scheme.

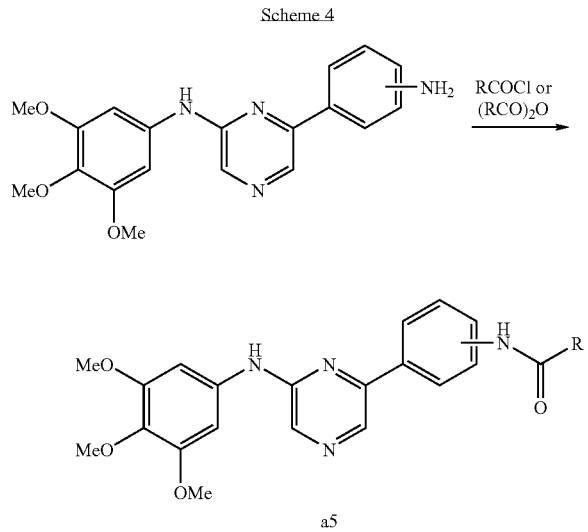

In another approach, sulfonamide compounds (a6) are prepared by reaction of phenylamines (e.g., CJS 364, CJS 366) with a sulphonyl chloride.

An example of such a method is illustrated in the following scheme.

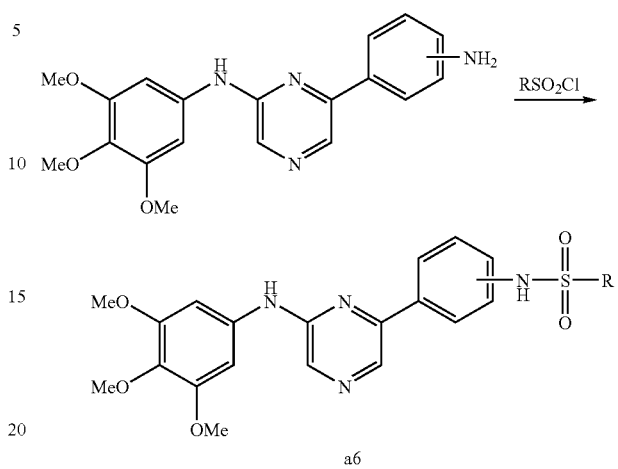

In another approach, compounds with an additional amino group on the pyrazine or pyridine rings (b7) are prepared by reaction of the corresponding halopyrazine or halopyridine compound (a7) with appropriate amines (e.g., aniline) under the conditions described above for amination.

An example of such a method is illustrated in the following scheme.

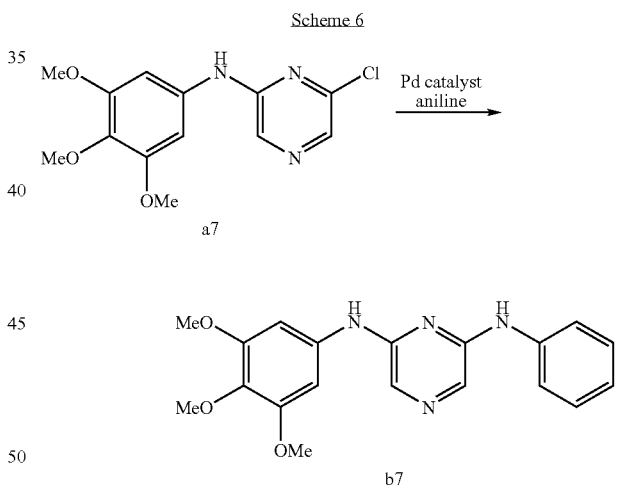

In another approach, 2,6-dichloropyrazine or 3,5-dichloropyridine is reacted with an amine and subsequently with an appropriate phenol or thiophenol (phenol shown) in the presence of suitable bases (e.g. potassium or sodium tert-butoxide) to generate the desired product (b8). Alternatively, the two steps may be reversed. This approach can also be extended to 2,5-dihalopyrazines and 2,5-dihalopyridines, and although this approach is exemplified using a dichloro compound, other halogens (e.g., Br, I) may be used.

An example of such a method is illustrated in the following scheme.

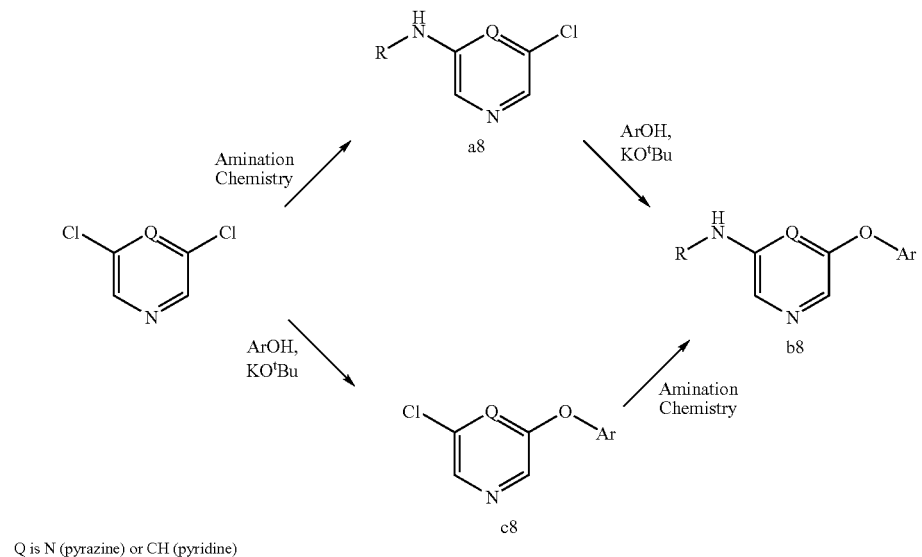

Scheme 7

Q is N (pyrazine) or CH (pyridine)

In another approach, 2-amino pyrazine compounds are prepared from 2,6-dihalo-3-amino pyrazine, wherein the 3-amino group is protected (e.g., as an acetyl or tert-butyloxy carbonyl (t-BOC) derivative). The protected pyrazine is subsequently reacted, for example, with a boronic acid via Suzuki coupling under the conditions already described for Suzuki couplings. The resulting intermediate is then further reacted with an amine, under the conditions already described for amination, to provide the desired compound. Although this approach is exemplified using a dibromo compound, other halogens (e.g., Cl, I) may be used.

An example of such a method is illustrated in the following scheme.

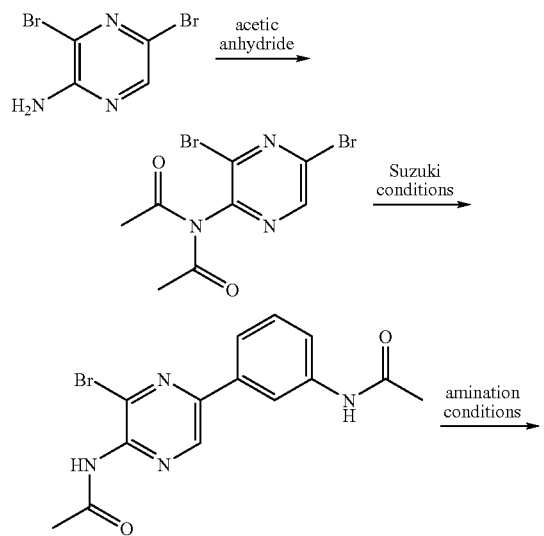

Scheme 8

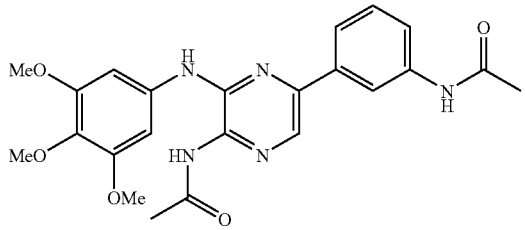

In another approach, a suitable ketone (e.g., b8) is reacted with hydroxylamine to generate the corresponding hydroxylamine derivative. An example of such a method is illustrated in the following scheme.

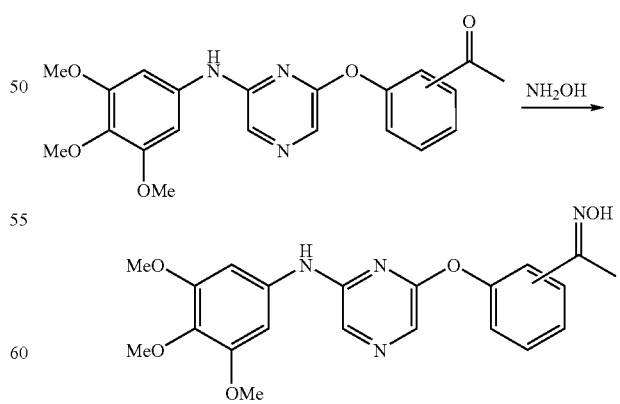

Scheme 9

In another approach, ureas with —O— linkers are constructed using the following strategy. 4-BOC-aminophenol is treated with 2,6-dichloropyrazine and potassium tert-butoxide to give the corresponding —O— linked derivative. This compound is reacted with a suitable aniline (for example 3,4,5-trimethoxyaniline) to furnish the corresponding t-BOC-protected amino compound. The t-BOC group is removed with trifluoroacetic acid and the resulting amine is treated with a suitable isocyanate to give the desired compound. An example of such a method is illustrated in the following scheme.

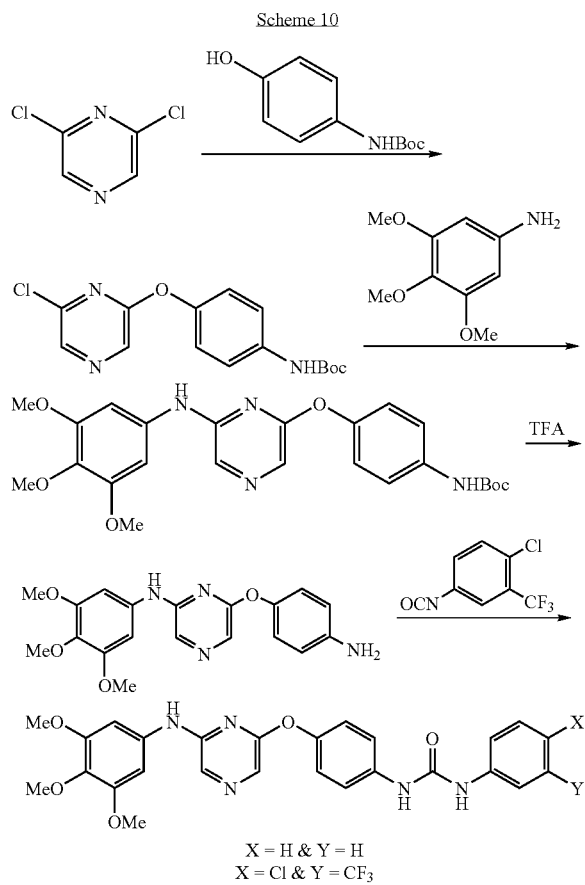

Scheme 10

X = H & Y = H
X = Cl & Y = CF$_3$

Uses

The pyrazines and pyridines, and dervatives thereof, described herein, are useful, for example, in the treatment of diseases and conditions that are ameliorated by the inhibition of RAF (e.g., B-RAF), such as, for example, proliferative conditions, cancer, etc.

Use in Methods of Inhibiting RAF (e.g., B-RAF)

One aspect of the present invention pertains to a method of inhibiting RAF (e.g., B-RAF) activity in a cell, e.g., in vitro or in vivo, comprising contacting the cell with an effective amount of a compound, as described herein.

Suitable assays for determining RAF (e.g., B-RAF) inhibition are described below, as well as in the Examples below.

B-RAF Assays:

B-RAF kinase activity is measured using a 4-tiered cascade enzyme assay similar to that described by Marais R., et al., 1997, *J. Biol. Chem.*, Vol. 272, pp. 4378-4383. B-RAF containing the V600E mutation (Davies, H., et al., 2002, *Nature*, Vol. 417, pp. 949-954) and an N-terminal MDRGSH6 tag is expressed in SF9 insect cells. Detergent soluble extracts from these cells are diluted 1:100 into an assay mixture containing GST-MEK-H6 (6.5 µg/ml) and GST-ERK-H6 (100 µg/ml) in a buffer containing 800 µM ATP and appropriate concentrations of inhibitor or diluent as control. The mixture is incubated for up to 10 minutes at 30° C. to activate the ERK in a B-RAF dependent manner within the cascade. The reaction is then stopped by addition of 20 mM EDTA. The extent of activation of the GST-ERK is then determined by adding a portion of this quenched reaction mixture to a further reaction mixture containing MBP and 100 µM ATP/gamma [$^{32}$P]ATP. After 12 minutes' incubation at 30° C., the incorporation of [$^{32}$P] into the MBP substrate, as a measure of B-RAF activity, is determined by precipitation with phosphoric acid and isolation by filtration on p81 phosphocellulose paper. The % inhibition of the B-RAF kinase activity is calculated and plotted in order to determine the concentration of test compound required to inhibit 50% of the B-RAF kinase activity (IC$_{50}$).

Alternatively, B-RAF kinase activity is measured using a different 4-tiered cascade enzyme assay. B-RAF containing the V600E mutation (Davies, H., et al., 2002, *Nature*, Vol. 417, pp. 949-954) and an N-terminal MDRGSH6 tag is expressed in SF9 insect cells. Detergent soluble extracts from these cells are diluted 1:250 into an assay mixture containing GST-MEK-H6 (25 µg/ml), GST-ERK-H6 (281.25 µg/ml) and MBP in a buffer containing appropriate concentrations of inhibitor or diluent as control. 0.03 µL (100 µM) ATP is added and the mixture is incubated for up to 10 minutes at 30° C. to activate the ERK in a B-RAF dependent manner within the cascade. The extent of activation of the GST-ERK is then determined by adding 0.033 µL (100 µM) HOT $^{32}$Pα. After 10 minutes' incubation at 30° C., the reaction is stopped by isolation of a portion of the reaction mixture on p81 phosphocellulose paper and submersion of this paper in 0.4% orthophosphoric acid. Incorporation of [$^{32}$P] into the MBP substrate, as a measure of B-RAF activity, is determined using a Packard Cernekov counter. The % inhibition of the B-RAF kinase activity is calculated and plotted in order to determine the concentration of test compound required to inhibit 50% of the B-RAF kinase activity (IC$_{50}$).

C-RAF Assay:

C-RAF (human) is diluted to a 10× working stock in 50 mM Tris pH 7.5, 0.1 mM EGTA, 0.1 mM sodium vanadate, 0.1% β-mercaptoethanol, 1 mg/ml BSA. One unit equals the incorporation of 1 nmol of phosphate per minute into myelin basic protein per minute. In a final reaction volume of 25 µl, C-RAF (5-10 mU) is incubated with 25 mM Tris pH 7.5, 0.02 mM EGTA, 0.66 mg/ml myelin basic protein, 10 mM MgAcetate, [γ-$^{33}$P-ATP] (specific activity approx 500 cpm/pmol, concentration as required) and appropriate concentrations of inhibitor or diluent as control. The reaction is initiated by the addition of Mg$^{2+}$+[γ-$^{33}$P-ATP]. After incubation for 40 minutes at room temperature, the reaction is stopped by the addition of 5 µl of a 3% phosphoric acid solution. 10 µl of the reaction is spotted onto a P30 filtermat and washed 3 times for 5 minutes in 75 mM phosphoric acid and once in methanol prior to drying and counting to determine the C-RAF activity. The % inhibition of the C-RAF kinase activity is calculated and plotted in order to determine the concentration of test compound required to inhibit 50% of the C-RAF kinase activity (IC$_{50}$).

Selectivity:

In one embodiment, the compound selectively inhibits one RAF (e.g., B-RAF), over at least one other RAF (e.g., A-RAF and/or C-RAF).

For example, in one embodiment, the ratio of the IC$_{50}$ value for B-RAF to the IC$_{50}$ value for the other RAF (e.g., A-RAF and/or C-RAF) is at least 10, more preferably at least 100, most preferably at least 1000.

Use in Methods of Inhibiting Cell Proliferation, Etc.

The compounds (i.e., certain pyrazines and pyridines, and derivatives thereof) described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, e.g., in vitro or in vivo, comprising contacting cells (or the cell) with an effective amount of a compound, as described herein.

In one embodiment, the method is a method of regulating (e.g., inhibiting) cell proliferation (e.g., proliferation of a cell), e.g., in vitro or in vivo, comprising contacting cells (or the cell) with an effective amount of a compound, as described herein.

In one embodiment, the method is performed in vitro.

In one embodiment, the method is performed in vivo.

In one embodiment, the compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described in the examples below.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a compound as described herein for use in a method of treatment of the human or animal body by therapy.

Use in the Manufacture of Medicaments

Another aspect of the present invention pertains to use of a compound, as described herein, in the manufacture of a medicament for use in treatment.

Methods of Treatment

Another aspect of the present invention pertains to a method of treatment comprising administering to a patient in need of treatment a therapeutically effective amount of a compound as described herein, preferably in the form of a pharmaceutical composition.

Conditions Treated—Conditions Ameliorated by the Inhibition of RAF

In one embodiment (e.g., of use in methods of therapy, of use in the manufacture of medicaments, of methods of treatment), the treatment is treatment of a disease or condition that is characterised by the up-regulation and/or activation of RAF (e.g., B-RAF), and/or is ameliorated by the inhibition of RAF (e.g., B-RAF).

In one embodiment, the treatment is treatment of cancer that is characterised by the up-regulation and/or activation of RAF (e.g., B-RAF), and/or is ameliorated by the inhibition of RAF (e.g., B-RAF).

Conditions Treated—Conditions Ameliorated by the Inhibition of RTKs

In one embodiment (e.g., of use in methods of therapy, of use in the manufacture of medicaments, of methods of treatment), the treatment is treatment of a disease or condition that is characterised by the up-regulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of cancer that is characterised by the up-regulation and/or activation of a receptor tyrosine kinase (RTK), and/or is ameliorated by the inhibition of a receptor tyrosine kinase (RTK).

Conditions Treated—Conditions Characterised by Angiogenesis

In one embodiment (e.g., of use in methods of therapy, of use in the manufacture of medicaments, of methods of treatment), the treatment is treatment of a disease or condition that is characterised by inappropriate, excessive, and/or undesirable angiogenesis (as "anti-angiogenesis agents"). Examples of such conditions are discussed above.

Conditions Treated—Prolifative Conditions and Cancer

The compounds of the present invention are useful in the treatment of proliferative conditions (as "anti-proliferative agents"), cancer (as "anti-cancer agents"), etc. The term "antiproliferative agent" as used herein, pertain to a compound which treats a proliferative condition (i.e., a compound which is useful in the treatment of a proliferative condition). The terms "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth.

The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

One of ordinary skill in the art is readily able to determine whether or not a candidate compound treats a proliferative condition, or treats cancer, for any particular cell type. For example, assays which may conveniently be used to assess the activity offered by a particular compound are described in the examples below.

Note that active compounds includes both compounds with intrinsic activity (drugs) as well as prodrugs of such compounds, which prodrugs may themselves exhibit little or no intrinsic activity.

In one embodiment (e.g., of use in methods of therapy, of use in the manufacture of medicaments, of methods of treatment), the treatment is treatment of a proliferative condition.

In one embodiment, the treatment is treatment of a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, skin cancer, squamous cancer, Kaposi's sarcoma, melanoma, malignant melanoma, lymphoma, or leukemia.

In one embodiment, the treatment is treatment of:
a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), esophagus, gall bladder, ovary, pancreas (e.g., exocrine pancreatic carcinoma), stomach, cervix, thyroid, prostate, skin (e.g., squamous cell carcinoma);
a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
a hematopoietic tumor of myeloid lineage, for example acute and chronic myelogenous leukemias, myelodysplastic syndrome, or promyelocytic leukemia;
a tumour of mesenchymal origin, for example fibrosarcoma or habdomyosarcoma;
a tumor of the central or peripheral nervous system, for example astrocytoma, neuroblastoma, glioma or schwannoma;
melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of melanoma or malignant melanoma.

In one embodiment, the treatment is treatment of colorectal cancer.

The compounds of the present invention may be used in the treatment of the cancers described herein, independent of the mechanisms discussed herein.

Conditions Treated—Prolifative Conditions and Cancer Associated with RAF

Cancers with, for example, activating mutations of RAS, RAF, and EGFR or over expression of RAS, RAF, and EGFR including any of the isoforms thereof, may be particularly sensitive to inhibitors of RAF (e.g., B-RAF) activity. Patients with activating mutants of RAF (e.g., B-RAF) may also find treatment with inhibitors of RAF (e.g., B-RAF) activity particularly beneficial. Cancers with other abnormalities leading to an upregulated RAF-MEK-ERK pathway signal may also be particularly sensitive to treatment with inhibitors of RAF (e.g., B-RAF) activity. Examples of such abnormalities include constitutive activation of a growth factor receptor; overexpression of one or more growth factor receptors; and overexpression of one or more growth factors.

In one embodiment (e.g., of use in methods of therapy, of use in the manufacture of medicaments, of methods of treatment), the treatment is treatment of a proliferative condition as described above, for example, cancer, that is characterised by:
(a) activating mutants of RAS or RAF;
(b) upregulation of RAS or RAF;
(c) upregulated RAF-MEK-ERK pathway signals;
(d) upregulation of growth factor receptors, such as ERBB2 and EGFR.

In one embodiment, the proliferative condition is characterised by cells which overexpress RAF (e.g., B-RAF) or express or overexpress mutant RAF (e.g., B-RAF). In one embodiment, the proliferative condition is characterised by cells which overexpress RAF (e.g., B-RAF). In one embodiment, the proliferative condition is characterised by cells which express or overexpress mutant RAF (e.g., B-RAF). In one embodiment, the proliferative condition is characterised by cells which overexpress RAF (e.g., B-RAF), or overexpress mutant RAF (e.g., B-RAF), as compared to corresponding normal cells. In one embodiment, the overexpression is by a factor of 1.5, 2, 3, 5, 10, or 20.

In one embodiment (e.g., of use in methods of therapy, of use in the manufacture of medicaments, of methods of treatment), the treatment is treatment of a condition associated with a mutated form of RAF (e.g., B-RAF), such as, for example, the mutations described in Wan, P., et al., 2004, *Cell*, Vol. 116, pp. 855-867 and Stratton et al., 2003, published international patent application publication number WO 03/056036.

Conditions Treated—Inflammation Etc.

The compounds of the present invention are useful in the treatment of conditions associated with inflammation (as "anti-inflammation agents"), etc.

The function of inflammatory cells is controlled by many factors the effects of which are mediated by different signal transduction pathways. Although some key pro-inflammatory functions are mediated by p38 Map kinase (e.g., TNF release), others are mediated by other pathways. The RAF-MEK-ERK pathway, in particular, is an important activating and proliferative signal in many inflammatory cells. B and T lymphocytyes, in particular, require activation of the RAF-MEK-ERK pathway for clonal expansion and generation of effector populations (see, e.g., Cantrell, D. A., 2003, *Immunol Rev.*, Vol. 192, pp. 122-130; Genot, E. and Cantrell, D. A., 2000, *Curr. Opin. Immunol.*, Vol. 12(3), pp. 289-294).

In one embodiment, the treatment is treatment of: inflammatory diseases, such as rheumatoid arthritis, osteoarthritis, rheumatoid spondylitis, gouty arthritis, traumatic arthritis, rubella arthritis, psoriatic arthritis, and other arthritic conditions; Alzheimer's disease; toxic shock syndrome, the inflammatory reaction induced by endotoxin or inflammatory bowel disease; tuberculosis; atherosclerosis; muscle degeneration; Reiter's syndrome; gout; acute synovitis; sepsis; septic shock; endotoxic shock; gram negative sepsis; adult respiratory distress syndrome; cerebral malaria; chronic pulmonary inflammatory disease; silicosis; pulmonary sarcoisosis; bone resorption diseases; reperfusion injury; graft versus host reaction; allograft rejections; fever and myalgias due to infection, such as influenza, cachexia, in particular cachexia secondary to infection or malignancy, cachexia secondary to acquired immune deficiency syndrome (AIDS); AIDS; ARC (AIDS related complex); keloid formation; scar tissue formation; Crohn's disease; ulcerative colitis; pyresis; chronic obstructive pulmonary disease (COPD); acute respiratory distress syndrome (ARDS); asthma; pulmonary fibrosis; bacterial pneumonia.

In one preferred embodiment, the treatment is treatment of: arthritic conditions, including rheumatoid arthritis and rheumatoid spondylitis; inflammatory bowel disease, including Crohn's disease and ulcerative colitis; and chronic obstructive pulmonary disease (COPD).

In one preferred embodiment, the treatment is treatment of: an inflammatory disorder characterized by T-cell proliferation (T-cell activation and growth), for example, tissue graft rejection, endotoxin shock, and glomerular nephritis.

Screening

Prior to treatment, a patient may be screened to determine whether a disease or condition from which the patient is or may be suffering is one which would be susceptible to treatment with a compound that inhibits RAF (e.g., B-RAF) activity or has activity against an RTK (e.g., FGFR-1, FGFR-2, FGFR-3, VEGFR-2, Tie2, EphB2). For example, a biological sample taken from a patient may be analysed to determine whether a condition or disease, such as cancer, that the patient is or may be suffering from is one which is characterised by elevated expression or activation of RAF (e.g., B-RAF), or an RTK (e.g., FGFR-1, FGFR-2, FGFR-3, VEGFR-2, Tie2, EphB2), or is the result of an activating mutation. Thus, the patient may be subjected to a diagnostic test to detect a marker characteristic of over-expression or activation of RAF (e.g., B-RAF) or an RTK (e.g., FGFR-1, FGFR-2, FGFR-3, VEGFR-2, Tie2, EphB2), or a mutation thereof.

As used herein, the term "marker" includes genetic markers (including, e.g., the measurement of DNA composition to identify mutations of RAF, RAS, MEK, ERK or a growth factor such as ERBB2 or EGFR) and markers which are characteristic of upregulation of RAF, RAS, MEK, ERK, growth factors receptors such as ERBB2 or EGFR including enzyme activity, enzyme levels, enzyme state (e.g. phosphorylated or not) and mRNA levels of the aforementioned proteins. Methods for identification and analysis of mutations are well known. See, for example, *Anticancer Research*, 1999, Vol. 19(4A), pp. 2481-2483; *Clin. Chem.*, 2002, Vol. 48, p. 428; *Cancer Research*, 2003, Vol. 63(14), pp. 3955-3957.

The term "marker" further includes genetic markers including, for example, the measurement of DNA composition to identify mutations of RTKs, e.g., FGFR-1, FGFR-2, FGFR-3, VEGFR-2, Tie2, and EphB2. The term "marker" also includes markers that are characteristic of up-regulation of RTKs, including enzyme activity, enzyme levels, enzyme state (e.g., phosphorylated or not) and mRNA levels of the aforementioned proteins.

Upregulation includes elevated expression or over expression, including gene amplification (i.e., multiple gene copies), increased expression by a transcriptional effect, hyperactivity, and activation, including activation by mutations.

Other tumours that have an upregulated RAF-MEK-ERK pathway signal may also be particularly sensitive to inhibitors of RAF (e.g., B-RAF) activity. A number of assays exist which can identify tumours that exhibit upregulation in the RAF-MEK-ERK pathway, including the commercially available MEK1/2 (MAPK Kinase) assay from Chemicon International. Upregulation can result from over expression or activation of growth factor receptors such as ERBB2 and EGFR, or mutant RAS or RAF proteins.

Typical methods for screening for over expression, upregulation or mutants include, but are not limited to, standard methods such as reverse-transcriptase polymerase chain reaction (RT-PCR) or in-situ hybridisation.

In screening by RT-PCR, the level of mRNA for the aforementioned proteins in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described, for example, in Ausubel, F. M. et al., eds., *Current Protocols in Molecular Biology*, 2004 (John Wiley & Sons Inc.); Innis, M. A. et-al., eds., *PCR Protocols: A Guide to Methods and Applications*, 1990 (Academic Press). Reactions and manipulations involving nucleic acid techniques are also described in Sambrook et al., *Molecular Cloning: A Laboratory Manual*, 3rd edition, 2001 (Cold Spring Harbor Laboratory Press). Alternatively, a commercially available kit for RT-PCR (e.g., Roche Molecular Biochemicals) may be used, or methodology as set forth in U.S. Pat. Nos. 4,666,828; 4,683,202; 4,801,531; 5,192,659, 5,272,057, 5,882,864, and 6,218,529.

An example of an in-situ hybridisation technique would be fluorescence in situ hybridisation (FISH) (see, e.g., Angerer, 1987, *Meth. Enzymol.*, Vol. 152, p. 649). Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, in order to enable specific hybridization with the target nucleic acid(s) under stringent conditions. Standard methods for carrying out FISH are described, for example, in Ausubel, F. M. et al., eds., *Current Protocols in Molecular Biology*, 2004 (John Wiley & Sons Inc.); Bartlett, John M. S., "Fluorescence In Situ Hybridization: Technical Overview," in: *Molecular Diagnosis of Cancer, Methods and Protocols, 2nd ed.* (*Series: Methods in Molecular Medicine*), March 2004, pp. 77-88 (ISBN: 1-59259-760-2).

Alternatively, the protein products expressed from the mRNAs may be assayed by immunohistochemistry of tumour sections, solid phase immunoassay with microtiter plates, Western blotting, 2-dimensional SDS-polyacrylamide gel electrophoresis, ELISA, and other methods known in the art for detection of specific proteins. Detection methods would include the use of site specific antibodies, such as, phospho RAF, phospho ERK, phospho MEK, or phosphotyrosine. In addition to tumour biopsies, other samples which could be utilised include pleural fluid, peritoneal fluid, urine, stool biopsies, sputum, blood (isolation and enrichment of shed tumour cells).

In addition, mutant forms of RAF, EGFR or ras can be identified by direct sequencing of, for example, tumour biopsies using PCR and methods to sequence PCR products directly, for example, using methods as described herein. These and other well-known techniques for detection of the over expression, activation, or mutations may be used.

Also, abnormal levels of proteins such as RAF, RAS and EGFR can be measured using standard enzyme assays, for example, for RAF, those assays described herein.

Alternative methods for the measurement of the over expression or activation of FGFR, Tie, VEGFR or Eph kinases, in particular VEGFR including the isoforms thereof, include the measurement of microvessel density. This can be measured, for example, using methods described by Orre and Rogers, 1999, *Int. J. Cancer*, Vol. 84(2), pp. 101-108. Assay methods also include the use of markers; for example, in the case of VEGFR, markers include CD31, CD34 and CD105 (Mineo et al., 2004, *J. Clin. Pathol.*, Vol. 57(6), pp. 591-597).

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of an active compound, or a material, composition or dosage form comprising an active compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development. Examples of such combinations are set out below.

In one embodiment, the compounds (i.e., certain pyrazines and pyridines, and derivatives thereof) described herein are combined with one or more (e.g., 1, 2, 3, 4) additional therapeutic agents, as described below.

One aspect of the present invention pertains to a compound as described herein, in combination with one or more additional therapeutic agents, as described below.

Examples of additional therapeutic agents that may be administered together (whether concurrently or at different time intervals) with the compounds described herein include:

(a) topoisomerase I inhibitors;
(b) antimetabolites;
(c) tubulin targeting agents;
(d) DNA binder and topoisomerase II inhibitors;
(e) alkylating agents;
(f) monoclonal antibodies;
(g) anti-hormones;
(h) signal transduction inhibitors;
(i) proteasome inhibitors;
(j) DNA methyl transferases;
(k) cytokines and retinoids.

The particular combination would be at the discretion of the physician who would select dosages using his common general knowledge and dosing regimens known to a skilled practitioner.

The agents (i.e., the compound described here, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use, as described below.

Other Uses

The compounds described herein may also be used as cell culture additives to inhibit cell proliferation, etc.

The compounds described herein may also be used as part of an in vitro assay, for example, in order to determine whether a candidate host is likely to benefit from treatment with the compound in question.

The compounds described herein may also be used as a standard, for example, in an assay, in order to identify other active compounds, other anti-proliferative agents, other anti-cancer agents, etc.

Kits

One aspect of the invention pertains to a kit comprising (a) an active compound as described herein, or a composition comprising an active compound as described herein, e.g., preferably provided in a suitable container and/or with suitable packaging; and (b) instructions for use, e.g., written instructions on how to administer the active compound or composition.

The written instructions may also include a list of indications for which the active ingredient is a suitable treatment.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one embodiment, the route of administration is topical, i.e., the compound or pharmaceutical composition comprising the active compound is administered topically.

The Subject/Patient

The subject/patient may be a chordate, a vertebrate, a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the active compound to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

In one embodiment, the pharmaceutical composition is a topical pharmaceutical composition, i.e., is formulated for use in topical administration.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 μg to about 250 mg (more typically about 100 μg to about 25 mg) per kilogram body weight of the subject per day. Where the active compound is a salt, an ester, an amide, a prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

All starting materials, reagents and solvents for reactions were reagent grade and used as purchased. Chromatography solvents were HPLC grade and were used without further purification. Reactions were monitored by thin layer chromatography (TLC) analysis using Merck silica gel 60 F-254 thin layer plates. Flash column chromatography was carried out on Merck silica gel 60 (0.015-0.040 mm) or in disposable Isolute Flash Si and Si II silica gel columns. Preparative TLC was performed on either Macherey-Nagel [809 023] pre-coated TLC plates SIL G-25 $UV_{254}$ or Analtech [2015] pre-coated preparative TLC plates, 2000 microns with $UV_{254}$. LCMS analyses were performed on a Micromass LCT/Water's Alliance 2795 HPLC system with a Discovery 5 μm, C18, 50 mm×4.6 mm i.d. column from Supelco at a temperature of 22° C. using the following solvent systems: Solvent A: Methanol; Solvent B: 0.1% Formic acid in water at a flow rate of 1 mL/min. Gradient starting with 10% A/90% B from 0-0.5 minutes then 10% A/90% B to 90% A/10% B from 0.5 minutes to 6.5 minutes and continuing at 90% A/10% B up to 10 minutes. From 10-10.5 minutes the gradient reverted back to 10% A/90% B where the concentrations remained until 12 minutes. UV detection was at 254 nm and ionisation was positive or negative ion electrospray. Molecular weight scan range is 50-1000. Samples were supplied as 1 mg/mL in DMSO or methanol with 3 μL injected on a partial loop fill. NMR spectra were recorded in DMSO-$d_6$ on a Bruker AC250 spectrometer (250 MHz) unless otherwise stated.

Example 1

2-(3,4,5-trimethoxyphenylamino)-6-chloropyrazine, 2a

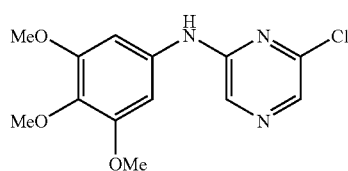

Method A: To 5.00 g (33.5 mmol) 2,6-dichloropyrazine dissolved in 200 mL dry toluene in an oven dried flask, were added under stirring: 0.42 g (0.46 mmol) Pd(0)$_2$ dba$_3$, 0.83 g (1.34 mmol) 2,2'-bis(diphenylphosphino)-1,1'-binaphtyl (BINAP), 7.36 g (40.2 mmol) 3,4,5-trimethoxyanilin and 4.41 g (46.9 mmol) Na-tert-butoxide. The reaction mixture was heated at 90° C. (bath temperature) for 4 hours under N$_2$. After cooling, the toluene solution was filtered. The solid was retaken in 100 mL Me$_2$CO, filtered through a 5 cm column of Kieselgel 60, and the resulting solution evaporated under vacuum. A portion of 2.53 g of title compound was obtained. The toluene filtrate was evaporated to dryness and then retaken in 70-80 mL boiling AcOEt. The solution was kept in a refrigerator over night and 2.57 g of solid title compound were collected by filtration. The filtrate was reduced to 18-20 mL and submitted to HPLC (Kieselgel 60, 0.015-0.043; eluent: AcOEt:cycloxane 2:1). A third fraction of 0.94 g of title compound was collected. The total yield was 6.04 g (61.1%). $^1$H-NMR (DMSO), δ (ppm), J (Hz): 3.63 (s, 3H, CH$_3$O$_{(4')}$), 3.77 (s, 6H, CH$_3$O$_{(3'+5')}$), 7.02 (s, 2H, H$_{arom(2'+6')}$), 7.96 (s, 1H, H$_{P5}$), 8.14 (s, 1H, H$_{P3}$), 9.79 (s, 1H, NH); MS, (C$_{13}$H$_{14}$ClN$_3$O$_3$), m/z: 296 [M$^+$+1, 100].

Example 2

2-(3-chloroanilin)-6-chloropyrazine, 2b

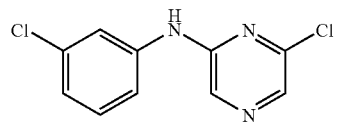

The title compound was prepared by a method analogous to Method A, using 3-chloroaniline. The work-up was different: to the reaction mixture 50 mL Et$_2$O were added and was extracted with 100 mL of H$_2$O. The aqueous layer was extracted again with 50 mL Et$_2$O and the organic solution pooled, dried (MgSO$_4$) and evaporated to dryness. 0.852 g of a solid were obtained and purified by preparative HPLC (Kieselgel 60, 0.015-0.043; eluent: AcOEt:cycloxane 1:2). A fraction of 0.419 g of title compound was collected (50.0%). $^1$H-NMR (DMSO), δ (ppm), J (Hz): 7.02 (m, 1H, H$_{arom\ (4'\ or\ 6')}$, J=7.90), 7.36 (t, 1H, H$_{arom\ 5}$ J=8.08), 7.51 (m, 1H, H$_{arom\ (6'\ or\ 4')}$, J=8.27) 7.83 (t, 1H, H$_{arom\ 2'}$ J=2.00), 8.03 (s, 1H, H$_{P5}$), 8.18 (s, 1H, H$_{P3}$), 10.03 (s, 1H, NH); MS, (C$_{10}$H$_7$Cl$_2$N$_3$), m/z: 296 [M−H]$^-$, 48].

Example 3

2-(4-methoxyanilin)-6-chloropyrazine, 2c

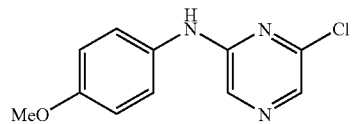

The title compound was prepared by a method analogous to Method A, using 4-methoxyanilin. Reaction time: 5 hours. 265 mg (33.7%) of title compound was obtained after purification by column chromatography (Kieselgel 60, 0.040-0.063; eluent: cyclohehane:AcOEt 1:1). $^1$H-NMR (DMSO), δ (ppm), J (Hz): 3.73 (s, 3H, CH$_3$O$_{(4')}$), 6.94 (d, 2H, H$_{arom\ 2+6}$, J=9.00), 7.51 (d, 2H, H$_{arom\ 3+5}$), 7.89 (s, 1H, H$_{P5}$), 8.08 (s, 1H, H$_{P3}$), 9.65 (s, 1H, NH).

Example 4

2-(3,4,5-trimethoxyphenylamino)-6-(3-acetamidophenyl)pyrazine, CJS 352

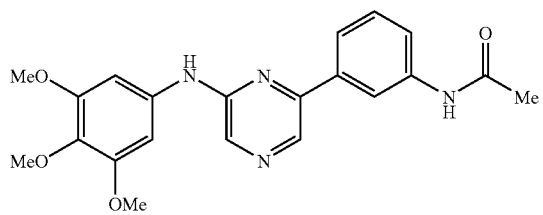

Method B. In an oven dried flask the catalyst is prepared by adding under stirring and Ar atmosphere 40 mg (0.09 mmol) dppb and 30 mg (0.077 mmol) $PdCl_2(benzonitrile)_2$ to 10 mL dry toluene. After 30 minutes, 225 mg (0.76 mmol) 2-(3,4,5-trimethoxyphenylamino)-6-chloropyrazine (2a) 161 mg (0.9 mmol) 3-acetamido-boronic acid, 1.60 mL EtOH and 1.5 mL aq. sol $Na_2CO_3$ 1M in 10 mL toluene were added and the reaction mixture was heated at 90° C. (bath temperature) for 8 hours. After cooling, 50 mL AcOEt were added to the reaction, and the mixture was washed (2×100 mL brine), dried and ($MgSO_4$) and evaporated to dryness. 165 mg of a solid were obtained and purified by preparative HPLC (Kieselgel 60, 0.015-0.043; eluent: AcOEt:EtOH 9:1). Finally, 55 mg pure title compound (18.4%) were obtained. $^1$H-NMR (DMSO), δ (ppm), J (Hz): 2.07 (s, 3H, $CH_3CO$), 3.63 (s, 3H, $CH_3O_{(4')}$), 3.80 (s, 6H, $CH_3O_{(3'+5')}$), 7.25 (s, 2H, $H_{arom(2'+6')}$), 7.43 (t, 1H, $H_{arom\ 5'}$, J=7.96), 7.65 (d, 1H, $H_{arom\ 6'\ or\ 4'}$, J=8.08), 7.65 (d, 1H, $H_{arom\ 4'\ or\ 6'}$, J=7.78), 8.16 (s, 1H, $H_{P5}$), 8.27 (s, 1H, $H_{arom\ 2'}$), 8.38 (s, 1H, $H_{P3}$), 9.57 (s, 1H, $NH_{amine}$), 10.06 (s, 1H, $NH_{amide}$);
MS, ($C_{21}H_{22}N_4O_4$), m/z: 395 [M$^+$+1, 100]

Example 5

2-(3,4,5-trimethoxyphenylamino)-6-(3-hydroxyphenyl)pyrazine, CJS 350

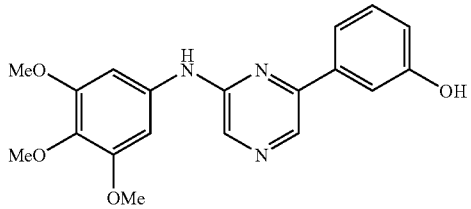

Using Method B with 112 mg (0.38 mmol) 2a and 100 mg (0.45 mmol) 3-(4,4,5,5-tetramethyl-1,3,2-dioxoborolan-2-yl)phenol, 74 mg pure title compound (55.2%) were obtained after purification by preparative HPLC (Kieselgel 60, 0.015-0.043; eluent: AcOEt). Reaction time: 16 hours. $^1$H-NMR (DMSO), δ (ppm), J (Hz): 3.63 (s, 3H, $CH_3O_{(4')}$), 3.82 (s, 6H, $CH_3O_{(3'+5')}$), 6.87 (d, 1H, $H_{arom\ 4'\ or\ 6'}$, J=9.80), 7.25 (s, 2H, $H_{arom(2'+6')}$), 7.29 (t, 1H, $H_{arom\ 5'}$, J=9.46), 7.52 (d, 1H, $H_{arom\ 6'\ or\ 4'}$, J=6.48), 7.53 (s, 1H, $H_{arom\ 2'}$), 8.14 (s, 1H, $H_{P5}$), 8.43 (s, 1H, $H_{P3}$), 9.54 (s, 1H, OH), 9.59 (s, 1H, $NH_{amine}$);
MS, ($C_{19}H_{19}N_3O_4$), m/z: 354.3 [M$^+$+1, 100]

Example 6

2-(3,4,5-trimethoxyphenylamino)-6-(4-hydroxyphenyl)pyrazine, CJS 351

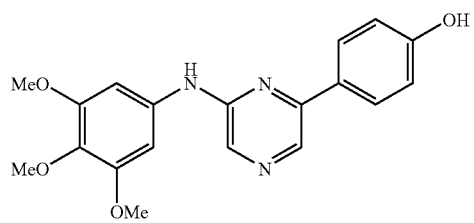

Using Method B with 275 mg (0.93 mmol) 2a and 242 mg (1.10 mmol) 4-(4,4,5,5-tetramethyl-1,3,2-dioxoborolan-2-yl)phenol, 83 mg pure title compound (59.7%) were obtained after purification by preparative HPLC (eluent:AcOEt). Reaction time: 48 hours.
$^1$H-NMR (DMSO), δ (ppm), J (Hz): 3.63 (s, 3H, $CH_3O_{(4')}$), 3.82 (s, 6H, $CH_3O_{(3'+5')}$), 6.88 (d, 2H, $H_{arom(2'+6')}$, J=8.52), 7.24 (s, 2H, $H_{arom(2+6)}$), 7.97 (d, 1H, $H_{arom\ (3'+5')}$), 8.05 (s, 1H, $H_{P5}$), 8.40 (s, 1H, $H_{P3}$), 9.46 (s, 1H, OH), 9.82 (s, 1H, $NH_{amine}$); MS, ($C_{19}H_{19}N_3O_4$), m/z: 354.3 [M$^+$+1, 100].

Example 7

2-(3,4,5-trimethoxyphenylamino)-6-(4-chlorophenyl)pyrazine, CJS 355

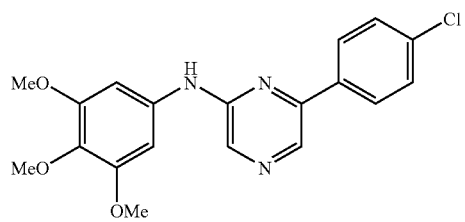

Using Method B with 212 mg (0.72 mmol) 2a and 135 mg (0.86 mmol) 4-chloro-phenylboronic acid, 190 mg pure title compound (59.7%) were obtained after purification by preparative HPLC (eluent:AcOEt). Reaction time: 18 hours.
$^1$H-NMR (DMSO), δ (ppm), J (Hz): 3.63 (s, 3H, $CH_3O_{(4')}$), 3.82 (s, 6H, $CH_3O_{(3'+5')}$), 6.88 (d, 2H, $H_{arom(2'+6')}$, J=8.52), 7.24 (s, 2H, $H_{arom(2+6)}$), 7.97 (d, 1H, $H_{arom\ (3'+5')}$), 8.05 (s, 1H, $H_{P5}$), 8.40 (s, 1H, $H_{P3}$), 9.46 (s, 1H, OH), 9.82 (s, 1H, $NH_{amine}$); MS, ($C_{19}H_{18}ClN_3O_4$), m/z: 354.3 [M$^+$+1, 100].

Example 8

2-(3,4,5-trimethoxyphenylamino)-6-(4-hydroxymethylphenyl)pyrazine, CJS 359

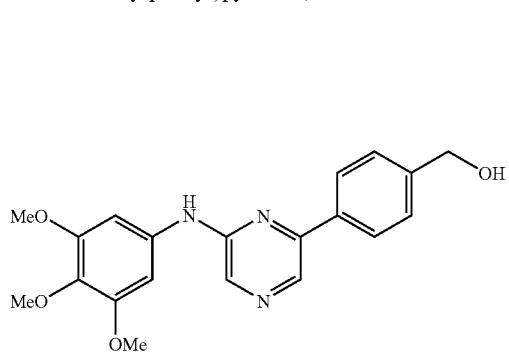

Using Method B with 212 mg (0.72 mmol) 2a and 131 mg (0.86 mmol) 4-hydroxy-methylphenyl boronic acid, 22 mg pure title compound (8.3%) were obtained after purification by preparative HPLC (eluent:AcOEt). Reaction time: 20 hours. $^1$H-NMR (DMSO), δ (ppm), J (Hz): 3.64 (s, 3H, CH$_3$O$_{(4')}$), 3.83 (s, 6H, CH$_3$O$_{(3'+5')}$), 4.57 (d, 2H, CH$_2$OH, J=5.66), 5.28 (t, 1H, CH$_2$OH), 7.26 (s, 2H, H$_{arom(2'+6')}$), 7.45 (s, 2H, H$_{arom(2+6)}$, J=8.23), 8.10 (d, 1H, H$_{arom(3'+5')}$), 8.14 (s, 1H, H$_{P5}$), 8.51 (s, 1H, H$_{P3}$), 9.56 (s, 1H, NH$_{amine}$);

MS, (C$_{20}$H$_{21}$N$_3$O$_4$), m/z: 368.3 [M$^+$+1, 100].

Example 9

2-(3,4,5-trimethoxyphenylamino)-6-(ethyl, 3-benzoate)pyrazine, CJS 362

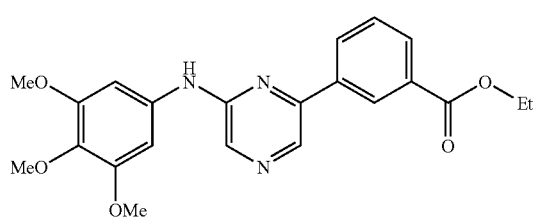

Using Method B with 400 mg (1.36 mmol) 2a and 450 mg (1.63 mmol) ethyl-3-(4,4,5,5-tetramethyl-1,3,2-dioxoborolan-2-yl)benzoate, 391 mg pure title compound (70.3%) were obtained after purification by preparative HPLC (eluent:AcOEt). Reaction time: 3 hours.

$^1$H-NMR (DMSO), δ (ppm), J (Hz): 1.34 (t, 3H, CH$_3$CH$_2$, J=7.09), 3.64 (s, 3H, CH$_3$O$_{(4')}$), 3.81 (s, 6H, CH$_3$O$_{(3'+5')}$), 4.36 (q, 2H, CH$_3$CH$_2$), 7.22 (s, 2H, H$_{arom(2+6)}$), 7.67 (t, 1H, H$_{arom 5'}$, J=7.77), 8.05 (d, 1H, H$_{arom (6' or 4')}$, J=7.24), 8.20 (s, 1H, H$_{P5}$), 8.36 (d, 1H, H$_{arom (4' or 6')}$, J=7.82), 8.57 (s, 1H, H$_{P3}$), 9.63 (s, 1H, NH$_{amine}$); MS, (C$_{22}$H$_{23}$N$_3$O$_5$), m/z: 410.1 [M$^+$+1, 100].

Example 10

2-(3-chlorophenylamino)-6-(3-acetamidophenyl) pyrazine, CJS 354

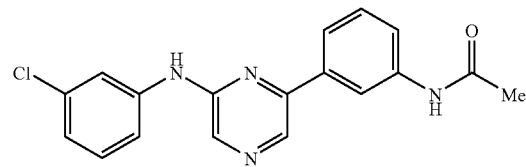

Using Method B with 300 mg (1.25 mmol) 2b and 268 mg (1.5 mmol) 3 acetamidoboronic acid, 78 mg pure title compound (28.1%) were obtained after purification by preparative HPLC (eluent:AcOEt). Reaction time: 16 hours. $^1$H-NMR (DMSO), δ (ppm), J (Hz): 2.09 (s, 3H, CH$_3$CONH), 7.03 (d, 1H, H$_{arom 6 or 4}$, J=7.12), 7.39 (t, 1H, H$_{arom 5}$, J=6.42), 7.45 (t, 1H, H$_{arom 5'}$, J=7.86), 7.63 (d, 1H, H$_{arom 4 or 6}$, J=7.86), 7.73 (d, 1H, H$_{arom 6' or 4'}$, J=7.74), 7.89 (m, 2H, H$_{arom 2'}$+H$_{arom 4' or 6'}$), 8.20 (s, 1H, H$_{P5}$), 8.48 (s, 1H, H$_{P3}$), 9.81 (s, 1H, NH$_{amine}$), 10.09 (s, 1H, NH$_{amide}$); MS, (C$_{18}$H$_{15}$ClN$_4$O), m/z: 339.3 [M$^+$+1, 100].

Example 11

2-(3-chlorophenylamino)-6-(4-hydroxyphenyl)pyrazine, CJS 357

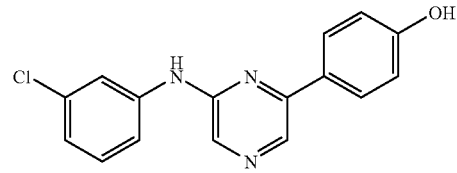

Using Method B with 300 mg (0.72 mmol) 2b and 330 mg (1.5 mmol) 4-(4,4,5,5-tetramethyl-1,3,2-borolan-2-yl)phenol, 221 mg pure title compound (59.5%) were obtained after purification by preparative HPLC (eluent:AcOEt). Reaction time: 24 hours. $^1$H-NMR (DMSO), δ (ppm), J (Hz): 6.90 (d, 2H, H$_{arom 2'+6'}$, J=8.63), 7.01 (m, 1H, H$_{arom 4 or 6}$, J=7.81), 7.36 (t, 1H, H$_{arom 5}$, J=8.10), 7.62 (d, 1H, H$_{arom 6 or 4}$, J=8.22), 7.62 (d, 2H, H$_{arom 3'+5'}$), 8.10 (s, 2H, H$_{arom 2}$+H$_{P5}$), 8.49 (s, 1H, H$_{P3}$), 9.72 (s, 1H, OH), 9.87 (s, 1H, NH$_{amine}$); MS, (C$_{16}$H$_{12}$ClN$_3$O), m/z: 298.3 [M$^+$+1, 100].

Example 12

2-(3,4,5-trimethoxyphenylamino)-6-(4-pyridyl)pyrazine, CJS 363

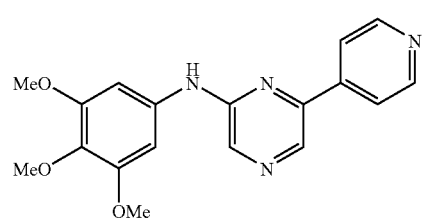

Method C. 200 mg (0.68 mmol) 2a, 55 mg (0.068 mmol) PdCl$_2$.dppf:DCM 1:1, 100 mg (0.82 mmol) 4-pyridyl boronic acid were dissolved in 15 mL DME. To this solution 1.4 mL aq. sol 1M of Na$_2$CO$_3$ were added under stirring and the reaction mixture was heated at 90° C. (bath temperature) for 24 hours. After cooling, 25 mL Et$_2$O and the organic solution washed (2×30 mL brine), dried (MgSO$_4$) and evaporated to dryness. A brown solid was obtained and recrystallised from AcOEt, giving 40 mg of pure title compound (17.4%).

$^1$H NMR (DMSO), δ (ppm), J (Hz): 3.64 (s, 3H, CH$_3$O$_{(4')}$), 3.83 (s, 6H, CH$_3$O$_{(3'+5')}$), 4.36 (q, 2H, CH$_3$CH$_2$), 7.22 (s, 2H, H$_{arom(2+6)}$), 8.07 (d, 2H, H$_{arom\ (2'+6')}$, J=4.73), 8.27 (s, 1H, H$_{P5}$), 8.65 (s, 1H, H$_{P3}$), 8.72 (d, 1H, H$_{arom\ (3'+5')}$), 9.70 (s, 1H, NH$_{amine}$); MS, (C$_{18}$H$_{18}$N$_4$O$_3$), m/z: 339.1 [M$^+$+1, 100].

Example 13

2-(3,4,5-trimethoxyphenylamino)-6-(3-aminophenyl)pyrazine, CJS 364

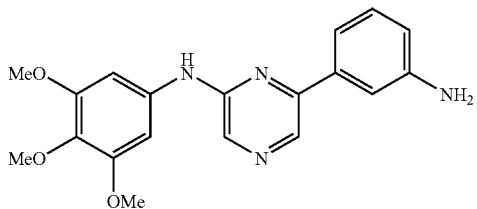

Using Method C with 1.0 g (3.4 mmol) 2a and 635 mg (4.1 mmol) 3-aminophenyl boronic acid, 463 mg pure title compound were obtained. The filtrate was submitted to purification by preparative HPLC (eluent:AcOEt) and another fraction of 412 mg was obtained. A total of 875 mg CJS 364 (72.9%) were obtained. Reaction time: 28 hours. $^1$H-NMR (DMSO), δ (ppm), J (Hz): 3.64 (s, 3H, CH$_3$O$_{(4')}$), 3.81 (s, 6H, CH$_3$O$_{(3'+5')}$), 5.19 (s, 2H, NH$_2$), 6.66 (d, 1H, H$_{arom\ 4'}$, J=7.70), 7.13 (t, 1H, H$_{arom\ 5'}$, J=7.77), 7.22 (d, 1H, H$_{arom\ 6'}$), 7.26 (s, 2H, H$_{arom(2+6)}$), 7.29 (s, 1H, H$_{arom\ 2'}$), 8.11 (s, 1H, H$_{P5}$), 8.33 (s, 1H, H$_{P3}$), 9.51 (s, 1H, NH$_{amine}$);

MS, (C$_{19}$H$_{20}$N$_4$O$_3$), m/z: 355.1 [M$^+$+1, 100].

Example 14

2-(3,4,5-trimethoxyphenylamino)-6-(ethyl, 4-benzoate)pyrazine, CJS 365

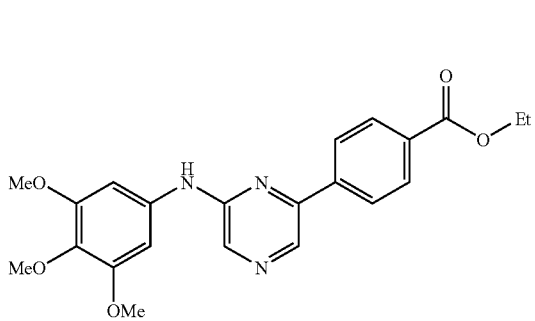

Using Method C with 200 mg (0.68 mmol) 2a and 215 μL (0.82 mmol) ethyl-4-(4,4,5,5-tetramethyl-1,3,2-borolan-2-yl)benzoate, 83 mg (29.8%) pure title compound were obtained after preparative HPLC (eluent:AcOEt) purification of the whole batch. Reaction time: 24 hours. $^1$H-NMR (DMSO), δ (ppm), J (Hz): 1.35 (t, 3H, CH$_3$CH$_2$, J=7.08), 3.65 (s, 3H, CH$_3$O$_{(4')}$), 3.83 (s, 6H, CH$_3$O$_{(3'+5')}$), 4.35 (q, 2H, CH$_3$CH$_2$), 7.24 (s, 2H, H$_{arom(2+6)}$), 8.07 (d, 2H, H$_{arom\ (2'+6')}$, J=8.39), 8.22 (s, 1H, H$_{P5}$), 8.26 (d, 2H, H$_{arom\ (2'+6')}$), 8.60 (s, 1H, H$_{P3}$), 9.65 (s, 1H, NH$_{amine}$); MS, (C$_{22}$H$_{23}$N$_3$O$_5$), m/z: 410 [M$^+$+1, 100].

Example 15

2-(3,4,5-trimethoxyphenylamino)-6-(4-aminophenyl)pyrazine, CJS 366

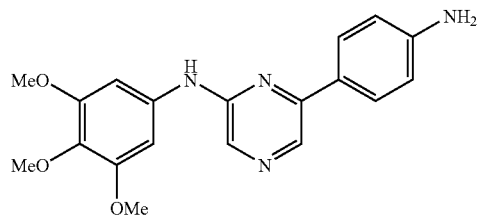

Using Method C with 500 mg (1.69 mmol) 2a and 438 mg (2.0 mmol) 4-(4,4,5,5-tetramethyl-1,3,2-borolan-2-yl)aniline, 248 mg pure title compound were obtained. The filtrate was submitted to purification by preparative HPLC (eluent:AcOEt) and another fraction of 102 mg was obtained. A total of 350 mg title compound (82.1%) were obtained. Reaction time: 18 hours. $^1$H-NMR (DMSO), δ (ppm), J (Hz): 3.63 (s, 3H, CH$_3$O$_{(4')}$), 3.82 (s, 6H, CH$_3$O$_{(3'+5')}$), 5.53 (s, 2H, NH$_2$), 6.64 (d, 2H, H$_{arom\ 2'+6'}$, J=8.47), 7.25 (s, 2H, H$_{arom(2+6)}$), 7.84 (d, 2H, H$_{arom\ 3'+5'}$), 7.97 (s, 1H, H$_{P5}$), 8.34 (s, 1H, H$_{P3}$), 9.38 (s, 1H, NH$_{amine}$); MS, (C$_{19}$H$_{20}$N$_4$O$_3$), m/z: 353 [M$^+$+1, 100].

Example 16

2-(3,4,5-trimethoxyphenylamino)-6-phenylpyrazine, CJS 371

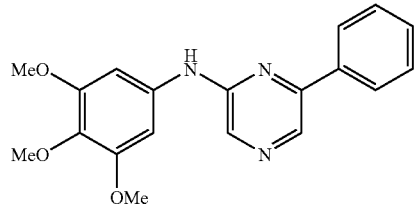

Using Method C with 200 mg (0.68 mmol) 2a and 100 mg (0.82 mmol) phenylboronic acid, 83 mg (22.9%) pure title compound were obtained after preparative HPLC (eluent: AcOEt) purification of the whole batch. Reaction time: 20 hours. $^1$H-NMR (DMSO), δ (ppm), J (Hz): 3.64 (s, 3H, CH$_3$O$_{(4')}$), 3.83 (s, 6H, CH$_3$O$_{(3'+5')}$), 7.26 (s, 2H, H$_{arom(2+6)}$), 7.51 (m, 3H, H$_{arom\ 3'+4'+5'}$), 8.14 (m, 2H, H$_{arom2'+6'}$), 8.16 (s, 1H, H$_{P5}$), 8.52 (s, 1H, H$_{P3}$), 9.58 (s, 1H, NH$_{amine}$); MS, (C$_{19}$H$_{19}$N$_3$O$_3$), m/z: 338 [M$^+$+1, 100].

Example 17

2-(3,4,5-trimethoxyphenylamino)-6-(4-acetamidophenyl)pyrazine, CJS 370

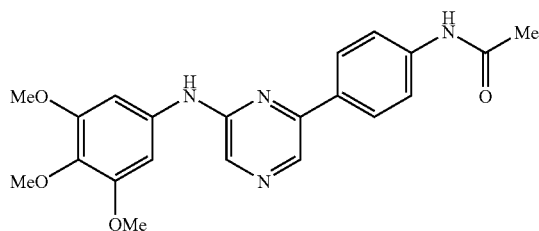

Using Method C with 200 mg (0.68 mmol) 2a and 214 mg (0.82 mmol) 4-(4,4,5,5-tetramethyl-1,3,2-borolan-2-yl)acetanilide, 206 mg (76.8%) pure title compound were obtained after preparative HPLC (eluent: AcOEt) purification of the whole batch. Reaction time: 48 hours. $^1$H-NMR (DMSO), δ (ppm), J (Hz): 2.07 (s, 3H, $CH_3CO$—) 3.63 (s, 3H, $CH_3O_{(4')}$), 3.82 (s, 6H, $CH_3O_{(3'+5')}$), 7.25 (s, 2H, $H_{arom(2+6)}$), 7.71 (d, 2H, $H_{arom\ 2'+6'}$, J=8.89), 8.07 (d, 2H, $H_{arom3'+5'}$), 8.11 (s, 1H, $H_{P5}$), 8.47 (s, 1H, $H_{P3}$), 9.53 (s, 1H, $NH_{amine}$), 10.12 (s, 1H, $NH_{amido}$); MS, ($C_{21}H_{22}N_4O_4$), m/z: 395 [M$^+$+1, 100].

Example 18

2-(3,4,5-trimethoxyphenylamino)-6-(4-formylphenyl)pyrazine, CJS 372

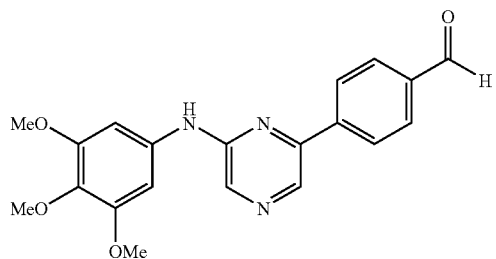

Using Method C with 200 mg (0.68 mmol) 2a and 123 mg (0.82 mmol) 4-formylphenylboronic acid, 153 mg (61.7%) pure title compound were obtained after preparative HPLC (eluent: AcOEt) purification of the whole batch. Reaction time: 24 hours. $^1$H-NMR (DMSO), δ (ppm), J (Hz): 3.64 (s, 3H, $CH_3O_{(4')}$), 3.83 (s, 6H, $CH_3O_{(3'+5')}$), 7.25 (s, 2H, $H_{arom(2+6)}$), 8.05 (d, 2H, $H_{arom\ 2'+6'}$, J=8.22), 8.23 (s, 1H, $H_{P5}$), 8.35 (d, 2H, $H_{arom3'+5'}$), 8.64 (s, 1H, $H_{P3}$), 9.68 (s, 1H, $NH_{amine}$), 10.08 (s, 1H, CHO); MS, ($C_{20}H_{19}N_3O_4$), m/z: 395 [M$^+$+1, 100].

Example 19

2-(3,4,5-trimethoxyphenylamino)-6-(3-pyridyl)pyrazine, CJS 373

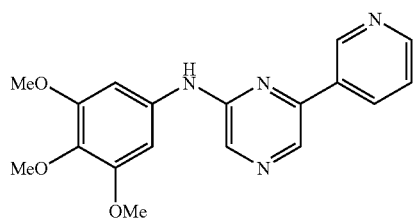

Using Method C with 200 mg (0.68 mmol) 2a and 100 mg (0.82 mmol) 3-pyridylboronic acid, 120 mg (52.1%) pure title compound were obtained after purification of the whole batch by column chromatography (Kieselgel 60, 0.040-0.063; eluent: AcOEt:MeOH 1:1). Reaction time: 3 hours. $^1$H-NMR (DMSO), δ (ppm), J (Hz): 3.67 (s, 3H, $CH_3O_{(4')}$), 3.85 (s, 6H, $CH_3O_{(3'+5')}$), 7.26 (s, 2H, $H_{arom(2+6)}$), 7.59 (m, 1H, $H_{arom\ 5'}$), 8.25 (s, 1H, $H_{P5}$), 8.49 (d, 1H, $H_{arom\ 6'}$, J=7.90), 8.63 (s, 1H, $H_{P3}$), 8.69 (d, 1H, $H_{arom\ 4'}$, J=3.18), 9.51 (d, 1H, $H_{arom\ 2'}$, J=2.21), 9.51 (s, 1H, $NH_{amine}$); MS, ($C_{18}H_{18}N_4O_3$), m/z: 339.1 [M$^+$+1, 100].

Example 20

2-(3,4,5-trimethoxyphenylamino)-6-(4-cyanophenyl)pyrazine, CJS 374

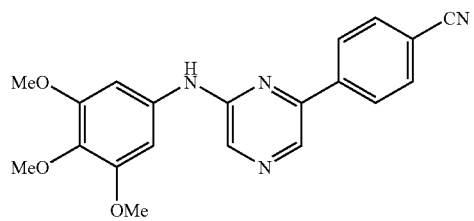

Using Method C with 200 mg (0.68 mmol) 2a and 188 mg (0.82 mmol) 4-(4,4,5,5-tetramethyl-1,3,2-borolan-2-yl)benzonitrile, 52 mg pure title compound were obtained. The filtrate was submitted to purification by preparative HPLC (eluent:AcOEt) and another fraction of 63 mg was obtained. A total of 115 mg title compound (46.7%) were obtained. Reaction time: 18 hours. $^1$H-NMR (DMSO), δ (ppm), J (Hz): 3.64 (s, 3H, $CH_3O_{(4')}$), 3.81 (s, 6H, $CH_3O_{(3'+5')}$), 7.21 (s, 2H, $H_{arom(2+6)}$), 6.64 (d, 2H, $H_{arom\ 2'+6'}$, J=8.47), 8.00 (d, 2H, $H_{arom\ 2'+6'}$, J=8.36), 8.23 (s, 1H, $H_{P5}$), 8.31 (d, 2H, $H_{arom\ 3'+5'}$), 8.63 (s, 1H, $H_{P3}$), 9.68 (s, 1H, $NH_{amine}$); MS, ($C_{20}H_{18}N_4O_3$), m/z: 363.2 [M$^+$+1, 100].

Example 21

2-(3,4,5-trimethoxyphenylamino)-6-(3-cyanophenyl)pyrazine, CJS 377

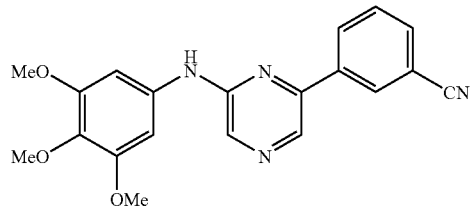

Using Method C with 200 mg (0.68 mmol) 2a and 188 mg (0.82 mmol) 3-(4,4,5,5-tetramethyl-1,3,2-borolan-2-yl)benzonitrile, 44 mg (17.9%) pure title compound were obtained after preparative HPLC (eluent: AcOEt) purification of the whole batch. Reaction time: 18 hours. $^1$H-NMR (DMSO), δ (ppm), J (Hz): 3.64 (s, 3H, $CH_3O_{(4')}$), 3.84 (s, 6H, $CH_3O_{(3'+5')}$), 7.23 (s, 2H, $H_{arom(2+6)}$), 7.73 (t, 1H, $H_{arom\ 5'}$, J=7.87), 7.93 (d, 1H, $H_{arom\ 6'}$, J=7.74), 8.22 (s, 1H, $H_{P5}$), 8.45 (d, 1H, $H_{arom\ 4'}$, J=8.01), 8.57 (2, 1H, $H_{arom\ 2'}$), 8.64 (s, 1H, $H_{P3}$), 9.68 (s, 1H, $NH_{amine}$); MS, ($C_{20}H_{18}N_4O_3$), m/z: 363.1 [M$^+$+1, 100].

Example 22

2-(3,4,5-trimethoxyphenylamino)-6-(N-tert-butoxy-carbonyl-pyrrol-2-yl) pyrazine, CJS 398

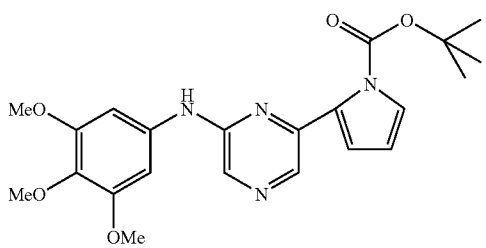

Using Method C with 100 mg (0.34 mmol) 2a and 86 mg (0.41 mmol) 1-tert-butoxycarbonyl-2-pyrrolyl boronic acid, 6 mg pure title compound were obtained. The filtrate was submitted to purification by preparative HPLC (eluent:A-cOEt) and a fraction of 52 mg of a product containing 25% (LC-MS) of the desired compound was obtained. A second purification using a semi-preparative Supelco discovery $C_{18}$ column (250×10 mm) (eluent: acetonitrile:$H_2O$ 9:1) led to 6 mg (4.1%) of pure title compound. Reaction time: 18 hours. $^1$H-NMR (DMSO), δ (ppm), J (Hz): 1.25 (s, 9H, t-Bu), 3.60 (s, 3H, $CH_3O_{(4')}$), 3.72 (s, 6H, $CH_3O_{(3'+5')}$), 6.33 (t, 1H, $H_{pyr\ 4'}$, J=3.30), 6.58-6.60 (m, 1H, $H_{pyr\ 3'\ or\ 5'}$), 7.16 (s, 2H, $H_{arom(2+6)}$), 7.42-7.44 (m, 1H, $H_{pyr\ 5'\ or\ 3'}$), 8.04 (s, 1H, $H_{P5}$), 8.12 (s, 1H, $H_{P3}$), 9.53 (s, 1H, $NH_{amine}$); MS, ($C_{22}H_{16}N_4O_5$), m/z: 427 [M$^+$+1, 100].

Example 23

2-(3,4,5-trimethoxyphenylamino)-6-(4-carboxami-dophenyl)pyrazine, CJS 400

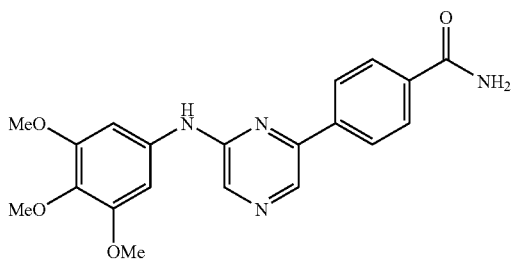

Using Method C with 100 mg (0.34 mmol) 2a and 73 mg (0.41 mmol) 4-aminocarbonylphenyl boronic acid, 23 mg (17.8%) pure title compound were obtained. Reaction time: 7 hours. $^1$H-NMR (DMSO), δ (ppm), J (Hz): 3.65 (s, 3H, $CH_3O_{(4')}$), 3.85 (s, 6H, $CH_3O_{(3'+5')}$), 7.27 (s, 2H, $H_{arom(2+6)}$), 7.47 (s broad, 1H, $CONH_2$), 8.02 (d, 2H, $H_{arom\ 2'+6'}$, J=8.44), 8.08 (s broad, 1H, $CONH_2$), 8.21 (s, 1H, $H_{P5}$), 8.23 (d, 2H, $H_{arom3'+5'}$), 8.61 (s, 1H, $H_{P3}$), 9.64 (s, 1H, $NH_{amine}$); MS, ($C_{20}H_{20}N_4O_4$), m/z: 381.18 [M$^+$+1, 100]; $^{13}$C NMR (75 MHZ, DMSO-$d_6$) δ 55.61, 60.14, 95.93, 126.15, 127.99, 130.27, 132.14, 134.23, 134.89, 136.76, 139.12, 146.73, 151.47, 152.83, 167.31.

Method D. In an alternative method, a tube suitable for microwave irradiation provided with stirring and an argon atmosphere were placed 2-(3,4,5-trimethoxyphenylamino)-6-chloropyrazine, (2a) (50 mg, 0.17 mmol), 4-aminocarbonylphenylboronic acid (36 mg, 0.22 mmol), tris(dibenzylideneacetone) dipalladium (0) (10 mg, 0.017 mmol), 1,3-bis(2,6-di-i-propylphenyl)-4,5-dihydro-imidazolium tetrafluoroborate (8 mg, 0.017 mmol), tetra-n-butylammonium bromide (5.6 mg, 0.017 mmol) and toluene (1 mL). The temperature was lowered to 0° C. and dropwise addition of a suspension of potassium methoxide (35.6 mg, 0.51 mmol) in methanol (0.4 mL) followed. This mixture was stirred for five minutes to allow equilibration at 0° C. once again and then microwave irradiation for 30 minutes at 65° C. followed. The same procedure was followed with double amounts of all substances (i.e., 100 mg of 2a, etc.) to ascertain the reproducibility of this method. The contents of both reactions were pooled together, dissolved in boiling ethyl acetate (25 mL for each reaction) and filtered. The resulting organic layer was evaporated under vacuo to give a solid that gave, upon column chromatography using ethyl acetate as the solvent, 124 mg of the title compound. Yield: 64%.

Example 24

2-(3-chlorophenylamino)-6-(4-pyridyl)pyrazine, CJS 361

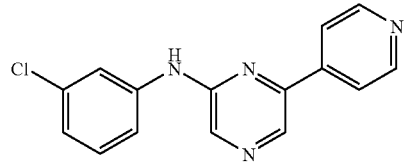

Using Method C with 175 mg (0.73 mmol) 2b and 108 mg (0.87 mmol) 4-pyridyl boronic acid, 79 mg pure title compound (38.3%) were obtained after purification by preparative HPLC (eluent:AcOEt). Reaction time: 24 hours. $^1$H-NMR (DMSO), δ (ppm), J (Hz): 7.05 (q, 1H, $H_{arom\ 6\ or\ 4}$, Jo=7.88, Jm=1.45), 7.39 (t, 1H, $H_{arom\ 5}$, J=8.11), 7.67 (q, 1H, $H_{arom\ 4\ or\ 6}$, Jo=8.22, Jm=1.37), 8.05 (m, 2H, $H_{arom\ 2'+6'}$), 8.05 (s, 1H, $H_{P5}$), 8.74 (s, 1H, $H_{P3}$), 8.75 (m, 2H, $H_{arom\ 3'+5'}$), 9.94 (s, 1H, $NH_{amine}$); MS, ($C_{15}H_{11}ClN_4$), m/z: 283.3 [M$^+$+1, 100].

Example 25

2-(4-methoxyphenylamino)-6-(3-acetamidophenyl) pyrazine, CJS 368

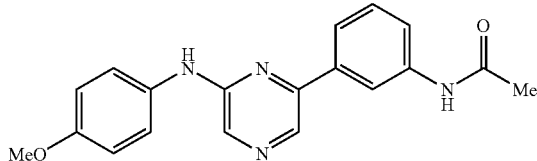

Using Method C with 228 mg (0.97 mmol) 2c and 147 mg (0.82 mmol) 3-acetamidophenyl boronic acid, 33 mg (10.2%) pure title compound were obtained. Reaction time: 24 hours. $^1$H-NMR (DMSO), δ (ppm), J (Hz): 2.09 (s, 3H, $CH_3CO$), 3.75 (s, 3H, $CH_3O_{(4')}$), 7.27 (s, 2H, $H_{arom(2+6)}$), 6.96 (d, 2H, $H_{arom\ 2+6}$, J=9.02), 7.42 (t, 1H, $H_{arom\ 5'}$, J=7.88), 7.63 (d, 2H, $H_{arom\ 4'\ or\ 6'}$, J=7.73), 7.71 (d, 2H, $H_{arom\ 6\ or\ 4'}$), 7.75 (d, 2H, $H_{arom\ 2+6}$), 8.11 (s, 1H, $H_{P5}$), 8.23 (d, 2H, $H_{arom3'+5'}$), 8.36 (s, 1H, H$_{P3}$), 9.41 (s, 1H, NH$_{amine}$), 10.09 (s, 1H, NH$_{amide}$); MS, (C$_{19}$H$_{18}$N$_4$O$_2$), m/z: 335.3 [M$^+$+1, 100].

Example 26

2-(3-acetamidophenyl)-6-chloropyrazine, 4a

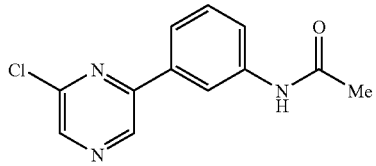

Method E. 1.00 g (6.70 mmol) 2,6 dichloropyrazine, 450 mg (0.54 mmol) PdCl$_2$.dppf:DCM 1:1, 1.44 g (8.04 mmol) 3-acetamidophenyl boronic acid were dissolved in 100 mL DME. To this solution 14 mL aq. sol Na$_2$CO$_3$ 1M were added under stirring and the reaction mixture was heated at 90° C. (bath temperature) for 5 hours. The reaction mixture was evaporated to dryness, the residue retaken in 50 mL AcOEt, filtered and the organic solution washed (2×30 mL brine), dried (MgSO$_4$) and evaporated to 20 mL. A pale yellow solid, 160 mg was obtained. After filtration the filtrate was submitted to preparative HPLC (Kieselgel 60, 0.015-0.040; eluent: AcOEt) and another fraction of 749 mg title compound was obtained. Total yield: 909 mg (54.7%). $^1$H-NMR (DMSO), δ (ppm), J (Hz): 2.07 (s, 3H, CH$_3$CO), 7.47 (t, 1H, H$_{arom\ 5}$, J=7.95), 7.79-7.84 (2d, 2H, H$_{arom\ 4+6}$), 8.28 (s, 1H, H$_{arom\ 2}$), 8.28 (s, 1H, H$_{P5}$), 8.76 (s, 1H, H$_{P3}$), 10.17 (s, 1H, NH$_{amide}$).

Example 27

2-(3,5-dimethoxyphenylamino)-6-(3-acetamidophenyl)pyrazine, CJS 367

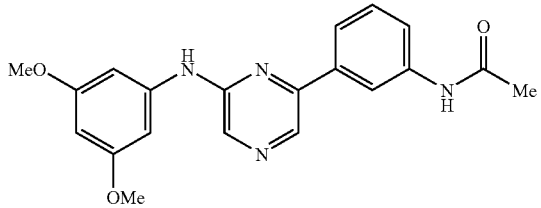

Method F. To 180 mg (0.73 mmol) 2-(3-acetamidophenyl)-6-chloropyrazine (4a) dissolved in 5 mL dry toluene in an oven dried flask, were added under stirring and argon: 24 mg (0.03 mmol) Pd(0)$_2$ dba$_3$, 75 mg (0.12 mmol) BINAP, 134 mg (0.88 mmol) 3,4,5-trimethoxyanilin and 98 mg (1.02 mmol) Na-tert-butoxide. The reaction mixture was heated at 90° C. (bath temperature) for 5 hours under N$_2$. After cooling, the toluene solution was filtered and evaporated under vacuum. The solid was retaken in 40 mL AcOEt, washed (2×40 mL water) and dried. The filtered catalyst was also extracted with 10 mL Me$_2$CO. The organic solutions was pooled, evaporated to 10 mL volume and left in a refrigerator over night. A portion of 160 mg of title compound was obtained. The filtrate submitted to HPLC (Kieselgel 60, 0.015-0.043; eluent: AcOEt). A fraction of 40 mg title compound was collected. The total yield was 170 mg (63.9%). $^1$H-NMR (DMSO), δ (ppm), J (Hz): 2.07 (s, 3H, CH$_3$CO), 3.75 (s, 6H, CH$_3$O$_{(3'+5')}$), 6.15 (s, 1H, H$_{arom\ 4}$), 7.12 (s, 2H, H$_{arom\ 2'+6'}$), 7.44 (t, 1H, H$_{arom\ 5'}$, J=7.77), 7.67 (d, 1H, H$_{arom\ 4'\ or\ 6'}$, J=7.92), 7.73 (d, 1H, H$_{arom\ 6'\ or\ 4'}$, J=7.63), 8.19 (s, 1H, H$_{P5}$), 8.24 (s, 1H, H$_{arom\ 2'}$), 8.39 (s, 1H, H$_{P3}$), 9.64 (s, 1H, NH$_{amino}$), 10.03 (s, 1H, NH$_{amido}$); MS, (C$_{20}$H$_{20}$N$_4$O$_3$), m/z: 365.3 [M$^+$+1, 100].

Example 28

2-(3,4-dimethoxyphenylamino)-6-(3-acetamidophenyl)pyrazine, CJS 369

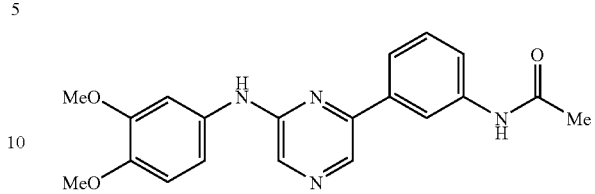

Using Method F with 180 mg (0.73 mmol) 4a and 134 mg (0.88 mmol) 3,4-dimethoxyaniline, 72 mg (27.1%) pure title compound were obtained after preparative HPLC (eluent: AcOEt) purification of the whole batch. Reaction time: 6 hours. $^1$H-NMR (DMSO), δ (ppm), J (Hz): 2.07 (s, 3H, CH$_3$CO), 3.73 (s, 3H, CH$_3$O$_{(4)}$), 3.77 (s, 3H, CH$_3$O$_{(3)}$), 6.95 (d, 1H, H$_{arom\ 5}$, J=8.71), 7.26 (q, 1H, H$_{arom\ 6}$, J$_o$=8.63, J$_m$=2.35), 7.42 (t, 1H, H$_{arom\ 5'}$, J=7.90), 7.62 (s, 1H, H$_{arom\ 2}$), 7.64 (d, 1H, H$_{arom\ 4'\ or\ 6'}$), 7.72 (d, 1H, H$_{arom\ 6'\ or\ 4'}$, J=7.63), 8.13 (s, 1H, H$_{P5}$), 8.30 (s, 1H, H$_{arom\ 2'}$), 8.35 (s, 1H, H$_{P3}$), 9.45 (s, 1H, NH$_{amino}$), 10.07 (s, 1H, NH$_{amido}$); MS, (C$_{20}$H$_{20}$N$_4$O$_3$), m/z: 365.3 [M$^+$+1, 100].

Example 29

2-(3,4-methylenedioxyphenylamino)-6-(3-acetamidophenyl)pyrazine, CJS 375

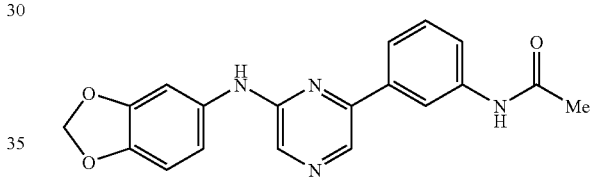

Using Method F with 200 mg (0.33 mmol) 4a and 138 mg (1.0 mmol) 3,4-methylendioxyaniline, 84 mg (29.0%) pure title compound were obtained after preparative HPLC (eluent: AcOEt) purification of the whole batch. Reaction time: 18 hours. $^1$H-NMR (DMSO), δ (ppm), J (Hz): 2.08 (s, 3H, CH$_3$CO), 5.99 (s, 2H, OCH$_2$O), 6.91 (d, 1H, H$_{arom\ 5}$, J=8.40), 7.32 (q, 1H, H$_{arom\ 6}$, J$_o$=8.43, J$_m$=1.99), 7.40 (d, 1H, H$_{arom\ 2}$, J=1.85), 7.43 (t, 1H, H$_{arom\ 5'}$, J=7.87), 7.65 (d, 1H, H$_{arom\ 4'\ or\ 6'}$, J=8.93), 7.68 (d, 1H, H$_{arom\ 6'\ or\ 4'}$, J=7.83), 8.12 (s, 1H, H$_{P5}$), 8.30 (s, 1H, H$_{arom\ 2'}$), 8.35 (s, 1H, H$_{P3}$), 9.42 (s, 1H, NH$_{amino}$), 10.09 (s, 1H, NH$_{amido}$); MS, (C$_{19}$H$_{16}$N$_4$O$_3$), m/z: 349.1 [M$^+$+1, 100].

Example 30

2-(3,4,5-trimethoxyphenylamino)-6-(N$_3$-benzyl-N$_1$-3-phenylureyl) pyrazine, CJS 378

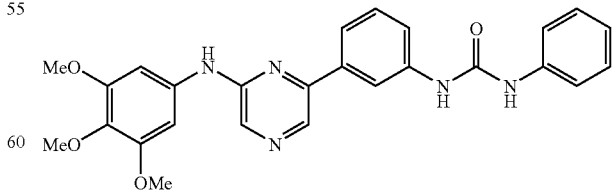

Method G. CJS 364, 50 mg (0.14 mmol) was dissolved in 5 mL DCM and 20 μL (0.15 mmol) of benzylisocyanate were added. The reaction mixture was stirred for 48 hours at room temperature. A solid precipitate was formed and filtered. 47 mg (69.1%) of pure title compound was obtained. $^1$H-NMR (DMSO), δ (ppm), J (Hz): 3.46 (s, 3H, CH$_3$O$_{(4')}$), 3.68 (s, 6H, CH$_3$O$_{(3'+5')}$), 4.32 (d, 2H, CH$_2$Ph, J=4.58), 6.72 (t, 1H, NHCH$_2$, J=5.52), 7.24 (s, 2H, H$_{arom(2'+6')}$), 7.26-7.45 (m, 6H, 5H$_{phenyl}$+H$_{arom\ 5'}$), 7.46 (d, 1H, H$_{arom\ 6'\ or\ 4'}$, J=7.74), 7.63 (d, 1H, H$_{arom\ 4'\ or\ 6'}$, J=7.11), 8.14 (s, 1H, H$_{arom\ 2'}$), 8.15 (s, 1H, H$_{P5}$), 8.39 (s, 1H, H$_{P3}$), 8.74 (s, 1H, NH$_{urea}$), 9.58 (s, 1H, NH$_{amine}$); MS, (C$_{27}$H$_{27}$N$_5$O$_4$), m/z: 484.3 [M$^+$+1, 100]

Example 31

2-(3,4,5-trimethoxyphenylamino)-6-(N$_3$-phenyl-N$_1$-3-phenylureyl) pyrazine, CJS 380

Using Method G with the same amount of CJS 364 (0.14 mmol), 52 mg (78.8%) pure title compound was obtained. Reaction time: 24 hours. $^1$H-NMR (DMSO), δ (ppm), J (Hz): 3.63 (s, 3H, CH$_3$O$_{(4')}$), 3.80 (s, 6H, CH$_3$O$_{(3'+5')}$), 6.98 (t, 1H, H$_{arom\ 5'}$, J=7.42), 7.25 (s, 2H, H$_{arom(2'+6')}$), 7.25-7.34 (m, 2H, 1H$_{phenyl}$+H$_{arom\ 6'\ or\ 4'}$), 7.38-7.53 (m, 4H, H$_{phenyl}$), 7.70 (d, 1H, H$_{arom\ 4'\ or\ 6'}$, J=7.90), 8.17 (s, 1H, H$_{P5}$), 8.22 (s, 1H, H$_{arom\ 2'}$), 8.43 (s, 1H, H$_{P3}$), 8.72 (s, 1H, NH$_{urea}$), 8.79 (s, 1H, NH$_{urea}$), 9.57 (s, 1H, NH$_{amine}$); MS, (C$_{26}$H$_{25}$N$_5$O$_4$), m/z: 470.2 [M$^-$−H], 100.

Example 32

2-(3,4,5-trimethoxyphenylamino)-6-(N$_3$-benzyl-N$_1$-3'-phenylthioureyl) pyrazine, CJS 379

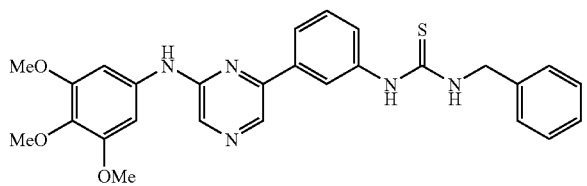

Using Method G with the same amount of CJS 364 (0.14 mmol), 12 mg (30.5%) pure title compound was obtained. Reaction time: 72 hours. $^1$H-NMR (DMSO), δ (ppm), J (Hz): 3.63 (s, 3H, CH$_3$O$_{(4')}$), 3.79 (s, 6H, CH$_3$O$_{(3'+5')}$), 4.76 (d, 2H, CH$_2$Ph, J=5.05), 7.25 (s, 2H, H$_{arom(2'+6')}$), 7.33-7.38 (m, 6H, 5H$_{phenyl}$+H$_{arom\ 5'}$), 7.47 (d, 1H, H$_{arom\ 6'\ or\ 4'}$, J=8.53), 7.88 (d, 1H, H$_{arom\ 4'\ or\ 6'}$), 8.16 (s, 1H, H$_{arom\ 2'}$), 8.17 (s, 1H, H$_{P5}$), 8.28 (s broad, 1H, NH-Bn), 8.47 (s, 1H, H$_{P3}$), 9.60 (s, 1H, NH$_{urea}$), 9.65 (s, 1H, NHPh); MS, (C$_{27}$H$_{27}$N$_5$O$_3$S), m/z: 502.2 [M$^+$+1, 100].

Example 33

2-(3,4,5-trimethoxyphenylamino)-6-(N$_3$-phenyl-N$_1$-3'-phenylthiourea) pyrazine, CJS 381

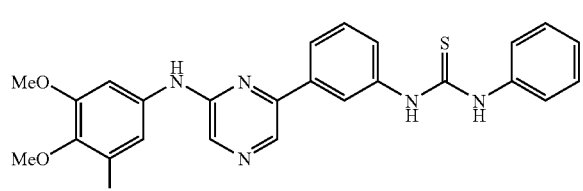

Using Method G with the same amount of CJS 364 (0.14 mmol), 20 mg (29.4%) pure title compound was obtained. Reaction time: 72 hours. $^1$H-NMR (DMSO), δ (ppm), J (Hz): 3.50 (s, 3H, CH$_3$O$_{(4')}$), 3.80 (s, 6H, CH$_3$O$_{(3'+5')}$), 7.26 (s, 2H, H$_{arom(2'+6')}$), 7.27-7.80 (m, 9H, NH+5H$_{phenyl}$+H$_{arom\ 6'}$+H$_{arom\ 4'}$+H$_{arom\ 5'}$), 8.14 (s, 1H, H$_{P5}$), 8.16 (s, 1H, H$_{arom\ 2'}$), 8.46 (s, 1H, H$_{P3}$), 9.67 (s, 1H, NH$_{amine}$), 10.07 (s broad, 1H, NH$_{thiourea}$); MS, (C$_{26}$H$_{25}$N$_5$O$_3$S), m/z: 488.2 [M$^-$−H], 100.

Example 34

2-(3,4,5-trimethoxyphenylamino)-6-(N$_3$-ethyl-N$_1$-3-phenylureyl) pyrazine, CJS 382

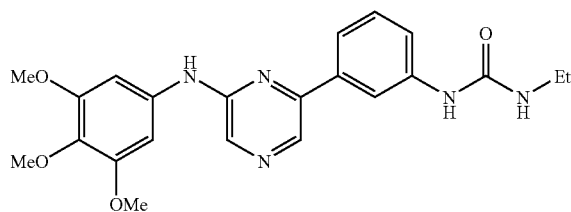

Using Method G with the same amount of CJS 364 (0.14 mmol), 18 mg (30.5%) pure title compound was obtained. Reaction time: 72 hours. $^1$H-NMR (DMSO), δ (ppm), J (Hz): 1.05 (t, 3H, CH$_3$CH$_2$, J=7.15), 3.05-3.19 (m, 2H, CH$_3$CH$_2$NH), 3.63 (s, 3H, CH$_3$O$_{(4')}$), 3.80 (s, 6H, CH$_3$O$_{(3'+5')}$), 6.16 (t, 1H, NHCH$_2$, J=5.37), 7.25 (s, 2H, H$_{arom(2'+6')}$), 7.35 (t, 1H, H$_{arom\ 5'}$, J=7.57), 7.45 (d, 1H, H$_{arom\ 6'\ or\ 4'}$, J=8.21), 7.61 (d, 1H, H$_{arom\ 4'\ or\ 6'}$, J=7.78), 8.13 (s, 1H, H$_{arom\ 2'}$), 8.15 (s, 1H, H$_{P5}$), 8.38 (s, 1H, H$_{P3}$), 8.54 (s, 1H, NH$_{urea}$), 9.56 (s, 1H, NH$_{amine}$); MS, (C$_{22}$H$_{25}$N$_5$O$_4$), m/z: 422.2 [M$^-$−H], 100.

Example 35

2-(3,4,5-trimethoxyphenylamino)-6-[3-(ethylcarbonylamino)phenyl] pyrazine, CJS 383

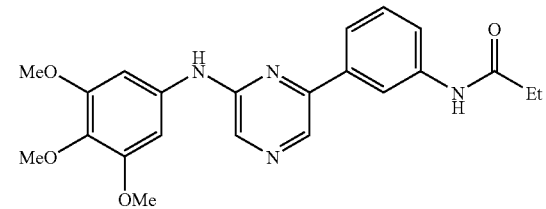

Method H. CJS 364, 50 mg (0.14 mmol) was dissolved in 5 mL THF dry and 17.5 µL (0.20 mmol) of propionyl chloride and 41.7 µL (0.30 mmol) triethylamine were added sequentially. The reaction mixture was stirred for 18 hours at room temperature. The solvent was evaporated and the residue retaken in 20-30 mL AcOEt. The solution was dried (MgSO$_4$), reduced to 10 mL, left overnight in a refrigerator and filtered. 9.5 mg of a solid was obtained and the filtrate was submitted to preparative HPLC (Kieselgel 60, 0.015-0.040; eluent: AcOEt). A second portion of 10 mg of title compound was separated. A total of 19.5 mg (23.9%) of pure title compound was obtained. $^1$H-NMR (DMSO), δ (ppm), J (Hz): 1.12 (t, 3H, CH$_3$CH$_2$, J=7.52), 2.34-2.37 (m, 2H, CH$_3$CH$_2$), 3.64 (s, 3H, CH$_3$O$_{(4')}$), 3.80 (s, 6H, CH$_3$O$_{(3'+5')}$), 7.26 (s, 2H, H$_{arom(2'+6')}$), 7.43 (t, 1H, H$_{arom\ 5'}$, J=7.89), 7.65 (d, 1H, H$_{arom\ 6'\ or\ 4'}$), 7.74 (d, 1H, H$_{arom\ 4'\ or\ 6'}$, J=7.75), 8.17 (s, 1H, H$_{P5}$), 8.32 (s, 1H, H$_{arom\ 2'}$), 8.40 (s, 1H, H$_{P3}$), 9.56 (s, 1H, NH$_{amine}$), 10.00 (s, 1H, NH$_{amide}$); MS, (C$_{22}$H$_{24}$N$_4$O$_4$), m/z: 409.17 [M$^+$+1], 100.

Example 36

2-(3,4,5-trimethoxyphenylamino)-6-[3-(n-propylcarbonylamino)phenyl] pyrazine, CJS 384

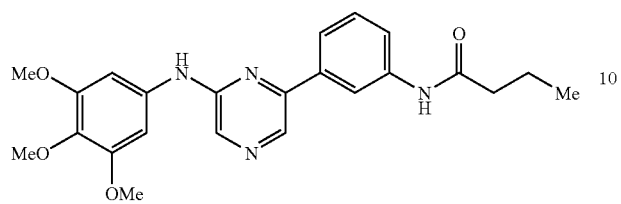

Using Method H with 0.14 mmol CJS 364 and 20.7 μL (0.2 mmol) propionyl chloride, 10 mg (12.3%) of pure title compound were obtained. $^1$H-NMR (DMSO), δ (ppm), J (Hz): 0.95 (t, 3H, CH$_3$CH$_2$, J=7.52), 1.63-1.70 (m, 2H, CH$_3$CH$_2$), 2.32 (t, 2H, CH$_2$NH, J=7.33), 3.64 (s, 3H, CH$_3$O$_{(4')}$), 3.80 (s, 6H, CH$_3$O$_{(3'+5')}$), 7.26 (s, 2H, H$_{arom(2'+6')}$), 7.44 (t, 1H, H$_{arom\ 5'}$, J=7.89), 7.68 (d, 1H, H$_{arom\ 6'\ or\ 4'}$), 7.74 (d, 1H, H$_{arom\ 4'\ or\ 6'}$, J=7.68), 8.18 (s, 1H, H$_{P5}$), 8.32 (s, 1H, H$_{arom\ 2'}$), 8.40 (s, 1H, H$_{P3}$), 9.59 (s, 1H, NH$_{amine}$), 10.01 (s, 1H, NH$_{amide}$); MS, (C$_{23}$H$_{26}$N$_4$O$_4$), m/z: 423.17 [M$^+$+1], 100.

Example 37

2-(3,4,5-trimethoxyphenylamino)-6-[3-(phenylcarbonylamino)phenyl] pyrazine, CJS 385

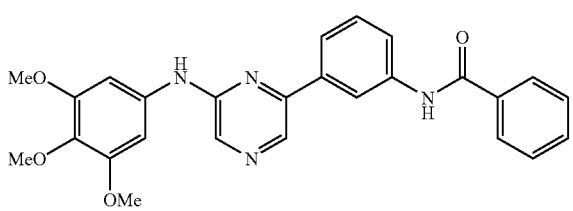

Using Method H with 0.14 mmol CJS 364 and 23.2 μL (0.2 mmol) benzoyl chloride, 34 mg (37.3%) of pure title compound were obtained. $^1$H-NMR (DMSO), δ (ppm), J (Hz): 3.62 (s, 3H, CH$_3$O$_{(4')}$), 3.78 (s, 6H, CH$_3$O$_{(3'+5')}$), 7.28 (s, 2H, H$_{arom(2'+6')}$), 7.44 (t, 1H, H$_{arom\ 5'}$, J=7.92), 7.64-7.73 (m, 3H, H$_{arom\ phenyl}$), 7.92-7.97 (m, 2H, H$_{arom\ 6'+4'}$), 8.05 (d, 2H, H$_{arom\ phenyl}$, J=6.31), 8.29 (s, 1H, H$_{P5}$), 8.55 (s, 1H, H$_{P3}$), 8.60 (s, 1H, H$_{arom\ 2'}$), 9.71 (s, 1H, NH$_{amine}$), 10.50 (s, 1H, NH$_{amide}$); MS, (C$_{26}$H$_{24}$N$_4$O$_4$), m/z: 457.2 [M$^+$+1], 100.

Example 38

2-(3,4,5-trimethoxyphenylamino)-6-[3-(benzylcarbonylamino)phenyl] pyrazine, CJS 386

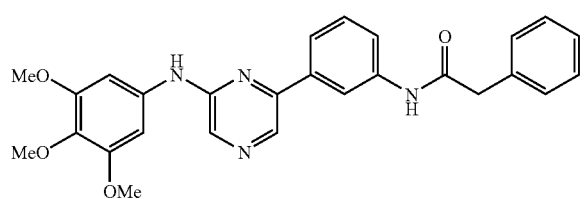

Using Method H with 0.14 mmol CJS 364 and 24.6 μL (0.2 mmol) phenylacetyl chloride, 14 mg (16.7%) of pure title compound were obtained. $^1$H-NMR (DMSO), δ (ppm), J (Hz): 3.64 (s, 3H, CH$_3$O$_{(4')}$), 3.68 (s, 2H, CH$_2$Ph), 3.75 (s, 6H, CH$_3$O$_{(3'+5')}$), 7.24 (s, 2H, H$_{arom(2'+6')}$), 7.27-7.37 (m, 5H, H$_{arom\ phenyl}$), 7.45 (t, 1H, H$_{arom\ 5'}$, J=7.88), 7.67 (d, 1H, H$_{arom\ 6'\ or\ 4'}$), 7.76 (d, 1H, H$_{arom\ 4'\ or\ 6'}$, J=7.65), 8.17 (s, 1H, H$_{P5}$), 8.32 (s, 1H, H$_{arom\ 2'}$), 8.39 (s, 1H, H$_{P3}$), 9.58 (s, 1H, NH$_{amine}$), 10.32 (s, 1H, NH$_{amide}$); MS, (C$_{27}$H$_{26}$N$_4$O$_4$), m/z: 471.2 [M$^+$+1], 100.

Example 39

2-(3,4,5-trimethoxyphenylamino)-6-[3-(phenyl-1-ethyl-2-carbonylamino) phenyl] pyrazine, CJS 387

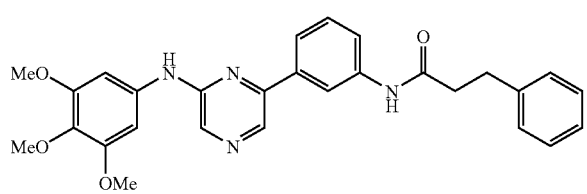

Using Method H with 0.14 mmol CJS 364 and 29.7 μL (0.2 mmol) phenylpropionyl chloride, 17 mg (17.5%) of pure title compound were obtained. $^1$H-NMR (DMSO), δ (ppm), J (Hz): 2.70 (t, 2H, CH$_2$Ph, J=6.72), 2.95 (t, 2H, CH$_2$CO, J=7.89), 3.64 (s, 3H, CH$_3$O$_{(4')}$), 3.79 (s, 6H, CH$_3$O$_{(3'+5')}$), 7.25 (s, 2H, H$_{arom(2'+6')}$), 7.20-7.40 (m, 5H, H$_{arom\ phenyl}$), 7.45 (t, 1H, H$_{arom\ 5'}$, J=7.92), 7.69 (d, 1H, H$_{arom\ 6'\ or\ 4'}$, J=6.79), 7.75 (d, 1H, H$_{arom\ 4'\ or\ 6'}$, J=8.21), 8.17 (s, 1H, H$_{P5}$), 8.29 (s, 1H, H$_{arom\ 2'}$), 8.40 (s, 1H, H$_{P3}$), 9.59 (s, 1H, NH$_{amine}$), 10.07 (s, 1H, NH$_{amide}$); MS, (C$_{28}$H$_{28}$N$_4$O$_4$), m/z: 485.2 [M$^+$+1], 100.

Example 40

2-(3,4,5-trimethoxyphenylamino)-6-[3-(thiophen-2-ylcarbonylamino) phenyl] pyrazine, CJS 388

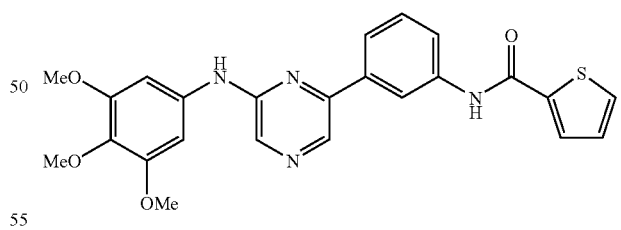

Using Method H with 0.14 mmol CJS 364 and 21.4 μL (0.2 mmol) 2-thiophenylcarboxyl chloride, 17 mg (18.4%) of pure title compound were obtained. $^1$H-NMR (DMSO), δ (ppm), J (Hz): 3.63 (s, 3H, CH$_3$O$_{(4')}$), 3.79 (s, 6H, CH$_3$O$_{(3'+5')}$), 7.26 (m, 3H, H$_{thio\ 4''}$+H$_{arom\ 2+6}$), 7.52 (t, 1H, H$_{arom\ 5'}$, J=7.87), 7.80-7.86 (m, 2H, H$_{arom\ 4'+6'}$), 7.90 (d, 1H, H$_{thio\ 3'''\ or\ 5'''}$, J=4.98), 8.07 (d, 1H, H$_{thio\ 5''\ or\ 3''}$, J=2.81), 8.20 (s, 1H, H$_{P5}$), 8.44 (s, 1H, H$_{arom\ 2'}$), 8.47 (s, 1H, H$_{P3}$), 9.61 (s, 1H, NH$_{amine}$), 10.39 (s, 1H, NH$_{amide}$); MS, (C$_{24}$H$_{22}$N$_4$O$_4$S), m/z: 463.1 [M$^+$+1], 100.

Example 41

2-(3,4,5-trimethoxyphenylamino)-6-[3-(thiophen-2-ylmethylcarbonylamino)phenyl] pyrazine, CJS 389

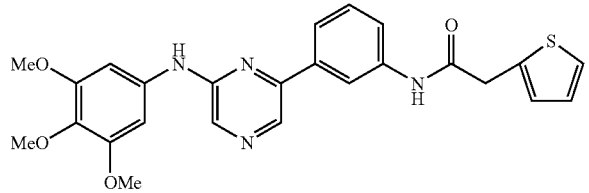

Using Method H with 0.14 mmol CJS 364 and 24.6 μL (0.2 mmol) 2-thiophenylacetyl chloride, 16 mg (16.8%) of pure title compound were obtained. $^1$H-NMR (DMSO), δ (ppm), J (Hz): 3.63 (s, 3H, $CH_3O_{(4')}$), 3.77 (s, 6H, $CH_3O_{(3'+5')}$), 3.91 (s, 2H, $CH_2Thio$), 7.02 (m, 2H, $H_{thio\ 3''+4''}$), 7.26 (s, 2H, $H_{arom\ 2+6}$), 7.43-7.46 (m, 1H, $H_{thio\ 2''}$), 7.46 (t, 1H, $H_{arom\ 5'}$, J=7.11), 7.70 (d, 1H, $H_{arom\ 6''\ or\ 4'}$, J=7.74), 7.78 (d, 1H, $H_{arom\ 4'\ or\ 6'}$), 8.17 (s, 1H, $H_{P5}$), 8.31 (s, 1H, $H_{arom\ 2'}$), 8.40 (s, 1H, $H_{P3}$), 9.58 (s, 1H, $NH_{amine}$), 10.36 (s, 1H, $NH_{amide}$); MS, ($C_{25}H_{24}N_4O_4S$), m/z: 477.1 [M$^+$+1], 100.

Example 42

2-(3,4,5-trimethoxyphenylamino)-6-[3-(furan-2-ylcarbonylamino)phenyl] pyrazine, CJS 390

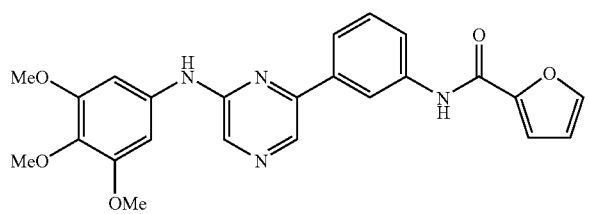

Using Method H with 0.14 mmol CJS 364 and 19.7 μL (0.2 mmol) 2-furylcarboxyl chloride, 22 mg (24.7%) of pure title compound were obtained. $^1$H-NMR (DMSO), δ (ppm), J (Hz): 3.63 (s, 3H, $CH_3O_{(4')}$), 3.80 (s, 6H, $CH_3O_{(3'+5')}$), 6.73-6.76 (m, 1H, $H_{furan\ 4''}$), 7.27 (s, 2H, $H_{arom\ 2+6}$), 7.38 (d, 1H, $H_{furan\ 5''\ or\ 3''}$, J=3.46), 7.53 (t, 1H, $H_{arom\ 5'}$, J=7.93), 7.83-7.88 (m, 2×d, 2H, $H_{arom\ 6'+4'}$, J=7.74), 7.78 (d, 1H, $H_{arom\ 5'\ or\ 6'}$), 7.99 (d, 1H, $H_{furan\ 3''\ or\ 5''}$, J=1.52), 8.19 (s, 1H, $H_{P5}$), 8.44 (s, 1H, $H_{arom\ 2'}$), 8.45 (s, 1H, $H_{P3}$), 9.61 (s, 1H, $NH_{amine}$), 10.32 (s, 1H, $NH_{amide}$); MS, ($C_{24}H_{22}N_4O_5$), m/z: 447.2 [M$^+$+1], 100.

Example 43

3-(3,4,5-trimethoxyphenylamino)-5-bromopyridine

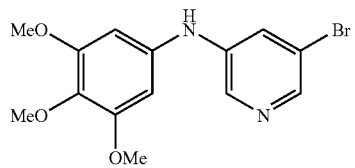

Method J. To 1.00 g (4.2 mmol) 3,5-dibromopyridine dissolved in 40 mL dry toluene in an oven dried flask, were added under stirring: 82 mg (0.09 mmol) Pd(0)$_2$ dba$_3$, 0.168 g (0.27 mmol) BINAP, 1.49 g (8.16 mmol) 3,4,5-trimethoxyanilin and 0.914 g (9.52 mmol) Na-tert-butoxide. The reaction mixture was heated at 90° C. (bath temperature) for 18 hours under N$_2$. After cooling, the toluene solution was filtered, and evaporated under vacuum. The residue was retaken in 30 mL AcOEt, washed (2×30 mL brine) dried, evaporated to a volume of 10 mL and submitted to HPLC (Kieselgel 60, 0.015-0.043; eluent: AcOEt:cycloxane 2:1). A fraction of 167 mg (11.7%) of title compound was collected. $^1$H-NMR (DMSO), δ (ppm), J (Hz): 3.63 (s, 3H, $CH_3O_{(4')}$), 3.78 (s, 6H, $CH_3O_{(3'+5')}$), 6.43 (s, 2H, $H_{arom\ 2+6}$), 7.53 (m, 1H, $H_{pyr\ 4}$, J=2.1), 8.04 (d, 1H, $H_{Pyr\ 2\ or\ 6}$, J=1.86), 8.14 (d, 1H, $H_{Pyr\ 6\ or\ 2}$), 8.48 (s, 1H, NH); MS, ($C_{14}H_{15}BrN_2O_3$), m/z: 339.05 [M$^+$+1, 100].

Example 44

3-(3,4,5-trimethoxyphenylamino)-5-(3-acetamidophenyl)pyridine, CJS 402

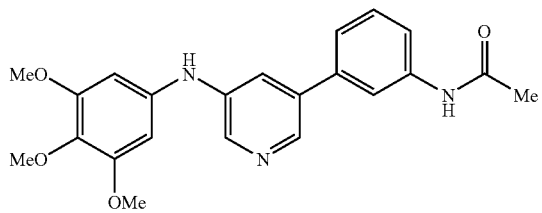

Using the procedure described for Suzuki coupling (Method C) and starting from 160 mg (0.97 mmol) 3-(3,4,5-trimethoxyphenylamino)-5-bromopyridine, 129 mg (69.7%) pure title compound were obtained after purification by preparative HPLC (eluent: AcOEt:EtOH 95:5). Reaction time: 4 hours. $^1$H-NMR (DMSO), δ (ppm), J (Hz): 2.06 (s, 3H, $CH_3CO$), 3.63 (s, 3H, $CH_3O_{(4')}$), 3.76 (s, 6H, $CH_3O_{(3'+5')}$), 6.46 (s, 2H, $H_{arom\ 2+6}$), 7.32 (d, 1H, $H_{arom\ 6'\ or\ 4'}$, J=7.61), 7.41 (t, 1H, $H_{arom\ 5'}$, J=7.98), 7.58 (s, 1H, $H_{pyr\ 4}$), 7.95 (d, 1H, $H_{Pyr\ 2\ or\ 6}$), 8.24 (d, 1H, $H_{Pyr\ 6\ or\ 2}$), 8.34 (d, 1H, $H_{Pyr\ 6\ or\ 2}$), 8.46 (s, 1H, $NH_{amine}$), 10.11 (s, 1H, $NH_{amine}$); MS, ($C_{22}H_{23}N_3O_4$), m/z: 394.2 [M$^+$+1, 100].

Example 45

3-(3-hydroxybenzylamino)-5-bromopyridine

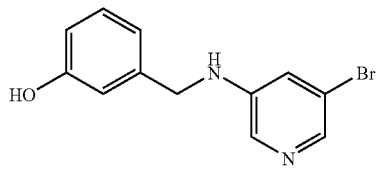

Using the amination procedure described for CJS 402 (Method A) and 86 mg (0.7 mmol) 3-hydroxybenzylamine, and starting from 200 mg (0.67 mmol) 3-(3,4,5-trimethoxyphenylamino)-5-bromopyridine, 174 mg (69.7%) intermediate were obtained.

$^1$H-NMR (DMSO), δ (ppm), J (Hz): 4.22 (d, 2H, $CH_2N$, J=4.21), 6.63 (dd, 1H, $H_{arom\ 6}$), 6.75-6.82 (m, 3H, NH+OH+$H_{arom\ 4}$), 7.07-7.14 (m, 2H, $H_{arom\ 5}$+$H_{pyr\ 4}$), 7.80 (d, 1H, H$_{Pyr\,2\,or\,6}$), 7.95 (d, 1H, H$_{Pyr\,6\,or\,2}$), 9.36 (s, 1H, NH); MS, (C$_{12}$H$_{11}$BrN$_2$O), m/z: 279.04 [M$^+$+1, 100].

Example 46

N-(3-(6-(2,3-dihydrobenzo[b][1,4]dioxin-6-ylamino) pyrazin-2-yl)phenyl)acetamide, CJS 391

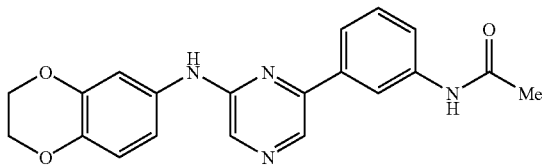

Method K. In a round-bottomed flask provided with stirring and an argon atmosphere, 2-(3-acetamidophenyl)-6-chloropyrazine (4a) (60 mg, 0.24 mmol), 6-amino-3,4-benzodioxane (45 mg, 0.29 mmol), Pd(0)$_2$ dba$_3$ (tris (dibenzylidene)acetone dipalladium(0)) (9 mg, 0.01 mmol), 2,2'-Bis(diphenylphosphino)-1,1'-binaphtyl (BINAP) (50 mg, 0.04 mmol), sodium tert-butoxide (33 mg, 0.34 mmol), and toluene (5 mL) were reacted at 90° C. for 12 hours. When the flask cooled down the solvent was evaporated under vacuo. The resulting solid was washed with 20 mL ethyl acetate and filtered. The volume was reduced to 1.5 mL and 0.5 mL of dichloromethane were added. This mixture was chromatographied in silica gel using ethyl acetate as eluent to furnish 40 mg of title compound. Yield: 45.8%. $^1$H NMR (250 MHz, DMSO-d$_6$) δ 2.09 (s, 3 H), 4.20-4.24 (m, 4H), 6.85 (d, 1 H, 8.7 Hz), 7.25-7.38 (m, 1 H), 7.43 (t, 1 H, 8.0 Hz), 7.68 (t, 1 H, 7.8 Hz), 8.11 (s, 1 H), 8.28 (s, 1 H), 8.34 (s, 1 H), 9.38 (s, 1 H), 10.08 (s, 1 H); $^{13}$C NMR (62.9 MHZ, DMSO-d$_6$) δ 24.64, 64.29, 64.51, 110.82, 115.00, 117.69, 118.20, 121.10, 122.61, 129.56, 130.37, 131.03, 132.75, 137.34, 138.58, 140.38, 143.82, 149.32, 151.99, 168.59; m/z 363.4 [(M+H)$^+$, calcd for C$_{20}$H$_{18}$N$_4$O$_3$ 362.1].

Example 47

N-(3-(6-(3-chloro-4-fluorophenylamino)pyrazin-2-yl)phenyl)acetamide, CJS 392

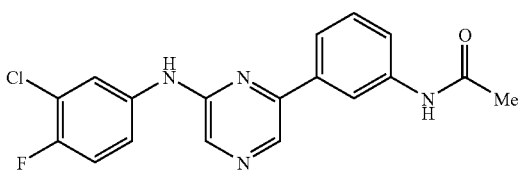

Using Method K. 2-(3-acetamidophenyl)-6-chloropyrazine (4a) (60 mg, 0.24 mmol), 3-chloro-4-fluoroaniline (42 mg, 0.29 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 80° C. for 12 hours. The same workup as for Method K and a combination of column chromatography and preparative TLC furnished 4 mg of title compound. Yield: 4.7%. $^1$H NMR (250 MHz, DMSO-d$_6$) δ 2.09 (s, 3 H), 7.38 (d, 1 H, J=9.5 Hz), 7.46 (d, 1 H. J=7.9 Hz), 7.61 (d, 1 H, J=7.9 Hz), 7.72 (d, 1 H, 7.5 Hz), 7.86-7.91 (m, 1 H), 8.00-8-04 (m, 1H), 8.18 (s, 1 H), 8.40 (bs, 1 H), 8.48 (s, 1 H), 9.80 (s, 1 H), 10.08 (s, 1 H); m/z 357.2 [(M+H)$^+$, calcd for C$_{18}$H$_{14}$ClFN$_4$O 356.1].

Example 48

N-(3-(6-(4-(trifluoromethoxy)phenylamino)pyrazin-2-yl)phenyl)acetamide, CJS 393

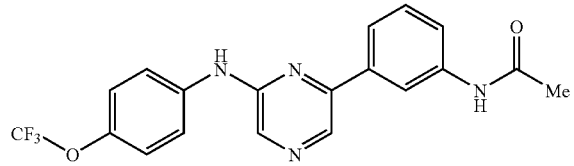

Using Method K, 2-(3-acetamidophenyl)-6-chloropyrazine (4a) (60 mg, 0.24 mmol), 4-(trifluoromethoxy)aniline (51 mg, 0.29 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 80° C. for 12 hours. The same workup as for Method K and a combination of column chromatography and preparative TLC furnished 19 mg of title compound. Yield: 20.4%. $^1$H NMR (250 MHz, DMSO-d$_6$) δ 2.10 (s, 3 H), 7.34-7.47 (m, 3 H), 7.60 (d, 1 H, 7.9 Hz), 7.74 (d, 1 H, 7.8 Hz), 8.00 (d, 2 H, 9.1 Hz), 8.21 (s, 1 H), 8.51 (bs, 2 H), 9.82 (s, 1 H), 10.10 (s, 1 H); $^{13}$C NMR (62.9 MHZ, DMSO-d$_6$) δ 24.09, 117.01, 119.09, 119.87, 120.94, 121.68, 129.15, 130.40, 133.52, 136.73, 139.92, 141.96, 141.99, 147.66, 151.00, 168.45; m/z 389.3 [(M+H)$^+$, calcd for C$_{19}$H$_{15}$F$_3$N$_4$O$_2$ 388.1].

Example 49

N-(3-(6-(2,4-dimethoxyphenylamino)pyrazin-2-yl) phenyl)acetamide, CJS 394

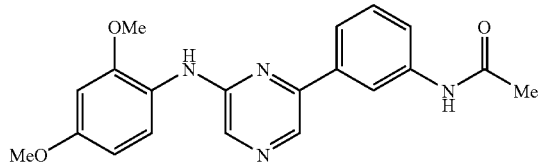

Method L. In a tube for parallel synthesis provided with stirring and an argon atmosphere, 2-(3-acetamidophenyl)-6-chloropyrazine (4a) (60 mg, 0.24 mmol), 1,3-dimethoxyaniline (53.6 mg, 0.35 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 85° C. for 16 hours. When the tube cooled down the solvent was evaporated under vacuo. The resulting solid was washed with 20 mL hot ethyl acetate and filtered. The volume was reduced to 2 mL. This mixture was chromatographied in silica gel using ethyl acetate as eluent to furnish 61 mg of a mixture of two products. Preparative TLC using ethyl acetate as eluent and crystallisation in chloroform afforded 11.9 mg of title compound. Yield: 13.6%. $^1$H NMR (250 MHz, DMSO-d$_6$) δ 2.08 (s, 3 H), 3.77 (s, 3 H), 3.85 (s, 3 H), 6.59 (dd, 1 H, Ja=8.9 Hz, Jb=2.7H), 6.68 (d, 1 H, J=2.6 Hz), 7.40 (t, 1 H, J=7.9 Hz), 7.65 (t, 2 H, J=9.27 Hz), 8.08 (d, 1 H, 8.8 Hz), 8.19 (s, 1 H), 8.29 (bs, 1 H), 8.32 (s, 1 H), 8.55 (s, 1 H), 10.07 (s, 1 H); m/z 365.1 [(M+H)$^+$, calcd for C$_{20}$H$_{20}$N$_4$O$_3$ 364.1].

Example 50

N-(3-(6-(3-(oxazol-5-yl)phenylamino)pyrazin-2-yl)phenyl)acetamide, CJS 407

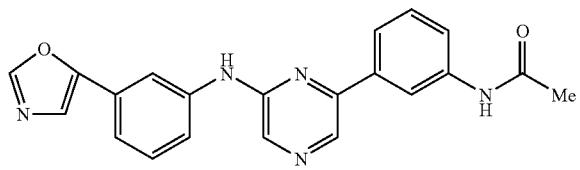

Using Method L, 2-(3-acetamidophenyl)-6-chloropyrazine (4a) (60 mg, 0.24 mmol), 3-(1,3-oxazol-5-yl)aniline (56.1 mg, 0.35 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 85° C. for 16 hours. The same workup as for Method L and a combination of column chromatography and preparative TLC afforded 23 mg of pure title compound. Yield: 25.8%. $^1$H NMR (250 MHz, DMSO-d$_6$) δ 2.08 (s, 3H), 7.36 (d, 1H, 8.0 Hz), 7.48 (t, 2H, 8.3 Hz), 7.61 (s, 1 H), 7.65 (d, 1 H, 8.4 Hz), 7.82 (d, 2 H, 7.3 Hz), 8.23 (s, 1 H), 8.39 (bs, 2 H), 8.46 (s, 1 H), 8.47 (s, 1 H), 9.82 (s, 1 H), 10.09 (s, 1 H); $^{13}$C NMR (62.9 MHZ, DMSO-d$_6$) δ 24.0, 113.4, 117.1, 117.3, 118.3, 120.3, 121.3, 121.8, 127.9, 129.3, 129.8, 130.3, 133.7, 137.0, 139.9, 141.4, 147.9, 150.8, 151.3, 151.7, 168.5; m/z 372.2 [(M+H)$^+$, calcd for C$_{21}$H$_{17}$N$_5$O$_2$ 371.1].

Example 51

N-(3-(6-(3,4-dihydro-2H-benzo[b][1,4]dioxepin-7-ylamino)pyrazin-2-yl)phenyl)acetamide, CJS 408

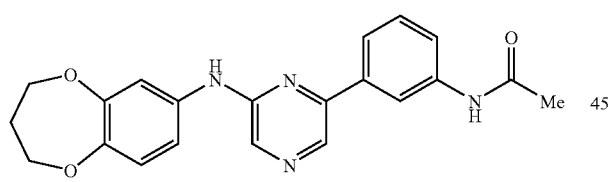

Using Method L. 2-(3-acetamidophenyl)-6-chloropyrazine (4a) (60 mg, 0.24 mmol), 3,4-dihydro-2H-1,5-benzodioxepin-7-aniline (57.8 mg, 0.35 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 85° C. for 16 hours. The same workup as for Method L and a combination of column chromatography and preparative TLC afforded 33 mg of title compound. Yield: 36.5%. $^1$H NMR (250 MHz, DMSO-d$_6$) δ 2.09 (bs, 5H), 4.00-4.13 (m, 4H), 6.98 (d, 1 H, 8.7 Hz), 7.33 (d, 1 H, 2.7 Hz), 7.43 (t, 1 H, 7.9 Hz), 7.54 (dd, 1 H, 8.7 Hz, 2.6 Hz), 7.62 (bd, 1 H, 6.8 Hz), 7.70 (bd, 1 H, 7.9 Hz), 8.12 (s, 1 H), 8.35 (bs, 1 H), 8.38 (s, 1 H), 9.47 (s, 1 H), 10.08 (s, 1 H); ); $^{13}$C NMR (62.9 MHZ, DMSO-d$_6$) δ 24.06, 31.99, 70.61, 111.53, 113.48, 117.21, 120.01, 121.08, 121.69, 129.21, 129.75, 133.29, 136.24, 137.10, 139.89, 145.73, 147.92, 151.17, 151.40, 168.42; m/z 377.2 [(M+H)$^+$, calcd for C$_{21}$H$_{20}$N$_4$O$_3$ 376.2].

Example 52

N-(3-(6-(4-(morpholinosulfonyl)phenylamino)pyrazin-2-yl)phenyl)acetamide, CJS 409

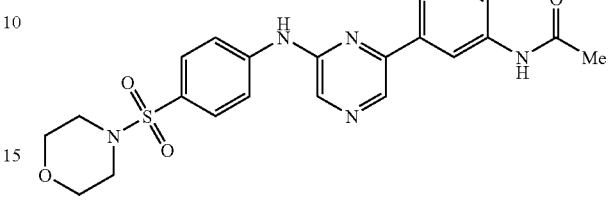

Using Method L, 2-(3-acetamidophenyl)-6-chloropyrazine (4a) (60 mg, 0.24 mmol), 4-(morpholinosulfonyl) aniline (84.8 mg, 0.35 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 85° C. and kept for 16 hours. The same workup as for Method L followed by column chromatography afforded 34 mg of title compound. Yield: 31.2%. $^1$H NMR (250 MHz, DMSO-d$_6$) δ 2.11 (s, 3 H), 2.86-2.89 (m, 4 H), 3.62-3.65 (m, 4 H), 7.45 (t, 1 H, 7.8 Hz), 7.54 (d, 1 H, 8.1 Hz), 7.73-7.80 (m, 3 H), 8.14 (d, 2 H, 8.9 Hz), 8.28 (s, 1 H), 8.57 (bs, 1 H), 8.61 (s, 1 H), 10.13 (s, 1 H), 10.18 (s, 1 H); $^{13}$C NMR (62.9 MHZ, DMSO-d$_6$) δ 24.19, 45.90, 65.28, 117.09, 117.50, 120.06, 121.09, 125.43, 129.22, 129.33, 131.54, 134.02, 136.56, 140.07, 145.24, 147.83, 150.66, 168.57; m/z 454.2 [(M+H)$^+$, calcd for C$_{22}$H$_{23}$N$_5$O$_4$S 453.2].

Example 53

N-(3-(6-(2,6-dichloropyridin-4-ylamino)pyrazin-2-yl)phenyl)acetamide, CJS 410

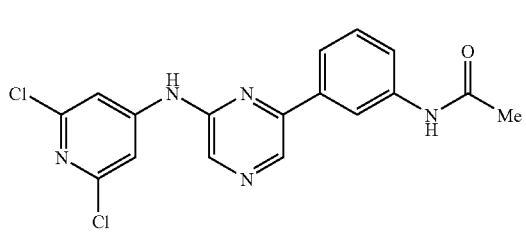

Using Method L, 2-(3-acetamidophenyl)-6-chloropyrazine (4a) (60 mg, 0.24 mmol), 2,6-dichloropyridin-4-amine (57.1 mg, 0.35 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 85° C. for 16 hours. The same workup as for Method L followed by preparative TLC afforded 7 mg of title compound. Yield: 7.8%. $^1$H NMR (250 MHz, DMSO-d$_6$) δ 2.08 (s, 3 H), 7.48 (t, 1 H, 7.9 Hz), 7.65 (d, 1 H, 8.0 Hz), 7.71 (d, 1 H, 7.6 Hz), 7.85 (s, 2 H), 8.30 (s, 1 H), 8.32 (bs, 1 H), 8.66 (s, 1 H), 10.10 (s, 1 H), 10.55 (s, 1 H); $^{13}$C NMR (62.9 MHZ, DMSO-d$_6$) δ 23.9, 110.3, 117.47, 120.6, 121.2, 129.4, 133.4, 134.2, 136.3, 140.0, 148.3, 149.5, 149.7, 151.4, 168.3; m/z 374.1 [(M+H)+, calcd for $C_{17}H_{13}Cl_2N_5O$ 373.0].

Example 54

N-(3-(6-(3-oxo-1,3-dihydroisobenzofuran-5-ylamino)pyrazin-2-yl)phenyl) acetamide, CJS 411

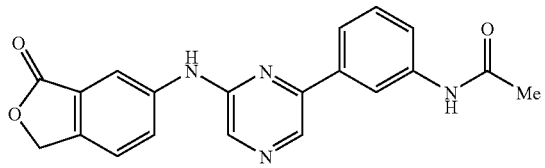

Using Method L, 2-(3-acetamidophenyl)-6-chloropyrazine (4a) (60 mg, 0.24 mmol), 6-amino-1,3-dihydroisobenzofuran-1-one (52.2 mg, 0.35 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 85° C. for 16 hours. The same workup as for Method L was followed by washing of the resulting solid with dichloromethane (30 mL) and filtration. The insoluble solid was then washed with acetone (60 mL). The acetone was evaporated under vacuo and the resulting solid was crystallised in cold dimethylformamide: dichloromethane mixtures to give 22.7 mg of title compound. Yield: 26.2%. $^1$H NMR (250 MHz, DMSO-d$_6$) δ 2.09 (s, 3 H), 5.39 (s, 2 H), 7.45 (t, 1 H, 8.0 Hz), 7.62-7.69 (m, 2 H), 7.76 (d, 1 H, 7.9 Hz), 8.23 (s, 1 H), 8.24-8.29 (m, 2 H), 8.39 (bs, 1 H), 8.50 (s, 1 H), 9.99 (s, 1 H), 10.06 (s, 1 H); $^{13}$C NMR (62.9 MHZ, DMSO-d$_6$) δ 24.05, 69.78, 112.78, 117.31, 120.16, 121.13, 123.36, 124.58, 125.59, 129.29, 130.73, 133.63, 136.83, 139.71, 139.94, 141.47, 147.88, 151.05, 168.47, 170.75; m/z 361.2 [(M+H)+, calcd for $C_{20}H_{16}N_4O_3$ 360.1].

Example 55

N-(3-(6-(4-tert-butylthiazol-2-ylamino)pyrazin-2-yl)phenyl)acetamide, CJS 413

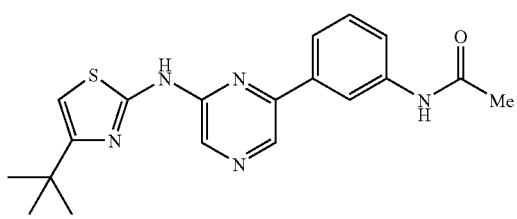

Following Method L, 2-(3-acetamidophenyl)-6-chloropyrazine (4a) (60 mg, 0.24 mmol), 4-(tert-butyl)-1,3-thiazol-2-amine (54.7 mg, 0.35 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 85° C. for 16 hours. The same workup as is Method L produced a solid that was washed with 50 mL dichloromethane and filtered. The dichloromethane slowly evaporated to produce white crystals that were removed by filtration and washing with dichloromethane (10 mL). The dichloromethane was then evaporated and the resulting crude was chromatographed in silica gel using ethyl acetate: dichloromethane, 2:1, as eluent to furnish 18.5 mg of title compound. Yield: 21.0%. $^1$H NMR (250 MHz, DMSO-d$_6$) δ 1.30 (s, 9H), 2.10 (s, 3 H), 6.69 (s, 1 H), 7.47 (t, 1 H, 7.9 Hz), 7.69 (d, 1 H, 8.0 Hz), 7.89 (d, 1 H, 7.8 Hz), 8.38 (s, 1 H), 8.45 (bs, 1 H), 8.58 (s, 1 H), 10.11 (s, 1 H), 11.78 (bs, 1 H);
$^{13}$C NMR (62.9 MHZ, DMSO-d$_6$) δ 24.05, 29.80, 34.12, 103.13, 117.42, 120.48, 121.54, 129.30, 131.54, 133.28, 136.40, 139.92, 147.95, 158.12, 160.43, 168.46; m/z 368.2 [(M+H)+, calcd for $C_{19}H_{21}N_5OS$ 367.1].

Example 56

N-(3-(6-(2,2,3,3-tetrafluoro-2,3-dihydrobenzo[b][1,4]dioxin-6-ylamino) pyrazin-2-yl)phenyl)acetamide, CJS 415

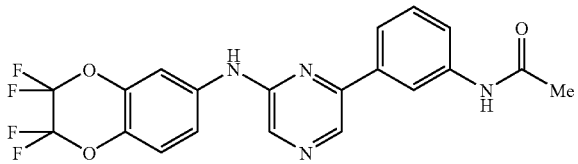

Following Method L, 2-(3-acetamidophenyl)-6-chloropyrazine (4a) (60 mg, 0.24 mmol), 2,2,3,3-tetrafluoro-6-amino-1,4-benzodioxene (78.1 mg, 0.35 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 85° C. for 16 hours. Evaporation under vacuo followed. The resulting solid was washed with 50 mL dichloromethane and filtered. The insoluble solid was dissolved in 3 mL of hot ethyl acetate. When this mixture was allowed to cool down in the freezer some crystals appeared. Filtration and washing with 2 mL of cold ethyl acetate gave 10.8 mg of the title compound. Yield: 10.4%. $^1$H NMR (250 MHz, DMSO-d$_6$) δ 2.08 (s, 3 H), 7.44 (d, 1 H, J=9.1 Hz), 7.47 (d, 1 H, J=7.8 Hz), 7.59 (bd, 1 H, J=7.6 Hz), 7.704-7.759 (m, 2 H), 7.96 (d, 1 H, 2.4 Hz), 8.21 (s, 1 H), 8.45 (bs, 1 H), 8.51 (s, 1 H), 9.95 (s, 1 H), 10.10 (s, 1 H); $^{13}$C NMR (62.9 MHZ, DMSO-d$_6$) δ 24.00, 106.13, 115.92, 117.34, 118.01, 120.13, 121.08, 129.31, 130.04, 130.98, 133.62, 136.16, 136.79, 139.03, 139.99, 147.90, 150.84, 168.40; m/z 435.1 [(M+H)+, calcd for $C_{20}H_{14}F_4N_4O_3$ 434.1].

Example 57

N-(3-(6-(2,2-difluorobenzo[d][1,3]dioxol-5-ylamino) pyrazin-2-yl)phenyl)acetamide, CJS 416

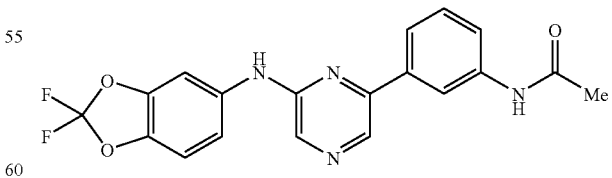

Following Method L, 2-(3-acetamidophenyl)-6-chloropyrazine (4a) (60 mg, 0.24 mmol), 5-amino-2,2-difluoro-1,3-benzodioxene (60.6 mg, 0.35 mmol), Pd(0)$_2$ dba$_3$ (9 mg, 0.01 mmol), BINAP (50 mg, 0.04 mmol), sodium tert-butoxide (33 mg, 0.34 mmol) and toluene (5 mL) were reacted at 85° C. for 16 hours. The solvent was evaporated under vacuo. The resulting crude was washed with dichloromethane (50 mL) and filtered. The liquid was collected and the volume reduced to 2 mL under vacuo. Five drops of cyclohexane were added and the content was cooled down in the fridger overnight. The resulting precipitate was collected by filtration and washed with cold dichloromethane: cyclohexane mixtures to provide 6 mg of title compound. Yield: 5.8%. $^1$H NMR (250 MHz, DMSO-d$_6$) δ 2.09 (s, 3 H), 7.37 (d, 1 H, 8.8 Hz), 7.44 (t, 7.9 Hz), 7.57-7.65 (m, 2 H), 7.70 (d, 1 H, 7.7 Hz), 7.94 (d, 1 H, 2.1 Hz), 8.20 (s, 1 H), 8.40 (bs, 1 H), 8.45 (s, 1 H), 9.88 (s, 1 H), 10.12 (s, 1 H);

$^{13}$C NMR (62.9 MHZ, DMSO-d$_6$) δ 24.00, 110.06, 113.48, 117.09, 119.91, 121.00, 129.20, 130.44, 133.49, 136.83, 136.95, 137.51, 139.91, 142.76, 147.81, 151.05, 168.38; m/z 385.1 [(M+H)$^+$, calcd for C$_{19}$H$_{14}$F$_2$N$_4$O$_3$ 384.1].

Example 58

N-(3-(6-(phenylamino)pyrazin-2-yl)phenyl)acetamide, CJS 438

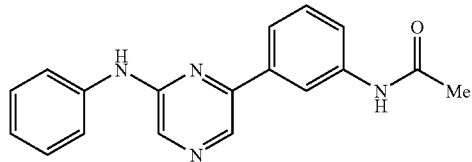

Method M. In a round-bottomed flask provided with stirring and an argon atmosphere, 2-(3-acetamidophenyl)-6-chloropyrazine (4a) (100 mg, 0.404 mmol), aniline (54 mg, 0.581 mmol), potassium tert-butoxide (68 mg, 0.605 mmol), 1,3-bis(2,6-di-1-propylphenyl)-4,5-dihydroimidazolium tetrafluoroborate, (19 mg, 0.0404 mmol), Pd(0)$_2$ dba$_3$ (18.5 mg, 0.0202 mmol) and dry dioxane (2.5 mL) were reacted at 95° C. for 3.5 hours. The solvent was evaporated under vacuo to yield a solid that was submitted to column chromatography using ethyl acetate as eluent to produce 32 mg of title compound. Yield: 26%. $^1$H NMR (250 MHz, DMSO-d$_6$) δ 2.11 (s, 3 H), 6.99 (t, 1 H, J=7.4 Hz), 7.33-7.49 (m, 3H), 7.62 (d, 1 H, J=7.9 Hz), 7.73 (d, 1 H, J=7.9 Hz), 7.87 (d, 1 H, J=7.6 Hz), 8.19 (s, 1 H), 8.44 (s, 1 H), 8.46 (bs, 1 H), 9.60 (s, 1 H), 10.10 (s, 1 H); $^{13}$C NMR (62.9 MHZ, DMSO-d$_6$) δ 24.11, 117.12, 118.21, 119.93, 121.04, 121.30, 128.91, 129.20, 129.96, 133.54, 137.05, 139.97, 140.66, 147.87, 151.46, 168.46; m/z 305.1 [(M+H)$^+$, calcd for C$_{18}$H$_{16}$N$_4$O 304.1].

Example 59

6-(naphthalen-1-yl)-N-(3,4,5-trimethoxyphenyl)pyrazin-2-amine, CJS 439

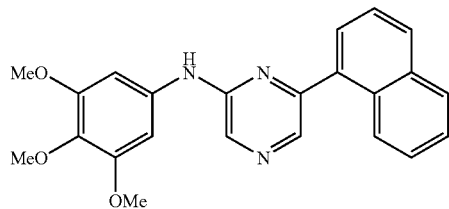

Method N. In a tube suitable for microwave irradiation provided with stirring, 2-(3,4,5-trimethoxyphenylamino)-6-chloropyrazine (2a) (150 mg, 0.507 mmol). 1-naphthylboronic acid (105 mg, 0.609 mmol), [1,1'-bis(diphenylphos-phino) ferrocene]dichloropalladium(II), complex with dichloromethane (1:1), (23 mg, 0.0286 mmol), ethylene glycol dimethyl ether (4 mL), sodium carbonate (250 mg, 2.36 mmol) and water (0.70 mL) were reacted at 100° C. for 30 minutes with microwave heating. The content of the reaction was passed through a very short silica-gel column to remove the palladium catalyst and everything was washed with 15 mL of ethyl acetate. The solvent was removed by vacuo and this gave 256 mg of a crude that was dissolved in a mixture of cyclohexane:ethanol (4:1), filtered and upon crystallisation produced 44 mg of the title compound. Yield: 22.4%. $^1$H NMR (250 MHz, DMSO-d$_6$) δ 3.52 (s, 6H), 3.56 (s, 3 H), 7.16 (s, 2 H), 7.54-7.59 (m, 2 H), 7.63 (d, 1 H, J=7.2 Hz), 7.72 (d, 1 H, J=7.1 Hz), 8.00-8.06 (m, 2 H), 8.20 (s, 1 H), 8.26-8.30 (m, 2 H), 9.65 (s, 1 H); $^{13}$C NMR (62.9 MHZ, DMSO-d$_6$) δ 55.36, 60.05, 96.15, 125.26, 125.39, 125.99, 126.66, 127.51, 128.44, 129.23, 130.50, 132.08, 133.21, 133.50, 135.20, 136.79, 150.10, 151.26, 152.73; m/z 388.2 [(M+H)$^+$, calcd for C$_{23}$H$_{21}$N$_3$O$_3$ 387.2].

Example 60

6-(naphthalen-2-yl)-N-(3,4,5-trimethoxyphenyl)pyrazin-2-amine, CJS 440

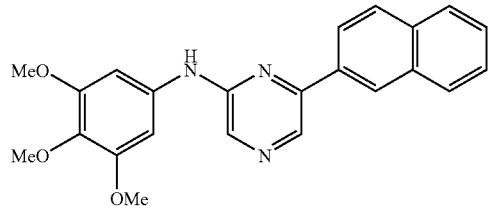

Using Method N, but using 2-naphthylboronic acid as the corresponding boronic acid, a crude was obtained after microwave irradiation and removal of the palladium catalyst. Column chromatography of the resulting crude (eluent dichloromethane: ethyl acetate; 2:1) generated 28 mg of the title compound. Yield: 14.4%. $^1$H NMR (250 MHz, DMSO-d$_6$) δ 3.65 (s, 3 H), 3.87 (s, 6H), 7.32 (s, 2 H), 7.56-7.60 (m, 2 H), 8.05 (d, 1 H, J=8.6 Hz), 8.20 (s, 1 H), 8.27 (d, 1 H, J=8.4 Hz), 8.68 (s, 1 H), 8.70 (bs, 1 H), 9.63 (s, 1 H); $^{13}$C NMR (62.9 MHZ, DMSO-d$_6$) δ 55.60, 60.14, 95.84, 123.96, 125.80, 126.73, 126.91, 127.65, 128.31, 128.39, 130.31, 132.06, 132.99, 133.35, 133.70, 134.08, 136.91, 147.63, 151.54, 152.85; m/z 388.2 [(M+H)$^+$, calcd for C$_{23}$H$_{21}$N$_3$O$_3$ 387.2].

Example 61

N-(3-(6-(3-methoxyphenylamino)pyrazin-2-yl)phenyl)acetamide, CJS 442

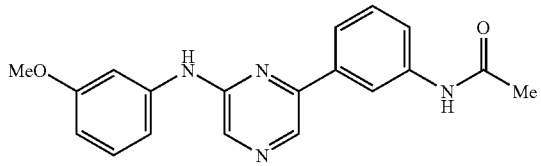

Method O. In a tube suitable for microwave irradiation provided with stirring and an argon atmosphere, 2-(3-acetamidophenyl)-6-chloropyrazine (150 mg, 0.61 mmol), m-anisidine (107.4 mg, 0.87 mmol), tris(dibenzylideneacetone)dipalladium (0) (28 mg, 0.030 mmol), 1,3-bis(2,6-di-I-propylphenyl)-4,5-dihydro-imidazolium tetrafluoroborate (29 mg, 0.061 mmol), potassium tert-butoxide (102 mg, 0.91 mmol) and dioxane (3.5 mL) were reacted at 100° C. for 30 minutes with microwave heating. The reaction crude was passed through a very short silica gel column (3-5 g silica), which was thoroughly washed with ethyl acetate (40 mL). The solvents were evaporated under vacuo and the resulting crude was chromatographied in silica gel using ethyl acetate as solvent to give 24 mg of product. Yield: 11.8%. $^1$H NMR (250 MHz, DMSO-$d_6$) δ 2.08 (s, 3 H), 3.77 (s, 3 H), 6.56 (d, 1 H, J=7.4 Hz), 7.25 (t, 1 H, J=8.1 Hz), 7.38-7.47 (m, 2 H), 7.56 (bs, 1 H), 7.65 (d, 1 H, J=7.8 Hz), 7.73 (d, 1 H, J=9.5 Hz), 8.20 (s, 1 H), 8.33 (bs, 1 H), 8.42 (s, 1 H), 9.61 (s, 1 H), 10.09 (s, 1 H); $^{13}$C NMR (62.9 MHZ, DMSO-$d_6$) δ 24.02, 54.78, 103.29, 107.48, 110.59, 117.26, 120.13, 121.21, 129.22, 129.65, 130.09, 133.66, 137.15, 139.88, 141.91, 147.98, 151.46, 159.67, 168.43; m/z 335.0 [(M+H)$^+$, calcd for $C_{19}H_{18}N_4O_2$ 334.1].

Example 62

N-(4-chloropyridin-2-yl)acetamide

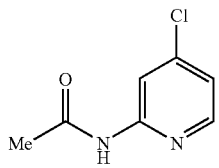

Method P. In a round-bottomed flask provided with stirring, 2-amino-4-chloropyridine (0.234 g, 1.83 mmol), acetic anhydride (2.5 mL) and triethylamine (1.00 g, 9.88 mmol) were reacted at 60° C. for 3 hours. The liquid was evaporated under powerful vacuo to give a black solid. Column chromatography using a mixture of dichloromethane and ethyl acetate (8:1) produced the title compound (0.220 g). Yield: 70.6%. $^1$H NMR (250 MHz, DMSO-$d_6$) δ 2.10 (s, 3 H), 7.22 (dd, 1 H, Ja=2.0 Hz, Jb=5.4 Hz), 8.16 (d, 1 H, J=1.9 Hz), 8.29 (d, 1 H, J=5.4 Hz), 10.74 (s, 1 H); $^{13}$C NMR (62.9 MHZ, DMSO-$d_6$) δ 23.88, 112.69, 119.18, 143.86, 149.36, 153.17, 169.75; m/z 171.0 [(M+H)$^+$, calcd for $C_7H_7N_2O$ 170.0].

Example 63

2-(3,4,5-trimethoxyphenylamino)-6-($N_3$-3-phenyl-$N_1$-3-phenylureyl)pyrazine, CJS 457

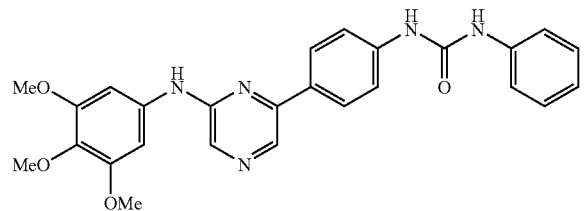

Method Q. CJS 366 (0.14 mmol) and 17 µL (0.15 mmol) phenylisocyanate in 5 mL DCM were stirred for 20 hours at 40° C. The urea precipitated and 26 mg (38.8%) pure title compound was obtained. $^1$H-NMR (DMSO), δ (ppm), J (Hz): 3.65 (s, 3H, $CH_3O_{(4')}$), 3.85 (s, 6H, $CH_3O_{(3'+5')}$), 7.00 (t, 1H, $H_{arom\ 5'}$, J=7.20), 7.27 (s, 2H, $H_{arom(2'+6')}$), 7.32 (d, 2H, 2$H_{phenyl}$, J=7.53), 7.48 (d, 2H, $H_{phenyl}$), 7.60 (d, 2H, $H_{arom\ 3''+5'''}$, J=8.69), 8.08 (d, 2H, $H_{arom\ 2''+6''}$) 8.11 (s, 1H, $H_{P5}$), 8.48 (s, 1H, $H_{P3}$), 8.75 (s, 1H, $NH_{urea}$), 8.92 (s, 1H, $NH_{urea}$), 9.58 (s, 1H, $NH_{amine}$); MS, ($C_{26}H_{25}N_5O_4$), m/z: 472.2 [M$^+$+H],−100.

Example 64

2-(3,4,5-trimethoxyphenylamino)-6-($N_3$-4-chloro-3-trifluorophenyl-$N_1$-3-phenylureyl) pyrazine, CJS 459

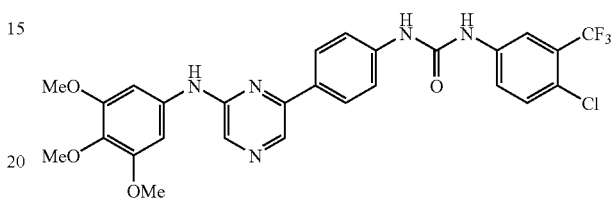

Using Method Q, 50 mg (0.14 mmol) of CJS 366 and 33 mg (0.15 mmol) 3-trifluoromethyl-4-chlorophenylisocyanate were stirred in 5 mL DCM for 20 hours at 40° C. The urea precipitated and 60 mg (74.8%) pure title compound was obtained. $^1$H-NMR (DMSO), δ (ppm), J (Hz): 3.65 (s, 3H, $CH_3O_{(4')}$), 3.84 (s, 6H, $CH_3O_{(3'+5')}$), 7.26 (s, 2H, $H_{arom(2'+6')}$), 7.58-7.70 (m, 4H, 2$H_{phenyl}$+$H_{arom\ 3''+5''}$), 8.08-8.16 (m, 3H, 1$H_{phenyl}$+$H_{arom2''+6''}$), 8.11 (s, 1H, $H_{P5}$), 8.49 (s, 1H, $H_{P3}$), 9.12 (s, 1H, $NH_{urea}$), 9.24 (s, 1H, $NH_{urea}$), 9.54 (s, 1H, $NH_{amine}$); MS, ($C_{27}H_{23}ClF_3N_5O_4$), m/z: 573.8 [M$^+$+H], 100.

Example 65

N-(3-(6-(4-morpholinophenylamino)pyrazin-2-yl)phenyl)acetamide, CJS 441

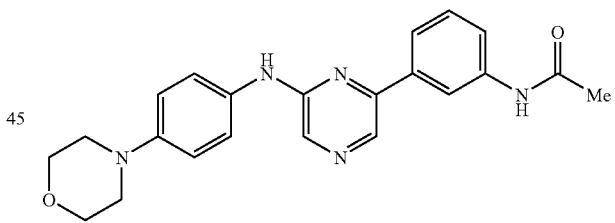

Using Method O, 2-(3-acetamidophenyl)-6-chloropyrazine (150 mg, 0.61 mmol), 4-morpholinoaniline (155.4 mg, 0.87 mmol), tris(dibenzylideneacetone) dipalladium (0) (28 mg, 0.030 mmol), 1,3-bis(2,6-di-1-propylphenyl)-4,5-dihydro-imidazolium tetrafluoroborate (29 mg, 0.061 mmol), potassium tert-butoxide (102 mg, 0.91 mmol), and dioxane (3.5 mL) were reacted at 100° C. for 30 minutes with microwave heating. The reaction crude was passed through a short silica gel column (2 g silica), which was thoroughly washed with ethyl acetate. The last fractions of this column were collected to give 9 mg of pure title compound. The first fractions were collected, the solvent was evaporated under vacuo and the resulting solid was crystallised in ethyl acetate to produce 61 mg of the title compound. Yield: 29.8%. $^1$H NMR (250 MHz, DMSO-$d_6$) δ 2.09 (s, 3 H), 3.03-3.07 (bt, 4 H), 3.72-3.76 (bt, 4 H), 6.97 (d, 2 H, J=9.0 Hz), 7.42 (t, 1 H, J=7.9 Hz), 7.65-7.68 (m, 2 H), 7.70 (d, 2H, J=8.9 Hz), 8.11 (s;

1 H), 8.33 (bs, 2 H), 9.36 (s, 1 H), 10.09 (s, 1 H); $^{13}$C NMR (62.9 MHZ, DMSO-d$_6$) δ 24.11, 49.24, 66.16, 116.01, 117.08, 119.61, 119.89, 121.08, 129.16, 133.03, 133.15, 137.23, 139.87, 146.10, 147.95, 151.70, 168.45; m/z 390.2 [(M+H)$^+$, calcd for C$_{22}$H$_{23}$N$_5$O$_2$ 389.2].

Example 66

N-(3-(6-(3-hydroxyphenylamino)pyrazin-2-yl)phenyl)acetamide, CJS 444

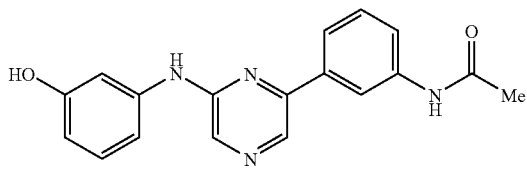

Using Method O, but replacing 4-morpholinoaniline by 3-hydroxyaniline (95 mg, 0.87 mmol) and adding 50 mg of tris(dibenzylideneacetone) dipalladium (0) instead of 28 mg. The reaction crude was passed through a very short silica gel column (2 g silica), which was thoroughly washed with ethyl acetate. The relevant fractions of this short column were collected to give 158 mg of the title compound. Yield: 80%. m/z 321.0 [(M+H)$^+$, calcd for C$_{18}$H$_{16}$N$_4$O$_2$ 320.1].

Example 67

N-(3-(6-(2-methoxyphenylamino)pyrazin-2-yl)phenyl)acetamide, CJS 446

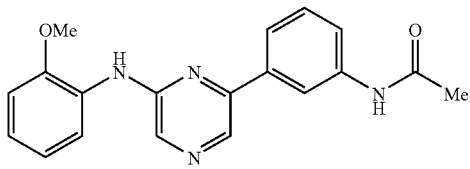

Using Method O, but replacing 4-morpholinoaniline by o-anisidine (107 mg, 0.87 mmol). The reaction crude was passed through a very short silica gel column (2-3 g silica), which was thoroughly washed with ethyl acetate. The relevant fractions of this short column were collected to give 8.3 mg of the title compound. Yield: 4%. m/z 335.1 [(M+H)$^+$, calcd for C$_{19}$H$_{18}$N$_4$O$_2$ 334.1].

Example 68

N-(4-(6-(3,4,5-trimethoxyphenylamino)pyrazin-2-ylamino)phenyl)acetamide, CJS 447

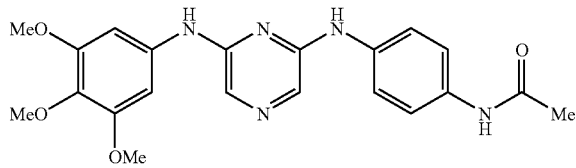

Method R. In a tube suitable for microwave irradiation provided with stirring and an argon atmosphere, 2-(3,4,5-trimethoxyphenylamino)-6-chloropyrazine, (2a) (150 mg, 0.51 mmol), 4-aminoacetanilide (114 mg, 0.76 mmol), tris(dibenzylideneacetone) dipalladium (0) (23 mg, 0.025 mmol), 1,3-bis(2,6-di-i-propylphenyl)-4,5-dihydro-imidazolium tetrafluoroborate (24 mg, 0.051 mmol) and potassium tert-butoxide (114 mg, 0.91 mmol), and dioxane (3.5 mL) were reacted at 100° C. for 30 minutes with microwave heating. The reaction content was filtered and the insoluble solid was thoroughly washed with boiling ethyl acetate (40 mL). This mixture was evaporated under vacuo and the resulting solid was chromatographied in silica gel using ethyl acetate as eluent to produce 86 mg of title compound. Yield: 29.8%. $^1$H NMR (250 MHz, DMSO-d$_6$) δ 2.01 (s, 3 H), 3.62 (s, 3 H), 3.63 (s, 6 H), 6.85 (s, 2 H), 7.40-7.52 (m, 6 H), 9.01 (s, 1 H), 9.04 (s, 1 H), 9.80 (s, 1 H);
$^{13}$C NMR (62.9 MHZ, DMSO-d$_6$) δ 23.82, 55.60, 60.13, 97.01, 119.17, 119.57, 121.33, 121.68, 132.23, 133.28, 136.07, 136.89, 150.22, 152.64, 167.70; m/z 410.2 [(M+H)$^+$, calcd for C$_{21}$H$_{23}$N$_5$O$_4$ 409.2].

Example 69

N$^2$-phenyl-N$^6$-(3,4,5-trimethoxyphenyl)pyrazine-2,6-diamine, CJS 448

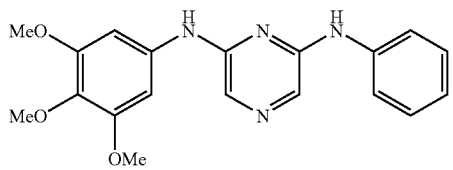

Using Method R, but replacing 4-aminoacetanilide with aniline (71 mg, 0.76 mmol). The reaction content was evaporated under vacuo and the resulting solid was chromatographied using a mixture of ethyl acetate and dichloromethane (7:3) as eluent to furnish 63 mg of the title compound. Yield: 35.2%. $^1$H NMR (250 MHz, DMSO-d$_6$) δ 3.62 (s, 3H), 3.63 (s, 6H), 6.86 (s, 2 H), 6.91 (t, 1 H, J=7.3 Hz), 7.22 (t, 2 H, J=9.4 Hz), 7.53 (s, 1 H), 7.54 (s, 1 H), 7.57 (d, 2 H, J=7.6 Hz), 9.05 (s, 1 H), 9.14 (s, 1 H); $^{13}$C NMR (62.9 MHZ, DMSO-d$_6$) δ 55.60, 60.11, 97.01, 118.59, 121.00, 121.87, 121.92, 128.65, 132.26, 136.85, 140.86, 150.00, 150.17, 152.84; m/z 353.1 [(M+H)$^+$, calcd for C$_{19}$H$_{20}$N$_4$O$_3$ 352.1].

Example 70

N-(3-(6-(3,4,5-trimethoxyphenylamino)pyrazin-2-ylamino)phenyl)acetamide, CJS 449

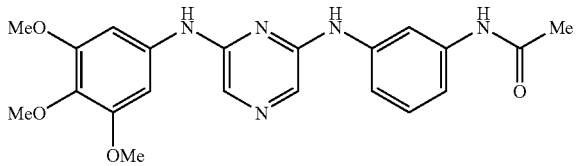

Using Method R, but replacing 4-aminoacetanilide with 3-aminoacetanilide (114 mg, 0.76 mmol). Workup: When the tube cooled down more tris(dibenzylideneacetone) dipalladium (0) (40 mg), 1,3-bis(2,6-di-i-propylphenyl)-4,5-dihydro-imidazolium tetrafluoroborate (50 mg) and potassium tert-butoxide (300 mg) were added to drive the reaction to completion. Microwave heating followed for 30 more minutes. The reaction content was passed through 2 g of silica gel and this column was washed with 40 mL of ethyl acetate. This liquid was evaporated under vacuo and the resulting solid was subsequently purified by a combination of chromatography and preparative TLC always using ethyl acetate as eluent. This procedure produced 12 mg of pure title compound. Yield: 6%. $^1$H NMR (250 MHz, DMSO-$d_6$) δ 2.01 (s, 3 H), 3.61 (s, 3 H), 3.62 (s, 6 H), 6.88 (s, 2 H), 7.04 (d, 1 H, J=8.4 Hz), 7.11 (t, 1 H, J=7.9 Hz), 7.50 (d, 1 H, J=7.9 Hz), 7.53 (s, 1 H), 7.56 (s, 1 H), 7.67 (bs, 1 H), 9.05 (s, 1 H), 9.13 (s, 1 H), 9.81 (s, 1 H); $^{13}$C NMR (62.9 MHZ, DMSO-$d_6$) δ 23.98, 55.58, 60.10, 96.74, 109.169, 112.22, 113.55, 121.87, 122.04, 128.74, 132.14, 136.92, 139.68, 141.08, 149.99, 150.18, 152.64, 168.15; m/z 410.1 [(M+H)$^+$, calcd for $C_{21}H_{23}N_5O_4$ 409.2].

Example 71

N$^1$-{4-[2-(3,4,5-trimethoxyphenylamino)-6-pyrazinyl]-phenyl}-N$^3$-(3,5-dimethyl-isoxazol-4-yl)-urea, CJS 466

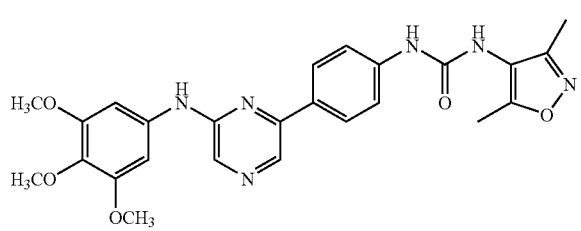

Using Method Q, 60 mg (0.17 mmol) CJS 366 and 26.3 mg (0.19 mmol) 3,5-dimethyl-isoxazol-4-yl isocyanate dissolved in 5 mL DCM were stirred for 24 hours under argon at 40° C. The precipitate formed was filtered and washed with DCM, giving 64.2 mg (77.0%) of title compound. $^1$H-NMR (DMSO), δ (ppm), J (Hz): 2.14 (s, 3H, 5-CH$_3$), 2.31 (s, 3H, 3-CH$_3$), 3.65 (s, 3H, CH$_3$O$_{4'}$), 3.84 (s, 6H, CH$_3$O$_{3'+5'}$), 7.25 (s, 2H, H$_{arom\ 2'+6'}$), 7.59 (d, 2H, H$_{arom\ 3''+5''}$, J=8.69), 7.79 (s, 1H, NH$_{het}$), 8.06 (d, 2H, H$_{arom\ 2''+6''}$), 8.10 (s, 1H, H$_{P5}$), 8.47 (s, 1H, H$_{P3}$), 9.07 (s, 1H, NH$_{Phe}$), 9.52 (s, 1H, NH$_{amino}$); MS, (C$_{25}$H$_{26}$N$_6$O$_5$), m/z: 491.2 [M$^+$+1], 100.

Example 72

N$^1$-{4-[2-(3,4,5-trimethoxyphenylamino)-6-pyrazinyl]-phenyl}-N$^3$-(2,6-dichloro-pyrid-4-yl)-urea, CJS 467

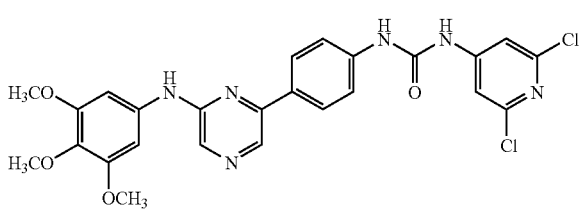

Using Method Q, with 60 mg (0.17 mmol) CJS 366 and 35.9 mg (0.19 mmol) 2,6-pyrid-4-yl isocyanate, 62.5 mg (74.9%) of title compound were obtained. $^1$H-NMR (DMSO), δ (ppm), J (Hz): 3.65 (s, 3H, CH$_3$O$_{4'}$), 3.84 (s, 6H, CH$_3$O$_{3'+5'}$), 7.26 (s, 2H, H$_{arom\ 2'+6'}$), 7.59 (s, 2H, H$_{Pyr3''+5''}$), 7.62 (d, 2H, H$_{arom\ 3''+''5}$, J=8.46), 8.11 (d, 2H, H$_{arom\ 2''+6''}$), 8.12 (s, 1H, H$_{P5}$), 8.50 (s, 1H, H$_{P3}$), 9.40 (s, 1H, NH$_{Phe}$), 9.54 (s, 1H, NH$_{amino}$), 9.62 (s, 1H, NH$_{Pyr}$); MS, (C$_{25}$H$_{22}$Cl$_2$N$_6$O$_4$), m/z: 541.1 [M$^+$+1], 100.

Example 73

N$^1$-{4-[2-(3,4,5-trimethoxyphenylamino)-6-pyrazinyl]-phenyl}-N$^3$-(2-thiophenyl)-urea, CJS 468

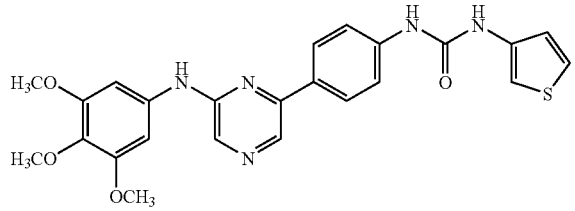

Using Method Q, with 60 mg (0.17 mmol) CJS 366 and 23.8 mg (0.19 mmol) 2-thiophenyl isocyanate, 62.3 mg (74.7%) of title compound were obtained. $^1$H-NMR (DMSO), δ (ppm), J (Hz): 3.65 (s, 3H, CH$_3$O$_{4'}$), 3.85 (s, 6H, CH$_3$O$_{3'+5'}$), 6.59-6.61 (m, 1H, H$_{Thio\ 5''}$), 6.81-6.92 (m, 2H, H$_{Thio\ 4''+3''}$), 7.26 (s, 2H, H$_{arom\ 2'+6'}$), 7.61 (d, 2H, H$_{arom\ 3''+5'''}$, J=8.74), 8.08 (d, 2H, H$_{arom\ 2''+6''}$), 8.11 (s, 1H, H$_{P5}$), 8.49 (s, 1H, H$_{P3}$), 8.98 (s, 1H, NH$_{Phe}$), 9.53 (s, 1H, NH$_{amino}$), 9.70 (s, 1H, NH$_{Thio}$); MS, (C$_{24}$H$_{23}$N$_5$O$_4$S), m/z: 478.1 [M$^+$+1], 100.

Example 74

N$^1$-{4-[2-(3,4,5-trimethoxyphenylamino)-6-pyrazinyl]-phenyl}-N$^3$-(2-fluorophenyl)-urea, CJS 469

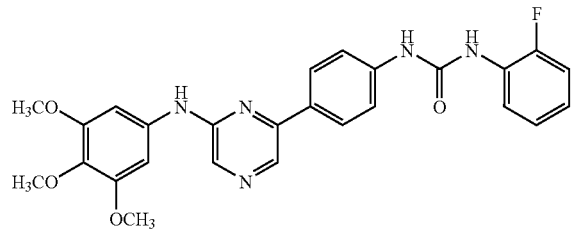

Using Method Q, with 60 mg (0.17 mmol) CJS 366 and 26.0 mg (0.19 mmol) 2-fluorophenyl isocyanate, 50.9 mg (61.0%) of title compound were obtained. $^1$H-NMR (DMSO), δ (ppm), J (Hz): 3.65 (s, 3H, CH$_3$O$_{4'}$), 3.85 (s, 6H, CH$_3$O$_{3'+5'}$), 7.05-7.30 (m, 2H, H$_{F-Phe\ 3''+4''}$), 7.27 (s, 2H, H$_{arom\ 2'+6'}$), 7.61 (d, 2H, H$_{arom\ 3''+5'''}$, J=8.78), 8.10 (d, 2H, H$_{arom\ 2''+6''}$), 8.11 (s, 1H, H$_{P5}$), 8.13-8.21 (m, 2H, H$_{F-Phe\ 5''+6''}$), 8.49 (s, 1H, H$_{P3}$), 8.62 (s, 1H, NH$_{F-Phe}$), 9.31 (s, 1H, NH$_{Phe}$), 9.53 (s, 1H, NH$_{amino}$); MS, (C$_{26}$H$_{24}$FN$_5$O$_4$), m/z: 490.1 [M$^+$+1], 100.

Example 75

N$^1$-{4-[2-(3,4,5-trimethoxyphenylamino)-6-pyrazinyl]-phenyl}-N$^3$-(3-fluorophenyl)-urea, CJS 470

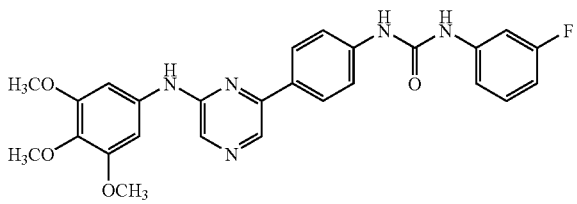

Using Method Q, with 60 mg (0.17 mmol) CJS 366 and 26.0 mg (0.19 mmol) 3-fluorophenyl isocyanate, 56.3 mg (67.5%) of title compound were obtained. $^1$H-NMR (DMSO), δ (ppm), J (Hz): 3.65 (s, 3H, CH$_3$O$_{4'}$), 3.85 (s, 6H, CH$_3$O$_{3'+5'}$), 6.77-6.85 (m, 1H, H$_{F-Phe\ 5'''}$), 7.15 (d, 1H, H$_{F-Phe\ 5'''}$, J=9.02), 7.26 (s, 2H, H$_{arom\ 2'+6'}$), 7.28-7.38 (m, 1H, H$_{F-Phe\ 4'''}$), 7.48-7.55 (m, 1H, H$_{F-Phe\ 2'''}$, J$_{HF}$=11.93), 7.61 (d, 2H, H$_{arom\ 3''+5''}$, J=8.78), 8.09 (d, 2H, H$_{arom\ 2''+6''}$), 8.11 (s, 1H, H$_{P5}$), 8.49 (s, 1H, H$_{P3}$), 8.62 (s, 1H, NH$_{F-Phe}$), 8.99 (s, 1H, NH$_{Phe}$), 9.53 (s, 1H, NH$_{amino}$); MS, (C$_{26}$H$_{24}$FN$_5$O$_4$), m/z: 490.1 [M$^+$+1], 100.

Example 76

N$^1$-{4-[2-(3,4,5-trimethoxyphenylamino)-6-pyrazinyl]-phenyl}-N$^3$-(4-fluorophenyl)-urea, CJS 471

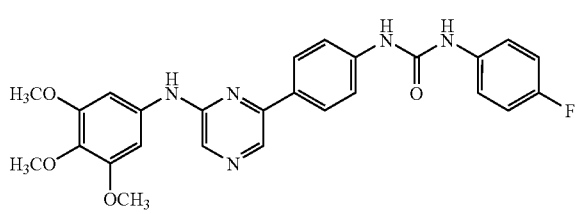

Using Method Q, with 60 mg (0.17 mmol) CJS 366 and 26.0 mg (0.19 mmol) 4-fluorophenyl isocyanate, 47.8 mg (57.3%) of title compound were obtained. $^1$H-NMR (DMSO), δ (ppm), J (Hz): 3.65 (s, 3H, CH$_3$O$_{4'}$), 3.84 (s, 6H, CH$_3$O$_{3'+5'}$), 7.10-7.20 (m, 2H, H$_{F-Phe\ 3'''+5'''}$, J=8.88), 7.26 (s, 2H, H$_{arom\ 2'+6'}$), 7.45-7.52 (m, 2H, H$_{F-Phe\ 2'''+6'''}$), 7.60 (d, 2H, H$_{arom\ 3''+5''}$, J=8.75), 8.08 (d, 2H, H$_{arom\ 2''+6''}$), 8.11 (s, 1H, H$_{P5}$), 8.48 (s, 1H, H$_{P3}$), 8.77 (s, 1H, NH$_{F-Phe}$), 8.92 (s, 1H, NH$_{Phe}$), 9.52 (s, 1H, NH$_{amino}$); MS, (C$_{26}$H$_{24}$FN$_5$O$_4$), m/z: 490.1 [M$^+$+1], 100.

Example 77

N$^1$-{4-[2-(3,4,5-trimethoxyphenylamino)-6-pyrazinyl]-phenyl}-N$^3$-(3-chlorophenyl)-urea, CJS 472

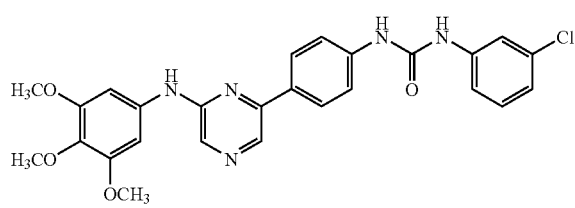

Using Method Q, with 60 mg (0.17 mmol) CJS 366 and 23.2 mg (0.19 mmol) 3-chlorophenyl isocyanate, 57.3 mg (68.7%) of title compound were obtained. $^1$H-NMR (DMSO), δ (ppm), J (Hz): 3.65 (s, 3H, CH$_3$O$_{4'}$), 3.85 (s, 6H, CH$_3$O$_{3'+5'}$), 7.03-7.07 (m, 1H, H$_{Cl-Phe\ 4'''}$), 7.26 (s, 2H, H$_{arom\ 2'+6'}$), 7.26-7.36 (m, 2H, H$_{Cl-Phe\ 5'''+6'''}$), 7.61 (d, 2H, H$_{arom\ 3''+5''}$, J=8.65), 7.74 (s, 1H, H$_{Cl-Phe\ 2'''}$) 8.09 (d, 2H, H$_{arom\ 2''+6''}$), 8.11 (s, 1H, H$_{P5}$), 8.48 (s, 1H, H$_{P3}$), 8.95 (s, 1H, NH$_{Cl-Phe}$), 9.00 (s, 1H, NH$_{Phe}$), 9.52 (s, 1H, NH$_{amino}$); MS, (C$_{26}$H$_{24}$ClN$_5$O$_4$), m/z: 506.1 [M$^+$+1], 100.

Example 78

N$^1$-{4-[2-(3,4,5-trimethoxyphenylamino)-6-pyrazinyl]-phenyl}-N$^3$-(4-chlorophenyl)-urea, CJS 473

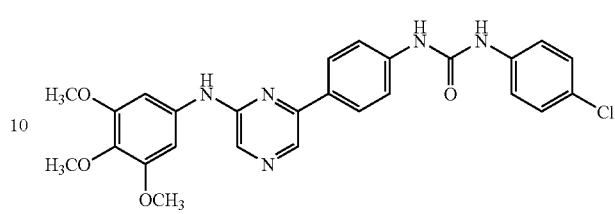

Using Method Q, with 60 mg (0.17 mmol) CJS 366 and 23.2 mg (0.19 mmol) 4-chlorophenyl isocyanate, 55.4 mg (66.4%) of title compound were obtained. $^1$H-NMR (DMSO), δ (ppm), J (Hz): 3.65 (s, 3H, CH$_3$O$_{4'}$), 3.84 (s, 6H, CH$_3$O$_{3'+5'}$), 7.26 (s, 2H, H$_{arom\ 2'+6'}$), 7.35 (d, 2H, H$_{Cl-Phe\ 3'''+5'''}$, J=8.83), 7.52 (d, 2H, H$_{Cl-Phe\ 2'''+6'''}$), 7.60 (d, 2H, H$_{arom\ 3''+5''}$, J=8.80), 8.08 (d, 2H, H$_{arom\ 2''+6''}$), 8.11 (s, 1H, H$_{P5}$), 8.48 (s, 1H, H$_{P3}$), 8.88 (s, 1H, NH$_{Cl-Phe}$), 8.96 (s, 1H, NH$_{Phe}$), 9.52 (s, 1H, NH$_{amino}$); MS, (C$_{26}$H$_{24}$ClN$_5$O$_4$), m/z: 506.1 [M$^+$+1], 100.

Example 79

N$^1$-{4-[2-(3,4,5-trimethoxyphenylamino)-6-pyrazinyl]-phenyl}-N$^3$-(3-trifluoromethyl-phenyl)-urea, CJS 474

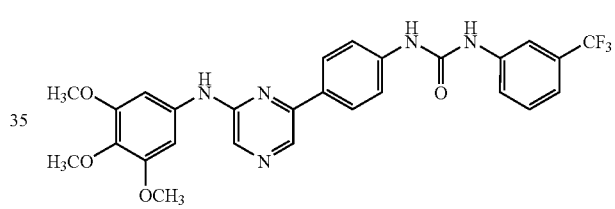

Using Method Q, with 60 mg (0.17 mmol) CJS 366 and 35.6 mg (0.19 mmol) 3-trifluoromethyl-phenyl isocyanate, 55.3 mg (66.3%) of title compound were obtained.

$^1$H-NMR (DMSO), δ (ppm), J (Hz): 3.65 (s, 3H, CH$_3$O$_{4'}$), 3.84 (s, 6H, CH$_3$O$_{3'+5'}$), 7.26 (s, 2H, H$_{arom\ 2'+6'}$), 7.34 (d, 2H, H$_{CF3-Phe\ 4'''\ or\ 6'''}$), 7.50-7.60 (m, 2H, H$_{CF3-Phe\ 5'''+4'''\ or\ 6'''}$), 7.62 (d, 2H, H$_{arom\ 3''+5''}$, J=8.83), 8.05 (s, 1H, H$_{CF3-Phe\ 2'''}$), 8.10 (d, 2H, H$_{arom\ 2''+6''}$), 8.11 (s, 1H, H$_{P5}$), 8.49 (s, 1H, H$_{P3}$), 9.05 (s, 1H, NH$_{CF3-Phe}$), 9.12 (s, 1H, NH$_{Phe}$), 9.53 (s, 1H, NH$_{amino}$); MS, (C$_{27}$H$_{24}$F$_3$N$_5$O$_4$), m/z: 540.1 [M$^+$+1], 100.

Example 80

N$^1$-{4-[2-(3,4,5-trimethoxyphenylamino)-6-pyrazinyl]-phenyl}-N$^3$-(4-trifluoromethyl-phenyl)-urea, CJS 475

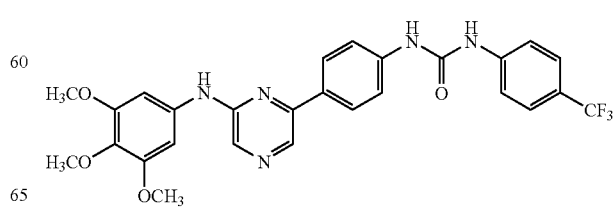

Using Method Q, with 60 mg (0.17 mmol) CJS 366 and 35.6 mg (0.19 mmol) 4-trifluoromethyl-phenyl isocyanate, 62.9 mg (75.4%) of title compound were obtained.

$^1$H-NMR (DMSO), δ (ppm), J (Hz): 3.65 (s, 3H, CH$_3$O$_{4'}$), 3.84 (s, 6H, CH$_3$O$_{3'+5'}$), 7.27 (s, 2H, H$_{arom\ 2'+6'}$), 7.60-7.72 (m, 6H, H$_{CF3\text{-}Phe\ 4'''+3'''+5'''+6'''}$+H$_{arom\ 3''+5''}$), 8.10 (d, 2H, H$_{arom\ 2''+6''}$, J=9.51), 8.11 (s, 1H, H$_{P5}$), 8.49 (s, 1H, H$_{P3}$), 9.09 (s, 1H, NH$_{Phe}$), 9.20 (s, 1H, NH$_{CF3\text{-}Phe}$), 9.53 (s, 1H, NH$_{amino}$); MS, (C$_{27}$H$_{24}$F$_3$N$_5$O$_4$), m/z: 540.1 [M$^+$+1], 100.

Example 81

N$^1$-{4-[2-(3,4,5-trimethoxyphenylamino)-6-pyrazinyl]-phenyl}-N$^3$-(3,4-difluorophenyl)-urea, CJS 476

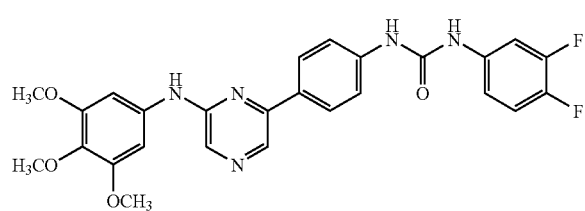

Using Method Q, with 60 mg (0.17 mmol) CJS 366 and 29.5 mg (0.19 mmol) 3,4-difluorophenyl isocyanate, 48.4 mg (58.0%) of title compound were obtained. $^1$H-NMR (DMSO), δ (ppm), J (Hz): 3.65 (s, 3H, CH$_3$O$_{4'}$), 3.84 (s, 6H, CH$_3$O$_{3'+5'}$), 7.14-7.19 (m, 1H, H$_{F\text{-}Phe\ 6'''}$), 7.27 (s, 2H, H$_{arom\ 2'+6'}$), 7.31-7.42 (m, 1H, H$_{F\text{-}Phe\ 5'''}$), 7.60 (d, 2H, H$_{arom\ 3''+5''}$, J=8.76), 8.02-8.08 (m, 1H, H$_{F\text{-}Phe\ 6'''}$), 8.10 (d, 2H, H$_{arom\ 2''+6''}$), 8.12 (s, 1H, H$_{P5}$), 8.49 (s, 1H, H$_{P3}$), 8.82 (s, 1H, NH$_{F\text{-}Phe}$), 9.38 (s, 1H, NH$_{Phe}$), 9.54 (s, 1H, NH$_{amino}$); MS, (C$_{26}$H$_{23}$F$_2$N$_5$O$_4$), m/z: 508.1 [M$^+$+1], 100.

Example 82

N$^1$-{4-[2-(3,4,5-trimethoxyphenylamino)-6-pyrazinyl]-phenyl}-N$^3$-(2,5-difluorophenyl)-urea, CJS 477

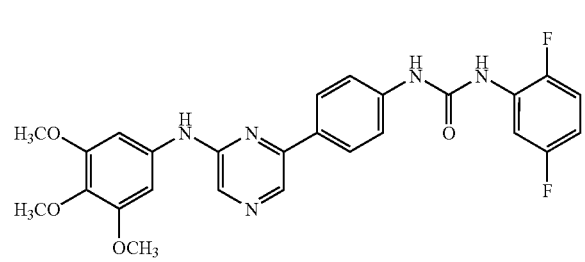

Using Method Q, with 60 mg (0.17 mmol) CJS 366 and 29.5 mg (0.19 mmol) 2,5-difluorophenyl isocyanate, 60.5 mg (72.6%) of title compound were obtained. $^1$H-NMR (DMSO), δ (ppm), J (Hz): 3.65 (s, 3H, CH$_3$O$_{4'}$), 3.84 (s, 6H, CH$_3$O$_{3'+5'}$), 6.81-6.89 (m, 1H, H$_{F\text{-}Phe\ 4'''}$), 7.26 (s, 2H, H$_{arom\ 2'+6'}$), 7.28-7.37 (m, 1H, H$_{F\text{-}Phe\ 3'''}$), 7.60 (d, 2H, H$_{arom\ 3''+5''}$, J=8.42), 7.64-7.74 (m, 1H, H$_{F\text{-}Phe\ 2'''}$), 8.08 (d, 2H, H$_{arom\ 2''+6''}$), 8.11 (s, 1H, H$_{P5}$), 8.49 (s, 1H, H$_{P3}$), 8.96 (s, 1H, NH$_{CF3\text{-}Phe}$), 9.00 (s, 1H, NH$_{Phe}$), 9.53 (s, 1H, NH$_{amino}$); MS, (C$_{26}$H$_{23}$F$_2$N$_5$O$_4$), m/z: 508.1 [M$^+$+1], 100.

Example 83

4-[2-(3,4,5-trimethoxyphenylamino)]-6-(4-phenylcarbonylamino)-phenyl]-pyrazine, CJS 481

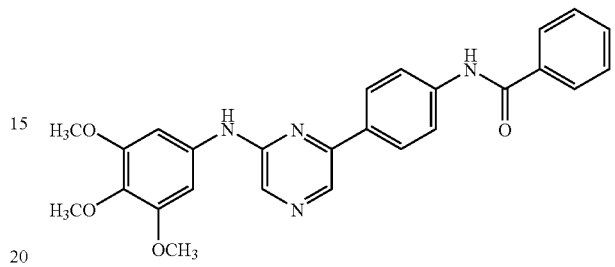

Method S. 50 mg (0.14 mmol) CJS 366, 33 mg (0.17 mmol) benzoyl chloride and 28 μL (0.20 mmol) triethylamine were refluxed under argon for 24 hours. The solvent was evaporated and the residue retaken in 10 mL AcOEt, washed with brine (2×10 mL) and evaporated under vacuum to a volume of 2 mL. This solution was subjected to flash chromatography (Isolute column, Sill, 10 g, 70 mL) and 53 mg (74.8%) of the title compound were obtained. $^1$H-NMR (DMSO), δ (ppm), J (Hz): 3.65 (s, 3H, CH$_3$O$_{4'}$), 3.84 (s, 6H, CH$_3$O$_{3'+5'}$), 7.26 (s, 2H, H$_{arom\ 2'+6'}$), 7.59-7.74 (m, 3H$_{Phe\ 3'''+5'''+(6'''\ or\ 2''')}$) 7.82 (t, 1H, H$_{Phe4'''}$), 7.89-8.01 (m, 3H, H$_{arom\ 3''+5''}$ and H$_{Phe\ 2'''\ or\ 6'''}$), 8.12 (s, 1H, H$_{P5}$), 8.15 (d, 2H, H$_{arom\ 2''+6''}$, J=8.46), 8.52 (s, 1H, H$_{P3}$), 9.55 (s, 1H, NH$_{amino}$), 10.44 (s, 1H, NH$_{amido}$); MS, (C$_{26}$H$_{24}$N$_4$O$_4$), m/z: 457.2 [M$^+$+1], 100.

Example 84

4-[2-(3,4,5-trimethoxyphenylamino)]-6-(4-phenyl sulphamidylamino-phenyl)-pyrazine, CJS 479

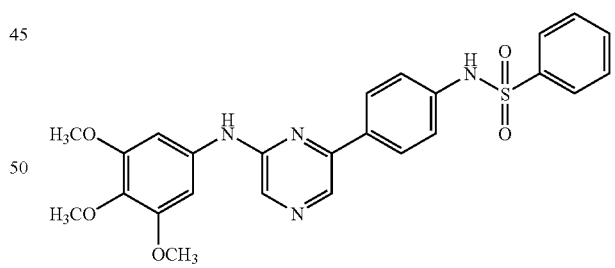

Method T. To 50 mg (0.14 mmol) CJS 366 dissolved in 5 mL DCM, were added under stirring and at room temperature, 30.0 mg (0.17 mmol) benzenesulphonyl chloride and 100 μL (0.17 mmol) pyridine. After 20 hours, the reaction mixture was evaporated to dryness, the residue retaken in 10 mL AcOEt, washed with brine (2×10 mL), dried (MgSO$_4$) and evaporated under vacuum. The residue was purified by flash chromatography (Isolute column, Flash Sill, 10 g, 70 mL) and 58.0 mg (84.1%) of the title compound were obtained. $^1$H-NMR (DMSO), δ (ppm), J (Hz): 3.64 (s, 3H, CH$_3$O$_{4'}$), 3.79 (s, 6H, CH$_3$O$_{3'+5'}$), 7.22 (d, 2H, H$_{arom\ 3''+5''}$, J=8.61), 7.24 (s, 2H, H$_{arom\ 2'+6'}$), 7.53-7.64 (m, 3H, $H_{Phe\ 3'''+4'''+5'''}$), 7.82 (d, 2H, $H_{Phe\ 2'''+6'''}$), 7.98 (d, 2H, $H_{arom\ 2''+6''}$, J=8.20), 8.11 (s, 1H, $H_{P5}$), 8.41 (s, 1H, $H_{P3}$), 9.53 (s, 1H, $NH_{amino}$), 10.56 (s, 1H, $NH_{sulphonamide}$); MS, ($C_{25}H_{24}N_4O_5S$), m/z: 493.1 [M$^+$+1], 100.

Example 85

4-[2-(3,4,5-trimethoxyphenylamino)]-6-(4-trifluorophenyl-sulphamidylamino-phenyl)-pyrazine, CJS 482

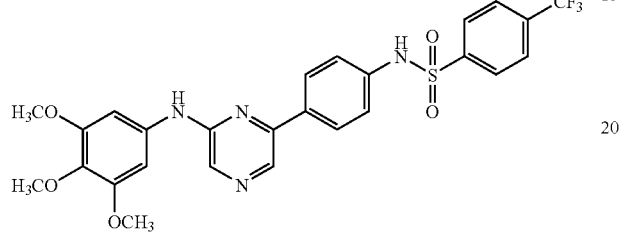

Using Method T with 60 mg (0.17 mmol) CJS 366 and 49.0 mg (0.20 mmol) 4-trifluoromethyl-phenylsulphonyl chloride, 70.0 mg (73.4%) of the title compound were obtained. $^1$H-NMR (DMSO), δ (ppm), J (Hz): 3.63 (s, 3H, $CH_3O_{4'}$), 3.78 (s, 6H, $CH_3O_{3'+5'}$), 7.19 (s, 2H, $H_{arom\ 2'+6'}$), 7.22 (d, 2H, $H_{arom\ 3''+5''}$), 7.95-8.02 (m, 6H, $H_{CF3arom}+H_{arom\ 3''+5''}$), 8.11 (s, 1H, $H_{P5}$), 8.42 (s, 1H, $H_{P3}$), 9.53 (s, 1H, $NH_{amino}$), 10.78 (s, 1H, $NH_{sulphonamide}$); MS, ($C_{26}H_{23}F_3N_4O_5S$), m/z: 561.1 [M$^+$+1], 100.

Example 86

4-[2-(3,4,5-trimethoxyphenylamino)]-6-(4-fluorophenyl-sulphamidylamino-phenyl)-pyrazine, CJS 483

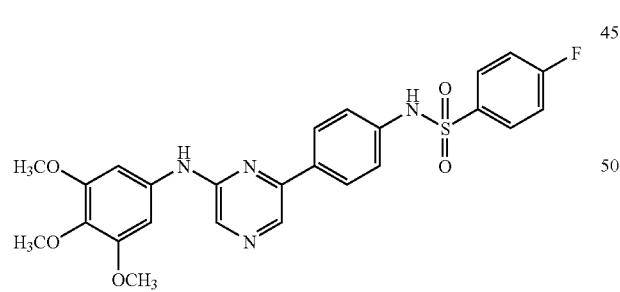

Using Method T with 60 mg (0.17 mmol) CJS 366 and 39.0 mg (0.20 mmol) 4-fluoromethyl-phenylsulphonyl chloride, 26.0 mg (30.0%) of the title compound were obtained. $^1$H-NMR (DMSO), δ (ppm), J (Hz): 3.64 (s, 3H, $CH_3O_{4'}$), 3.79 (s, 6H, $CH_3O_{3'+5'}$), 7.21 (s, 2H, $H_{arom\ 2'+6'}$), 7.22 (d, 2H, $H_{arom\ 3''+5''}$), 7.39-7.46 (m, 2H, $H_{FPhearom\ 3'''+5'''}$), 7.84-7.89 (m, 2H, $H_{FPhearom\ 2'''+6'''}$), 8.00 (d, 2H, $H_{arom\ 2''+6''}$, J=8.51), 8.11 (s, 1H, $H_{P5}$), 8.42 (s, 1H, $H_{P3}$), 9.54 (s, 1H, $NH_{amino}$), 10.58 (s, 1H, $NH_{sulphonamide}$); MS, ($C_{25}H_{23}FN_4O_5S$), m/z: 511.2 [M$^+$+1], 100.

Example 87

4-[2-(3,4,5-trimethoxyphenylamino)]-6-{[4-(4-chlorophenyl)-sulphamidylamino]-phenyl}-pyrazine, CJS 484

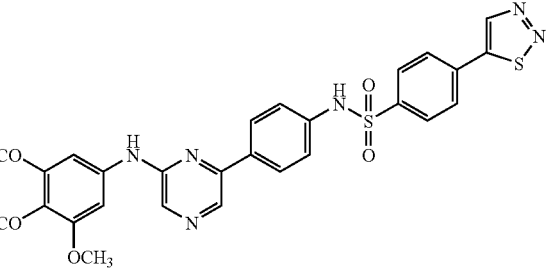

Using Method T with 60 mg (0.17 mmol) CJS 366 and 42.0 mg (0.20 mmol) 4-chlorophenyl-sulphonyl chloride, 67.0 mg (74.8%) of the title compound were obtained. $^1$H-NMR (DMSO), δ (ppm), J (Hz): 3.64 (s, 3H, $CH_3O_{4'}$), 3.80 (s, 6H, $CH_3O_{3'+5'}$), 7.13 (d, 2H, $H_{arom\ 3''+5''}$, J=8.65), 7.21 (s, 2H, $H_{arom\ 2'+6'}$), 7.61 (d, 2H, $H_{ClPhe\ 3'''+5'''}$, J=8.55), 7.79 (d, 2H, $H_{ClPhe\ 2'''+6'''}$), 7.94 (d, 2H, $H_{arom\ 2''+6''}$), 8.07 (s, 1H, $H_{P5}$), 8.39 (s, 1H, $H_{P3}$), 9.51 (s, 1H, $NH_{amino}$); MS, ($C_{25}H_{23}ClN_4O_5S$), m/z: 527.1 [M$^+$+1], 100.

Example 88

4-[2-(3,4,5-trimethoxyphenylamino)]-6-[4-(1,2,3-thiadiazol-4-yl) phenyl-sulphamidylamino-phenyl] pyrazine, CJS 486

Using Method T with 60 mg (0.17 mmol) CJS 366 and 52.0 mg (0.20 mmol) 4-(1,2,3-thiadiazol-4-yl)-phenylsulphonyl chloride, 73.0 mg (74.5%) of the title compound were obtained. $^1$H-NMR (DMSO), δ (ppm), J (Hz): 3.63 (s, 3H, $CH_3O_{4'}$), 3.78 (s, 6H, $CH_3O_{3'+5'}$), 7.20 (s, 2H, $H_{arom\ 2'+6'}$), 7.27 (d, 2H, $H_{arom\ 3''+5''}$, J=8.41), 7.98 (d, 2H, $H_{Phearom\ 3'''+5'''}$, J=7.87), 8.01 (d, 2H, $H_{Phearom\ 2'''+6'''}$), 8.10 (s, 1H, $H_{P5}$), 8.34 (d, 2H, $H_{arom\ 2''+6''}$), 8.41 (s, 1H, $H_{P3}$), 9.53 (s, 1H, $NH_{amino}$), 9.77 (s, 1H, $H_{Het}$), 10.66 (s, 1H, $NH_{sulphonamide}$); MS, ($C_{27}H_{24}N_6O_5S_2$), m/z: 577.2 [M$^+$+1], 100.

Example 89

4-[2-(3,4,5-trimethoxyphenylamino)]-6-[4-(1-methyl-1H-imidazolyl)-sulphamidylamino-phenyl] pyrazine, CJS 488

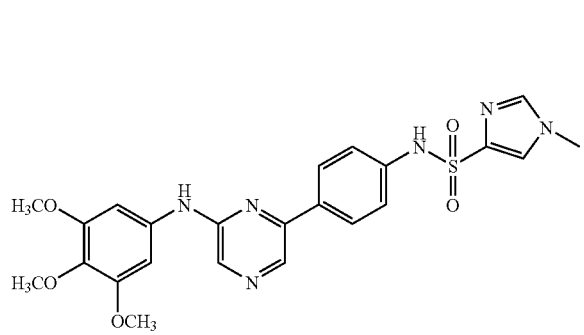

Using Method T with 60 mg (0.17 mmol) CJS 366 and 36.0 mg (0.20 mmol) 1-methyl-1H-imidazol-4-yl-sulphonyl chloride, 74.0 mg (87.7%) of the title compound were obtained.
$^1$H-NMR (DMSO), δ (ppm), J (Hz): 3.65 (s, 3H, $CH_3O_{4'}$), 3.67 (s, 3H, N—$CH_3$), 3.82 (s, 6H, $CH_3O_{3'+5'}$), 7.22 (s, 2H, $H_{arom\ 2'+6'}$), 7.27 (d, 2H, $H_{arom\ 3''+5''}$, J=8.59), 7.76 (s, 1H, $H_{Het}$), 7.92 (s, 1H, $H_{Het}$), 7.99 (d, 2H, $H_{arom\ 2''+6''}$), 8.10 (s, 1H, $H_{P5}$), 8.43 (s, 1H, $H_{P3}$), 9.53 (s, 1H, $NH_{amino}$), 10.49 (s, 1H, $NH_{sulphonamide}$); MS, ($C_{23}H_{24}N_6O_5S$), m/z: 497.2 [M$^+$+1], 100.

Example 90

4-[2-(3,4,5-trimethoxyphenylamino)]-6-[4-(5-chloro-1,3-dimethyl-1H-pyrazolyl)-sulphamidylamino-phenyl]-pyrazine, CJS 490

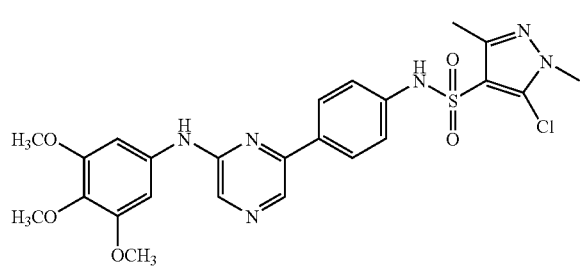

Using Method T with 60 mg (0.17 mmol) CJS 366 and 46.0 mg (0.20 mmol) 5-chloro-1,3-dimethyl-1H-pyrazole-4-sulphonyl chloride, 33.0 mg (35.6%) of the title compound were obtained. $^1$H-NMR (DMSO), δ (ppm), J (Hz): 2.28 (s, 3H, 3-$CH_3$) 3.62 (s, 3H, $CH_3O_{4'}$), 3.71 (s, 3H, N—$CH_3$), 3.81 (s, 6H, $CH_3O_{3'+5'}$), 7.21 (s, 2H, $H_{arom\ 2'+6'}$), 7.22 (d, 2H, $H_{arom\ 3''+5''}$, J=8.60), 7.99 (d, 2H, $H_{arom\ 2''+6''}$), 8.10 (s, 1H, $H_{P5}$), 8.43 (s, 1H, $H_{P3}$), 9.52 (s, 1H, $NH_{amino}$), 10.78 (s, 1H, $NH_{sulphonamide}$); MS, ($C_{24}H_{25}ClN_6O_5S$), m/z: 541.1 [M$^+$+1], 100.

Example 91

4-[2-(3,4,5-trimethoxyphenylamino)]-6-{[3-(6-morpholin-4-yl-pyridyl)-sulphamidylamino]-4-phenyl}pyrazine, CJS 491

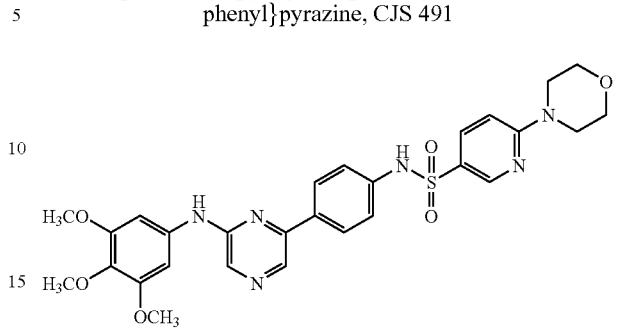

Using Method T with 60 mg (0.17 mmol) CJS 366 and 53.0 mg (0.20 mmol) 6-morpholin-4-yl-pyridyl-3-sulphonyl chloride, 78.0 mg (95.8%) of the title compound were obtained.
$^1$H-NMR (DMSO), δ (ppm), J (Hz): 3.56-3.64 (m, 8H, $H_{morpholin}$), 3.64 (s, 3H, $CH_3O_{4'}$), 3.80 (s, 6H, $CH_3O_{3'+5'}$), 6.90 (d, 1H, $H_{Pyr5'''}$, J=9.23), 7.21 (s, 2H, $H_{arom\ 2'+6'}$), 7.23 (d, 2H, $H_{arom\ 3''+5''}$), 7.76-7.81 (m, 1H, $H_{Pyr4'''}$), 8.00 (d, 2H, $H_{arom\ 2''+6''}$, J=8.50), 8.11 (s, 1H, $H_{P5}$), 8.42 (s, 1H, $H_{P3}$), 8.44-8.46 (m, 1H, $H_{Pyr5'''}$), 9.53 (s, 1H, $NH_{amino}$), 10.40 (s, 1H, $NH_{sulphonamide}$); MS, ($C_{28}H_{30}N_6O_6S$), m/z: 579.2 [M$^+$+1], 100.

Example 92

$N^2$-(pyridin-4-yl)-$N^6$-(3,4,5-trimethoxyphenyl)pyrazine-2,6-diamine, CJS 705

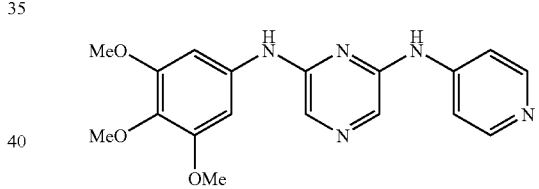

Using Method R, with 200 mg of 2-(3,4,5-trimethoxyphenylamino)-6-chloropyrazine (all amounts scaled accordingly) and 4-aminopyridine, 25 mg of title compound were obtained. Yield: 10%. $^1$H NMR (250 MHz, DMSO-$d_6$) δ 3.64 (s, 3 H), 3.68 (s, 6 H), 6.83 (s, 2 H), 7.55 (d, 2 H, J=6.3 Hz), 7.62 (s, 1 H), 7.69 (s, 1 H), 8.25 (d, 2 H, J=6.3 Hz), 9.23 (s, 1 H), 9.66 (s, 1 H). $^{13}$C NMR (62.5 MHz, DMSO-$d_6$) δ 55.66, 60.14, 97.52, 112.07, 122.57, 123.96, 132.67, 136.40, 147.39, 148.88, 149.83, 150.18, 152.93. m/z 354.2 [(M+H)$^+$ calcd for $C_{18}H_{19}N_5O_3$ 353.2].

Example 93

$N^2$-(3-fluorophenyl)-$N^6$-(3,4,5-trimethoxyphenyl)pyrazine-2,6-diamine, CJS 707

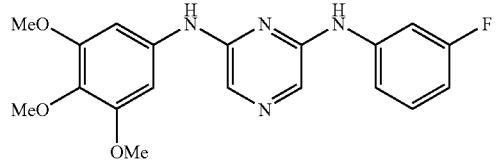

Using Method R, with 200 mg of 2-(3,4,5-trimethoxyphenylamino)-6-chloropyrazine (all amounts scaled accordingly) and 3-fluoroaniline, 60 mg of title compound were obtained. Yield: 23%. $^1$H NMR (250 MHz, DMSO-d$_6$) δ 3.62 (s, 3H), 3.65 (s, 6H), 6.65-6.72 (m, 1H), 6.81 (s, 2H), 7.24 (m, 2H), 7.56 (s, 1H), 7.58 (s, 1H), 7.67 (d, 1H, J=13.0 Hz), 9.12 (s, 1H), 9.41 (s, 1H). $^{13}$C NMR (62.5 MHz, DMSO-d$_6$) δ 55.45, 60.07, 97.24, 106.71, 107.05, 114.04, 122.16, 122.49, 130.14, 132.43, 136.55, 142.71, 142.89, 149.52, 150.10, 152.89.

Example 94

N$^2$-(4-fluorophenyl)-N$^6$-(3,4,5-trimethoxyphenyl)pyrazine-2,6-diamine, CJS 709

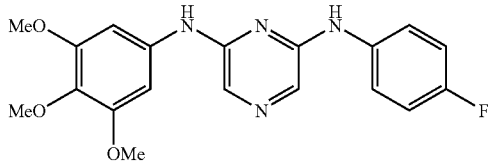

Using Method R, with 200 mg of 2-(3,4,5-trimethoxyphenylamino)-6-chloropyrazine (all amounts scaled accordingly) and 4-fluoroaniline, 72 mg of title compound were obtained. Yield: 28%. $^1$H NMR (250 MHz, DMSO-d$_6$) δ 3.62 (s, 9H), 6.83 (s, 2H), 7.06 (t, 2H, J=9.0 Hz), 7.51 (s, 1H), 7.57 (d, 2H, J=9.1 Hz), 9.05 (s, 1H), 9.14 (s, 1H). $^{13}$C NMR (62.5 MHz, DMSO-d$_6$) δ 55.56, 60.12, 97.01, 114.94, 115.29, 120.38, 120.50, 121.62, 121.83, 132.29, 137.19, 137.22, 150.15, 152.84. m/z 371.2 [(M+H)$^+$ calcd for C$_{19}$H$_{19}$FN$_4$O$_3$ 370.1].

Example 95 tert-butyl 2-(3-aminophenoxy)ethylcarbamate, CJS 700

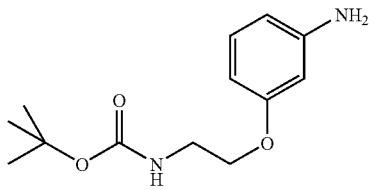

Method U. To a round-bottomed flask provided with an Argon atmosphere were added 3-aminophenol (600 mg, 5.48 mmol), potassium carbonate (380 mg, 2.76 mmol), potassium tert-butoxide (648 mg, 5.76 mmol) and dry DMF (8 mL). The reaction mixture was stirred for 10 minutes and a solution of 2-(Boc-amino) ethyl bromide (1.23 g, 5.50 mmol) in 6 mL of dry DMF was added dropwise and the temperature increased to 90° C. for 3 hours. To this solution was added a solution of sodium hydroxide (3.5 g) in water (100 mL). This mixture was extracted with ethyl acetate (40 mL×3 times). The organic layers were combined and dried with anhydrous magnesium sulphate, filtered and evaporated under powerful vacuo to produce a crude that was chromatographed using a mixture of ethyl acetate:dichloromethane (ratio 15:85) to furnish 713 mg of the title compound. Yield: 49%. $^1$H-NMR (250 MHz, DMSO-d$_6$) δ 1.38 (s, 9H), 3.24 (c, 2H, J=5.8 Hz), 3.33 (s, 1H), 3.82 (t, 2H, J=5.9), 5.02 (s, 2H), 6.06 (d, 1H, J=9.1 Hz), 6.12-6.16 (m, 2H), 6.88 (t, 1H, J=7.7 Hz), 6.95 (bt, 1H, J=5.2 Hz). $^{13}$C (62.5 MHz, DMSO-d$_6$) δ 28.19, 65.81, 77.70, 99.98, 101.90, 106.91, 129.49, 149.93, 155.64, 159.37.

Example 96 tert-butyl 2-(3-(6-(3-acetamidophenyl)pyrazin-2-ylamino)phenoxy)ethylcarbamate, CJS 702

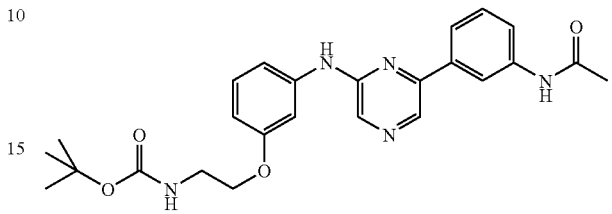

Using Method O, 2-(3-acetamidophenyl)-6-chloropyrazine (150 mg, 0.61 mmol), tert-butyl 2-(3-aminophenoxy)ethylcarbamate (CJS 700, 190 mg, 0.753 mmol), tris(dibenzylideneacetone) dipalladium (0) (28 mg, 0.030 mmol), 1,3-bis(2,6-di-i-propylphenyl)-4,5-dihydro-imidazolium tetrafluoroborate (29 mg, 0.061 mmol) and potassium tert-butoxide (102 mg, 0.91 mmol), and dioxane (3.5 mL) were reacted at 100° C. for 20 minutes with microwave heating. The reaction mixture was filtered and washed with ethyl acetate (45 mL). The resulting liquid was dried under vacuo to give a paste that was chromatographed using a mixture of ethyl acetate:dichloromethane (1:1) as eluent to furnish 120 mg of the title compound. Yield: 43%. $^1$H NMR (250 MHz, DMSO-d$_6$) δ 1.37 (s, 9H), 2.09 (s, 3H), 3.32 (m, 2H), 3.98 (m, 2H), 6.56 (dd, 1H, Ja=8.0 Hz, Jb=2.4 Hz), 7.01 (bt, 1H), 7.25 (t, 1H, J=8.1 Hz), 7.36 (bd, 1H, J=8.4 Hz), 7.45 (t, 1H, J=7.9 Hz), 7.59 (bs, 1H), 7.66 (bd, 1H, J=9.2 Hz), 7.74 (bd, 1H, J=8.0 Hz), 8.19 (s, 1H), 8.34 (bs, 1H), 8.42 (s, 1H), 9.60 (s, 1H), 10.09 (s, 1H). $^{13}$C NMR (62.5 MHz, DMSO-d$_6$) δ 23.99, 28.18, 66.23, 77.77, 103.95, 107.82, 110.74, 117.11, 120.07, 121.24, 129.24, 129.66, 130.08, 133.66, 137.10, 139.90, 141.88, 147.96, 151.44, 155.65, 158.87, 168.53. m/z 364.2 [(M-Boc+H)$^+$ calc for C$_{20}$H$_{21}$N$_5$O$_2$ 363.2].

Example 97

N-(3-(6-(3(2-aminoethoxy)phenylamino)pyrazin-2-yl)phenyl)acetamide, CJS 703

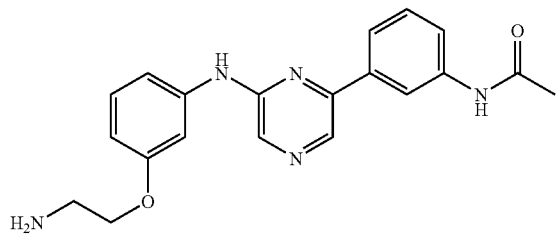

Method V. In a round-bottomed flask provided with stirring were placed tert-butyl 2-{3-[6-(3-acetamidophenyl)pyrazin-2-ylamino]phenoxy}ethylcarbamate (60 mg, 01294 mmol) and trifluoroacetic acid (2.5 mL) and this mixture was stirred for 3 hours. The TFA was evaporated under vacuo and triethylamine was added (250 mg). The resulting paste was chromatographed using initially a mixture of ethyl acetate and ethanol (85:15) and subsequently increasing the polarity of the eluent up to 50:50 to give 15 mg of the title compound.

Yield: 32%. $^1$H NMR (250 MHz, DMSO-d$_6$) δ 2.09 (s, 3 H), 2.90 (t, 2 H, J=5.5 Hz), 3.96 (t, 2 H, J=5.7 Hz), 6.56 (d, 1 H, J=8.0 Hz), 7.24 (t, 1 H, J=8.0 Hz), 7.34 (d, 1 H, J=6.8 Hz), 7.44 (t, 1 H, J=7.9 Hz), 7.64 (bs, 1 H), 7.66 (d, 1 H, J=9.0 Hz), 7.73 (d, 1 H, J=8.0 Hz), 8.20 (s, 1 H), 8.34 (bs, 1 H), 8.42 (s, 1 H), 9.64 (s, 1 H), 10.16 (s, 1 H). $^{13}$C NMR (62.5 MHz, DMSO-d$_6$) δ 23.98, 40.82, 69.56, 103.92, 107.96, 110.61, 117.24, 120.19, 121.26, 129.22, 129.61, 130.08, 133.68, 137.15, 139.90, 141.89, 147.98, 151.47, 159.08, 168.51. m/z 364.2 [(M+H)$^+$ calc for C$_{21}$H$_{20}$N$_5$O$_2$ 363.2].

Example 98

N-(4-hydroxy-naphthalen-1-yl)acetamide, CJS 704

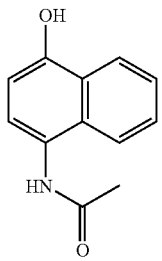

Method W. In a round-bottomed flask provided with stirring were mixed 4-amino-1-naphthol hydrochloride (1.00 g, 5.111 mmol), triethylamine (517 mg, 5.110 mmol) and acetic anhydride (522 mg, 5.111 mmol). The temperature was raised to 50° C. and maintained for 1 hour. When the reaction cooled down the solvent was evaporated under powerful vacuo and the resulting crude was chromatographed using a mixture of ethyl acetate and dichloromethane (1:3) as eluent to give 863 mg of title compound. Yield: 84%. $^1$H NMR (250 MHz, DMSO-d$_6$) δ 2.12 (s, 3H), 6.82 (d, 1 H, J=8.0 Hz), 7.30 (d, 1 H, J=8.0 Hz), 7.43-7.54 (m, 2 H), 7.88 (d, 1 H, J=7.7 Hz), 8.15 (d, 1 H, J=7.6 Hz), 9.61 (s, 1 H), 10.08 (s, 1 H). $^{13}$C NMR (62.5 MHz, DMSO-d$_6$) δ 23.11, 107.24, 122.22, 122.80, 123.60, 124.51, 124.67, 124.94, 125.94, 129.76, 151.15, 168.86. m/z 201.1 [(M+H)$^+$ calcd for C$_{12}$H$_{11}$NO$_2$ 201.1].

Example 99

2-(3,4,5-trimethoxyphenylamino)-6-(naphthalen-1-yloxy)pyrazine, CJS 706

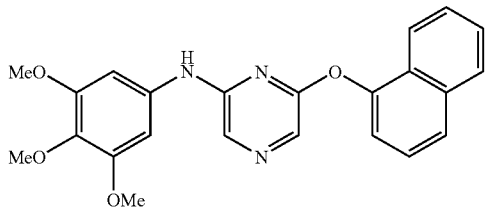

Method X. In a tube suitable for microwave irradiation provided with stirring and an argon atmosphere were placed 1-naphthol (73.1 mg, 0.5072 mmol), potassium carbonate (35 mg, 0.2536 mmol), potassium tert-butoxide (60 mg, 0.53.26 mmol), and dry dimethylformamide (3.5 mL). This mixture was stirred for 10 minutes and 2-(3,4,5-trimethoxyphenylamino)-6-chloropyrazine, (2a) (150 mg, 0.51 mmol) was added. The tube was heated under microwaves for 30 minutes at 120° C. When the mixture cooled down, the reaction crude was mixed with a solution of NaOH (2.5 g) in water (40 mL) and extracted with dichloromethane (40 mL×3 times). The organic layers were combined and dried with magnesium sulphate. Filtration and evaporation under powerful vacuum produced a solid that was chromatographed using a mixture of dichloromethane and ethyl acetate (7:3) as eluent to produce 66 mg of pure title compound. Yield: 32%. $^1$H NMR (250 MHz, DMSO-d$_6$) δ 3.19 (s, 6H), 3.47 (s, 3H), 6.58 (s, 2H), 7.32 (d, 1H, J=8.5 Hz), 7.50-7.60 (m, 3H), 7.83 (d, 1H, J=8.3 Hz), 7.91 (s, 1H), 7.96 (s, 1H), 7.98-8.03 (m, 2H), 9.49 (s, 1H). $^{13}$C NMR (62.5 MHz, DMSO-d$_6$) δ 55.17, 59.96, 95.53, 117.11, 120.88, 121.28, 124.80, 126.03, 126.54, 126.65, 126.72, 127.96, 128.32, 132.07, 134.45, 136.16, 149.40, 150.61, 152.58, 158.19. m/z 404.2 [(M+H)$^+$ calcd for C$_{23}$H$_{21}$N$_3$O$_4$ 403.2].

Example 100

N-{4-[6-(3,4,5-trimethoxyphenylamino)pyrazin-2-yloxy]naphthalen-1-yl}acetamide, CJS 712

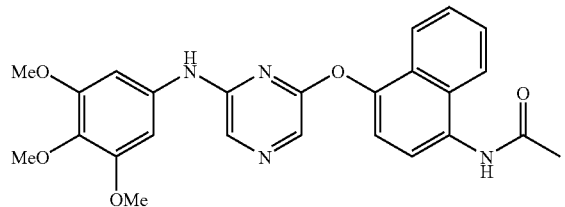

Using Method X, with 200 mg of 2-(3,4,5-trimethoxyphenylamino)-6-chloropyrazine (all amounts scaled accordingly) and N-(4-hydroxynaphthalen-1-yl)acetamide (CJS 704), using an identical workup and chromatography using a mixture of ethyl acetate and dichloromethane (7:3) furnished 31 mg of the title compound. Yield: 6.7%. $^1$H NMR (250 MHz, DMSO-d$_6$) δ 2.21 (s, 3H), 3.20 (s, 9H), 3.48 (s, 3H), 6.61 (s, 2H), 7.31 (d, 1H, J=8.2 Hz), 7.59 (t, 2H, J=7.6 Hz), 7.70 (d, 1H, J=8.3 Hz), 7.91 (s, 1H), 7.96-7.99 (m, 2H), 8.13 (d, 1H, J=7.8 Hz), 9.49 (s, 1H), 9.93 (s, 1H). $^{13}$C NMR (62.5 MHz, DMSO-d$_6$) δ 23.44, 55.10, 59.95, 95.38, 116.77, 120.89, 121.48, 121.61, 123.18, 126.38, 126.53, 127.11, 128.23, 128.71, 130.90, 131.98, 136.18, 146.44, 150.64, 152.59, 158.26, 168.93. m/z [(M+H)$^+$ calcd for C$_{25}$H$_{24}$N$_4$O$_5$ 460.2].

Example 101

2-(3,4,5-trimethoxyphenylamino)-6-(naphthalen-2-yloxy)pyrazine, CJS 717

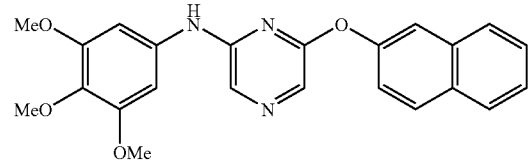

Using Method X, with 200 mg of 2-(3,4,5-trimethoxyphenylamino)-6-chloropyrazine (all amounts scaled accordingly) and 2-naphthol, 78 mg of the title compound were obtained.

Yield: 38%. $^1$H NMR (250 MHz, DMSO-$d_6$) δ 3.06 (s, 9H), 3.45 (s, 3H), 6.69 (s, 2H), 7.37 (dd, 1H, Ja=2.3 Hz, Jb=8.9 Hz), 7.49-7.54 (m, 2H), 7.72 (d, 1H, J=2.0 Hz), 7.84-7.89 (m, 2H), 7.92-7.99 (m, 3H), 9.55 (s, 1H). m/z 404.2 [(M+H)$^+$ calcd for $C_{23}H_{21}N_3O_4$ 403.2].

Example 102

N-Acetyl-N-(3,5-dibromo-pyrazin-2-yl)-acetamide, CJS 720

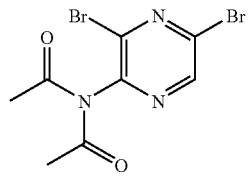

Method Y. N-(3,5-Dibromo-pyrazin-2-yl)-acetamide (1.01 g, 4 mmol) and sodium bicarbonate (1.02, 12 mmol) were refluxed in acetyl chloride (20 mL) for 2 days. The solvent was evaporated and the residue was partitioned between $CH_2Cl_2$ and water. The organic layer was dried and evaporated to give 1.31 g (97%) of title compound as crystals. $^1$H NMR δ (DMSO-$d_6$) 2.26 (6H, s, $CH_3$), 9.00 (1H, s, CH). MS m/z (electrospray) 358/60/2 (M+Na$^+$).

Example 103

2-Bromo-3-acetamido-6-(3-acetamidophenyl)pyrazine, CJS 713

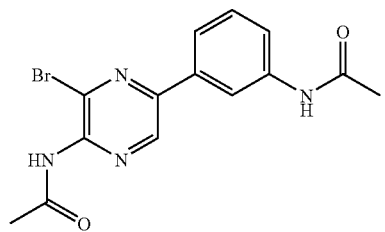

Method Z. In a tube suitable for microwave irradiation provided with stirring and an argon atmosphere were placed N-Acetyl-N-(3,5-dibromo-pyrazin-2-yl)-acetamide (200 mg, 0.5940 mmol), 3-acetamidobenzeneboronic acid (106 mg, 0.594 mmol), [1,1'-bis(diphenylphosphino)ferrocene]dichloropalladium (II) complex with dichloromethane (1:1) (36 mg, 0.0445 mmol), ethyleneglycoldimethylether (3.0 mL), water (0.6 mL) and sodium carbonate (126 mg, 1.19 mmol). The tube was heated by microwave irradiation at 90° C. for 30 minutes. This reaction was repeated again and the reaction mixtures from both reactions were joined and worked up together. The combined reaction was filtered and the precipitate washed with hot ethyl acetate (60 mL). The organic layer was evaporated under vacuum and the resulting crude was chromatographed (eluent: ethyl acetate) to give 26 mg of title compound. Yield: 7%. $^1$H NMR (250 MHz, DMSO-$d_6$) δ 2.07 (s, 3H), 2.12 (s, 3H), 7.46 (t, 1H, J=7.9 Hz), 7.77 (d, 1H, J=7.8 Hz), 7.82 (d, 1H, J=7.7 Hz), 8.21 (bs, 1H), 9.05 (s, 1H), 10.17 (s, 1H), 10.46 (s, 1H). $^{13}$C NMR (62.5 MHz, DMSO-$d_6$) δ 23.04, 23.99, 117.03, 120.73, 121.29, 129.54, 134.45, 136.31, 138.55, 140.15, 145.67, 148.90, 168.55, 168.92. m/z 349.1 [(M+H)$^+$ calcd for $C_{14}H_{13}BrN_4O_2$ 348.0].

Example 104

2-(3,4,5-Trimethoxyphenylamino)-3-acetamido-6-(3-acetamidophenyl)pyrazine, CJS 711

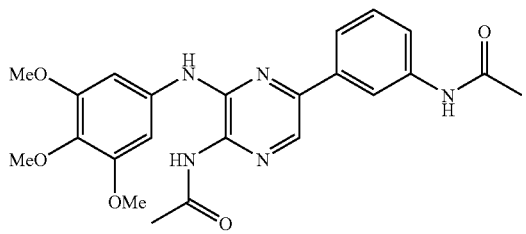

Method AA. In a tube suitable for microwave irradiation provided with stirring and an argon atmosphere were placed 2-bromo-3-acetamido-6-(3-acetamidophenyl)pyrazine (32 mg, 0.09164 mmol), 3,4,5-trimethoxyaniline (33.6 mg, 0.1833 mmol), sodium tert-butoxide (18 mg, 0.1833 mmol), Pd(0)$_2$ dba$_3$ (8.4 mg, 9.164 μmol), 4,5-bis(diphenylphosphino)-9,9-dimethylxanthene (Xant phos) (5.3 mg, 9.164 μmol) and dry toluene 1.5 mL). The tube was heated by microwave irradiation at 110° C. for 30 minutes. The reaction crude was filtered and the precipitate washed with boiling ethyl acetate (30 mL). The organic layers were evaporated under vacuum and the resulting crude was chromatographed (eluent: mixture of ethyl acetate and methanol; 9:1) to produce 7 mg of title compound. Yield: 17%. $^1$H NMR (250 MHz, DMSO-$d_6$) δ 2.06 (s, 3H), 2.17 (s, 3H), 3.64 (s, 3H), 3.77 (s, 9H), 7.24 (s, 2H), 7.42 (t, 1H, J=8.0 Hz), 7.64 (d, 1H, J=7.7 Hz), 7.73 (d, 1H, J=7.9 Hz), 8.22 (bs, 1H), 8.28 (s, 1H), 8.52 (s, 1H), 10.07 (s, 1H), 10.21 (s, 1H). m/z 452.2 [(M+H)$^+$ calcd for $C_{23}H_{25}N_5O_5$ 451.2].

Example 105

2,6-[di(3,4,5-trimethoxybenzylamino)]-pyrazine, CJS 461

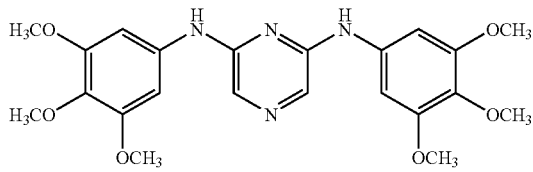

Method BB. 50 mg (0.17 mmol) 2-chloro-6-(3,4,5-trimethoxyphenylamino)-pyrazine were reacted with 31.0 mg (0.17 mmol) 3,4,5-trimethoxyaniline, in toluene (5 mL) and in the presence of 8.5 mg (0.018 mmol, 5%) palladacycle2 and 32 mg (0.34 mmol) NaO-tert-Bu. The reaction mixture was stirred at 100° C. for 18 hours and then filtered. The filtrate was evaporated under vacuum, the solid residue dissolved in 15 mL AcOEt, the organic solution washed (2×15 mL) brine, dried and evaporated to 2 mL volume. The solution was purified by preparative HPLC (Kieselgel 60, 0.015-0.040; eluentAcOEt), to give 67.0 mg (89.1%) of the title compound. $^1$H-NMR (DMSO), δ (ppm), J (Hz): 3.59 (s, 6H, CH$_3$O$_{4'}$), 3.61 (s, 12H, CH$_3$O$_{3'+5'}$), 6.88 (s, 4H, H$_{arom\ 2'+6'}$), 7.52 (s, 2H, H$_{P3+5}$), 9.11 (s, 2H, NH$_{amino}$);

MS, (C$_{22}$H$_{26}$N$_4$O$_6$), m/z: 443.1 [M$^+$+1], 100.

Example 106

2-(3,4,5-trimethoxybenzylamino)-6-(4-aminophenyloxy)-pyrazine, CJS 462

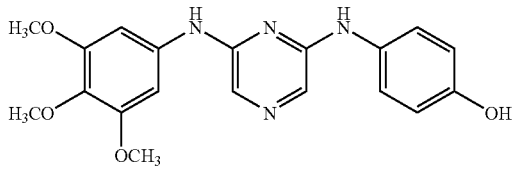

Method CC. To 58.0 mg (0.53 mmol) 4-hydroxyaniline, in 5 mL dimethylformamide were added under stirring and argon 67 mg (0.60 mmol) K-tert-BuO and 42 mg (0.3 mmol) K$_2$CO$_3$. After 5 minutes, 150 mg (0.51 mmol) 2-chloro-6-(3,4,5-trimethoxyphenylamino)-pyrazine were added and the reaction mixture submitted to microwave (30 minutes, 110° C., 200 W). The reaction mixture was filtered and poured in 20 mL water. The emulsion was extracted with (2×20 mL) AcOEt, the organic layer pooled, dried and evaporated to a volume of 2-3 mL. After purification by flash chromatography (Isolute column, Flash Sill, 50 g, 150 mL; eluent; AcOEt), 48.9 mg (26.0%) of the title compound were obtained. $^1$H-NMR (DMSO), δ (ppm), J (Hz): 3.59 (s, 12H, CH$_3$O$_{3'+4+5'}$), 6.68 (d, 2H, H$_{arom\ 3''+5''}$, J=8.42), 6.87 (s, 2H, H$_{arom\ 2'+6'}$), 7.32 (d, 2H, H$_{arom\ 2''+6''}$), 7.43 (s, 2H, H$_{P3+5}$), 8.75 (s, 2H, NH$_{amino}$), 8.96 (s, 2H, NH$_{amino}$), 9.07 (s, 2H, OH$_{phenol}$); MS, (C$_{19}$H$_{20}$N$_4$O$_4$), m/z: 369.1 [M$^+$+1], 100.

Example 107

2-Chloro-6-(coumarin-1-yl-6-oxy)-pyrazine, CJS 426(A)

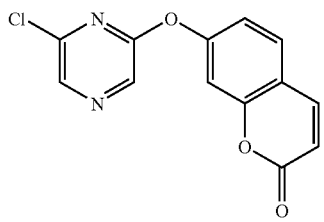

Method DD. In a carousel tube suitable for parallel synthesis were added 2,6-dichloropyrazine (200 mg, 1.35 mmol), 6-hydroxycoumarine (242 mg, 1.49 mmol), dry degassed DMF (10 mL), and potassium tert-butoxide (165 mg, 1.49 mmol). This mixture was stirred at 90° C. for 5 hours. The reaction mixture was diluted with AcOEt (20 mL), washed with brine (20 mL×2 times), dried and evaporated to 2 mL volume. The desired compound crystallized, yielding 370 mg of the title compound. Yield: 100%. $^1$H NMR (250 MHz, DMSO-d$_6$) δ 6.50 (d, 1H, H$_{arom\ 3}$, J=9.6 Hz), 7.29 (dd, 1H, H$_{arom\ 6}$, J$_o$=8.2 Hz, J$_m$=2.2 Hz), 7.44 (d, 1H, H$_{arom\ 7}$, J=2.2 Hz), 7.84 (d, 1H, H$_{arom\ 5}$, J=8.4 Hz), 8.10 (d, 1H, H$_{arom\ 4}$, J=9.6 Hz), 8.60 (s, 1H, H$_{Pz\ 5}$), 8.65 (s, 1H, H$_{Pz\ 3}$). m/z: 274.0 [(M)$^+$, calcd for C$_{13}$H$_7$ClN$_2$O$_3$ 274.0].

Example 108

2-Chloro-6-(tetralon-1-yl-5-oxy)-pyrazine, CJS 428 (A)

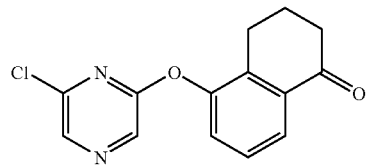

Using Method DD with 2,6-dichloropyrazine (200 mg, 1.34 mmol) and 5-hydroxy-tetralone (238 mg, 1.49 mmol), and purification by column chromatography (AcOEt:cyclohexane, 1:1), the title compound was obtained (366 mg). Yield: 100%. $^1$H NMR (250 MHz, DMSO-d$_6$) δ 1.97-2.07 (m, 2H, H$_3$), 2.64 (t, 2H, H$_4$, J=7.1 Hz), 2.77 (t, 2H, H$_2$, J=6.8 Hz), 7.46-7.45 (m, 2H, H$_{arom\ 7+8}$), 7.86 (dd, 1H, H$_{arom\ 6}$, J$_o$=7.4 Hz, J$_m$=1.6 Hz), 8.54 (s, 1H, H$_{Pz\ 5}$), 8.63 (s, 1H, H$_{Pz\ 3}$). m/z: 274.1 [(M)$^+$, calcd for C$_{14}$H$_{11}$ClN$_2$O$_2$ 274.1].

Example 109

2-Chloro-6-(tetralon-1-yl-6-oxy)-pyrazine, CJS 429 (A)

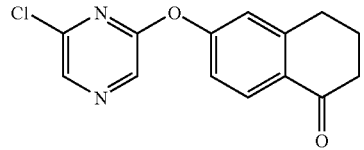

Using Method DD with 2,6-dichloropyrazine (200 mg, 1.34 mmol) and 6-hydroxy-tetralone (238 mg, 1.49 mmol), and crystallisation in AcOEt, the title compound was obtained (365 mg). Yield: 100%. $^1$H NMR (250 MHz, DMSO-d$_6$) δ 2.02-2.12 (m, 2H, H$_3$), 2.63 (t, 2H, H$_4$, J=5.9 Hz), 2.97 (t, 2H, H$_2$, J=6.5 Hz), 7.20-7.26 (m, 2H, H$_{arom\ 5+8}$), 7.96 (d, 1H, H$_{arom\ 6}$, J=8.3 Hz), 8.59 (s, 1H, H$_{Pz\ 5}$), 8.62 (s, 1H, H$_{Pz\ 3}$). m/z: 274.1 [(M)$^+$, calcd for C$_{14}$H$_{11}$ClN$_2$O$_2$ 274.1].

Example 110

2-Chloro-6-(2-fluorophenyl-oxy)-pyrazine, CJS 430(A)

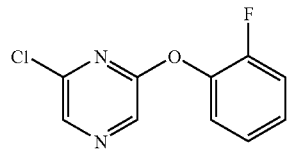

Using Method DD with 2,6-dichloropyrazine (250 mg, 1.69 mmol) and 2-fluorophenol (166 μL, 1.86 mmol, d=1.26 g/mL), and purification by column chromatography (AcOEt: cyclohexane, 1:1), the title compound was obtained (302 mg). Yield: 80%. $^1$H NMR (250 MHz, DMSO-d$_8$) δ 7.31-7.45 (m, 4H, H$_{arom}$), 8.56 (s, 1H, H$_{Pz\ 5}$), 8.67 (s, 1H, H$_{Pz\ 3}$).

m/z: 224.0 [(M)$^+$, calcd for C$_{10}$H$_6$ClFN$_2$O 224.0].

Example 111

2-Chloro-6-(3-fluorophenyl-oxy)-pyrazine, CJS 454(A)

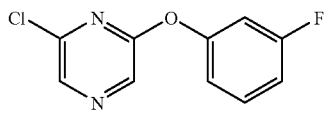

Using Method DD with 2,6-dichloropyrazine (250 mg, 1.69 mmol) and 3-fluorophenol (166 µL, 1.86 mmol, d=1.25 g/mL), and purification by column chromatography (AcOEt: cyclohexane, 1:1), the title compound was obtained (347 mg). Yield: 92%. $^1$H NMR (250 MHz, DMSO-d$_6$) δ 7.13-7.17 (m, 2H, H$_{arom\,4+6}$), 7.25 (d, 1H, H$_{arom\,2}$, J$_F$=10.0 Hz), 7.52 (q, 1H, H$_{arom\,5}$, J=8.1 Hz), 8.54 (s, 1H, H$_{Pz\,5}$), 8.56 (s, 1H, H$_{Pz\,3}$). m/z: 224.0 [(M)$^+$, calcd for C$_{10}$H$_6$ClFN$_2$O 224.0].

Example 112

2-Chloro-6-(6-acetamido-naphthyl-1-oxy)-pyrazine, CJS 485(A)

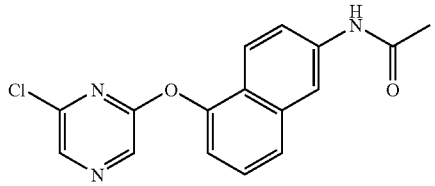

Using Method DD with 2,6-dichloropyrazine (250 mg, 1.68 mmol) and 6-acetamido-1-naphthol (350 mg, 1.72 mmol), and crystallisation in AcOEt, the title compound was obtained (526 mg). Yield: 100%. $^1$H NMR (250 MHz, DMSO-d$_6$) δ 2.12 (s, 3H, CH$_3$—N), 7.29 (d, 1H, H$_{arom\,4}$, J=7.4 Hz), 7.53 (t, 1H, H$_{arom\,3}$, J=7.9 Hz), 7.57-7.62 (m, 1H, H$_{arom\,7}$), 7.80 (d, 1H, H$_{arom\,2\,or\,8}$, J=8.2 Hz), 7.85 (d, 1H, H$_{arom\,8\,or\,2}$, J=9.1 Hz), 8.42 (d, 1H, H$_{arom\,5}$, J=1.3 Hz), 8.53 (s, 1H, H$_{Pz\,5}$), 8.67 (s, 1H, H$_{Pz\,3}$), 10.23 (s, 1H, NH). m/z: 313.1 [(M)$^+$, calcd for C$_{16}$H$_{12}$ClN$_3$O$_2$ 313.1].

Example 113

2-Chloro-6-(5-acetamido-naphtyl-1-oxy)-pyrazine, CJS 487(A)

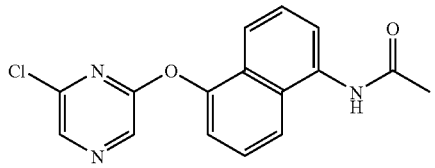

Using Method DD with 2,6-dichloropyrazine (200 mg, 1.34 mmol) and 6-acetamido-1-naphthol (270 mg, 1.49 mmol), and crystallisation in AcOEt, the title compound was obtained (379 mg). Yield: 90%. $^1$H NMR (250 MHz, DMSO-d$_6$) δ 2.27 (s, 3H, CH$_3$—N), 7.54 (t, 1H, H$_{arom\,7}$, J=8.0 Hz), 7.59 (d, 1H, H$_{arom\,4}$, J=7.5 Hz), 7.68 (t, 1H, H$_{arom\,3}$, J=8.0 Hz), 7.80 (d, 1H, H$_{arom\,6}$, J=7.2 Hz), 7.83 (d, 1H, H$_{arom\,8}$, J=6.4 Hz), 8.13 (d, 1H, H$_{arom\,2}$, J=8.4 Hz), 8.59 (s, 1H, H$_{Pz\,5}$), 8.78 (s, 1H, H$_{Pz\,3}$), 10.10 (s, 1H, NH). $^{13}$C NMR (62.9 MHz, DMSO-d$_6$) δ 23.47, 117.94, 118.14, 120.98, 122.31, 125.65, 126.51, 127.12, 129.19, 133.58, 134.22, 137.59, 144.42, 148.21, 158.81, 168.99. m/z 314.0 [(M+H)$^+$ calcd for C$_{16}$H$_{12}$ClN$_3$O$_2$ 313.0].

Example 114

N-(4-(6-Chloropyrazin-2-yloxy)naphthalen-1-yl) acetamide

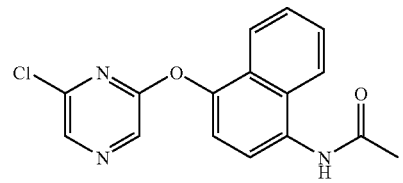

Method DD was followed (in a round-bottomed flask, reaction time: 20 hours) with N-(4-hydroxynaphthalen-1-yl)acetamide (1.22 g, 6.08 mmol) and 2,6-dichloropyrazine (1.09 g, 7.30 mmol). The DMF was evaporated in vacuo. The resulting crude was dissolved in a mixture (hot) of AcOEt (25 mL) and acetone (175 mL) and filtered. The volume of the filtrate was reduced to 100 mL and this filtrate crystallised upon storage at low temperature to yield the title compound (1.30 g). Yield: 68%. $^1$H NMR (500 MHz, DMSO-d$_6$) δ 2.21 (s, 3H), 7.42 (d, 1H, J=8.2 Hz), 7.57 (t, 1H, J=7.5 Hz), 7.64 (t, 1H, J=7.6 Hz), 7.72 (d, 1H, J=8.1 Hz), 7.90 (d, 1H, J=8.3 Hz), 8.16 (d, 1H, J=8.5 Hz), 8.52 (s, 1H), 8.72 (s, 1H), 10.02 (s, 1H). $^{13}$C NMR (125.8 MHz, DMSO-d$_6$) δ 23.42, 117.59, 121.40, 121.65, 123.42, 126.53, 126.71, 126.85, 128.90, 131.85, 133.59, 137.50, 144.40, 145.04, 158.92, 169.04. m/z 314.0 [(M+H)$^+$ calcd for C$_{16}$H$_{12}$ClN$_3$O$_2$ 313.1].

Example 115

2-Chloro-6-(2-chlorophenyl-oxy)-pyrazine, CJS 489(A)

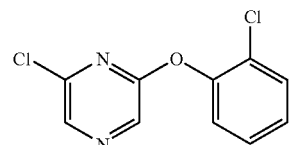

Using Method DD with 2,6-dichloropyrazine (250 mg, 1.69 mmol) and 2-chlorophenol (193 µL, 1.86 mmol, d=1.24 g/mL), and purification by column chromatography (AcOEt: cyclohexane, 1:1), the title compound was obtained (363 mg). Yield: 89%. $^1$H NMR (250 MHz, DMSO-d$_6$) δ 7.37-7.39 (m, 1H, H$_{arom\,4}$), 7.46-7.47 (m, 2H, H$_{arom\,5+6}$), 7.64 (d, 1H, $H_{arom\ 3}$, J=8.2 Hz), 8.55 (s, 1H, $H_{Pz\ 5}$), 8.65 (s, 1H, $H_{Pz\ 3}$). m/z: 240.0 [(M)$^+$, calcd for $C_{10}H_6Cl_2N_2O$ 240.0].

Example 116

2-Chloro-6-(3-chlorophenyl-oxy)-pyrazine, CJS 504(A)

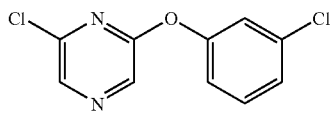

Using Method DD with 2,6-dichloropyrazine (250 mg, 1.69 mmol) and 3-chlorophenol (193 µL, 1.86 mmol, d=1.24 g/mL), and purification by column chromatography (AcOEt:cyclohexane, 1:1), the title compound was obtained (346 mg). Yield: 85%. $^1$H NMR (250 MHz, DMSO-d$_6$) δ 7.32 (dd, 1H, $H_{arom\ 4}$, $J_o$=8.2 Hz, $J_m$=1.9 Hz), 7.43 (d, 1H, $H_{arom\ 6}$, J=8.0 Hz), 7.50 (d, 1H, $H_{arom\ 2}$, $J_m$=1.9 Hz), 7.56 (t, 1H, $H_{arom\ 5}$, J=8.1 Hz), 8.59 (s, 1H, $H_{Pz\ 5}$), 8.62 (s, 1H, $H_{Pz\ 3}$). m/z: 241.1 [(M+H)$^+$, calcd for $C_{10}H_6Cl_2N_2O$ 240.0].

Example 117

2-Chloro-6-(2-phenyl-phenyl-oxy)-pyrazine, CJS 492(A)

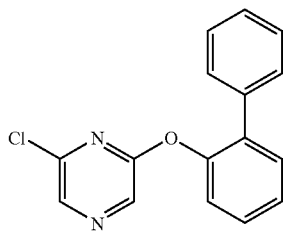

Using Method DD (reaction time: 20 hours) with 2,6-dichloropyrazine (200 mg, 1.34 mmol) and 2-phenyl-phenol (268 mg, 1.49 mmol), and purification by column chromatography (AcOEt:cyclohexane, 1:2), the title compound was obtained (238 mg). Yield: 65%. $^1$H NMR (250 MHz, DMSO-d$_6$) δ 7.31-7.61 (m, 9H, $H_{arom}$), 8.43 (s, 1H, $H_{Pz\ 5}$), 8.46 (s, 1H, $H_{Pz\ 3}$). m/z: 283.1 [(M+H)$^+$, calcd for $C_{16}H_{11}ClN_2O$ 282.1].

Example 118

2-Chloro-6-(3-phenyl-phenyl-oxy)-pyrazine, CJS 493(A)

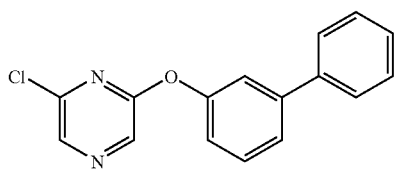

Using Method DD (reaction time: 20 hours) with 2,6-dichloropyrazine (200 mg, 1.34 mmol) and 3-phenyl-phenol (268 mg, 1.49 mmol), and purification by column chromatography (AcOEt:cyclohexane, 1:2), the title compound was obtained (370 mg). Yield: 98%. $^1$H NMR (250 MHz, DMSO-d$_6$) δ 7.35-7.72 (m, 9H, $H_{arom}$), 8.53 (s, 1H, $H_{Pz\ 5}$), 8.59 (s, 1H, $H_{Pz\ 3}$). m/z: 283.1 [(M+H)$^+$, calcd for $C_{16}H_{11}ClN_2O$ 282.1].

Example 119

2-Chloro-6-(4-phenyl-phenyl-oxy)-pyrazine, CJS 494(A)

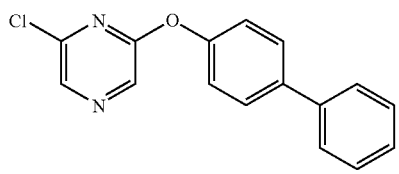

Using Method DD (reaction time: 20 hours) with 2,6-dichloropyrazine (200 mg, 1.34 mmol) and 4-phenyl-phenol (268 mg, 1.49 mmol), and purification by column chromatography (AcOEt:cyclohexane, 1:2), the title compound was obtained (376 mg). Yield: 99%. $^1$H NMR (250 MHz, DMSO-d$_6$) δ 7.40-7.60 (m, 5H, $H_{arom}$), 7.76 (d, 2H, $H_{arom\ 3+5}$, J=7.1 Hz), 7.82 (d, 2H, $H_{arom\ 2+6}$, J=8.7 Hz), 8.59 (s, 1H, $H_{Pz\ 5}$), 8.65 (s, 1H, $H_{Pz\ 3}$). m/z: 283.1 [(M+H)$^+$, calcd for $C_{16}H_{11}ClN_2O$ 282.1].$^-$ Example 120

2-Chloro-6-(3-acetamidophenyl-oxy)-pyrazine, CJS 505(A)

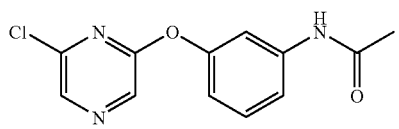

Using Method DD with 2,6-dichloropyrazine (200 mg, 1.34 mmol) and 3-acetamidophenol (202 mg, 1.49 mmol), and crystallisation in AcOEt, the title compound was obtained (350 mg). Yield: 99%. $^1$H NMR (250 MHz, DMSO-d$_6$) δ 2.06 (s, 3H, CH$_3$—NH), 6.90-6.95 (m, 1H, $H_{arom\ 5}$), 7.76 (dd, 2H, $H_{arom\ 4+6}$, $J_m$=2.0 Hz, $J_o$=7.6 Hz), 7.59 (s, 1H, $H_{arom\ 2}$), 8.52 (s, 1H, $H_{Pz\ 5}$), 8.54 (s, 1H, $H_{Pz\ 3}$), 10.12 (s, 1H, NH).

m/z: 264.0 [(M+H)$^+$, calcd for $C_{12}H_{10}ClN_3O_2$ 263.0].

Example 121

2-Chloro-6-(4-acetamidophenyl-oxy)-pyrazine, CJS 506(A)

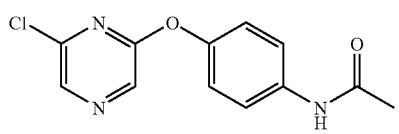

Using Method DD with 2,6-dichloropyrazine (200 mg, 1.34 mmol) and 4-acetamidophenol (202 mg, 1.49 mmol), and crystallisation in AcOEt, the title compound was obtained (327 mg). Yield: 92%. $^1$H NMR (250 MHz, DMSO-d$_6$) δ 2.12 (s, 3H, CH$_3$—NH), 7.25 (d, 2H, $H_{arom\ 3+5}$, J=8.9 Hz), 7.71 (d, 2H, H$_{arom\ 2+6}$, J=8.9 Hz), 8.55 (s, 1H, H$_{Pz\ 5}$), 8.57 (s, 1H, H$_{Pz\ 3}$), 10.10 (s, 1H, NH). m/z: 264.0 [(M+H)$^+$, calcd for C$_{12}$H$_{10}$ClN$_3$O$_2$ 263.0].

Example 122

2-chloro-6-(acetophenone-3-oxy)-pyrazine, CJS 508(A)

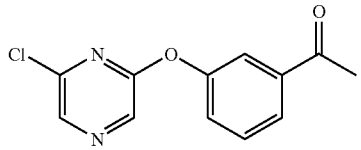

Using Method DD with 2,6-dichloropyrazine (220 mg, 1.49 mmol) and 3-hydroxyacetophenone (200 mg, 1.47 mmol), and crystallisation in AcOEt, the title compound was obtained (370 mg). Yield: 96%. $^1$H NMR (250 MHz, DMSO-d$_6$) δ 2.61 (s, 3H, CH$_3$—CO), 7.57 (dd, 1H, H$_{arom\ 4}$, J$_m$=1.2 Hz, J$_o$=9.0 Hz), 7.65 (t, 1H, H$_{arom\ 5}$, J=7.8 Hz), 7.82 (d, 1H, H$_{arom\ 2}$, J$_m$=2.0 Hz), 7.88 (dd, 1H, H$_{arom\ 6}$, J$_m$=1.3 Hz, J$_o$=7.5 Hz), 8.55 (s, 1H, H$_{P5}$), 8.61 (s, 1H, H$_{Pz\ 3}$) m/z: 249.0 [(M+H)$^+$, calcd for C$_{12}$H$_9$ClN$_2$O$_2$ 248.0].

Example 123

2-Chloro-6-(acetophenone-4-oxy)-pyrazine, CJS 509(A)

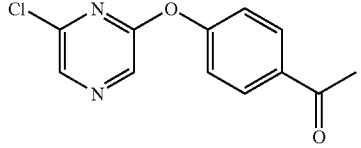

Using Method DD with 2,6-dichloropyrazine (220 mg, 1.49 mmol) and 3-hydroxyacetophenone (200 mg, 1.47 mmol), and crystallisation in AcOEt, the title compound was obtained (365 mg). Yield: 99%. $^1$H NMR (250 MHz, DMSO-d$_6$) δ 2.61 (s, 3H, CH$_3$—CO), 7.42 (d, 2H, H$_{arom\ 3+5}$, J=8.7 Hz), 8.08 (d, 2H, H$_{arom\ 2+6}$, J=8.7 Hz), 8.59 (s, 1H, H$_{Pz\ 5}$), 8.63 (s, 1H, H$_{Pz\ 3}$). m/z: 249.0 [(M+H)$^+$, calcd for C$_{12}$H$_9$ClN$_2$O$_2$ 248.0].

Example 124

2-Chloro-6-(indanone-4-oxy)-pyrazine, CJS 510(A)

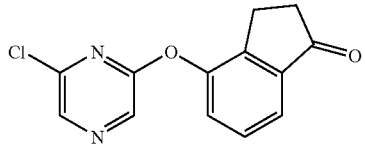

Using Method DD with 2,6-dichloropyrazine (200 mg, 1.34 mmol) and 4-hydroxyindanone (219 mg, 1.49 mmol), and crystallisation in AcOEt, the title compound was obtained (314 mg). Yield: 90%. $^1$H NMR (250 MHz, DMSO-d$_6$) δ 2.70 (t, 2H, H$_3$, J=5.7 Hz), 2.94 (t, 2H, H$_2$, J=5.7 Hz), 7.55-7.64 (m, 3H, H$_{arom}$), 8.57 (s, 1H, H$_{Pz\ 5}$), 8.66 (s, 1H, H$_{Pz\ 3}$). m/z: 261.0 [(M+H)$^+$, calcd for C$_{13}$H$_9$ClN$_2$O$_2$ 260.0].

Example 125

2-Chloro-6-(indanone-5-oxy)-pyrazine, CJS 511(A)

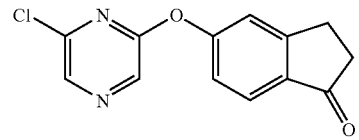

Using Method DD with 2,6-dichloropyrazine (200 mg, 1.34 mmol) and 5-hydroxyindanone (219 mg, 1.49 mmol), and crystallisation in AcOEt, the title compound was obtained (350 mg). Yield: 100%. $^1$H NMR (250 MHz, DMSO-d$_6$) δ 2.67 (t, 2H, H$_3$, J=5.9 Hz), 3.13 (t, 2H, H$_2$, J=5.5 Hz), 7.31 (dd, 1H, H$_{arom\ 6}$, J$_m$=1.9 Hz, J$_o$=8.3 Hz), 7.47 (d, 1H, H$_{arom\ 4}$, J=1.3 Hz), 7.73 (d, 1H, H$_{arom\ 7}$, J=8.3 Hz), 8.59 (s, 1H, H$_{Pz\ 5}$), 8.64 (s, 1H, H$_{Pz\ 3}$). m/z: 261.0 [(M+H)$^+$, calcd for C$_{13}$H$_9$ClN$_2$O$_2$ 260.0].

Example 126

2-Chloro-6-(indanone-6-oxy)-pyrazine, CJS 512(A)

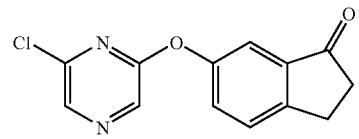

Using Method DD with 2,6-dichloropyrazine (200 mg, 1.34 mmol) and 6-hydroxyindanone (219 mg, 1.49 mmol), and crystallisation in AcOEt, the title compound was obtained (330 mg). Yield: 94%. $^1$H NMR (250 MHz, DMSO-d$_6$) δ 2.74 (t, 2H, H$_3$, J=5.8 Hz), 3.15 (t, 2H, H$_2$, J=6.0 Hz), 7.50 (d, 1H, H$_{arom\ 7}$, J=2.2 Hz), 7.60 (dd, 1H, H$_{arom\ 5}$, J$_m$=2.3 Hz, J$_o$=8.3 Hz), 7.70 (d, 1H, H$_{arom\ 4}$, J=8.3 Hz), 8.53 (s, 1H, H$_{Pz\ 5}$), 8.59 (s, 1H, H$_{Pz\ 3}$). m/z: 261.1 [(M+H)$^+$, calcd for C$_{13}$H$_9$ClN$_2$O$_2$ 260.0].

Example 127

2-Chloro-6-(indanone-7-oxy)-pyrazine, CJS 513(A)

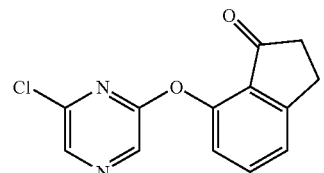

Using Method DD with 2,6-dichloropyrazine (200 mg, 1.34 mmol) and 7-hydroxyindanone (219 mg, 1.49 mmol), and crystallisation in AcOEt, the title compound was obtained (348 mg). Yield: 100%. $^1$H NMR (250 MHz, DMSO-d$_6$) δ 2.56-2.61 (m, 2H, H$_3$), 3.16 (t, 2H, H$_3$, J=5.6 Hz), 7.25 (d, 1H, H$_{arom\ 4}$, J=7.9 Hz), 7.54 (d, 1H, H$_{arom\ 6}$, J=7.6 Hz), 7.78 (t, 1H, H$_{arom\ 5}$, J=8.3 Hz), 8.49 (s, 1H, H$_{Pz\ 5}$), 8.62 (s, 1H, H$_{Pz\ 3}$). m/z: 261.0 [(M+H)$^+$, calcd for C$_{13}$H$_9$ClN$_2$O$_2$ 260.0].

Example 128

2-Chloro-6-(quinoline-4-oxy)-pyrazine, CJS 523(A)

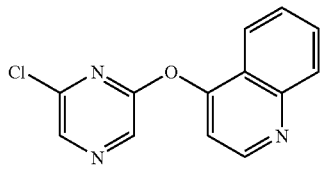

Using Method DD with 2,6-dichloropyrazine (250 mg, 1.69 mmol) and 4-hydroxyquinoline (270 mg, 1.49 mmol), and purification by column chromatography (AcOEt cyclohexane, 1:1), the title compound was obtained (60 mg). Yield: 14%. $^1$H NMR (250 MHz, DMSO-d$_6$) δ 7.45 (d, 1H, H$_{arom\ 3}$, J=4.9 Hz), 7.67 (t, 1H, H$_{arom\ 7}$, J=7.6 Hz), 7.86 (t, 1H, H$_{arom\ 6}$, J=7.8 Hz), 8.12 (d, 2H, H$_{arom\ 3+5}$, J=8.7 Hz), 8.67 (s, 1H, H$_{Pz\ 5}$), 8.82 (s, 1H, H$_{Pz\ 3}$), 8.94 (d, 1H, H$_{arom\ 2}$, J=4.9 Hz). m/z: 258.0 [(M+H)$^+$, calcd for C$_{13}$H$_8$ClN$_3$O 257.0].

Example 129

2-Chloro-6-(quinoline-5-oxy)-pyrazine, CJS 524(A)

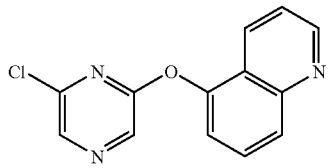

Using Method DD with 2,6-dichloropyrazine (250 mg, 1.69 mmol) and 5-hydroxyquinoline (270 mg, 1.49 mmol), and purification by column chromatography (AcOEt:cyclohexane, 1:1), the title compound was obtained (264 mg). Yield: 61%. $^1$H NMR (250 MHz, DMSO-d$_6$) δ 7.54-7.58 (m, 2H, H$_{arom\ 3+8}$), 7.84 (t, 1H, H$_{arom\ 7}$, J=8.1 Hz), 8.01 (d, 1H, H$_{arom\ 6}$, J=8.5 Hz), 8.37 (d, 1H, H$_{arom\ 4}$, J=8.0 Hz), 8.55 (s, 1H, H$_{Pz\ 5}$), 8.73 (s, 1H, H$_{Pz\ 3}$), 8.98 (dd, 1H, H$_{arom\ 2}$, J=1.4 Hz, J=4.0 Hz). m/z: 258.0 [(M+H)$^+$, calcd for C$_{13}$H$_8$ClN$_3$O 257.0].

Example 130

2-Chloro-6-(quinoline-6-oxy)-pyrazine, CJS 525(A)

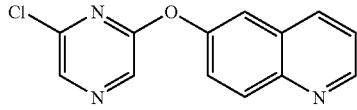

Using Method DD with 2,6-dichloropyrazine (250 mg, 1.69 mmol) and 6-hydroxyquinoline (270 mg, 1.49 mmol), and purification by column chromatography (AcOEt cyclohexane, 1:1), the title compound was obtained (324 mg). Yield: 75%. $^1$H NMR (250 MHz, DMSO-d$_6$) δ 7.56-7.59 (m, 1H, H$_{arom\ 3}$), 7.70 (dd, 1H, H$_{arom\ 7}$, J$_m$=2.6 Hz, J$_o$=9.1 Hz), 7.87 (d, 1H, H$_{arom\ 5}$, J=2.4 Hz), 8.12 (d, 1H, H$_{arom\ 8}$, J=9.0 Hz), 8.37 (d, 1H, H$_{arom\ 4}$, J=8.1 Hz), 8.56 (s, 1H, H$_{Pz\ 5}$) 8.65 (s, 1H, H$_{Pz\ 3}$), 8.93 (dd, 1H, H$_{arom\ 2}$, J=1.0 Hz, J=4.9 Hz). m/z: 258.0 [(M+H)$^+$, calcd for C$_{13}$H$_8$ClN$_3$O 257.0].

Example 131

2-Chloro-6-(isoquinoline-5-oxy)-pyrazine, CJS 526(A)

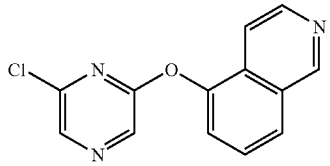

Using Method DD with 2,6-dichloropyrazine (250 mg, 1.69 mmol) and 4-hydroxyisoquinoline (270 mg, 1.49 mmol), and purification by column chromatography (AcOEt: cyclohexane, 1:1), the title compound was obtained (263 mg). Yield: 61%. $^1$H NMR (250 MHz, DMSO-d$_6$) δ 7.72-7.78 (m, 3H, H$_{arom\ 3+6+7}$), 8.11 (d, 1H, H$_{arom\ 5}$, J=7.8 Hz), 8.53 (d, 1H, H$_{arom\ 2}$, J=5.9 Hz), 8.55 (s, 1H, H$_{Pz\ 5}$), 8.75 (s, 1H, H$_{Pz\ 3}$), 9.43 (s, 1H, H$_{arom\ 8}$).

m/z: 258.1 [(M+H)$^+$, calcd for C$_{13}$H$_8$ClN$_3$O 257.0].

Example 132

2-Chloro-6-(4-N—BOC-aminophenyl-oxy)-pyrazine

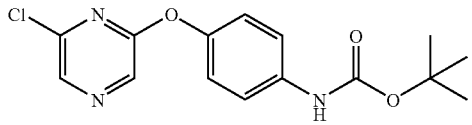

Using Method DD with 2,6-dichloropyrazine (700 mg, 4.69 mmol) and 4-N—BOC-aminophenol (912 mg, 1.49 mmol), and purification by column chromatography (AcOEt: cyclohexane, 1:1), the title compound was obtained (1.17 g). Yield: 69%. $^1$H NMR (250 MHz, DMSO-d$_6$) δ 1.99 (s, 9H, 3×CH$_3$), 7.16 (d, 2H, H$_{arom\ 3+5}$, J=8.9 Hz), 7.53 (d, 2H, H$_{arom\ 2+6}$, J=8.9 Hz), 8.49 (s, 1H, H$_{Pz\ 5}$), 8.51 (s, 1H, H$_{Pz\ 3}$), 9.48 (s, 1H, NH). m/z: 322.1 [(M+H)$^+$, calcd for C$_{15}$H$_{16}$ClN$_3$O$_3$ 321.1].

Example 133

2-(3,4,5-Trimethoxyphenylamino)-6-(coumarin-1-yl-6-oxy)-pyrazine, CJS 426

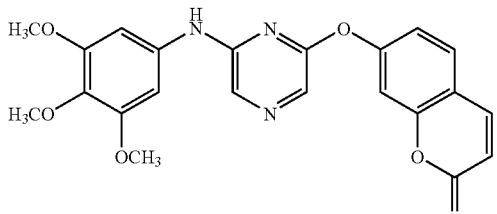

Method EE. In a carousel tube suitable for parallel synthesis, 2-chloro-6-(coumarin-1-yl-6-oxy)-pyrazine (200 mg, 0.72 mmol) was reacted with 3,4,5-trimethoxyaniline (158 mg, 0.86 mmol) in dry degassed toluene (10 mL) in the presence of Pd(0)$_2$.dba$_3$ (20 mg, 0.022 mmol, 3 mol %), 2-dicyclohexylphosphino-2'-(N,N-dimethylamino)-biphenyl (16 mg, 0.044 mmol, 6 mol %) and sodium tert-butoxide (138 mg, 1.44 mmol). This mixture was stirred at 90° C. for 20 hours under a nitrogen atmosphere. The reaction content was evaporated to dryness in vacuo and the solid residue was retaken in hot AcOEt (10 mL×2 times). The solutions were filtered, pooled, washed with 0.1 N HCl (10 mL), water, dried (MgSO$_4$), and evaporated again. The solid residue was purified by column chromatography (AcOEt:ethanol, 1:1) to give the title compound (102 mg). Yield: 34%.

$^1$H NMR (250 MHz, DMSO-d$_6$) δ 3.38 (s, 6H, [CH$_3$O]$_{3+5}$), 3.54 (s, 3H, [CH$_3$O]$_4$), 6.47 (d, 1H, H$_{arom\ 3}$, J=9.6 Hz), 6.77 (s, 2H, H$_{arom2'+6'}$), 7.22 (dd, 1H, H$_{arom\ 6}$, J$_o$=8.5 Hz, J$_m$=2.3 Hz), 7.34 (d, 1H, H$_{arom2'+6'}$, J=2.2 Hz), 7.72 (d, 1H, H$_{arom\ 5}$, J=8.5 Hz), 7.84 (s, 1H, H$_{Pz\ 5}$), 8.03 (s, 1H, H$_{Pz\ 3}$), 8.10 (d, 1H, H$_{arom\ 4}$, J=9.62 Hz), 9.63 (s, 1H, NH). m/z: 422.1 [(M+H)$^+$, calcd for C$_{22}$H$_{19}$N$_3$O$_6$ 421.1].

Example 134

2-(3,4,5-trimethoxyphenylamino)-6-(tetralon-1-yl-5-oxy)-pyrazine, CJS 428

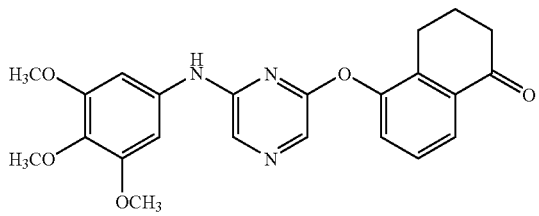

Using Method EE with 2-chloro-6-(tetralon-1-yl-5-oxy)-pyrazine (200 mg, 0.73 mmol) and 3,4,5-trimethoxyaniline (160 mg, 0.87 mmol), and purification by column chromatography (AcOEt), the title compound was obtained (193 mg). Yield: 63%. $^1$H NMR (250 MHz, DMSO-d$_6$) δ 1.99-2.02 (m, 2H, H$_3$), 2.60 (t, 2H, H$_4$, J=5.9 Hz), 2.77 (t, 2H, H$_2$, J=5.9 Hz), 3.41 (s, 6H, [CH$_3$O]$_{3+5}$), 3.55 (s, 3H, [CH$_3$O]$_4$), 6.69 (s, 2H, H$_{arom2'+6'}$), 7.40-7.44 (m, 2H, H$_{arom\ 7+8}$), 7.88 (d, 1H, H$_{arom\ 6}$, J=6.8 Hz), 7.81 (s, 1H, H$_{Pz\ 5}$), 7.95 (s, 1H, H$_{Pz\ 3}$), 9.52 (s, 1H, NH). m/z: 422.2 [(M+H)$^+$, calcd for C$_{23}$H$_{23}$N$_3$O$_6$ 421.2].

Example 135

2-(3,4,5-Trimethoxyphenylamino)-6-(tetralon-1-yl-6-oxy)-pyrazine, CJS 429

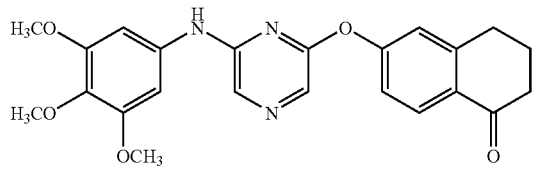

Using Method EE with 2-chloro-6-(tetralon-1-yl-6-oxy)-pyrazine (200 mg, 0.73 mmol) and 3,4,5-trimethoxyaniline (160 mg, 0.87 mmol), and purification by column chromatography (AcOEt), the title compound was obtained (182 mg). Yield: 59%. $^1$H NMR (250 MHz, DMSO-d$_6$) δ 2.02-2.09 (m, 2H, H$_3$), 2.62 (t, 2H, H$_4$, J=6.8 Hz), 2.92 (t, 2H, H$_2$, J=5.8 Hz), 3.40 (s, 6H, [CH$_3$O]$_{3+5}$), 3.55 (s, 3H, [CH$_3$O]$_4$), 6.79 (s, 2H, H$_{arom2'+6'}$), 7.13 (dd, 1H, H$_{arom\ 8}$, J$_o$=8.5 Hz, J$_m$=2.4 Hz), 7.18 (d, 1H, H$_{arom\ 5}$, J=2.2 Hz), 7.82 (s, 1H, H$_{Pz\ 5}$), 7.92 (d, 1H, H$_{arom\ 6}$, J=8.5 Hz), 8.02 (s, 1H, H$_{Pz\ 3}$), 9.63 (s, 1H, NH). m/z: 422.2 [(M+H)$^+$, calcd for C$_{23}$H$_{23}$N$_3$O$_6$ 421.1].

Example 136

2-(3,4,5-Trimethoxyphenylamino)-6-(2-fluorophenyl-oxy)-pyrazine, CJS 430

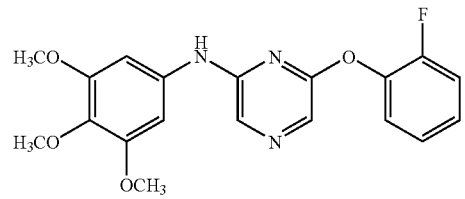

Using Method EE with 2-chloro-6-(2-fluorophenyloxy)-pyrazine (200 mg, 0.89 mmol) and 3,4,5-trimethoxyaniline (196 mg, 1.07 mmol), and purification by column chromatography (AcOEt:cyclohexane, 1:1), the title compound was obtained (234 mg). Yield: 71%. $^1$H NMR (250 MHz, DMSO-d$_6$) δ 3.42 (s, 6H, [CH$_3$O]$_{3+5}$), 3.54 (s, 3H, [CH$_3$O]$_4$), 6.69 (s, 2H, H$_{arom2'+6'}$), 7.24-7.41 (m, 4H, H$_{arom}$), 7.83 (s, 1H, H$_{Pz\ 5}$), 7.96 (s, 1H, H$_{Pz\ 3}$), 9.57 (s, 1H, NH).

m/z: 372.1 [(M+H)$^+$, calcd for C$_{19}$H$_{18}$FN$_3$O$_4$ 371.1].

Example 137

2-(3,4,5-Trimethoxyphenylamino)-6-(3-fluorophenyl-oxy)-pyrazine, CJS 454

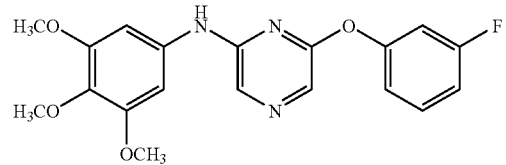

Using Method EE with 2-chloro-6-(3-fluorophenyloxy)-pyrazine (200 mg, 0.89 mmol) and 3,4,5-trimethoxyaniline (196 mg, 1.07 mmol), and purification by column chromatography (AcOEt:cyclohexane, 1:1), the title compound was obtained (200 mg). Yield: 61%. $^1$H NMR (250 MHz, DMSO-d$_6$) δ 3.44 (s, 6H, [CH$_3$O]$_{3+5}$), 3.55 (s, 3H, [CH$_3$O]$_4$), 6.77 (s, 2H, H$_{arom\ 2'+6'}$), 7.02-7.09 (m, 2H, H$_{arom\ 4+6}$), 7.16 (d, 1H, H$_{arom\ 2}$, J$_F$=8.8 Hz), 7.43 (q, 1H, H$_{arom\ 5}$, J=8.5 Hz), 7.78 (s, 1H, H$_{Pz\ 5}$), 7.98 (s, 1H, H$_{Pz\ 3}$), 9.61 (s, 1H, NH). m/z: 372.1 [(M+H)$^+$, calcd for C$_{19}$H$_{18}$FN$_3$O$_4$ 371.1].

Example 138

2-(3,4,5-Trimethoxyphenylamino)-6-(6-acetamido-naphtyl-1-oxy)-pyrazine, CJS 485

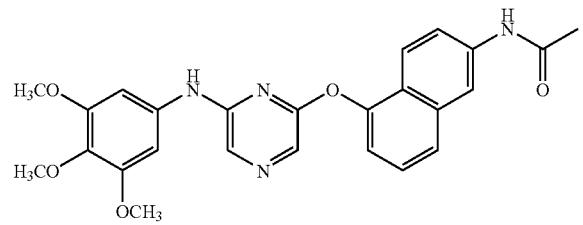

Using Method EE with 2-chloro-6-(6-acetamidonaphtyl-oxy)-pyrazine (200 mg, 0.64 mmol) and 3,4,5-trimethoxyaniline (140 mg, 0.76 mmol), and purification by column chromatography (AcOEt), the title compound was obtained (75 mg). Yield: 25%. $^1$H NMR (250 MHz, DMSO-$d_6$) δ 2.16 (s, 3H, $CH_3$—N), 3.38 (s, 6H, $[CH_3O]_{3+5}$), 3.54 (s, 3H, $[CH_3O]_4$), 6.67 (s, 2H, $H_{arom2'+6'}$), 7.24 (d, 1H, $H_{arom\,4}$, J=7.4 Hz), 7.52 (t, 1H, $H_{arom\,3}$, J=7.8 Hz), 7.62 (dd, 1H, $H_{arom\,7}$, $J_m$=1.9 Hz, $J_o$=9.0 Hz), 7.76 (d, 1H, $H_{arom\,2}$, J=8.2 Hz), 7.94-7.97 (m, 1H, $H_{arom\,8}$), 7.95 (s, 1H, $H_{Pz\,5}$), 8.02 (s, 1H, $H_{Pz\,3}$), 8.44 (d, 1H, $H_{arom\,5}$, J=1.4 Hz), 9.54 (s, 1H, NH), 10.25 (s, 1H, NH). m/z: 461.2 [(M+H)$^+$, calcd for $C_{25}H_{24}N_4O_5$ 460.2].

Example 139

2-(3,4,5-Trimethoxyphenylamino)-6-(5-acetamido-naphtyl-1-oxy)-pyrazine, CJS 487

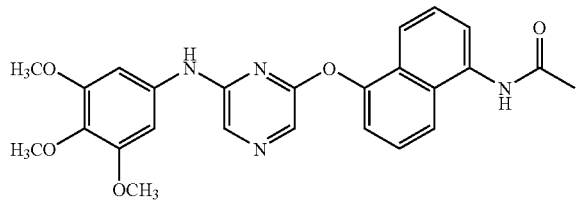

Using Method EE with 2-chloro-6-(5-acetamidonaphtyl-oxy)-pyrazine (200 mg, 0.64 mmol) and 3,4,5-trimethoxyaniline (140 mg, 0.76 mmol), and purification by column chromatography (AcOEt), the title compound was obtained (72 mg). Yield: 24%. $^1$H NMR (250 MHz, DMSO-$d_6$) δ 2.23 (s, 3H, $CH_3$—N), 3.32 (s, 6H, $[CH_3O]_{3+5}$), 3.49 (s, 3H, $[CH_3O]_4$), 6.60 (s, 2H, $H_{arom2'+6'}$), 7.35 (d, 1H, $H_{arom\,4}$, J=7.4 Hz), 7.52 (t, 1H, $H_{arom\,7}$, J=7.9 Hz), 7.56 (t, 1H, $H_{arom\,3}$, J=7.9 Hz), 7.75 (d, 1H, $H_{arom\,8}$, J=7.3 Hz), 7.84 (d, 1H, $H_{arom\,6}$, J=8.4 Hz), 7.93 (s, 1H, $H_{Pz\,5}$), 7.97 (s, 1H, $H_{Pz\,3}$), 7.99 (d, 1H, $H_{arom\,2}$, J=7.7 Hz), 9.50 (s, 1H, NH), 9.97 (s, 1H, NH). m/z: 461.2 [(M+H)$^+$, calcd for $C_{25}H_{24}N_4O_5$ 460.2].

Example 140

2-(3,4,5-Trimethoxyphenylamino)-6-(2-chlorophenyl-oxy)-pyrazine, CJS 489

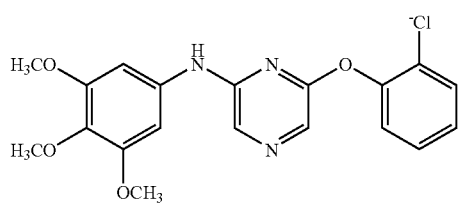

Using Method EE with 2-chloro-6-(2-chlorophenyloxy)-pyrazine (200 mg, 0.83 mmol) and 3,4,5-trimethoxyaniline (183 mg, 1.00 mmol), and purification by column chromatography (AcOEt:cyclohexane, 1:1), the title compound was obtained (227 mg). Yield: 71%. $^1$H NMR (250 MHz, DMSO-$d_6$) δ 3.43 (s, 6H, $[CH_3O]_{3+5}$), 3.54 (s, 3H, $[CH_3O]_4$), 6.68 (s, 2H, $H_{arom2'+6'}$), 7.26-7.30 (m, 1H, $H_{arom\,4}$), 7.37-7.40 (m, 2H, $H_{arom\,5+6}$), 7.59 (d, 1H, $H_{arom\,3}$, J=7.8 Hz), 7.82 (s, 1H, $H_{Pz\,5}$), 7.95 (s, 1H, $H_{Pz\,3}$), 9.56 (s, 1H, NH). m/z: 388.1 [(M+H)$^+$, calcd for $C_{19}H_{18}ClN_3O_4$ 387.1].

Example 141

2-(3,4,5-Trimethoxyphenylamino)-6-(3-chlorophenyl-oxy)-pyrazine, CJS 504

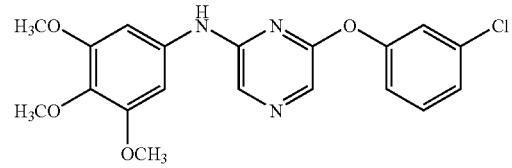

Using Method EE with 2-chloro-6-(3-chlorophenyloxy)-pyrazine (200 mg, 0.83 mmol) and 3,4,5-trimethoxyaniline (183 mg, 1.00 mmol), and purification by column chromatography (AcOEt:cyclohexane, 1:1), the title compound was obtained (165 mg). Yield: 43%. $^1$H NMR (250 MHz, DMSO-$d_6$) δ 3.43 (s, 6H, $[CH_3O]_{3+5}$), 3.54 (s, 3H, $[CH_3O]_4$), 6.76 (s, 2H, $H_{arom2'+6'}$), 7.18 (d, 1H, $H_{arom\,4}$, J=6.5 Hz), 7.28 (d, 1H, $H_{arom\,6}$, J=6.7 Hz), 7.36 (s, 1H, $H_{arom\,2}$), 7.43 (t, 1H, $H_{arom\,5}$, J=8.1 Hz), 7.79 (s, 1H, $H_{Pz\,5}$), 7.98 (s, 1H, $H_{Pz\,3}$), 9.62 (s, 1H, NH).

m/z: 387.2 [(M+H)$^+$, calcd for $C_{25}H_{23}N_3O_4$ 387.1].

Example 142

2-(3,4,5-Trimethoxyphenylamino)-6-[(2-phenyl)-phenyl-oxy]-pyrazine, CJS 492

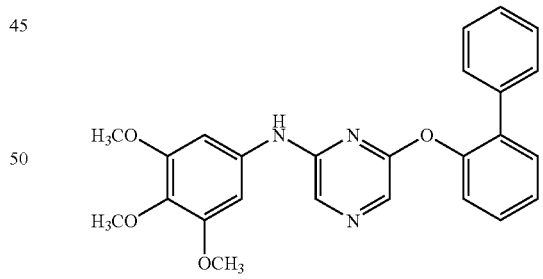

Using Method EE with 2-chloro-6-[(2-phenyl)-phenyl-oxy]-pyrazine (110 mg, 0.39 mmol) and 3,4,5-trimethoxyaniline (84 mg, 0.46 mmol), and purification by column chromatography (AcOEt), the title compound was obtained (101 mg). Yield: 60%. $^1$H NMR (250 MHz, DMSO-$d_6$) δ 3.41 (s, 6H, $[CH_3O]_{3+5}$), 3.55 (s, 3H, $[CH_3O]_4$), 6.79 (s, 2H, $H_{arom2'+6'}$), 7.22-7.49 (m, 9H, $H_{arom}$), 7.66 (s, 1H, $H_{Pz\,5}$) 7.88 (s, 1H, $H_{Pz\,3}$), 9.51 (s, 1H, NH).

m/z: 430.2 [(M+H)$^+$, calcd for $C_{25}H_{23}N_3O_4$ 429.2].

Example 143

2-(3,4,5-Trimethoxyphenylamino)-6-[(3-phenyl)-phenyl-oxy]-pyrazine, CJS 493

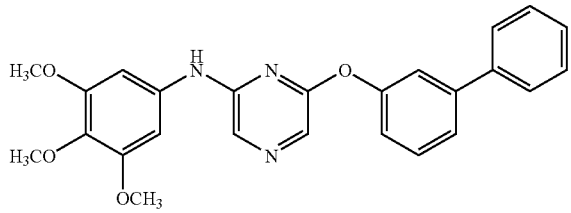

Using Method EE (reaction time: 4 hours) with 2-chloro-6-[(3-phenyl)-phenyl-oxy]-pyrazine (100 mg, 0.35 mmol) and 3,4,5-trimethoxyaniline (84 mg, 0.46 mmol), and purification by column chromatography (AcOEt), the title compound was obtained (117 mg). Yield: 78%.

$^1$H NMR (250 MHz, DMSO-$d_6$) δ 3.51 (s, 6H, [CH$_3$O]$_{3+5}$), 3.67 (s, 3H, [CH$_3$O]$_4$), 6.79 (s, 2H, H$_{arom2'+6'}$), 7.17-7.22 (m, 2H, H$_{arom\ 5+6}$), 7.30-7.52 (m, 6H, H$_{arom}$), 7.63 (dd, 1H, H$_{arom\ 2}$, J$_o$=7.6 Hz, J$_m$=1.3 Hz), 7.81 (s, 1H, H$_{Pz\ 5}$), 7.98 (s, 1H, H$_{Pz\ 3}$), 9.57 (s, 1H, NH). m/z: 430.2 [(M+H)$^+$, calcd for C$_{25}$H$_{23}$N$_3$O$_4$ 429.2].

Example 144

2-(3,4,5-Trimethoxyphenylamino)-6-[(4-phenyl)-phenyl-oxy]-pyrazine, CJS 494

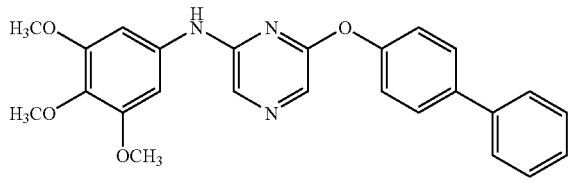

Using Method EE with 2-chloro-6-[(4-phenyl)-phenyl-oxy]-pyrazine (110 mg, 0.39 mmol) and 3,4,5-trimethoxyaniline (84 mg, 0.46 mmol), and purification by column chromatography (AcOEt), the title compound was obtained (105 mg). Yield: 63%. $^1$H NMR (250 MHz, DMSO-$d_6$) δ 3.38 (s, 6H, [CH$_3$O]$_{3+5}$), 3.52 (s, 3H, [CH$_3$O]$_4$), 6.81 (s, 2H, H$_{arom2'+6'}$), 7.29 (d, 2H, H$_{arom\ 3+5}$, J=8.6 Hz), 7.36-7.53 (m, 1H, H$_{arom4''}$), 7.68 (d, 2H, H$_{arom\ 2''+6''}$, J=7.9 Hz), 7.71 (d, 2H, H$_{arom\ 2+6}$, J=8.7 Hz), 7.81 (s, 1H, H$_{Pz\ 5}$), 7.98 (s, 1H, H$_{Pz\ 3}$), 9.58 (s, 1H, NH). m/z: 430.2 [(M+H)$^+$, calcd for C$_{25}$H$_{23}$N$_3$O$_4$ 429.2].

Example 145

2-(3,4,5-Trimethoxyphenylamino)-6-(3-acetamidophenyl-oxy)-pyrazine, CJS 505

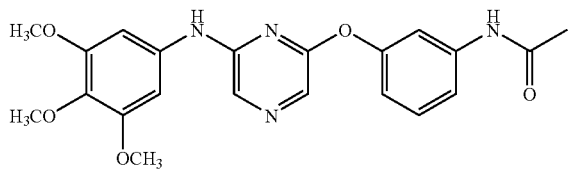

Using Method EE with 2-chloro-6-(3-acetamidophenyl-oxy)-pyrazine (150 mg, 0.57 mmol) and 3,4,5-trimethoxyaniline (125 mg, 0.68 mmol), and crystallisation (AcOEt), the title compound was obtained (81 mg). Yield: 35%. $^1$H NMR (250 MHz, DMSO-$d_6$) δ 2.03 (s, 3H, CH$_3$—NH), 3.44 (s, 6H, [CH$_3$O]$_{3+5}$), 3.56 (s, 3H, [CH$_3$O]$_4$), 6.80 (s, 2H, H$_{arom2'+6'}$), 6.82-6.87 (m, 1H, H$_{arom\ 5}$), 7.31-7.49 (m, 2H, H$_{arom\ 4+6}$), 7.50 (s, 1H, H$_{arom\ 2}$), 7.76 (s, 1H, H$_{Pz\ 5}$), 7.97 (s, 1H, H$_{Pz\ 3}$), 9.55 (s, 1H, NH), 10.04 (s, 1H, NH). m/z: 411.2 [(M+H)$^+$, calcd for C$_{21}$H$_{22}$N$_4$O$_5$ 410.2].

Example 146

2-(3,4,5-Trimethoxyphenylamino)-6-(4-acetamidophenyl-oxy)-pyrazine, CJS 506

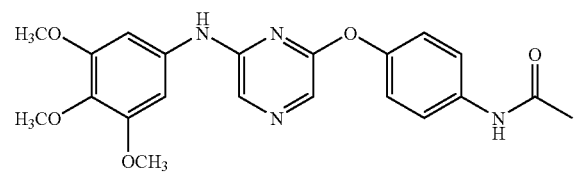

Using Method EE with 2-chloro-6-(4-acetamidophenyl-oxy)-pyrazine (150 mg, 0.57 mmol) and 3,4,5-trimethoxyaniline (125 mg, 0.68 mmol), and crystallisation (AcOEt), the title compound was obtained (87 mg). Yield: 37%. $^1$H NMR (250 MHz, DMSO-$d_6$) δ 2.07 (s, 3H, CH$_3$—NH), 3.43 (s, 6H, [CH$_3$O]$_{3+5}$), 3.55 (s, 3H, [CH$_3$O]$_4$), 6.77 (s, 2H, H$_{arom2'+6'}$), 7.13 (d, 2H, H$_{arom\ 3+5}$, J=8.9 Hz), 7.60 (d, 2H, H$_{arom\ 2+6}$, J=8.9 Hz), 7.73 (s, 1H, H$_{Pz\ 5}$), 7.93 (s, 1H, H$_{Pz\ 3}$), 9.51 (s, 1H, NH), 9.98 (s, 1H, NH). m/z: 411.2 [(M+H)$^+$, calcd for C$_{21}$H$_{22}$N$_4$O$_5$ 410.2].

Example 147

2-(3,4,5-Trimethoxyphenylamino)-6-(acetophenone-3-oxy)-pyrazine, CJS 508

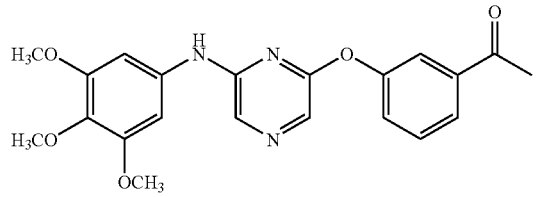

Using Method EE with 2-chloro-6-(acetophenone-3-oxy)-pyrazine (200 mg, 0.80 mmol) and 3,4,5-trimethoxyaniline (176 mg, 0.96 mmol), and purification by column chromatography (AcOEt:cyclohexane, 9:1), the title compound was obtained (85 mg).

Yield: 27%. $^1$H NMR (250 MHz, DMSO-$d_6$) δ 2.61 (s, 3H, CH$_3$—CO), 3.39 (s, 6H, [CH$_3$O]$_{3+5}$), 3.54 (s, 3H, [CH$_3$O]$_4$), 6.74 (s, 2H, H$_{arom\ 2'+6'}$), 7.49 (dd, 1H, H$_{arom\ 4}$, J$_m$=2.3 Hz, J$_o$=9.3 Hz), 7.59 (t, 1H, H$_{arom\ 5}$, J=8.0 Hz), 7.73 (d, 1H, H$_{arom\ 2}$, J$_m$=2.0 Hz), 7.81 (s, 1H, H$_{Pz\ 5}$), 7.82 (d, 1H, H$_{arom\ 6}$, J=6.8 Hz), 7.99 (s, 1H, H$_{Pz\ 3}$), 9.57 (s, 1H, NH). m/z: 396.2 [(M+H)$^+$, calcd for C$_{21}$H$_{21}$N$_3$O$_5$ 395.1].

Example 148

2-(3,4,5-Trimethoxyphenylamino)-6-(acetophenone-4-oxy)-pyrazine, CJS 509

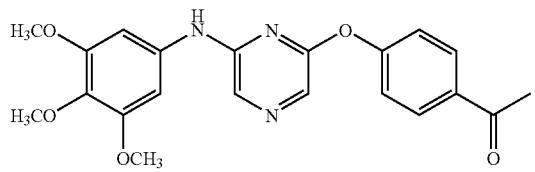

Using Method EE with 2-chloro-6-(acetophenone-4-oxy)-pyrazine (150 mg, 0.60 mmol) and 3,4,5-trimethoxyaniline (148 mg, 0.72 mmol), and purification by column chromatography (AcOEt:cyclohexane, 9:1), the title compound was obtained (85 mg).

Yield: 34%. $^1$H NMR (250 MHz, DMSO-$d_6$) δ 2.56 (s, 3H, $CH_3$—CO), 3.43 (s, 6H, $[CH_3O]_{3+5}$), 3.59 (s, 3H, $[CH_3O]_4$), 6.82 (s, 2H, $H_{arom2'+6'}$), 7.37 (d, 2H, $H_{arom\ 3+5}$, J=8.7 Hz), 7.89 (s, 1H, $H_{Pz\ 5}$), 8.07 (d, 2H, $H_{arom\ 2+6}$, J=6.7 Hz), 8.08 (s, 1H, $H_{Pz\ 3}$), 9.68 (s, 1H, NH).
m/z: 397.1 [(M+H)$^+$, calcd for $C_{21}H_{21}N_3O_5$ 396.1].

Example 149

2-(3,4,5-Trimethoxyphenylamino)-6-(indanone-4-oxy)-pyrazine, CJS 510

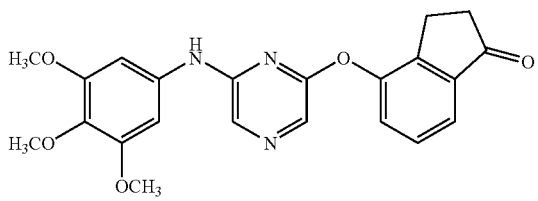

Using Method EE with 2-chloro-6-(indanone-4-oxy)-pyrazine (200 mg, 0.77 mmol) and 3,4,5-trimethoxyaniline (169 mg, 0.92 mmol), and purification by column chromatography (AcOEt), the title compound was obtained (71 mg). Yield: 23%. $^1$H NMR (250 MHz, DMSO-$d_6$) δ 2.69 (t, 2H, $H_3$, J=3.7 Hz), 2.98 (t, 2H, $H_2$, J=5.2 Hz), 3.43 (s, 6H, $[CH_3O]_{3+5}$), 3.59 (s, 3H, $[CH_3O]_4$), 6.75 (s, 2H, $H_{arom2'+6'}$), 7.56-7.62 (m, 3H, $H_{arom}$), 7.90 (s, 1H, $H_{Pz\ 5}$), 8.04 (s, 1H, $H_{Pz\ 3}$), 9.62 (s, 1H, NH). m/z: 408.1 [(M+H)$^+$, calcd for $C_{22}H_{21}N_3O_5$ 407.1].

Example 150

2-(3,4,5-Trimethoxyphenylamino)-6-(indanone-5-oxy)-pyrazine, CJS 511

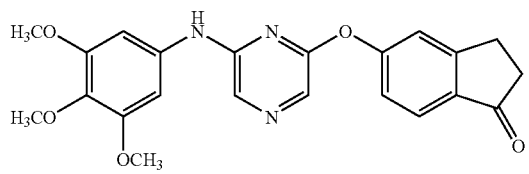

Using Method EE with 2-chloro-6-(indanone-5-oxy)-pyrazine (200 mg, 0.77 mmol) and 3,4,5-trimethoxyaniline (169 mg, 0.92 mmol), and purification by column chromatography (AcOEt), the title compound was obtained (61 mg).

Yield: 20%. $^1$H NMR (250 MHz, DMSO-$d_6$) δ 2.68 (t, 2H, $H_3$, J=5.6 Hz), 3.08 (t, 2H, $H_2$, J=5.0 Hz), 3.39 (s, 6H, $[CH_3O]_{3+5}$), 3.55 (s, 3H, $[CH_3O]_4$), 6.77 (s, 2H, $H_{arom2'+6'}$), 7.21 (dd, 1H, $H_{arom\ 6}$, $J_m$=1.9 Hz, $J_o$=8.3 Hz), 7.40 (s, 1H, $H_{arom\ 4}$), 7.68 (d, 1H, $H_{arom\ 7}$, J=8.3 Hz), 7.84 (s, 1H, $H_{Pz\ 5}$), 8.02 (s, 1H, $H_{Pz\ 3}$), 9.62 (s, 1H, NH). m/z: 408.1 [(M+H)$^+$, calcd for $C_{22}H_{21}N_3O_5$ 407.1].

Example 151

2-(3,4,5-Trimethoxyphenylamino)-6-(indanone-6-oxy)-pyrazine, CJS 512

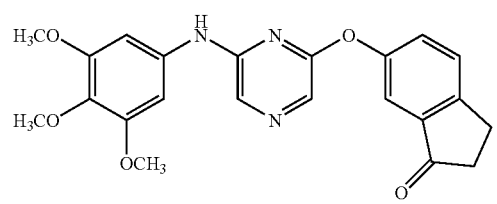

Using Method EE with 2-chloro-6-(indanone-6-oxy)-pyrazine (200 mg, 0.77 mmol) and 3,4,5-trimethoxyaniline (169 mg, 0.92 mmol), and purification by column chromatography (AcOEt), the title compound was obtained (30 mg). Yield: 10%. $^1$H NMR (250 MHz, DMSO-$d_6$) δ 2.73 (t, 2H, $H_3$, J=5.4 Hz), 3.13 (t, 2H, $H_2$, J=5.8 Hz), 3.37 (s, 6H, $[CH_3O]_{3+5}$), 3.54 (s, 3H, $[CH_3O]_4$), 6.72 (s, 2H, $H_{arom2'+6'}$), 7.37 (d, 1H, $H_{arom\ 7}$, J=2.2 Hz), 7.52 (dd, 1H, $H_{arom\ 5}$, $J_m$=2.3 Hz, $J_o$=7.2 Hz), 7.64 (d, 1H, $H_{arom\ 4}$, J=8.3 Hz), 7.81 (s, 1H, $H_{Pz\ 5}$), 7.98 (s, 1H, $H_{Pz\ 3}$), 9.57 (s, 1H, NH). m/z: 408.1 [(M+H)$^+$, calcd for $C_{22}H_{21}N_3O_5$ 407.1].

Example 152

2-(3,4,5-Trimethoxyphenylamino)-6-(indanone-7-oxy)-pyrazine, CJS 513

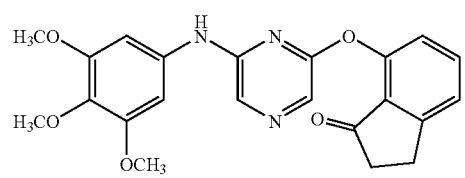

Using Method EE with 2-chloro-6-(indanone-7-oxy)-pyrazine (200 mg, 0.77 mmol) and 169 mg (0.92 mmol) 3,4,5-trimethoxyaniline (169 mg, 0.92 mmol), and purification by column chromatography (AcOEt), the title compound was obtained (11 mg). Yield: 4%.

$^1$H NMR (250 MHz, DMSO-$d_6$) δ 2.49-2.52 (m, 2H, $H_3$), 3.10 (t, 2H, $H_3$, J=5.5 Hz), 3.35 (s, 6H, $[CH_3O]_{3+5}$), 3.54 (s, 3H, $[CH_3O]_4$), 6.64 (s, 2H, $H_{arom2'+6'}$), 7.18 (d, 1H, $H_{arom\ 4}$, J=7.9 Hz), 7.35 (d, 1H, $H_{arom\ 6}$, J=7.5 Hz), 7.70 (t, 1H, $H_{arom\ 5}$, J=7.8 Hz), 7.79 (s, 1H, $H_{Pz\ 5}$), 7.90 (s, 1H, $H_{Pz\ 3}$), 9.46 (s, 1H, NH). m/z: 408.1 [(M+H)$^+$, calcd for $C_{22}H_{21}N_3O_5$ 407.1].

Example 153

2-(3,4,5-Trimethoxyphenylamino)-6-(quinolyl-4-oxy)-pyrazine, CJS 523

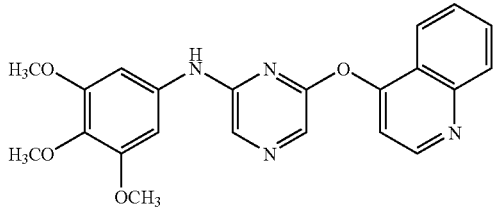

Using Method EE with 2-chloro-6-(quinolyl-4-oxy)-pyrazine (150 mg, 0.58 mmol) and 3,4,5-trimethoxyaniline (128 mg, 0.70 mmol), and crystallisation (AcOEt), the title compound was obtained (48 mg). Yield: 20%. $^1$H NMR (250 MHz, DMSO-$d_6$) δ 3.22 (s, 6H, [$CH_3O$]$_{3+5}$), 3.49 (s, 3H, [$CH_3O$]$_4$), 6.67 (s, 2H, $H_{arom2'+6'}$), 7.16 (d, 1H, $H_{arom\,3}$, J=5.0 Hz), 7.66 (t, 1H, $H_{arom\,7}$, J=7.7 Hz), 7.84 (t, 1H, $H_{arom\,6}$), 8.02 (s, 1H, $H_{Pz\,5}$), 8.08 (d, 1H, $H_{arom\,8}$, J=8.1 Hz), 8.09 (s, 1H, $H_{Pz\,3}$), 8.16 (d, 1H, $H_{arom\,5}$, J=8.1 Hz), 8.80 (d, 1H, $H_{arom\,2}$, J=5.0 Hz), 9.71 (s, 1H, NH). m/z: 405.1 [(M+H)$^+$, calcd for $C_{22}H_{20}N_4O_4$ 404.1].

Example 154

2-(3,4,5-Trimethoxyphenylamino)-6-(quinolyl-5-oxy)-pyrazine, CJS 524

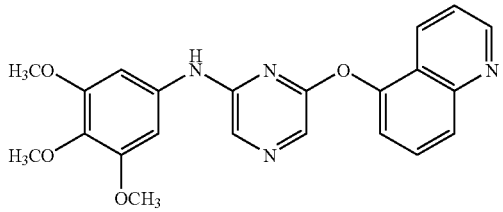

Using Method EE with 2-chloro-6-(quinolyl-5-oxy)-pyrazine (150 mg, 0.58 mmol) and 3,4,5-trimethoxyaniline (128 mg, 0.70 mmol), and crystallisation (AcOEt), the title compound was obtained (77 mg). Yield: 33%. $^1$H NMR (250 MHz, DMSO-$d_6$) δ 3.18 (s, 6H, [$CH_3O$]$_{3+5}$), 3.47 (s, 3H, [$CH_3O$]$_4$), 6.57 (s, 2H, $H_{arom2'+6'}$), 7.43 (d, 1H, $H_{arom\,8}$, J=7.5 Hz), 7.53-7.57 (m, 1H, $H_{arom\,3}$), 7.78 (t, 1H, $H_{arom\,7}$, J=8.5 Hz), 7.93 (d, 1H, $H_{arom\,6}$, J=8.3 Hz), 8.37 (d, 1H, $H_{arom\,8}$, J=8.0 Hz), 7.94 (s, 1H, $H_{Pz\,5}$), 7.99 (s, 1H, $H_{Pz\,3}$), 8.40 (d, 1H, $H_{arom\,4}$, J=8.3 Hz), 8.96 (dd, 1H, $H_{arom\,2}$, J=1.5 Hz, J=3.7 Hz), 9.56 (s, 1H, NH). m/z: 405.1 [(M+H)$^+$, calcd for $C_{22}H_{20}N_4O_4$ 404.1].

Example 155

2-(3,4,5-Trimethoxyphenylamino)-6-(quinolyl-6-oxy)-pyrazine, CJS 525

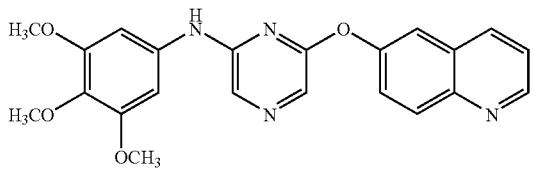

Using Method EE with 2-chloro-6-(quinolyl-6-oxy)-pyrazine (150 mg, 0.58 mmol) and 3,4,5-trimethoxyaniline (128 mg, 0.70 mmol), and crystallisation (AcOEt), the title compound was obtained (149 mg). Yield: 64%. $^1$H NMR (250 MHz, DMSO-$d_6$) δ 3.06 (s, 6H, [$CH_3O$]$_{3+5}$), 3.45 (s, 3H, [$CH_3O$]$_4$), 6.68 (s, 2H, $H_{arom2'+6'}$), 7.50-7.55 (m, 1H, $H_{arom\,3}$), 7.63 (d, 1H, $H_{arom\,7}$, J=9.1 Hz), 7.80 (s, 1H, $H_{arom\,5}$), 7.87 (s, 1H, $H_{Pz\,5}$), 8.00 (s, 1H, $H_{Pz\,3}$), 8.08 (d, 1H, $H_{arom\,8}$, J=9.1 Hz), 8.33 (d, 1H, $H_{arom\,4}$, J=8.2 Hz), 8.89 (d, 1H, $H_{arom\,2}$, J=2.5 Hz), 9.60 (s, 1H, NH). m/z: 405.2 [(M+H)$^+$, calcd for $C_{22}H_{20}N_4O_4$ 404.1].

Example 156

2-(3,4,5-Trimethoxyphenylamino)-6-(isoquinolyl-7-oxy)-pyrazine, CJS 526

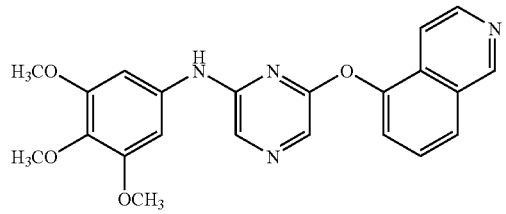

Using Method EE with 2-chloro-6-(quinolyl-6-oxy)-pyrazine (150 mg, 0.58 mmol) and 3,4,5-trimethoxyaniline (128 mg, 0.70 mmol), crystallisation (AcOEt), and purification by column chromatography (AcOEt), the title compound was obtained (67 mg). Yield: 29%.

$^1$H NMR (250 MHz, DMSO-$d_6$) δ 3.20 (s, 6H, [$CH_3O$]$_{3+5}$), 3.48 (s, 3H, [$CH_3O$]$_4$), 6.55 (s, 2H, $H_{arom2'+6'}$), 7.62 (d, 1H, $H_{arom\,7}$, J=7.5 Hz), 7.71 (t, 1H, $H_{arom\,6}$, J=7.9 Hz), 7.80 (d, 1H, $H_{arom\,3}$, J=5.8 Hz), 7.95 (s, 1H, $H_{Pz\,5}$), 7.99 (s, 1H, $H_{Pz\,3}$), 8.03 (d, 1H, $H_{arom\,5}$, J=8.1 Hz), 8.52 (d, 1H, $H_{arom\,2}$, J=5.8 Hz), 9.41 (s, 1H, $H_{arom\,8}$), 9.55 (s, 1H, NH). m/z: 405.1 [(M+H)$^+$, calcd for $C_{22}H_{20}N_4O_4$ 404.1].

Example 157

2-(3,4,5-Trimethoxyphenylamino)-6-(4-N—BOC-aminophenyl-oxy)-pyrazine, CJS 522

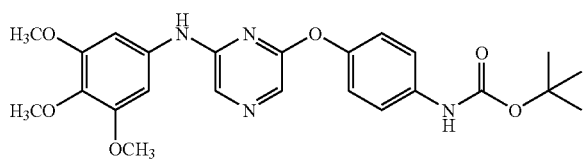

Using Method EE with 2-chloro-6-(4-N—BOC-aminophenyl-oxy)-pyrazine (100 mg, 0.31 mmol) and 3,4,5-trimethoxyaniline (70 mg, 0.38 mmol), and purification by column chromatography (AcOEt:cyclohexane, 1:1), the title compound was obtained (44 mg).

Yield: 30%. $^1$H NMR (250 MHz, DMSO-$d_6$) δ 31.50 (s, 9H, 3×$CH_3$), 3.52 (s, 3H, [$CH_3O$]$_4$), 3.67 (s, 6H, [$CH_3O$]$_{3+5}$), 6.77 (s, 2H, $H_{arom2'+6'}$), 7.09 (d, 2H, $H_{arom\,3+5}$, J=8.8 Hz), 7.47 (d, 2H, $H_{arom\,2+6}$, J=8.8 Hz), 7.72 (s, 1H, $H_{Pz\,5}$), 7.92 (s, 1H, $H_{Pz\,3}$), 9.39 (s, 1H, NH), 9.50 (s, 1H, NH). m/z: 469.2 [(M+H)$^+$, calcd for $C_{24}H_{28}N_4O_6$ 468.2].

Example 158

2-(3,4,5-Trimethoxyphenylamino)-6-(acetophenone oxime-3-oxy)-pyrazine, CJS 514

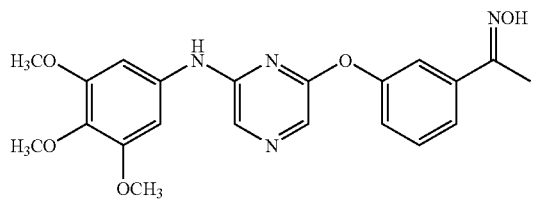

Method FF. 2-(3,4,5-Trimethoxyphenylamino)-6-(acetophenone-3-oxy)-pyrazine (90 mg, 0.22 mmol) and hydrazine hydrate solution 50% (40 μL, 0.96 mmol) were refluxed for 1.5 hours in EtOH (5 mL). The reaction mixture was evaporated to dryness. Purification by column chromatography (AcOEt:EtOH, 9:1) furnished the title compound (37 mg). Yield: 41%. $^1$H NMR (250 MHz, DMSO-$d_6$) δ 2.61 (s, 3H, $CH_3$—CO), 3.39 (s, 6H, $[CH_3O]_{3+5}$), 3.54 (s, 3H, $[CH_3O]_4$), 7.18-7.21 (m, 1H, $H_{arom}$), 7.43-7.50 (m, 3H, $H_{arom}$), 7.79 (s, 1H, $H_{Pz\ 5}$), 7.97 (s, 1H, $H_{Pz\ 3}$), 9.55 (s, 1H, NH), 11.29 (s, 1H, NHOH). m/z: 411.2 [(M+H)$^+$, calcd for $C_{21}H_{22}N_4O_5$ 410.2].

Example 159

2-(3,4,5-Trimethoxyphenylamino)-6-(acetophenone-oxime-4-oxy)-pyrazine, CJS 515

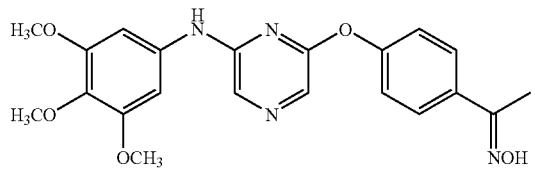

Using Method FF with 2-(3,4,5-trimethoxyphenylamino)-6-(acetophenone-4-oxy)-pyrazine (90 mg, 0.22 mmol) and hydrazine hydrate solution 50% (40 μL, 0.96 mmol), and purification by column chromatography (AcOEt:EtOH, 9:1), the title compound was obtained (30 mg). Yield: 33%. $^1$H NMR (250 MHz, DMSO-$d_6$) δ 2.56 (s, 3H, $CH_3$—CO), 3.44 (s, 6H, $[CH_3O]_{3+5}$), 3.60 (s, 3H, $[CH_3O]_4$), 6.83 (s, 2H, $H_{arom2'+6'}$), 7.26 (d, 2H, $H_{arom\ 3+5}$, J=8.7 Hz), 7.74 (d, 2H, $H_{arom\ 2+6}$, J=8.7 Hz), 7.84 (s, 1H, $H_{Pz\ 5}$), 8.02 (s, 1H, $H_{Pz\ 3}$), 9.63 (s, 1H, NH), 11.25 (s, 1H, NHOH). m/z: 411.2 [(M+H)$^+$, calcd for $C_{21}H_{22}N_4O_5$ 410.2].

Example 160

2-(3,4,5-Trimethoxyphenylamino)-6-(indanone-oxime-4-oxy)-pyrazine, CJS 516

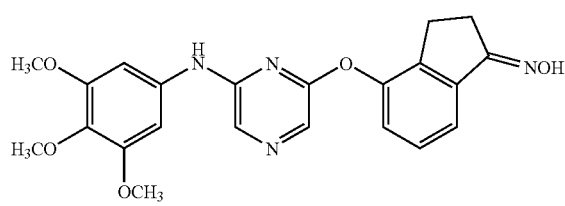

Using Method FF (reaction time: 5 hours) with 2-(3,4,5-trimethoxyphenylamino)-6-(indanone-4-oxy)-pyrazine (70 mg, 0.17 mmol) and hydrazine hydrate solution (32 μL, 0.51 mmol), and crystallisation (AcOEt), the title compound was obtained (30 mg). Yield: 42%. $^1$H NMR (250 MHz, DMSO-$d_6$) δ 2.78 (m, 2H, $H_3$), 3.36 (m, 2H, $H_2$), 3.38 (s, 6H, $[CH_3O]_{3+5}$), 3.53 (s, 3H, $[CH_3O]_4$), 6.72 (s, 2H, $H_{arom\ 2'+6'}$), 7.18 (d, 1H, $H_{arom\ 7}$, J=7.6 Hz), 7.33 (t, 1H, $H_{arom\ 6}$, J=7.7 Hz), 7.44 (d, 1H, $H_{arom\ 5}$, J=7.3 Hz), 7.80 (s, 1H, $H_{Pz\ 5}$), 7.96 (s, 1H, $H_{Pz\ 3}$), 9.57 (s, 1H, NH), 11.02 (s, 1H, NHOH). m/z: 423.2 [(M+H)$^+$, calcd for $C_{22}H_{22}N_4O_5$ 422.1].

Example 161

2-(3,4,5-Trimethoxyphenylamino)-6-(indanone-oxime-5-oxy)-pyrazine, CJS 517

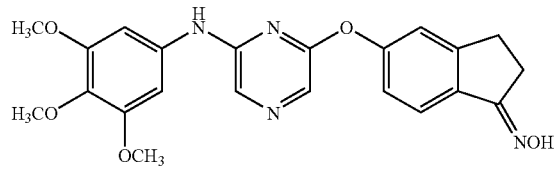

Using Method FF (reaction time: 5 hours) with 2-(3,4,5-trimethoxyphenylamino)-6-(indanone-5-oxy)-pyrazine (70 mg, 0.17 mmol) and hydrazine hydrate solution (32 μL, 0.51 mmol), and crystallisation (AcOEt), the title compound was obtained (41 mg). Yield: 51%. $^1$H NMR (250 MHz, DMSO-$d_6$) δ 2.68 (t, 2H, $H_3$, J=5.6 Hz), 3.08 (t, 2H, $H_2$, J=5.3 Hz), 3.37 (s, 6H, $[CH_3O]_{3+5}$), 3.54 (s, 3H, $[CH_3O]_4$), 6.77 (s, 2H, $H_{arom2'+6'}$), 7.22 (dd, 1H, $H_{arom\ 6}$, $J_m$=2.0 Hz, $J_o$=7.3 Hz), 7.40 (d, 1H, $H_{arom\ 4}$, J=1.7 Hz), 7.68 (d, 1H, $H_{arom\ 7}$, J=8.4 Hz), 7.85 (s, 1H, $H_{Pz\ 5}$), 8.02 (s, 1H, $H_{Pz\ 3}$), 9.67 (s, 1H, NH), 10.87 (s, 1H, NHOH). m/z: 423.2 [(M+H)$^+$, calcd for $C_{22}H_{22}N_4O_5$ 422.1].

Example 162

2-(3,4,5-Trimethoxyphenylamino)-6-(tetralonyl-1-oxime-5-oxy)-pyrazine, CJS 519

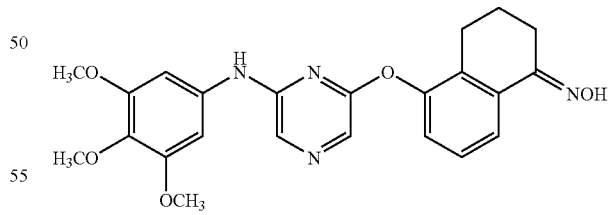

Using Method FF (reaction time: 4.5 hours) with 2-(3,4,5-trimethoxy phenylamino)-6-(tetralon-1-yl-5-oxy)-pyrazine (100 mg, 0.24 mmol) and hydrazine hydrate solution (44 μL, 0.70 mmol), and crystallisation (AcOEt), the title compound was obtained (55 mg). Yield: 53%. $^1$H NMR (250 MHz, DMSO-$d_6$) δ 1.69 (t, 2H, $H_3$, J=5.9 Hz), 2.64-2.65 (m, 4H, $H_{2+4}$), 3.40 (s, 6H, $[CH_3O]_{3+5}$), 3.53 (s, 3H, $[CH_3O]_4$), 6.71 (s, 2H, $H_{arom2'+6'}$), 7.13 (d, 1H, $H_{arom\ 8}$, J=7.9 Hz), 7.25 (t, 2H, $H_{arom\ 7}$, J=7.9 Hz), 7.76 (d, 1H, $H_{arom\ 6}$, J=5.2 Hz), 7.77 (s, 1H, $H_{Pz\,5}$), 7.93 (s, 1H, $H_{Pz\,3}$), 9.53 (s, 1H, NH), 11.27 (s, 1H, NHOH). m/z: 437.2 [(M+H)$^+$, calcd for $C_{23}H_{24}N_4O_5$ 436.2].

Example 163

2-(3,4,5-trimethoxyphenylamino)-6-(tetralonyl-1-oxime-6-oxy)-pyrazine, CJS 520

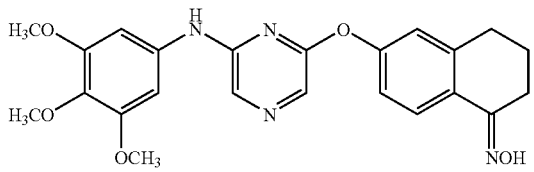

Using Method FF (reaction time: 4.5 hours) with 2-(3,4,5-trimethoxy phenylamino)-6-(tetralon-1-yl-6-oxy)-pyrazine (100 mg, 0.24 mmol) and hydrazine hydrate solution (44 μL, 0.70 mmol), and crystallisation (AcOEt), the title compound was obtained (32 mg). Yield: 30%. $^1$H NMR (250 MHz, DMSO-d$_6$) δ 1.75 (t, 2H, H$_3$, J=5.2 Hz), 2.61-2.68 (m, 4H, H$_{2+4}$), 3.40 (s, 6H, [CH$_3$O]$_{3+5}$), 3.54 (s, 3H, [CH$_3$O]$_4$), 6.79 (s, 2H, H$_{arom2'+6'}$), 7.03-7.18 (m, 2H, H$_{arom\,5+8}$), 7.78 (s, 1H, H$_{Pz\,5}$) 7.87 (d, 1H, H$_{arom\,7}$, J=8.4 Hz), 7.96 (s, 1H, H$_{Pz\,3}$), 9.60 (s, 1H, NH), 11.10 (s, 1H, NHOH). m/z: 437.2 [(M+H)$^+$, calcd for $C_{23}H_{24}N_4O_5$ 436.2].

Example 164

2-(3,4,5-Trimethoxyphenylamino)-6-(4-aminophenyl-oxy)-pyrazine, CJS 480

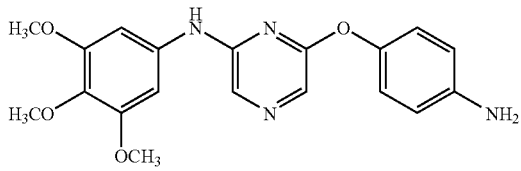

Method GG. 2-(3,4,5-Trimethoxyphenylamino)-6-(4-N—BOC-aminophenyl-oxy)-pyrazine (140 mg, 0.30 mmol) was stirred at room temperature for 1 hour in TFA (6 mL). The solvent was evaporated in vacuo. Purification by column chromatography (AcOEt) gave the title compound (90 mg). Yield: 82%. $^1$H NMR (250 MHz, DMSO-d$_6$) δ 3.56 (s, 6H, [CH$_3$O]$_{3+5}$), 3.73 (s, 3H, [CH$_3$O]$_4$), 6.81 (s, 2H, H$_{arom2'+6'}$), 6.94 (d, 2H, H$_{arom\,3+5}$, J=8.8 Hz), 7.07 (d, 2H, H$_{arom\,2+6}$, J=8.8 Hz), 7.71 (s, 1H, H$_{Pz\,5}$), 7.93 (s, 1H, H$_{Pz\,3}$), 9.53 (s, 1H, NH).

Example 165

2-(3,4,5-trimethoxyphenylamino)-6-(N$^1$-phenyl-ureyl-N$^3$-phenyl-oxy)-pyrazine, CJS 464

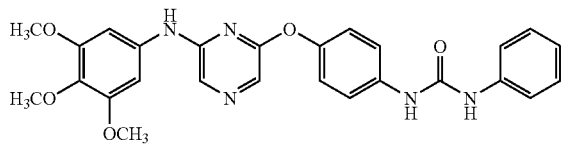

Method HH. 2-(3,4,5-Trimethoxyphenylamino)-6-(4-aminophenyl-oxy)-pyrazine (50 mg, 0.14 mmol) was suspended in DCM (5 mL) and phenylisocyanate (17 μL, 0.15 mmol) was added under stirring. The reaction mixture was kept at 40° C. for 60 hours. The precipitate formed was filtered, yielding the title compound (20 mg). Yield: 30%. $^1$H NMR (250 MHz, DMSO-d$_6$) δ 3.46 (s, 6H, [CH$_3$O]$_{3+5}$), 3.55 (s, 3H, [CH$_3$O]$_4$), 6.79 (s, 2H, H$_{arom2'+6'}$), 6.98 (t, 1H, H$_{arom\,4'''}$, J=7.3 Hz), 7.13 (d, 2H, H$_{arom\,3+5}$, J=8.8 Hz), 7.28 (d, 1H, H$_{arom\,6'''}$, J=8.1 Hz), 7.31 (d, 1H, H$_{arom\,2''}$, J=7.7 Hz), 7.48 (d, 4H, H$_{arom\,2+6\,and\,3''+5'''}$, J=8.8 Hz), 7.74 (s, 1H, H$_{Pz\,5}$), 7.93 (s, 1H, H$_{Pz3}$), 8.69 (s, 1H, NH$_{urea}$), 8.76 (s, 1H, NH$_{urea}$), 9.52 (s, 1H, NH). m/z: 488.2 [(M+H)$^+$, calcd for $C_{26}H_{25}N_6O_5$ 487.2].

Example 166

2-(3,4,5-Trimethoxyphenylamino)-6-[N$^1$-(4-chloro-3-fluoromethyl-phenyl)-ureyl-N$^3$-phenyl-oxy]-pyrazine, CJS 465

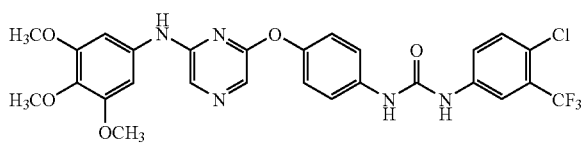

Using Method HH with 2-(3,4,5-trimethoxyphenylamino)-6-(4-aminophenyl-oxy)-pyrazine (50 mg, 0.14 mmol) and 4-chloro-3-fluoromethyl-phenylisocyanate (33 mg, 0.15 mmol), the title compound was obtained (30 mg). Yield: 36%. $^1$H NMR (250 MHz, DMSO-d$_6$) δ 3.45 (s, 6H, [CH$_3$O]$_{3+5}$), 3.54 (s, 3H, [CH$_3$O]$_4$), 6.79 (s, 2H, H$_{arom2'+6'}$), 7.14 (d, 2H, H$_{arom\,3+5}$, J=8.9 Hz), 7.49 (d, 2H, H$_{arom\,2+6}$, J=8.9 Hz), 7.60-7.70 (m, 2H, H$_{arom5'''+6'''}$), 7.74 (s, 1H, H$_{Pz\,5}$), 7.93 (s, 1H, H$_{Pz3}$), 8.14 (m, 1H, H$_{arom2'''}$), 8.97 (s, 1H, NH$_{urea}$), 9.22 (s, 1H, NH$_{urea}$), 9.52 (s, 1H, NH). m/z: 590.2 [(M+H)$^+$, calcd for $C_{27}H_{23}ClF_3N_5O_5$ 589.1].

Example 167

N-(5-Hydroxynaphthalen-1-yl)acetamide, CJS 726

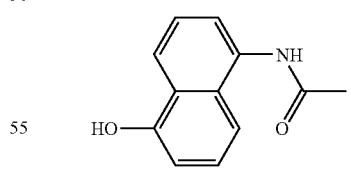

Using Method W with 5-amino-1-naphthol (10.0 g, 62.8 mmol) and not using triethylamine, the target compound was obtained (15.6 g). Yield: 99%. $^1$H NMR (250 MHz, DMSO-d$_6$) δ 2.16 (s, 3H), 6.89 (d, 1H, J=7.3 Hz), 7.28-7.43 (m, 2H), 7.51 (d, 1H, J=8.5 Hz), 7.66 (d, 1H, J=7.4 Hz), 7.98 (d, 1H, J=8.3 Hz), 9.78 (s, 1H), 10.13 (s, 1H). $^{13}$C NMR (62.9 MHz, DMSO-d$_6$) δ 23.44, 108.09, 113.19, 119.08, 121.78, 123.95, 125.26, 126.10, 129.10, 133.36, 153.33, 168.76. m/z 202.1 [(M+H)$^+$ calcd for $C_{12}H_{11}NO_2$ 201.1].

Example 168

6-Phenoxy-N-(3,4,5-trimethoxyphenyl)pyrazin-2-amine, CJS 718

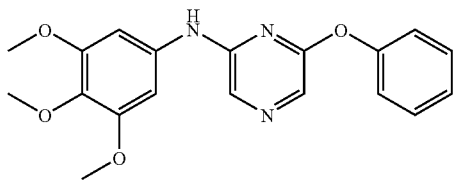

Using Method X (but with no addition of K₂CO₃) with 2-(3,4,5-trimethoxyphenylamino)-6-chloropyrazine (150 mg) and phenol, the title compound was obtained (127 mg). Yield: 71%. ¹H NMR (250 MHz, DMSO-d₆) δ 3.31 (s, 9H), 3.54 (s, 3H), 6.77 (s, 2H), 7.16-7.23 (m, 3H), 7.41 (t, 2H, J=7.9 Hz), 7.75 (s, 1H), 7.95 (s, 1H), 9.53 (s, 1H). ¹³C NMR (62.9 MHz, DMSO-d₆) δ 55.33, 60.03, 95.77, 120.55, 121.17, 124.47, 128.42, 129.74, 132.15, 136.29, 150.52, 152.69, 153.86, 153.86, 157.23. m/z 354.1 [(M+H)⁺ calcd for C₁₉H₁₉N₃O₄ 353.1].

Example 169

6-(Pyridin-4-yloxy)-N-(3,4,5-trimethoxyphenyl)pyrazin-2-amine, CJS 719

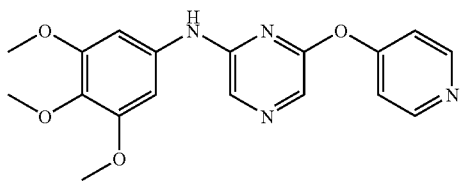

Using Method X with 150 mg of 2-(3,4,5-trimethoxyphenylamino)-6-chloropyrazine and 4-hydroxypyridine, the title compound was obtained (89 mg). Yield: 50%. ¹H NMR (250 MHz, DMSO-d₆) δ 3.64 (s, 3H), 3.79 (s, 6H), 6.29 (d, 2H, J=7.9 Hz), 7.07 (s, 2H), 8.19 (s, 1H), 8.32 (s, 1H), 8.43 (d, 2H, J=8.0 Hz), 9.91 (bs, 1H). ¹³C NMR (62.9 MHz, DMSO-d₆) δ 55.61, 60.11, 96.50, 117.94, 121.98, 132.71, 132.79, 135.77, 136.52, 145.43, 150.31, 152.85, 178.22. m/z 355.1 [(M+H)⁺ calcd for C₁₈H₁₈N₄O₄ 354.1].

Example 170

6-(Pyridin-3-yloxy)-N-(3,4,5-trimethoxyphenyl)pyrazin-2-amine, CJS 721

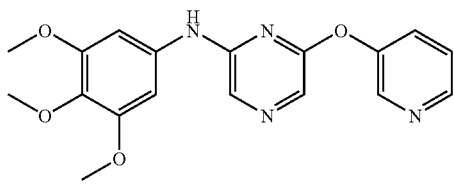

Using Method X with 150 mg of 2-(3,4,5-trimethoxyphenylamino)-6-chloropyrazine and 3-hydroxypyridine, the title compound was obtained (46 mg). Yield: 26%. ¹H NMR (250 MHz, DMSO-d₆) δ 3.41 (s, 6H), 3.54 (s, 3H), 6.71 (s, 2H), 7.47 (ddd, 1H, J₁=0.6 Hz, J₂=4.7 Hz, J₃=8.4 Hz), 7.69 (ddd, 1H, J₁=1.4 Hz, J₂=2.8 Hz, J₃=8.4 Hz), 7.82 (s, 1H), 7.98 (s, 1H), 8.43 (dd, 1H, J₁=1.4 Hz, J₂=4.7 Hz), 8.54 (dd, 1H, J₁=0.5 Hz, J₂=2.8 Hz), 9.61 (s, 1H). ¹³C NMR (62.9 MHz, DMSO-d₆) δ 55.32, 60.04, 95.95, 120.94, 124.52, 128.42, 128.91, 132.34, 136.10, 142.68, 145.66, 150.31, 150.38, 152.71, 156.84. m/z 355.1 [(M+H)⁺ calcd for C₁₈H₁₈N₄O₄ 354.1].

Example 171

6-(Naphthalen-1-ylthio)-N-(3,4,5-trimethoxyphenyl)pyrazin-2-amine, CJS 723

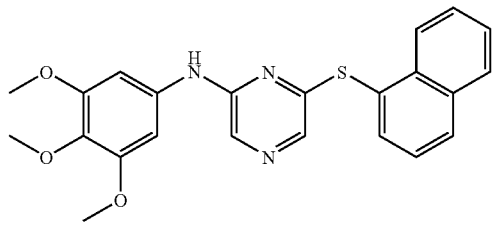

Using Method X with 150 mg of 2-(3,4,5-trimethoxyphenylamino)-6-chloropyrazine and 1-thionaphthol, the title compound was obtained (68 mg). Yield: 32%. ¹H NMR (250 MHz, DMSO-d₆) δ 3.60 (s, 3H), 3.61 (s, 6H), 6.94 (s, 2H), 7.25 (s, 1H), 7.57-7.63 (m, 3H), 7.91 (s, 1H), 7.95 (dd, 1H, J₁=1.2 Hz, J₂=7.1 Hz), 8.03-8.07 (m, 1H), 8.11 (d, 1H, J=8.3 Hz), 8.26-8.30 (m, 1H), 9.54 (s, 1H). ¹³C NMR (62.9 MHz, DMSO-d₆) δ 55.55, 60.09, 96.41, 124.82, 126.23, 126.58, 126.74, 127.65, 128.90, 129.90, 130.63, 131.09, 132.52, 133.33, 133.97, 134.60, 136.13, 151.27, 152.55, 152.74. m/z 420.1 [(M+H)⁺ calcd for C₂₃H₂₁N₃O₃S 419.1].

Example 172

6-(5,6,7,8-Tetrahydronaphthalen-1-yloxy)-N-(3,4,5-trimethoxyphenyl)pyrazin-2-amine, CJS 724

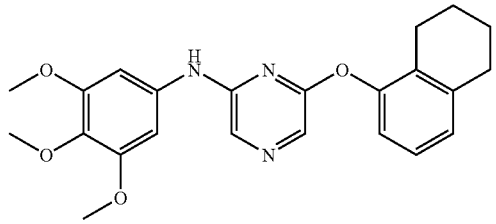

Using Method X with 150 mg of 2-(3,4,5-trimethoxyphenylamino)-6-chloropyrazine and 5,6,7,8-tetrahydro-1-naphthol, the title compound was obtained (27 mg). Yield: 13%. ¹H NMR (250 MHz, DMSO-d₆) δ 1.65-1.69 (m, 4H), 2.53-2.56 (m, 2H), 2.72-2.77 (m, 2H), 3.42 (s, 6H), 3.54 (s, 3H), 6.74 (s, 2H), 6.89 (d, 1H, J=7.9 Hz), 6.95 (d, 1H, J=6.6 Hz), 7.11 (t, 1H, J=7.8 Hz), 7.71 (s, 1H), 7.91 (s, 1H), 9.55 (bs, 1H). ¹³C NMR (62.9 MHz, DMSO-d₆) δ 22.01, 22.26, 23.12, 28.78, 55.36, 60.03, 95.72, 118.40, 120.56, 125.66, 126.09, 127.60, 129.06, 132.10, 136.39, 138.76, 150.59, 151.46, 152.70, 157.65. m/z 408.2 [(M+H)⁺ calcd for C₂₃H₂₅N₃O₄ 407.2].

Example 173

6-(1H-Indol-4-yloxy)-N-(3,4,5-trimethoxyphenyl)pyrazin-2-amine, CJS 725

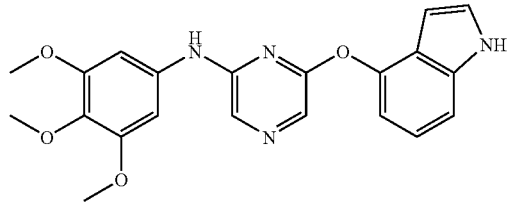

Using Method X with 150 mg of 2-(3,4,5-trimethoxyphenylamino)-6-chloropyrazine and 4-hydroxyindole, the title compound was obtained (34 mg). Yield: 17%. $^1$H NMR (250 MHz, DMSO-$d_6$) δ 3.24 (s, 6H), 3.49 (s, 3H), 6.10-6.12 (m, 1H), 6.66 (s, 2H), 6.79 (d, 1H, J=7.1 Hz), 7.07 (t, 1H, J=7.8 Hz), 7.25-7.29 (m, 2H), 7.79 (s, 1H), 7.92 (s, 1H), 9.44 (s, 1H), 11.26 (s, 1H). $^{13}$C NMR (62.9 MHz, DMSO-$d_6$) δ 55.12, 59.96, 95.43, 98.04, 108.42, 109.87, 120.50, 120.91, 121.37, 125.36, 127.87, 131.91, 136.34, 138.13, 146.33, 150.59, 152.58, 157.84. m/z 393.1 [(M+H)$^+$ calcd for $C_{21}H_{20}N_4O_4$ 392.1].

Example 174

N-(5-(6-(3-(Oxazol-5-yl)phenylamino)pyrazin-2-yloxy)naphthalen-1-yl)acetamide, CJS 727

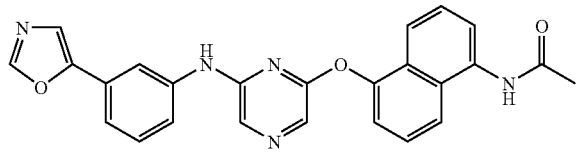

Method II. This method is similar to Method R but employs conventional (rather than microwave) heating and a reaction time of 20 hours. Using 2-chloro-6-(5-acetamidonaphtyl-oxy)-pyrazine (150 mg, 0.48 mmol) and 3-(1,3-oxazol-5-yl-aniline) (96 mg, 0.60 mmol), the title compound was obtained (71 mg). Yield: 34%. $^1$H NMR (250 MHz, DMSO-$d_6$) δ 2.22 (s, 3H), 6.95 (t, 1H, J=7.9 Hz), 7.06 (d, 1H, J=8.5 Hz), 7.15 (d, 1H, J=7.6 Hz), 7.44-7.46 (m, 2H), 7.49-7.52 (m, 2H), 7.57 (d, 1H, J=7.6 Hz), 7.74 (d, 1H, J=6.6 Hz), 7.77 (d, 1H, J=8.2 Hz), 7.94 (s, 1H), 7.96 (s, 1H), 8.02 (d, 1H, J=8.4 Hz), 8.36 (s, 1H), 9.68 (bs, 1H), 9.99 (bs, 1H). $^{13}$C NMR (125.8 MHz, DMSO-$d_6$) δ 23.44, 113.35, 117.19, 117.82, 117.99, 118.40, 120.07, 120.86, 121.74, 122.02, 125.49, 126.10, 127.53, 127.61, 127.69, 129.22, 134.08, 140.57, 149.18, 149.98, 150.28, 151.61, 154.70, 158.28, 168.90. m/z 438.1 [(M+H)$^+$ calcd for $C_{25}H_{19}N_5O_3$ 437.1].

Example 175

N-(5-(6-(3-Oxo-1,3-dihydroisobenzofuran-5-ylamino)pyrazin-2-yloxy)naphthalen-1-yl)acetamide, CJS 728

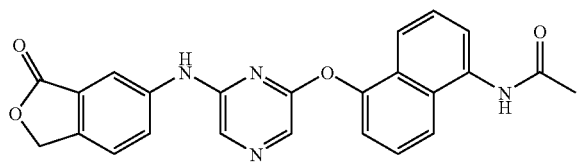

Method JJ. This method is identical to Method II, but uses microwave heating. Using Method JJ (heating time: 30 minutes) with 2-chloro-6-(5-acetamidonaphtyl-oxy)-pyrazine (150 mg, 0.48 mmol) and 6-amino-1,3-dihydroisobenzofuran-1-one (89 mg, 0.60 mmol), the title compound was obtained (8 mg). Yield: 4%. $^1$H NMR (250 MHz, DMSO-$d_6$) δ 2.21 (s, 3H), 5.24 (s, 2H), 7.17 (d, 1H, J=8.5 Hz), 7.45-7.51 (m, 3H), 7.63 (d, 1H, J=8.2 Hz), 7.68-7.75 (m, 3H), 7.92 (s, 1H), 7.98 (s, 1H), 8.05 (d, 1H, J=8.7 Hz), 9.92 (bs, 1H), 10.00 (bs, 1H). m/z 427.1 [(M+H)$^+$ calcd for $C_{24}H_{18}N_4O_4$ 426.1].

Example 176

N-(4-(6-(3-(Oxazol-5-yl)phenylamino)pyrazin-2-yloxy)naphthalen-1-yl)acetamide, CJS 734

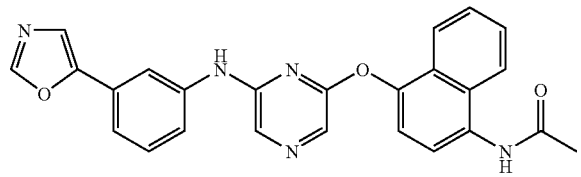

Using Method JJ with N-(4-(6-chloropyrazin-2-yloxy)naphthalen-1-yl)acetamide (150 mg, 0.48 mmol) and 3-(1,3-oxazol-5-yl-aniline) (115 mg, 0.71 mmol), the title compound was obtained (97 mg). Yield: 46%. $^1$H NMR (500 MHz, DMSO-$d_6$) δ 2.22 (s, 3H), 6.95 (t, 1H, J=7.9 Hz), 7.10 (d, 1H, J=8.2 Hz), 7.14 (d, 1H, J=7.7 Hz), 7.41 (d, 1H, J=8.2 Hz), 7.44 (bs, 2H), 7.54 (t, 1H, J=7.5 Hz), 7.60 (t, 1H, =7.4 Hz), 7.70 (d, 1H, J=8.1 Hz), 7.91 (d, 1H, J=8.5 Hz), 7.95 (bs, 2H), 8.16 (d, 1H, J=8.4 Hz), 8.37 (s, 1H), 9.70 (bs, 1H), 9.99 (bs, 1H). $^{13}$C NMR (125.8 MHz, DMSO-$d_6$) δ 23.43, 113.25, 117.10, 117.70, 117.81, 120.71, 121.66, 121.77, 123.32, 126.27, 126.53, 127.31, 127.45, 127.53, 128.92, 129.39, 131.23, 140.63, 146.10, 149.99, 150.27. m/z 438.1 [(M+H)$^+$ calcd for $C_{25}H_{19}N_5O_3$ 437.1].

Example 177

N-(4-(6-Chloropyrazin-2-yloxy)naphthalen-1-yl)acetamide, CJS 733

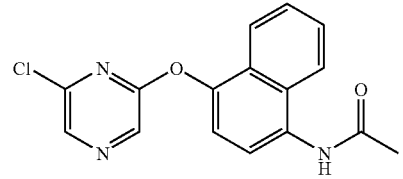

Method KK. A mixture of N-(4-hydroxynaphthalen-1-yl)acetamide (1.22 g, 6.08 mmol) and potassium tert-butoxide (0.68 g, 6.08 mmol) in dry DMF (19 mL) was stirred for 1 hour under argon. To this mixture, 2,6-dichloropyrazine (1.09 g, 7.30 mmol) was added and the temperature was raised to 90° C. and maintained for 20 hours. The DMF was evaporated in vacuo. The resulting crude was dissolved in a (hot) mixture of AcOEt (25 mL) and acetone (175 mL) and filtered. The volume of the filtrate was reduced to 100 mL and this filtrate crystallised upon storage at low temperature to yield the title compound (1.30 g). Yield: 68%. $^1$H NMR (500 MHz, DMSO-$d_6$) δ 2.21 (s, 3H), 7.42 (d, 1H, J=8.2 Hz), 7.57 (t, 1H, J=7.5 Hz), 7.64 (t, 1H, J=7.6 Hz), 7.72 (d, 1H, J=8.1 Hz), 7.90 (d, 1H, J=8.3 Hz), 8.16 (d, 1H, J=8.5 Hz), 8.52 (s, 1H), 8.72 (s, 1H), 10.02 (s, 1H). $^{13}$C NMR (125.8 MHz, DMSO-$d_6$) δ 23.42, 117.59, 121.40, 121.65, 123.42, 126.53, 126.71, 126.85, 128.90, 131.85, 133.59, 137.50, 144.40, 145.04, 158.92, 169.04. m/z 314.0 [(M+H)$^+$ calcd for $C_{16}H_{12}ClN_3O_2$ 313.1].

Example 178

2-(3,4,5-Trimethoxyphenylamino)-6-[4-(4-fluorophenylcarbonyl)-aminophenyl]-pyrazine, CJS 495

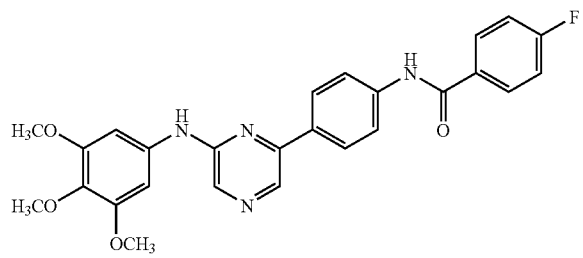

Method LL. In a tube suitable for parallel synthesis, 2-(3,4,5-trimethoxyphenylamino)-6-(4-aminophenyloxy)-pyrazine (50 mg, 0.14 mmol) and 4-fluorophenylcarbonyl chloride (21 µL, 0.17 mmol) were stirred under nitrogen for 20 hours in dry dioxane (5 mL) in the presence of triethylamine (25 mL, 1.2 eq). The reaction mixture was evaporated to dryness, redissolved in 10 mL AcOEt, the solution washed (2×10 mL brine), dried, and purified by column chromatography (AcOEt) to give the title compound (33 mg). Yield: 50%. $^1$H NMR (250 MHz, DMSO-d$_6$) δ 3.69 (s, 3H, [CH$_3$O]$_4$), 3.89 (s, 6H, [CH$_3$O]$_{3+5}$), 7.32 (s, 2H, H$_{arom2'+6'}$), 7.44 (t, 2H, H$_{arom\ 2''+6''}$, J=8.8 Hz), 7.98 (d, 2H, H$_{arom\ 3+5}$, J=8.6 Hz), 8.10-8.21 (m, 4H, H$_{arom\ 3''+5''}$ and H$_{arom\ 2+6}$), 8.18 (s, 1H, H$_{Pz\ 5}$), 8.57 (s, 1H, H$_{Pz\ 3}$), 9.61 (s, 1H, NH), 10.50 (s, 1H, NH$_{amide}$). m/z 475.2 [(M+H)$^+$ calcd for C$_{26}$H$_{23}$FN$_4$O$_4$ 474.2].

Example 179

2-(3,4,5-Trimethoxyphenylamino)-6-[4-(4-trifluoromethyl-phenylcarbonyl)-aminophenyl]-pyrazine, CJS 496

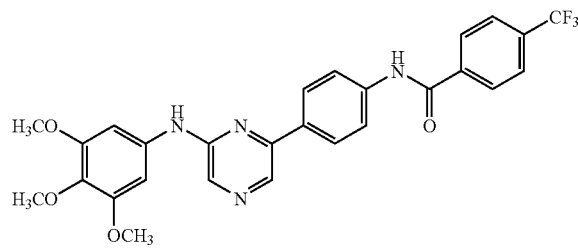

Using Method LL with 2-(3,4,5-trimethoxyphenylamino)-6-(4-aminophenyloxy)-pyrazine (50 mg, 0.14 mmol) and 4-trifluoromethyl-phenylcarbonyl chloride (35 mg, 0.17 mmol), and purification by column chromatography (AcOEt), the title compound was obtained (34 mg). Yield: 46%. $^1$H NMR (250 MHz, DMSO-d$_6$) δ 3.65 (s, 3H, [CH$_3$O]$_4$), 3.85 (s, 6H, [CH$_3$O]$_{3+5}$), 7.28 (s, 2H, H$_{arom2'+6'}$), 7.95 (d, 4H, H$_{arom\ 3+5}$ and H$_{arom\ 2''+6''}$ J=8.5 Hz), 8.15-8.21 (m, 4H, and H$_{arom\ 2+6}$, H$_{arom\ 3''+5''}$ and H$_{Pz\ 5}$), 8.53 (s, 1H, H$_{Pz\ 3}$), 9.57 (s, 1H, NH), 10.66 (s, 1H, NH$_{amide}$). m/z 525.2 [(M+H)$^+$ calcd for C$_{27}$H$_{23}$F$_3$N$_4$O$_4$ 524.2].

Example 180

2-(3,4,5-Trimethoxyphenylamino)-6-[4-(4-chlorophenylcarbonyl)-aminophenyl]-pyrazine, CJS 497

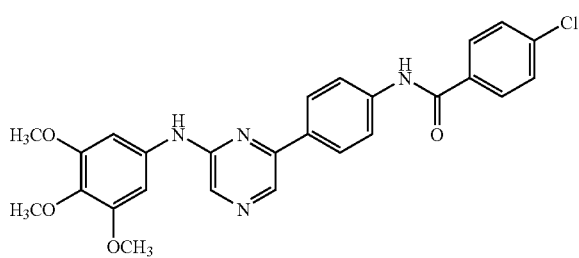

Using Method LL with 2-(3,4,5-trimethoxyphenylamino)-6-(4-aminophenyloxy)-pyrazine (50 mg, 0.14 mmol) and 4-chlorophenylcarbonyl chloride (22 µL, 0.17 mmol), and purification by column chromatography (AcOEt), the title compound was obtained (23 mg). Yield: 34%. $^1$H NMR (250 MHz, DMSO-d$_6$) δ 3.65 (s, 3H, [CH$_3$O]$_4$), 3.85 (s, 6H, [CH$_3$O]$_{3+5}$), 7.28 (s, 2H, H$_{arom2'+6'}$), 7.64 (d, 2H, H$_{arom\ 3+5}$, J=8.5 Hz), 7.93 (d, 2H, H$_{arom\ 3''+5''}$, J=8.6 Hz), 7.93 (m, 2H, H$_{arom\ 2''+6''}$), 8.03 (m, 2H, H$_{arom\ 2+6}$), 8.14 (s, 1H, H$_{Pz\ 5}$), 8.53 (s, 1H, H$_{Pz\ 3}$), 9.56 (s, 1H, NH), 10.50 (s, 1H, NH$_{amide}$). m/z 491.1 [(M+H)$^+$ calcd for C$_{26}$H$_{23}$ClN$_4$O$_4$ 490.1].

Example 181

2-(3,4,5-Trimethoxyphenylamino)-6-[4-(4-di-n-propylaminosulphamidyl-phenyl carbonyl)-aminophenyl]-pyrazine, CJS 501

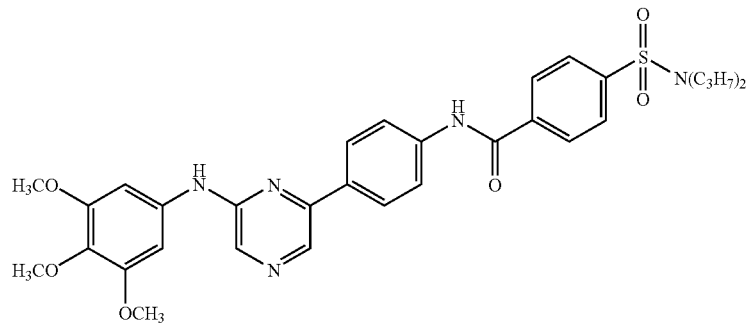

Using Method LL with 2-(3,4,5-trimethoxyphenylamino)-6-(4-aminophenyloxy)-pyrazine (50 mg, 0.14 mmol) and with 4-(di-n-propylaminosulphamidyl)-phenylcarbonyl chloride (52 mg, 0.17 mmol), and purification by column chromatography (AcOEt), the title compound was obtained (51 mg). Yield: 55%. $^1$H NMR (250 MHz, DMSO-$d_6$) δ 0.84 (t, 6H, $CH_3$, J=7.3 Hz), 1.46-1.56 (m, 4H, $CH_2$), 3.08 (m, 4H, N—$CH_2$, J=7.7 Hz), 3.64 (s, 3H, $[CH_3O]_4$), 3.85 (s, 6H, $[CH_3O]_{3+5}$), 7.27 (s, 2H, $H_{arom2'+6'}$), 7.93-7.99 (m, 4H, $H_{arom\ 3+5}$ and $H_{arom\ 3''+5''}$), 8.14-8.18 (m, 4H, $H_{arom\ 2+6}$ and $H_{arom2''+6''}$), 8.14 (s, 1H, $H_{Pz\ 5}$), 8.54 (s, 1H, $H_{Pz\ 3}$), 9.60 (s, 1H, NH), 10.68 (s, 1H, $NH_{amide}$). m/z 620.2 [(M+H)$^+$ calcd for $C_{32}H_{37}N_5O_6S$ 619.2].

Example 182

2-(3,4,5-Trimethoxyphenylamino)-6-[4-(2,6-difluorophenylcarbonyl)-amino phenyl]-pyrazine, CJS 502

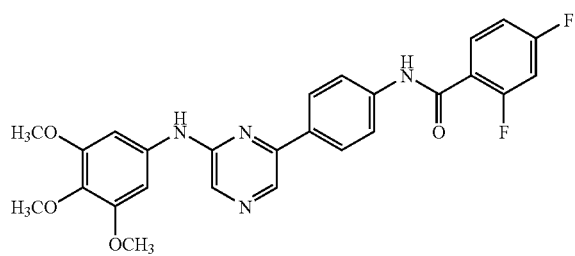

Using Method LL with 2-(3,4,5-trimethoxyphenylamino)-6-(4-aminophenyloxy)-pyrazine (50 mg, 0.14 mmol) and 2,6-difluoro-phenylcarbonyl chloride (30 mg, 0.17 mmol), and purification by column chromatography (AcOEt), the title compound was obtained (21 mg). Yield: 30%. $^1$H NMR (250 MHz, DMSO-$d_6$) δ 3.65 (s, 3H, $[CH_3O]_4$), 3.85 (s, 6H, $[CH_3O]_{3+5}$), 7.27 (s, 2H, $H_{arom2'+6'}$), 7.45-7.47 (m, 1H, $H_{arom\ 3''}$), 7.79-7.84 (m, 2H, $H_{arom\ 4''+5''}$), 7.86 (d, 2H, $H_{arom\ 3+5}$, J=8.3 Hz), 8.14 (s, 1H, $H_{Pz\ 5}$), 8.15 (d, 2H, $H_{arom\ 2+6}$, J=6.7 Hz), 8.52 (s, 1H, $H_{Pz\ 3}$), 9.56 (s, 1H, NH), 10.61 (s, 1H, $NH_{amide}$). m/z 493.2 [(M+H)$^+$ calcd for $C_{26}H_{22}F_2N_4O_6$ 492.2].

Biological Methods—Kinase Assay No. 1

Compounds were assessed by a kinase assay performed according to the following protocol.

1. Prepare three stock solutions: AB Solution, Start Mix, and Dilution Buffer.

| AB solution: 1 ml | |
|---|---|
| Tris pH 7.5 (1M) | 50 µL |
| β-Mercaptoethanol | 3 µL |
| EDTA pH 8 (0.5M) | 2 µL |
| Triton (10%) | 10 µL |
| NaF (5 mM) | 30 µL |
| $NaVO_4$ (20 µM) | 25 µL |
| Bovine Serum Albumin (20 mg/ml) | 50 µL |
| *Myelin Basic Protein (30 mg/mL) | 60 µL |
| *MEK (5 mg/ml) | 5 µL |
| *ERK (7.5 mg/ml) | 37.5 µL |
| $H_2O$ | 727.5 µL |
| Start mix: 300 µL | |
| ATP (100 mM) | 1.8 µL |
| $MgCl_2$ (1M) | 14.4 µL |
| $H_2O$ | 281.8 µL |
| HOT $^{32}$Pα | 2 µL |

| Dilution buffer: 1 ml | |
|---|---|
| Tris pH 7.5 (1M) | 50 µL |
| EDTA pH 8 (0.5M) | 0.2 µL |
| NaCl (5M) | 20 µL |
| Triton (10%) | 10 µL |
| NaF (5 mM) | 10 µL |
| $NaVO_4$ (20 µM) | 10 µL |
| β-Mercaptoethanol | 3 µL |
| Bovine Serum Albumin (20 mg/mL) | 50 µL |
| $H_2O$ | 847 µL |

*= Added just prior to use

2. Prepare the B-RAF dilutions:

B-RAF dilution (1)=Mix 7.5 µL $^{V600E}$B-RAF+30 µL dilution buffer.

(This is a 1 in 5 dilution.)

B-RAF dilution (0.1)=Mix 20 µL $^{V600E}$B-RAF dilution (1)+180 µL dilution buffer.

(This is a further 1 in 10 dilution, so the total B-RAF dilution is 50×.)

3. Mix 700 µL AB solution+175 µL B-RAF dilution (0.1). This solution is now referred to as AB0.1.
4. Add 24.5 µL AB0.1 solution into numbered tubes, as indicated below.

(Note: Each Reaction is Tested in Triplicate.)

5. Add 20 µL AB solution to the blowout and empty vector control tubes.
6. Add DMSO, $H_2O$ etc. to the control tubes, as below.
7. Add 0.5 µL of test compound of the desired concentration (diluted in DMSO) to the appropriate tubes, as below. (Note: stock test compound concentration is 100 mM.)

| Tube | AB0.1 | AB | Test Compound concentration | Controls | Amount of B-RAF per tube |
|---|---|---|---|---|---|
| 1 | 24.5 µL | — | 1000 µM | — | 0.1 µL |
| 2 | 24.5 µL | — | 100 µM | — | 0.1 µL |
| 3 | 24.5 µL | — | 10 µM | — | 0.1 µL |
| 4 | 24.5 µL | — | 1 µM | — | 0.1 µL |
| 5 | 24.5 µL | — | 0.1 µM | — | 0.1 µL |
| 6 | 24.5 µL | — | 0.01 µM | — | 0.1 µL |
| 7 | 24.5 µL | — | — | DMSO 0.5 µL | 0.1 µL |
| 8 | 24.5 µL | — | — | $H_2O$ 0.5 µL | 0.1 µL |
| 9 (blowout) | — | 20 µL | — | B-RAF dilution (1) 5 µL | 1 µL |
| 10 | — | 20 µL | — | Empty vector 5 µL | 0 µL |
| 11 (positive control) | 24.5 µL | — | — | PD (10 µM) 0.5 µL | 0.1 µL |

8. Incubate tubes at 30° C. for 10 minutes.
9. Add 5 µL of start mix to each tube in 15-second intervals, gently spinning each tube after adding the start solution, and incubate at 30° C. for 10 minutes.
10. Stop the reaction by placing 20 µL of the reaction solution in the tube onto a small piece of P81 paper (pre-numbered), and drop this paper into 75 mM orthophosphoric acid. Repeat this every 15 seconds with each tube.
11. When all reactions have been stopped, replace the acid with fresh acid.
12. Do two more of these washes every 15 minutes.

13. Remove the paper from the acid and put into pre-numbered tubes.
14. Count the radiation levels using a Packard Cerenkov counter.

Biological Methods—Kinase Assay No. 2 (DELFIA)

Compounds were assessed by a kinase assay performed according to the following protocol.

The following reagents were prepared:

DELFIA Kinase Buffer (DKB):

| Reagent | Stock Concentration | Volume per mL (μL) | Volume per 10 mL plate (μL) |
|---|---|---|---|
| 20 mM MOPS pH 7.2 | 0.2 M | 100 | 1000 |
| 0.5 M EGTA pH 8.0 | 0.5 M | 10 | 100 |
| 10 mM MgCl$_2$ | 1 M | 10 | 100 |
| 0.1% β-mercaptoethanol |  | 1 | 10 |
| 25 mM β-glycerophosphate | 0.5 M | 50 | 500 |
| Water | 100% | 829 | 8290 |

MOPS = 3-[N-Morpholino] propanesulfonic acid (Sigma M3183).
EGTA = Ethylene glycol-bis(2-aminoethylether)-N,N,N',N'-tetraacetic acid (Sigma E3889).

DKB1 (DKB with B-RAF and MEK Protein):

Combine 4950 μL of DKB and 50 μL of 2.5 mg/ml GST-MEK stock (to give 1 mg of MEK per 40 μL). Then add 22.5 μL of B-RAF to give ~0.2 μL of B-RAF per 40 μL.

DKB2 (DKB with MEK Protein):

Combine 4950 μL of DKB and 50 μL of 2.5 mg/ml GST-MEK stock (to give 1 mg of MEK per 40 μL). Use 500 μL of this for the blow out (BO) and the empty vector (EV) control.

ATP:

100 mM stock, dilute to 500 μM to give 100 μM final concentration in assay.

Inhibitors (Test Compounds):

100 mM stock, dilute to 10, 3, 1, 0.3, 0.1, 0.03, 0.01, 0.003, 0.001, 0.0003, 0.0001 mM in DMSO in drug plate, resulting in concentration of 100, 30, 10, 3, 1, 0.3, 0.1, 0.03, 0.01, 0.003, 0.001 μM in the assay.

Primary Antibody:

Phospho-MEK1/2 CST #9121S diluted 1:1000 in DELFIA assay buffer (AB). Preincubate antibody in the AB for 30 minutes at room temperature prior-to-use.

Secondary Antibody:

Anti-rabbit-Eur labelled secondary Perkin Elmer #AD0105 diluted 1:1000 in DELFIA assay buffer (AB). Pre-incubate antibody in the AB for 30 minutes at room temperature prior to use. (Primary and secondary antibodies were incubated together,)

Tween:

0.1% Tween 20 in water

Assay Buffer:

DELFIA assay buffer Perkin Elmer #4002-0010

Enhancement Solution:

DELFIA enhancement solution Perkin Elmer #4001-0010

Assay Plates:

96 well glutathione-coated black plate Perbio #15340

Procedure:
1. Preblock wells with 5% milk in TBS for 1 hour.
2. Wash wells with 3× with 200 μL TBS.
3. Plate out 40 μL of DKB1 for all inhibitors (test compounds), DMSO control, and optionally other control compounds.
4. Plate out 40 μL of DKB2 for BO and EV wells.
5. Add inhibitors (test compounds) at 0.5 μL per well according to desired plate layout.
6. Add 0.5 μL DMSO to vehicle control wells.
7. Add 2 μL of B-RAF to BO and EV wells.
8. Pre-incubate with inhibitors (test compounds) for 10 minutes at room temperature with shaking.
9. Add 10 μL of 500 μM ATP stock, in DKB, to give 100 μM assay concentration.
10. Seal plates with TopSeal and incubate at room temperature with shaking for 45 minutes.
11. Wash plates 3× with 200 μL 0.1% Tween20/Water to terminate reaction.
12. Add 50 μL per well of antibody mix and incubate for 1 hour at room temperature with shaking.
13. Wash plates 3× with 200 μL 0.1% Tween20/Water.
14. Add 100 μL DELFIA enhancement solution per well, cover in foil, and incubate at room temperature for 30 minutes with shaking.
15. Read on Victor using Europium protocol.

Biological Methods—Cell Based Assays

Compounds were assessed using cell-based assays which were performed according to the following protocol.

Day 0:
Plate out 16,000 cells/well in 99 μL medium in a 96-well plate.

Day 1:
1. Add 1 μL inhibitor to the cells (total 1 μL solution).
2. Incubate the cells with test compound for 6 hours at 37° C.
3. Aspirate off the solution from all of the wells.
4. Fixate the cells with 100 μL 4% formaldehyde/0.25% Triton X-100 PBS per well.
5. Incubate the plate for 1 hour at 4° C.
6. Aspirate off the fixing solution and add 300 μL TBS per well.
7. Leave the plate overnight at 4° C.

Day 2:
1. Wash the plate 2× with 200 μL PBS per well.
2. Block with 100 μL 5% dried milk in TBS.
3. Incubate the plate for 20 minutes at 37° C.
4. Wash the plate 2× with 0.1% tween/H$_2$O.
5. Add 50 μL of 3 μg/mL primary antibody ppERK (Sigma M8159), diluted in 5% milk powder/TBS, to each well.
6. Incubate the plate for 2 hours at 37° C.
7. Wash the plate 3× with 0.1% tween/H$_2$O.
8. Add 50 μL of 0.45 μg/mL secondary Europium-labelled anti-mouse antibody (Perkin Elmer) to each well.
9. Incubate the plate for 1 hour at 37° C.
10. Wash the plate 3× with 0.1% tween/H$_2$O.
11. Add 100 μL enhancement solution (Perkin Elmer) to each well.
12. Leave the plate for approximately 10 minutes at room temperature before gently shaking the plate.
13. Read Europium Time Resolved Fluorescence in Victor2.
14. Wash the plate 2× with 0.1% tween/H$_2$O.
15. Measure the protein concentration with BCA (Sigma) by adding 200 μL of solution per well.
16. Incubate the plate for 30 minutes at 37° C.
17. Read absorbance levels at 570 nm in a plate reader.

Note that Europium counts are normalised for protein levels by dividing counts by absorbance.

Biological Methods—Cell Proliferation Assay (SRB IC$_{50}$)

Cultures of WM266.4 melanoma cells are routinely cultured in DMEM/10% foetal bovine serum, at 37° C., in 5% CO$_2$ water saturated atmosphere. Cultures are maintained in exponential growth phase by sub-culturing before having become confluent (3-5 day intervals). Single cell suspensions are prepared by harvesting an 80 cm² tissue culture flask with 5 mL commercial trypsin EDTA. After 5 minutes, the detached cells are mixed with 5 mL fully complemented culture medium and centrifugally pelleted (1000 rpm for 7 minutes). After aspirating the supernatant, the cell pellet is re-suspended in 10 mL fresh medium and the cells fully disaggregated by drawing the whole volume up/down 5 times through a 19-gauge needle. The concentration of the cells is determined using a haemocytometer (1/10 dilution). A suitable volume to give at least a 2-fold excess for the number of tests being conducted, typically 100-200 mL, is prepared by diluting the cell suspension to 10,000/mL, and 100 µL/well dispensed into 96 well plates using a programmable 8-channel peristaltic pump, giving 1000 cells/well, leaving column 12 blank. The plates are returned to the incubator for 24 hours to allow the cells to re-attach. The compounds being tested are prepared at 20 mM in dimethylsulphoxide. Aliquots (200 µL) are diluted into 20 mL culture medium giving 200 µM, and 10 serial dilutions of 3× performed by transferring 5 mL to 10 mL. Aliquots (100 µL) of each dilution are added to the wells, using an 8-channel pipettor, thus performing a final further 2× dilution, and giving doses ranging from 100 µM to 0.005 µM. Column 11 receives plain culture medium only. Each compound is tested in quadruplicate, each replicate being the average of four wells, and two plates per compound. After a further 6 days growth, the plates are emptied, and the cells are fixed in 10% trichloroacteic acid for 10 minutes on ice. After thorough rinsing in running tap water, the plates are dried, and stained by adding 50 µL of a solution of 0.1% sulphorhodamine-B in 1% acetic acid, for 10 minutes at room temperature. The stain is poured out and the plates thoroughly rinsed under a stream of 1% acetic acid, thus removing unbound stain, and dried. The bound stain is taken into solution by addition of 150 µL Tris buffer pH 8, followed by 10 minutes on a plate-shaker (approximately 500 rpm). The absorbance at 540 nm in each well (being proportional to the number of cells present) is determined using a plate reader. After averaging the results in rows A-D and E-H, the blank value (row 12) is subtracted, and results expressed as percentage of the untreated value (row 11). The 10 values so derived (in quadruplicate) are plotted against the logarithm of the drug concentration, and analysed by non-linear regression to a four parameter logistic equation, setting constraints-if suggested by inspection. The $IC_{50}$ generated by this procedure is the concentration of the drug that produces a percentage control $A_{540}$ midway between the saturation, and zero-effect plateaus.

Biological Methods—B-RAF High Throughput Screen $^{V600E}$B-RAF was used in a cascade assay that included MEK1, ERK2 and Elk. Phosphorylation through this cascade was measured using a specific phospho-Elk antibody and a Europium-labelled anti-mouse IgG secondary antibody in a DELFIA ELISA assay.

High-binding 384-well clear polystyrene plates (Greiner 00360148) were coated overnight (4° C.) with 25 µL Elk (2.5 µg/mL in PBS).

The plates were washed three times with PBS and the wells blocked with 5% milk (Marvel) in PBS. After 30 minutes at room temperature, the plates were again washed three times with PBS.

$^{V600E}$B-RAF lysate, MEK1 and ERK2 were pre-mixed in B-RAF buffer (Tris 50 mM, pH 7.5, containing 10 mM MgCl₂, 100 µM EGTA, 0.1% mercaptoethanol, 5 mM sodium fluoride, 200 µM sodium orthovanadate and 0.5 mg/ml BSA) so that the equivalent of 0.05 µL B-RAF, 81.25 ng MEK1 and 1 µg ERK2 were added to each well in a total volume of 17 µL. Inhibitors (200 µM) or DMSO control (2%) 3 µL were added to the plates prior to enzyme mix. The enzyme reaction was started by the addition of 5 µL ATP solution (125 µM in B-RAF buffer) (final concentration 25 µM) and the reaction stopped by washing the plates three times in 0.1% Tween/water. Anti-phospho Elk (Ser 383 monoclonal antibody) (Cell Signalling Technology #9186) diluted 1/4000 and Eu-labelled anti-mouse IgG (Perkin Elmer Life Sciences, AD0124) diluted to 1/50, were pre-mixed (30 minutes at room temperature) in DELFIA assay buffer (Perkin Elmer Life Sciences 4002-0010) and 25 µL added to each well. After 1.5 hours, the plates were washed again (3×) in 0.1% Tween/water.

35 µL of Enhancement solution (Perkin Elmer Life Sciences 4001-0010) was then added and after 20 minutes at room temperature, the plates were read on a Victor2 at 615 nm (excitation 340 nm in time resolved fluorescence mode). Percent inhibition was calculated in relation to DMSO only controls. Staurosporin was used as a positive control.

In a high throughput screen (HTS) context, hits were identified as compounds that inhibited the enzyme cascade by more than 3 standard deviations of the mean of the compound wells (n=320) on each plate.

Biological Data

The following compounds were tested using one or more of a BRAF V599E kinase assay, a phospho-ERK cell-based assay, and a cell proliferation (SRB) assay:

CJS 350, CJS 351, CJS 352, CJS 354, CJS 355, CJS 357, CJS 359, CJS 361, CJS 362, CJS 363, CJS 364, CJS 365, CJS 366, CJS 367, CJS 368, CJS 369, CJS 370, CJS 371, CJS 372, CJS 373, CJS 374, CJS 375, CJS 377, CJS 378, CJS 379, CJS 380, CJS 381, CJS 382, CJS 383, CJS 384, CJS 385, CJS 386, CJS 387, CJS 388, CJS 389, CJS 390, CJS 391, CJS 392, CJS 393, CJS 394, CJS 398, CJS 400, CJS 402, CJS 407, CJS 408, CJS 409, CJS 410, CJS 411, CJS 413, CJS 415, CJS 416, CJS 426, CJS 428, CJS 429, CJS 430, CJS 438, CJS 439, CJS 440, CJS 441, CJS 442, CJS 444, CJS 446, CJS 447, CJS 448, CJS 449, CJS 454, CJS 457, CJS 459, CJS 461, CJS 462, CJS 464, CJS 465, CJS 466, CJS 467, CJS 468, CJS 469, CJS 470, CJS 471, CJS 472, CJS 473, CJS 474, CJS 475, CJS 476, CJS 477, CJS 479, CJS 480, CJS 481, CJS 482, CJS 483, CJS 484, CJS 485, CJS 486, CJS 487, CJS 488, CJS 489, CJS 490, CJS 491, CJS 492, CJS 493, CJS 494, CJS 495, CJS 496, CJS 497, CJS 501, CJS 502, CJS 504, CJS 505, CJS 506, CJS 508, CJS 509, CJS 510, CJS 511, CJS 512, CJS 513, CJS 514, CJS 515, CJS 516, CJS 517, CJS 519, CJS 520, CJS 523, CJS 524, CJS 525, CJS 526, CJS 702, CJS 703, CJS 705, CJS 706, CJS 707, CJS 709, CJS 711, CJS 712, CJS 717, CJS 718, CJS 719, CJS 721, CJS 723, CJS 724, CJS 725, CJS 727, CJS 728, CJS 734.

About 80% had an IC50 of less than 20 µM in at least one of the three assays.

About 90% had an $IC_{50}$ of less than 50 µM in at least one of the three assays.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The present invention is not limited to those embodiments which are encompassed by the appended claims, which claims pertain to only some of many preferred embodiments, and which claims are included at this time primarily for initial search purposes. This is particularly true for the claims to compounds per se.

What is claimed is:
1. A compound selected from compounds of the following formula and pharmaceutically acceptable salts thereof:

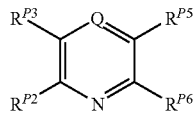

wherein:
Q is independently —N═;
$R^{P3}$ is independently a group of the formula -$J^1$-$L^1$-Z;
-$J^1$-$L^1$-Z is independently —NH—Z;
$R^{P2}$ is independently —H;
$R^{P5}$ is independently a group of the formula —W—Y;
W is independently —O—;
$R^{P6}$ is independently —H;
Z is independently $C_{6-14}$ carboaryl and is independently unsubstituted or substituted with one or more of the following substituents:
—C(═O)OH, —C(═O)OMe, —C(═O)OEt, —C(═O)O(iPr), —C(═O)O(tBu), —C(═O)O(cPr), —C(═O)OCH₂CH₂OH, —C(═O)OCH₂CH₂OMe, —C(═O)OCH₂CH₂OEt, —C(═O)OPh, —C(═O)OCH₂Ph, —(C═O)NH₂, —(C═O)NMe₂, —(C═O)NEt₂, —(C═O)N(iPr)₂, —(C═O)N(CH₂CH₂OH)₂, —(C═O)-morpholino, —(C═O)NHPh, —(C═O)NHCH₂Ph, —C(═O)H, —(C═O)Me, —(C═O)Et, —(C═O)(tBu), —(C═O)-cHex, —(C═O)Ph, —(C═O)CH₂Ph, —F, —Cl, —Br, —I, —OH, —OMe, —OEt, —O(iPr), —O(tBu), —OPh, —OCH₂Ph, —OCF₃, —OCH₂CF₃, —OCH₂CH₂OH, —OCH₂CH₂OMe, —OCH₂CH₂OEt, —OCH₂CH₂OEt, —OCH₂CH₂NH₂, —OCH₂CH₂NMe₂, —OCH₂CH₂N(iPr)₂, —OPh-Me, —OPh-OH, —OPh-OMe, —OPh-F, —OPh-Cl, —OPh-Br, —OPh-I, —SH, —SMe, —SEt, —SPh, —SCH₂Ph, —OC(═O)Me, —OC(═O)Et, —OC(═O)(iPr), —OC(═O)(tBu), —OC(═O)(cPr), —OC(═O)CH₂CH₂OH, —OC(═O)CH₂CH₂OMe, —OC(═O)CH₂CH₂OEt, —OC(═O)Ph, —OC(═O)CH₂Ph, —OC(═O)NH₂, —OC(═O)NHMe, —OC(═O)NMe₂, —OC(═O)NHEt, —OC(═O)NEt₂, —OC(═O)NHPh, —OC(═O)NCH₂Ph, —NH₂, —NHMe, —NHEt, —NH(iPr), —NMe₂, —NEt₂, —N(iPr)₂, —N(CH₂CH₂OH)₂, —NHPh, —NHCH₂Ph, piperidino, piperazino, morpholino, —NH(C═O)Me, —NH(C═O)Et, —NMe(C═O)nPr, —NH(C═O)Ph, —NHC(═O)CH₂Ph, —NMe(C═O)Me, —NMe(C═O)Et, —NMe(C═O)Ph, —NMeC(═O)CH₂Ph, —NHSO₂Me, —NHSO₂Et, —NHSO₂Ph, —NHSO₂PhMe, —NHSO₂CH₂Ph, —NMeSO₂Me, —NMeSO₂Et, —NMeSO₂Ph, —NMeSO₂PhMe, —NMeSO₂CH₂Ph, —SO₂Me, —SO₂CF₃, —SO₂Et, —SO₂Ph, —SO₂PhMe, —SO₂CH₂Ph, —SO₂NH₂, —SO₂NHMe, —SO₂NHEt, —SO₂NMe₂, —SO₂NEt₂, —SO₂-morpholino, —SO₂NHPh, —SO₂NHCH₂Ph, —CH₂Ph, —CH₂Ph-Me, —CH₂Ph-OH, —CH₂Ph-F, —CH₂Ph-Cl, -Ph, -Ph-Me, -Ph-OH, -Ph-OMe, -Ph-NH₂, -Ph-F, -Ph-Cl, -Ph-Br, -Ph-I, pyridyl, pyrazinyl, pyrimidinyl, pyridazinyl, furanyl, thiophenyl, pyrrolyl, imidazoyl, pyrazolyl, oxazoyl, thiazolyl, thiadiazolyl, pyrrolidinyl, imidazolidinyl, pyrazolidinyl, piperidinyl, piperazinyl, azepinyl, tetrahydrofuranyl, tetrahydropyranyl, morpholinyl, azetidinyl, -Me, -Et, -nPr, iPr, -nBu, -iBu, -sBu, -tBu, -nPe, -cPr, -cHex, —CH═CH₂, —CH₂—CH═CH₂, —CF₃, —CHF₂, —CH₂F, —CCl₃, —CBr₃, —CH₂CH₂F, —CH₂CHF₂, and —CH₂F₃, —CH₂OH, —CH₂OMe, —CH₂OEt, —CH₂NH₂, —CH₂NMe₂, —CH₂CH₂OH, —CH₂CH₂OMe, —CH₂CH₂OEt, —CH₂CH₂CH₂NH₂, and —CH₂CH₂NMe₂; and
Y is independently $C_{6-14}$ carboaryl and is independently unsubstituted or substituted with one or more of the following substituents:
(1) —C(═O)OH;
(2) —C(═O)OMe, —C(═O)OEt, —C(═O)O(iPr), —C(═O)O(tBu); —C(═O)O(cPr); —C(═O)OCH₂CH₂OH, —C(═O)OCH₂OMe, —C(═O)OCH₂CH₂OEt; —C(═O)OPh, —C(═O)OCH₂Ph;
(3) —(C═O)NH₂, —(C═O)NMe₂, —(C═O)NEt₂, —(C═O)N(iPr)₂, —(C═O)N(CH₂CH₂OH)₂; —(C═O)-morpholino, —(C═O)NHPh, —(C═O)NHCH₂Ph;
(4) —C(═O)H, —(C═O)Me, —(C═O)Et, —(C═O)(tBu), —(C═O)-cHex, —(C═O)Ph; —(C═O)CH₂Ph;
(5) —F, —Cl, —Br, —I;
(6) —CN;
(7) —NO₂;
(8) —OH;
(9) —OMe, —OEt, —O(iPr), —O(tBu), —OPh, —OCH₂Ph; —OCF₃, —OCH₂CF₃; —OCH₂CH₂OH, —OCH₂CH₂OMe, —OCH₂CH₂Et; —OPh-Me, —OPh-OH, —OPh-OMe, —OPh-F, —OPh-Cl, —OPh-Br, —OPh-I;
(10) —SH;
(11) —SMe, —SEt, —SPh, —SCH₂Ph;
(12) —OC(═C)Me, —OC(═O)Et, —OC(═O)(iPr), —OC(═O)(tBu); —OC(═O)(cPr); —OC(═O)CH₂CH₂OH, —OC(═O)CH₂CH₂OMe, —OC(═O)CH₂CH₂OEt; —OC(═O)Ph, —OC(═O)CH₂Ph;
(13) —OC(═O)NH₂, —OC(═O)NHMe, —OC(═O)NMe₂, —OC(═O)NHEt; —OC(═O)NEt₂, —OC(═O)NCHPh, —OC(═O)NCH₂Ph;
(14) —NH₂, —NHMe, —NHEt, —NH(iPr), —NMe₂, —NEt₂, —N(iPr)₂, —N(CH₂CH₂OH)₂; —NHPh, —NHCH₂Ph; piperidino, piperazino, morpholino;
(15) —NH(C═O)Me, —NH(C═O)Et, —NH(C═O)nPr, —NH(C═O)Ph, —NHC(═O)CH₂Ph;
(16) —NH(C═O)NH₂, —NH(C═O)NHMe, —NH(C═O)NHEt, —NH(C═O)NPh, —NH(C═O)NHCH₂Ph; —NH(C═S)NH₂, —NH(C═S)NHMe, —NH(C═S)NHEt, —NH(C═O)NPh, —NH(C═S)NHCH₂Ph;
(17) —NHSO₂Me, —NHSO₂Et, —NHSO₂Ph, —NHSO₂PhMe, —NHSO₂CH₂Ph; —NMeSO₂Me, —NMeSO₂Et, —NMeSO₂Ph, —NMeSO₂PhMe, —NMeSO₂CH₂Ph;
(18) —SO₂Me, —SO$_{CF3}$, —SO₂Ph, —SO₂PhMe, —SO₂CH₂Ph;
(19) —OSO₂Me, —OSO₂CF₃, —OSO₂Et, —OSO₂Ph, —OSO₂PhMe, —OSO₂CH₂Ph;
(20) —SO₂NH₂, —SO₂NHMe, —SO₂NHEt, —SO₂NMe₂, —SO₂NEt₂, —SO₂-morpholino, —SO₂NHPh, —SO₂NHCH₂Ph;
(21) —CH₂Ph, —CH₂Ph-Me, —CH₂Ph-OH, —CH₂Ph-F, —CH₂-Ph-Cl;
(22) -Ph, -Ph-Me, -Ph-OH, -Ph-OMe, -Ph-NH₂, -Ph-F, -Ph-Cl, -Ph-Br, -Ph-I; pyridyl, pyrazinyl, pyrimidinyl, pyridazinyl, furanyl, thiophenyl, pyrrolyl, imidazolyl, pyrazolyl, oxazolyl, thiazolyl, thiadiazolyl;
(23) pyrrolidinyl, imidazolidinyl, pyrazolidinyl, piperidinyl, piperazinyl, azepinyl, tetrahydrofuranyl, tetrahydropyranyl, morpholinyl, azetidinyl;
(24) -Me, -Et, -nPr, iPr, -nBu, iBu, -sBu, -tBu, -nPe; -cPr, -cHex; —CH═CH₂, —CH₂—CH═CH₂; —CF₃, —CHF₂, —CH₂F, —CCl₃, —CBr₃, —CH₂CH₂F, —CH₂CHF₂, and —CH₂CF₃; —CH₂OH, —CH₂OMe, —CH₂OEt, —CH₂NH₂, —CH₂NMe₂;
—CH₂CH₂OH, —CH₂CH₂OMe, —CH₂CH₂OEt,
—CH₂CH₂CH₂NH₂, —CH₂CH₂NMe₂;
(25) =O;
(26) =NH, =NMe; =NEt;
(27) =NOH, =NOMe, =NOEt, =NO(nPn), =NO(iPr), =NO(cPr), =NO(CH₂-cPr);
(28) —OP(=O)(OH)₂, —P(=O)(OH)₂, —OP(=O)(OMe)₂, —P(=O)(OMe)₂;
(29) —O—CH₂—O—, —O—CH₂—CH₂—O—, —O—CH₂—CH₂—CH₂—O—, —O—CF₂—O—, and —O—CF₂—CF₂—O—.

2. A compound according to claim 1, wherein Z is independently $C_{6-14}$ carboaryl and is independently unsubstituted or substituted with one or more of the following substituents:
—F, —Cl, —Br, —I,
—OMe, —OEt, —OCF₃,
-Ph, pyridyl, furanyl, pyrrolyl, oxazolyl, thiadiazolyl,
-Me, -Et, -tBu, —CF₃, and —CH₂OH.

3. A compound selected from compounds of the following formula and pharmaceutically acceptable salts thereof:

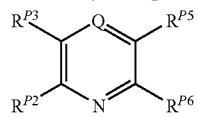

wherein:
Q is independently —N=;
$R^{P3}$ is independently a group of the formula -$J^1$-$L^1$-Z;
-$J^1$-$L^1$-Z is independently —NH—Z;
Z is independently $C_{6-14}$ carboaryl and is independently unsubstituted or substituted with one or more of the following substituents:
(1) carboxylic acid; (2) carboxylic acid ester; (3) amido or thioamido; (4) acyl; (5) halo; (6) cyano; (7) nitro; (8) hydroxy; (9) ether; (10) thiol; (11) thioether; (12) acyloxy; (13) carbamate; (14) amino; (15) acylamino or thioacylamino; (16) aminoacylamino or aminothioacylamino; (17) sulfonamino; (18) sulfonyl; (19) sulfonate; (20) sulfonamido; (21) $C_{5-20}$aryl-$C_{1-7}$alkyl; (22) $C_{5-20}$aryl; (23) $C_{3-20}$heterocyclyl; (24) $C_{1-7}$alkyl; (25) oxo; (26) imino; (27) hydroxyimino; (28) phosphate; and (29) bi-dentate di-oxy groups;
$R^{P2}$ is independently —H;
$R^{P5}$ is independently a group of the formula —W—Y;
W is independently —O—;
Y is independently $C_{6-14}$ carboaryl and is independently unsubstituted or substituted with one or more of the following substituents:
(1) carboxylic acid; (2) carboxylic acid ester; (3) amido or thioamido; (4) acyl; (5) halo; (6) cyano; (7) nitro; (8) hydroxy; (9) ether; (10) thiol; (11) thioether; (12) acyloxy; (13) carbamate; (14) amino; (15) acylamino or thioacylamino; (16) aminoacylamino or aminothioacylamino; (17) sulfonamino; (18) sulfonyl; (19) sulfonate; (20) sulfonamido; (21) $C_{5-20}$aryl-$C_{1-7}$alkyl; (22) $C_{5-20}$aryl; (23) $C_{3-20}$heterocyclyl; (24) $C_{1-7}$alkyl; (25) oxo; (26) imino; (27) hydroxyimino; (28) phosphate; and (29) bi-dentate di-oxy groups; and
$R^{P6}$ is independently —H.

4. A compound according to claim 3, wherein Y is independently naphthyl; and is independently unsubstituted or substituted.

5. A compound according to claim 3, wherein Y is independently phenyl; and is independently unsubstituted or substituted.

6. A compound according to claim 3, wherein Z is independently naphthyl; and is independently unsubstituted or substituted.

7. A compound according to claim 3, wherein Z is independently phenyl; and is independently unsubstituted or substituted.

8. A compound according to claim 3, wherein the compound has a molecular weight of 275 to 1000.

9. A composition comprising a compound according to claim 3 and a pharmaceutically acceptable carrier or diluent.

10. A compound selected from compounds of the following formula and pharmaceutically acceptable salts thereof:

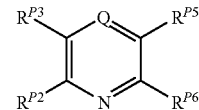

wherein:
Q is independently —N=;
$R^{P3}$ is independently a group of the formula -$J^1$-$L^1$-Z;
-$J^1$-$L^1$-Z is independently —NH—Z;
Z is independently phenyl, and is independently unsubstituted or substituted with one or more substituents selected from: —C(=O)OH, —C(=O)OMe, —C(=O)OEt, —C(=O)O(iPr), —C(=O)O(tBu), —C(=O)O(cPr), —C(=O)OCH₂CH₂OH, —C(=O)OCH₂CH₂OMe, —C(=O)OCH₂CH₂OEt, —C(=O)OPh, —C(=O)OCH₂Ph, —(C=O)NH₂, —(C=O)NMe₂, —(C=O)NEt₂, —(C=O)N(iPr), —C(=O)N(CH₂CH₂OH)₂, —(C=O)-morpholino, —(C=O)NHPh, —(C=O)NHCH₂Ph, —C(=O)H, —(C=O)Me, —(C=O)Et, —(C=O)(tBu), —(C=O)-cHex, —(C=O)Ph, —(C=O)CH₂Ph, —F, —Cl, —Br, —I, —OH, —OMe, —OEt, —O(iPr), —O(tBu), 13 OPh, —OCH₂Ph, —OCF₃, —OCH₂CF₃, —OCH₂CH₂OH, —OCH₂CH₂OMe, —OCH₂CH₂OEt, —OCH₂CH₂NH₂, —OCH₂CH₂NMe₂, —OCH₂CH₂N(iPr), —OPh-Me, —OPh-OH, —OPh-OMe, —OPh-F, —OPh-F, —OPh-Cl, —OPh-Br, —OPh-I, —SH, —SMe, —SEt, —SPh, —SCH₂Ph, —OC(=O)Me, —OC(=O)Et, —OC(=O)(iPr), —OC(=O)(tBu), —OC(=O)(cPr), —OC(=O)CH₂CH₂OH, —OC(=O)CH₂CH₂OMe, —OC(=O)CH₂CH₂OEt, —OC(=O)Ph, —OC(=O)CH₂Ph, —OC(=O)NH₂, —OC(=O)NHMe, —OC(=O)NMe₂, —OC(=O)NHEt, —OC(=O)NEt₂, —OC(=O)NHPh, —OC(=O)NCH₂Ph, —NH₂, —NHMe, —NHEt, —NH(iPr), —NMe₂, —NEt₂, —N(iPr)₂, —N(CH₂CH₂OH)₂, —NHPh, —NHCH₂Ph, piperidino, piperazino, morpholino, —NH(C=O)Me, —NH(C=O)Et, —NH(C=O)nPr, —NH(C=O)Ph, —NCH(=O)CH₂Ph, —NMe(C=O)Me, —NMe(C=)Et, —NMe(C=O)Ph, —NMeC(=O)CH₂Ph, —NHSO₂Me, —NHSO₂Et, —NHSO₂Ph, —NMeSO₂PhMe, —NMeSO₂CH₂Ph, —NMeSO₂Me, —NMeSO₂Et, —NMeSO₂Ph, —NMeSO₂PhMe, —NMeSO₂CH₂Ph, —SO₂Me, —SO₂CF₃, —SO₂Et, —SO₂Ph, —SO₂PhMe, —SO₂CH₂Ph, —SO₂NH₂, —SO₂NHMe, —SO₂NHEt, —SO₂NMe₂, —SO₂NEt₂, —SO₂-morpholino, —SO₂NHPh, —SO₂NHCH₂Ph, —CH₂Ph, —CH₂Ph-Me, —CH₂Ph-OH, —CH₂Ph-F, —CH₂Ph-Cl, -Ph, -Ph-Me, -Ph-OH, -Ph-OMe, -Ph-NH₂, -Ph-F, -Ph-Cl, -Ph-Br, -Ph-I, pyridyl, pyrazinyl, pyrimidinyl, pyridazinyl, furanyl, thiophenyl, pyrrolyl, imidazolyl, pyrazolyl, oxazolyl, thiazolyl, thiadiazolyl, pyrrolidinyl, imidazolidinyl, pyrazolidinyl, piperidinyl, piperazinyl, azepinyl, tetrahydrofuranyl, tetrahydropyranyl, morpholinyl, azetidinyl, -Me, -Et, -nPr, -iPr, -nBu, -iBu, -sBu, -tBu, -tBu, -nPe, -cPr, -cHex, —CH=CH₂, —CH₂—CH=CH₂, —CF₃, —CHF₂, —CH₂F, —CCl₃, —CBr₃, —CH₂CH₂F, —CH₂CHF₂, —CH₂CF₃, —CH₂OH, —CH₂OMe, —CH₂OEt, —CH₂NH₂, —CH₂NMe₂, —CH₂CH₂OH, —CH₂CH₂OMe, —CH₂CH₂OEt, —CH₂CH₂CH₂NH₂, and —CH₂CH₂NMe₂;

R^P2 is independently —H;

R^P5 is independently a group of the formula —W—Y;

W is independently —O—;

Y is independently phenyl or naphthyl, and is independently unsubstituted or substituted with one or more substituents selected from: —C(=O)OMe, —C(=O)OEt, —C(=O)O(iPr), —C(=O)O(tBu), —C(=O)O(cPr), —C(=O)OCH₂CH₂OH, —C(=O)OCH₂CH₂OMe, —C(=O)OCH₂CH₂OEt, —C(=O)OPh, —C(=O)OCH₂Ph, —(C=O)NH₂, —(C=O)NMe₂, —(C=O)NEt₂, —(C=O)N(iPr)₂, —(C=O)N(CH₂CH₂OH)₂, —C(=O)-morpholino, —(C=O)NHPh, —(C=O)NHCH₂Ph, —C(=O)H, —C(=O)Me, —C(=O)Et, —(C=O)(tBu), —(C=O)-cHex, —(C=O)Ph, —(C=O)CH₂Ph, —F, —Cl, —Br, —I, —CN, —OH, —NH₂, —NHMe, —NHEt, —NH(iPr), —NMe₂, —NEt₂, —N(iPr)₂, —N(CH₂CH₂OH)₂, —NHPh, —NHCH₂Ph, piperidino, piperazino, morpholino, —NH(C=O)Me, —NH(C=O)Et, —(C=O)Pr, —NH(C=O)Ph, —NCH(=O)CH₂Ph, —NMe(C=O)Me, —NMe(C=O)Et, —NMe(C=O)Ph, —NMeC(=O)CH₂Ph, —NH(C=O)NH₂, —NH(C=O)NHMe, —NH(C=O)NHEt, —NH(C=S)NHEt, —NH(C=S)NPh, —NH(C=S)NHCH₂Ph, —NHSO₂Me, —NHSO₂Et, —NHSO₂Ph, —NHSO₂PhMe, —NHSO₂CH₂Ph, —NMeSO₂Me, —NMeSO₂Et, —NMeSO₂Ph, —NMeSO₂PhMe, —NMeSO₂CH₂Ph, —SO₂NH₂, —SO₂NHMe, —SO₂NHEt, —SO₂NMe₂, —SO₂NEt₂, —SO₂-morpholino, —SO₂NHPh, —SO₂NHCH₂Ph, -Me, -Et, -nPr, -iPr, -nBu, -iBu, -sBu, -tBu, -nPe, -cPr, -cHex, —CH=CH₂, —CH₂CH=CH₂, —CF₃, —CHF₂, —CH₂F, —CCl₃, —CBr₃, —CH₂CH₂F, —CH₂CHF₂, —CH₂CF₃, —CH₂OH, —CH₂OMe, —CH₂OEt, —CH₂NH₂, —CH₂NMe₂, —CH₂CH₂OH, —CH₂CH₂OMe, —CH₂CH₂OEt, —CH₂CH₂CH₂NH₂, and —CH₂CH₂NMe₂; and R^P6 is independently —H.

11. A compound according to claim 10, wherein Z is independently phenyl and is independently unsubstituted or substituted with one or more substituents selected from: —C(=O)OMe, —C(=O)OEt, —C(=O)O(iPr), —C(=O)O(tBu), —C(=O)O(cPr), —C(=O)OCH₂CH₂OH, —C(=O)OCH₂CH₂OMe, —C(=O)OCH₂CH₂OEt, —C(=O)OPh, —C(=O)OCH₂Ph, —F, —Cl, —Br, —I, —OH, —OMe, —OEt, —O(iPr), —O(tBu), —OPh, —OCH₂Ph, —OCF₃, —OCH₂CF₃, —OCH₂CH₂OH, —OCH₂CH₂OMe, —OCH₂CH₂OEt, —OCH₂CH₂NH₂, —OCH₂CH₂NMe₂, —OCH₂CH₂N(iPr)₂, —OPh, -Me, —OPh, —OH, —OPh-OMe, —OPh-F, —OPh-Cl, —OPh-Br, —OPh-I, —SH, —SMe, —SEt, —SPh, —SCH₂Ph, —OC(=O)Me, —OC(=O)Et, —OC(=O)(iPr), —OC(=O)(tBu), —OC(=O)(cPr), —OC(=O)CH₂CH₂OH, —OC(=O)CH₂CH₂OMe, —OC(=O)CH₂CH₂OEt, —OC(=O)Ph, —OC(=O)CH₂Ph, —SO₂Me, —SO₂CF₃, —SO₂Et, —SO₂Ph, —SO₂PhMe, —SO₂CH₂Ph, -Ph, -Ph-Me, -Ph-OH, -Ph-OMe, -Ph-NH₂, -Ph-F, -Ph-Cl, -Ph-Br, -Ph-I, pyridyl, pyrazinyl, pyrimidinyl, pyridazinyl, furanyl, thiophenyl, pyrrolyl, imidazolyl, pyrazolyl, oxazolyl, thiazolyl, thiadiazolyl, pyrrolidinyl, imidazolidinyl, pyrazolidinyl, piperidinyl, piperazinyl, azepinyl, tetrahydrofuranyl, tetrahydropyranyl, morpholinyl, azetidinyl, -Me, -Et, -nPr, -iPr, -nBu, -iBu, -sBu, -tBu, -nPe, -cPr, -cHex, —CH=CH₂, —CH₂—CH=CH₂, —CF₃, —CHF₂, —CH₂F, —CCl₃, —CBr₃, —CH₂CH₂F, —CH₂CHF₂, —CH₂CF₃, —CH₂OH, —CH₂OMe, —CH₂OEt, —CH₂NH₂, —CH₂CH₂OH, —CH₂CH₂OMe, —CH₂CH₂OEt, —CH₂CH₂CH₂NH₂, and —CH₂CH₂NMe₂.

12. A compound according to claim 10, wherein Z is independently phenyl and is independently unsubstituted or substituted with one or more substituents selected from: —F, —Cl, —Br, —I, —OMe, —OEt, —OCF₃, —SO₂-morpholino, -Ph, pyridyl, furanyl, pyrrolyl, oxazolyl, thiadiazolyl, -Me, -Et, -tBu, —CF₃, and —CH₂OH.

13. A compound according to claim 10, wherein Y is independently phenyl and is independently, unsubstituted or substituted with one or more substituents selected from: —C(=O)OMe, —C(=O)OEt, —C(=O)O(tBu), —(C=O)NH₂, —C(=O)H, —F, —Cl, —Br, —I, —CN, —OH, —NH₂, —NHPh, —NH(C=O)Me, —NH(C=O)Et, —NH(C=O)Pr, —NH(C=O)Ph, —NHC(=O)CH₂Ph, —NHC(=O)CH(Me)Ph, —NHC(=O)(thiophenyl), —NHC(=O)CH₂(thiophenyl), —NHC(=O)furanyl, —NH(C=O)NH₂, —NH(C=O)NHMe, —NH(C=O)NHEt, —NH(C=O)NPh, —NH(C=O)NHCH₂Ph, —NH(C=S)NH₂, —NH(C=S)NHMe, —NH(C=S)NHEt, —NH(C=S)NPh, —NH(C=S)NHCH₂Ph, —NHSO₂Me, —NHSO₂Et, —NHSO₂Ph, —NHSO₂PhMe, —NHSO₂CH₂Ph, —NMeSO₂Me, —NHSO₂Et, —NMeSO₂Ph, —NMeSO₂PhMe, —NMeSO₂CH₂Ph, —SO₂NH₂, —SO₂NHMe, —SO₂NHEt, —SO₂NMe₂, —SO₂NEt₂, —SO₂-morpholino, —SO₂NHPh, —SO₂NHCH₂Ph, and —CH₂OH.

14. A compound according to claim 13, wherein Y is independently phenyl and is independently unsubstituted or substituted with one or more substituents selected from: —NH₂, —NH(C=O)Me, —NH(C=O)Et, —NH(C=O)Pr, —NH(C=O)Ph, and —NHC(=O)CH₂Ph.

15. A composition comprising a compound according to claim 10 and a pharmaceutically acceptable carrier or diluent.

16. A composition comprising a compound according to claim 14 and a pharmaceutically acceptable carrier or diluent.

17. A compound selected from compounds of the following formula and pharmaceutically acceptable salts thereof:

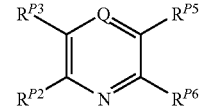

wherein:

Q is independently —N=;

R^P3 is independently a group of the formula -J¹-L¹-Z;

-J¹-L¹-Z is independently —NH—Z;

Z is independently phenyl and is independently unsubstituted or substituted with one or more substituents selected from: —C(=O)OH, —C(=O)OMe, —C(=O)OEt, —C(=O)O(iPr), —C(=O)O(tBu), —C(=O)O(cPr), —C(=O)OCH₂CH₂OH, —C(=O)OCH₂CH₂OMe, —C(=O)OCH₂CH₂OEt, —C(=O)OPh, —C(=O)OCH₂Ph, —(C=O)NH₂, —(C=O)NMe₂, —(C=O)NEt₂, —(C=O)N(iPr)₂, —(C=O)N(CH₂CH₂OH)₂, —(C=O)-morpholino, —(C=O)NHPh, —(C=O)NHCH₂Ph, —C(=O)H, —(C=O)Me, —(C=O)Et, —(C=O)(tBu), —(C=O)-cHex, —(C=O)Ph, —(C=O)CH₂Ph, —F, —Cl, —Br, —I, —OH, —OMe, —OEt, —O(iPr), —O(tBu), —OPh, —OCH₂Ph, —OCF₃, —OCH₂CF₃, —OCH₂CH₂OH, —OCH₂CH₂OMe, —OCH₂CH₂OEt, —OCH₂CH₂NH₂, —OCH₂CH₂NMe₂, —OCH₂CH₂N(iPr)₂, —OPh-Me, —OPh-OH, —OPh-OMe, —OPh-F, —OPh-Cl, —OPh-Br, —OPh-I, —SH, —SMe, —SEt, —SPh, —SCH₂Ph, —OC(=O)Me, —OC(=O)Et, —OC(=O)(iPr), —OC(=O)(tBu), —OC(=O)(cPr), —OC(=O)CH₂CH₂OH, —OC(=O)CH₂CH₂OMe, —OC(=O)CH₂CH₂OEt, —OC(=O)Ph, —OC(=O)CH₂Ph, —OC(=O)NH₂, —OC(=O)NHMe, —OC(=O)NMe₂, —OC(=O)NHEt, —OC(=O)NEt₂, —OC(=O)NHPh, —OC(=O)NCH₂Ph, —NH₂, —NHMe, —NHEt, —NH(iPr), —NMe$_2$, —NEt$_2$, —N(iPr)$_2$, —N(CH$_2$CH$_2$OH)$_2$, —NHPh, —NHCH$_2$Ph, piperidino, piperazino, morpholino, —NH(C=O)Me, —NH(C=O)Et, —NH(C=O)nPr, —NH(C=O)Ph, —NHC(=O)CH$_2$Ph, —NMe(C=O)Me, —NMe(C=O)Et, —NMe(C=O)Ph, —NMeC(=O)CH$_2$Ph, —NHSO$_2$Me, —NHSO$_2$Et, —NHSO$_2$Ph, —NHSO$_2$PhMe, —NHSO$_2$CH$_2$Ph, —NMeSO$_2$Me, —NMeSO$_2$Et, —NMeSO$_2$Ph, —NMeSO$_2$PhMe, —NMeSO$_2$CH$_2$Ph, —SO$_2$Me, —SO$_2$CF$_3$, —SO$_2$Et, —SO$_2$Ph, —SO$_2$PhMe, —SO$_2$CH$_2$Ph, —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph, —CH$_2$Ph, —CH$_2$Ph-Me, —CH$_2$Ph-OH, —CH$_2$Ph-F, —CH$_2$Ph-Cl, -Ph, -Ph-Me, -Ph-OH, -Ph-OMe, -Ph-NH$_2$, -Ph-F, -Ph-Cl, -Ph-Br, -Ph-I, pyridyl, pyrazinyl, pyrimidinyl, pyridazinyl, furanyl, thiophenyl, pyrrolyl, imidazolyl, pyrazolyl, oxazolyl, thiazolyl, thiadiazolyl, pyrrolidinyl, imidazolidinyl, pyrazolidinyl, piperidinyl, piperazinyl, azepinyl, tetrahydrofuranyl, tetrahydropyranyl, morpholinyl, azetidinyl, -Me, -Et, -nPr, -iPr, -nBu, -iBu, -sBu, -tBu, -nPe, -cPr, -cHex, —CH=CH$_2$, —CH$_2$—CH=CH$_2$, —CF$_3$, —CHF$_2$, —CH$_2$F, —CCl$_3$, —CBr$_3$, —CH$_2$CH$_2$F, —CH$_2$CHF$_2$, —CH$_2$CF$_3$, —CH$_2$OH, —CH$_2$OMe, —CH$_2$OEt, —CH$_2$NH$_2$, —CH$_2$NMe$_2$, —CH$_2$CH$_2$OH, —CH$_2$CH$_2$OMe, —CH$_2$CH$_2$OEt, —CH$_2$CH$_2$CH$_2$NH$_2$, and —CH$_2$CH$_2$NMe$_2$;

R$^{P2}$ is independently —H;

R$^{P5}$ is independently a group of the formula —W—Y;

W is independently —O—;

Y is independently naphthyl and is independently unsubstituted or substituted with one or more substituents selected from: —C(=O)OMe, —C(=O)OEt, —C(=O)O(iPr), —C(=O)O(tBu), —C(=O)O(cPr), —C(=O)OCH$_2$CH$_2$OH, —C(=O)OCH$_2$CH$_2$OMe, —C(=O)OCH$_2$CH$_2$OEt, —C(=O)OPh, —C(=O)OCH$_2$Ph, —(C=O)NH$_2$, —(C=O)NMe$_2$, —(C=O)NEt$_2$, —(C=O)N(iPr)$_2$, —(C=O)N(CH$_2$CH$_2$OH)$_2$, —(C=O)-morpholino, —(C=O)NHPh, —(C=O)NHCH$_2$Ph, —C(=O)H, —(C=O)Me, —(C=O)Et, —(C=O)(tBu), —(C=O)-cHex, —(C=O)Ph, —(C=O)CH$_2$Ph, —F, —Cl, —Br, —I, —CN, —OH, —NH$_2$, —NHMe, —NHEt, —NH(iPr), —NMe$_2$, —NEt$_2$, —N(iPr)$_2$, —N(CH$_2$CH$_2$OH)$_2$, —NHPh, —NHCH$_2$Ph, piperidino, piperazino, morpholino, —NH(C=O)Me, —NH(C=O)Et, —NH(C=O)Pr, —NH(C=O)Ph, —NHC(=O)CH$_2$Ph, —NMe(C=O)Me, —NMe(C=O)Et, —NMe(C=O)Ph, —NMeC(=O)CH$_2$Ph, —NH(C=O)NH$_2$, —NH(C=O)NHMe, —NH(C=O)NHEt, —NH(C=O)NPh, —NH(C=O)NHCH$_2$Ph, —NH(C=S)NH$_2$, —NH(C=S)NHMe, —NH(C=S)NHEt, —NH(C=S)NPh, —NH(C=S)NHCH$_2$Ph, —NHSO$_2$Me, —NHSO$_2$Et, —NHSO$_2$Ph, —NHSO$_2$PhMe, —NHSO$_2$CH$_2$Ph, —NMeSO$_2$Me, —NMeSO$_2$Et, —NMeSO$_2$Ph, —NMeSO$_2$PhMe, —NMeSO$_2$CH$_2$Ph, —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph, -Me, -Et, -nPr, -iPr, -nBu, -iBu, -sBu, -tBu, -nPe, -cPr, -cHex, —CH=CH$_2$, —CH$_2$—CH=CH$_2$, —CF$_3$, —CHF$_2$, —CH$_2$F, —CCl$_3$, —CBr$_3$, —CH$_2$CH$_2$F, —CH$_2$CHF$_2$, —CH$_2$CF$_3$, —CH$_2$OH, —CH$_2$OMe, —CH$_2$OEt, —CH$_2$NH$_2$, —CH$_2$NMe$_2$, —CH$_2$CH$_2$OH, —CH$_2$CH$_2$OMe, —CH$_2$CH$_2$OEt, —CH$_2$CH$_2$CH$_2$NH$_2$, and —CH$_2$CH$_2$NMe$_2$; and R$^{P6}$ is independently —H.

18. A compound according to claim 17, wherein Z is independently phenyl and is independently unsubstituted or substituted with one or more substituents selected from: —C(=O)OMe, —C(=O)OEt, —C(=O)O(iPr), —C(=O)O(tBu), —C(=O)O(cPr), —C(=O)OCH$_2$CH$_2$OH, —C(=O)OCH$_2$CH$_2$OMe, —C(=O)OCH$_2$CH$_2$OEt, —C(=O)OPh, —C(=O)OCH$_2$Ph, —F, —Cl, —Br, —I, —OH, —OMe, —OEt, —O(iPr), —O(tBu), —OPh, —OCH$_2$Ph, —OCF$_3$, —OCH$_2$CF$_3$, —OCH$_2$CH$_2$OH, —OCH$_2$CH$_2$OMe, —OCH$_2$CH$_2$OEt, —OCH$_2$CH$_2$NH$_2$, —OCH$_2$CH$_2$NMe$_2$, —OCH$_2$CH$_2$N(iPr)$_2$, —OPh -Me, —OPh —OH, —OPh-OMe, —OPh-F, —OPh-Cl, —OPh-Br, —OPh-I, —SH, —SMe, —SEt, —SPh, —SCH$_2$Ph, —OC(=O)Me, —OC(=O)Et, —OC(=O)(iPr), —OC(=O)(tBu), —OC(=O)(cPr), —OC(=O)CH$_2$CH$_2$OH, —OC(=O)CH$_2$CH$_2$OMe, —OC(=O)CH$_2$CH$_2$OEt, —OC(=O)Ph, —OC(=O)CH$_2$Ph, —SO$_2$Me, —SO$_2$CF$_3$, —SO$_2$Et, —SO$_2$Ph, —SO$_2$PhMe, —SO$_2$CH$_2$Ph, -Ph, -Ph-Me, -Ph-OH, -Ph-OMe, -Ph-NH$_2$, -Ph-F, -Ph-Cl, -Ph-Br, -Ph-I, pyridyl, pyrazinyl, pyrimidinyl, pyridazinyl, furanyl, thiophenyl, pyrrolyl, imidazolyl, pyrazolyl, oxazolyl, thiazolyl, thiadiazolyl, pyrrolidinyl, imidazolidinyl, pyrazolidinyl, piperidinyl, piperazinyl, azepinyl, tetrahydrofuranyl, tetrahydropyranyl, morpholinyl, azetidinyl, -Me, -Et, -nPr, -iPr, -nBu, -iBu, -sBu, -tBu, -nPe, -cPr, -cHex, —CH=CH$_2$, —CH$_2$—CH=CH$_2$, —CF$_3$, —CHF$_2$, —CH$_2$F, —CCl$_3$, —CBr$_3$, —CH$_2$CH$_2$F, —CH$_2$CHF$_2$, —CH$_2$CF$_3$, —CH$_2$OH, —CH$_2$OMe, —CH$_2$OEt, —CH$_2$NH$_2$, —CH$_2$NMe$_2$, —CH$_2$CH$_2$OH, —CH$_2$CH$_2$OMe, —CH$_2$CH$_2$OEt, —CH$_2$CH$_2$CH$_2$NH$_2$, and —CH$_2$CH$_2$NMe$_2$.

19. A compound according to claim 17, wherein Y is independently naphthyl and is independently unsubstituted or substituted with one or more substituents selected from: —C(=O)OMe, —C(=O)OEt, —C(=O)O(tBu), —(C=O)NH$_2$, —C(=O)H, —F, —Cl, —Br, —I, —CN, —OH, —NH$_2$, —NHPh, —NH(C=O)Me, —NH(C=O)Et, —NH(C=O)Pr, —NH(C=O)Ph, —NHC(=O)CH$_2$Ph, —NHC(=O)CH(Me)Ph, —NHC(=O)(thiophenyl), —NHC(=O)CH$_2$(thiophenyl), —NHC(=O)furanyl, —NH(C=O)NH$_2$, —NH(C=O)NHMe, —NH(C=O)NHEt, —NH(C=O)NPh, —NH(C=O)NHCH$_2$Ph, —NH(C=S)NH$_2$, —NH(C=S)NHMe, —NH(C=S)NHEt, —NH(C=S)NPh, —NH(C=S)NHCH$_2$Ph, —NHSO$_2$Me, —NHSO$_2$Et, —NHSO$_2$Ph, —NHSO$_2$PhMe, —NHSO$_2$CH$_2$Ph, —NMeSO$_2$Me, —NMeSO$_2$Et, —NMeSO$_2$Ph, —NMeSO$_2$PhMe, —NMeSO$_2$CH$_2$Ph, —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph, and —CH$_2$OH.

20. A composition comprising a compound according to claim 17 and a pharmaceutically acceptable carrier or diluent.

21. A compound according to claim 17, wherein Z is independently phenyl and is independently unsubstituted or substituted with one or more substituents selected from: —F, —Cl, —Br, —I, —OMe, —OEt, —OCF$_3$, —SO$_2$-morpholino, -Ph, pyridyl, furanyl, pyrrolyl, oxazolyl, thiadiazolyl, -Me, -Et, -tBu, —CF$_3$, and —CH$_2$OH.

22. A compound according to claim 21, wherein Y is independently naphthyl and is independently unsubstituted or substituted with one or more substituents selected from: —NH$_2$, —NH(C=O)Me, —NH(C=O)Et, —NH(C=O)Pr, —NH(C=O)Ph, and —NHC(=O)CH$_2$Ph.

23. A composition comprising a compound according to claim 22 and a pharmaceutically acceptable carrier or diluent.

24. A compound selected from the following compounds and pharmaceutically acceptable salts thereof:

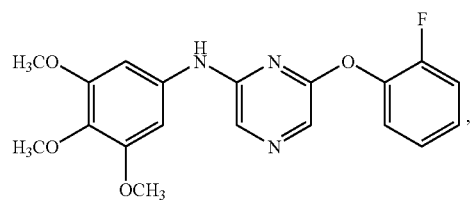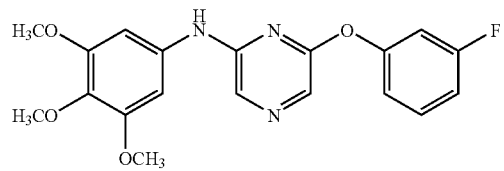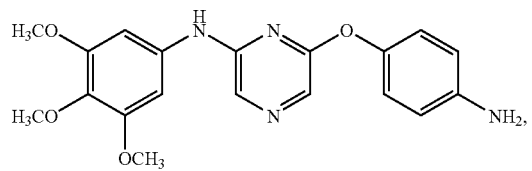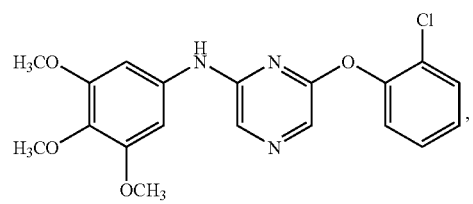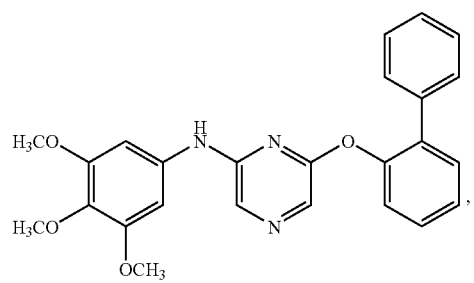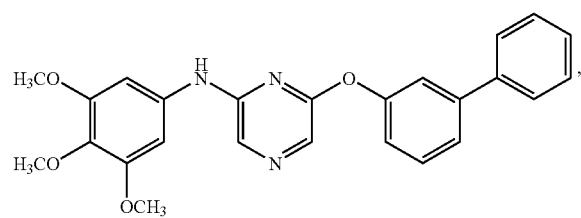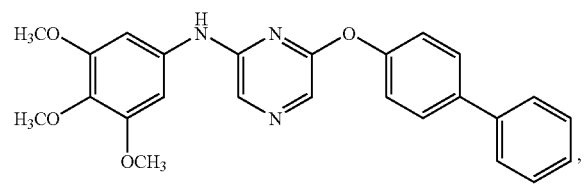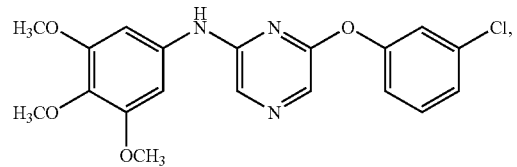
-continued
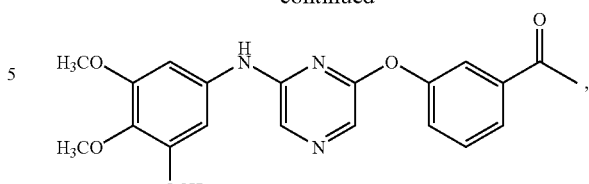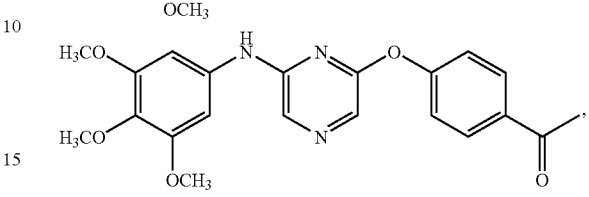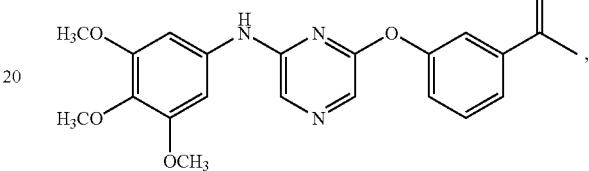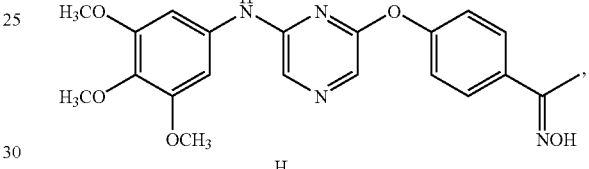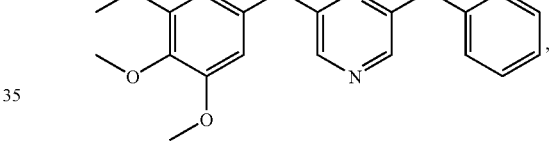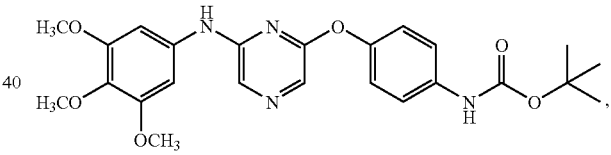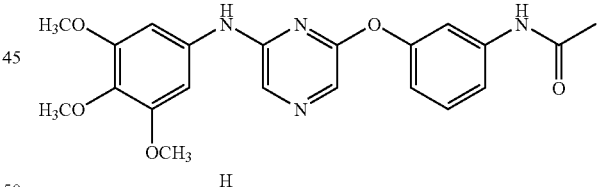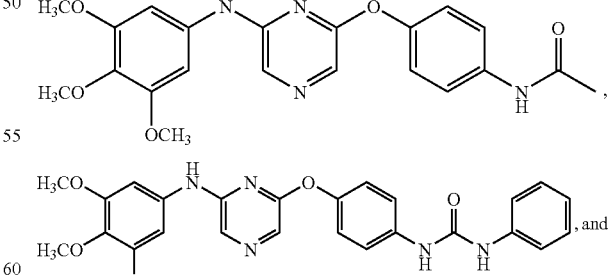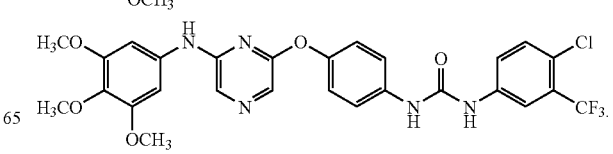

25. A composition comprising a compound according to claim 24 and a pharmaceutically acceptable carrier or diluent.
26. A compound selected from the following compounds and pharmaceutically acceptable salts thereof:
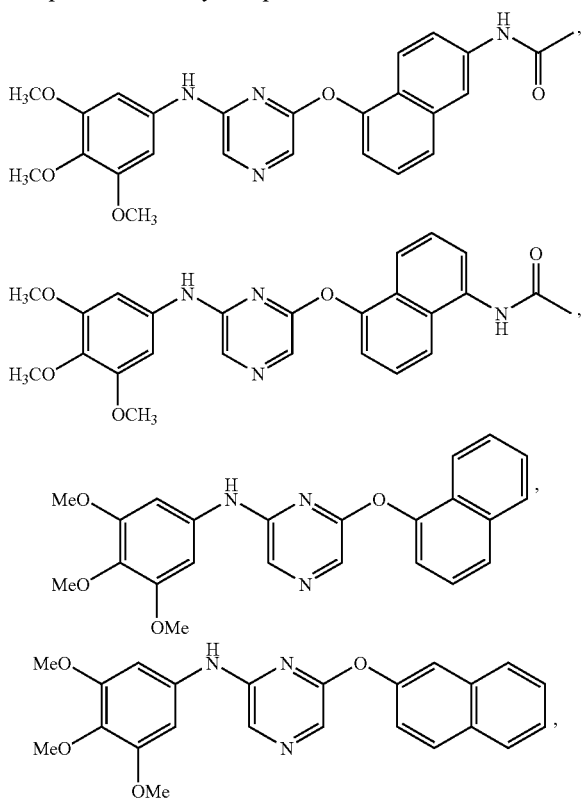
-continued
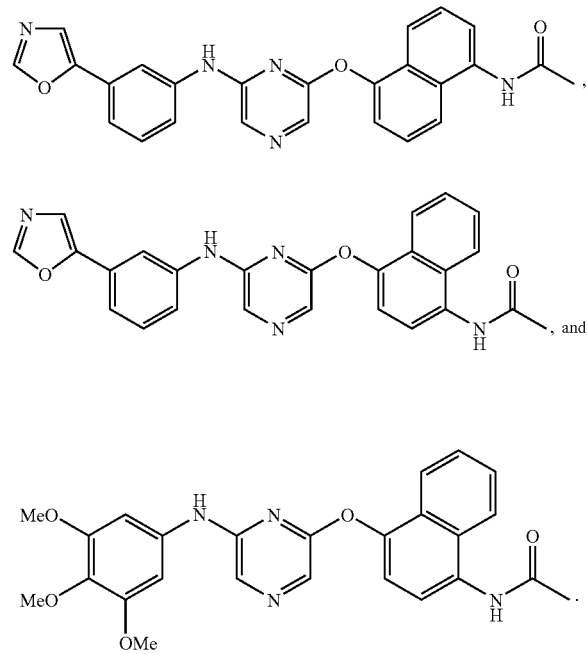
27. A composition comprising a compound according to claim 26 and a pharmaceutically acceptable carrier or diluent.
* * * * *